US009498778B2

(12) United States Patent
Corey et al.

(10) Patent No.: US 9,498,778 B2
(45) Date of Patent: Nov. 22, 2016

(54) INSTRUMENT FOR PROCESSING CARTRIDGE FOR PERFORMING ASSAYS IN A CLOSED SAMPLE PREPARATION AND REACTION SYSTEM

(71) Applicant: GENMARK DIAGNOSTICS, INC., Carlsbad, CA (US)

(72) Inventors: Scott Corey, Hydes, MD (US); Brian Murphy, Carlsbad, CA (US); Eric Schneider, Carlsbad, CA (US); David Walter Wright, Littleton, CO (US); Dominic Aiello, Denver, CO (US); Andrew Fish, Carlsbad, CA (US); Jay Srinivasan, Carlsbad, CA (US); George Maltezos, Merrick, NY (US)

(73) Assignee: GENMARK DIAGNOSTICS, INC., Carlsbad, CA (US)

( * ) Notice: Subject to any disclaimer, the term of this patent is extended or adjusted under 35 U.S.C. 154(b) by 158 days.

(21) Appl. No.: 14/538,565

(22) Filed: Nov. 11, 2014

(65) Prior Publication Data
US 2016/0129445 A1   May 12, 2016

(51) Int. Cl.
*B01L 7/00* (2006.01)
*B01L 3/00* (2006.01)

(52) U.S. Cl.
CPC ............... *B01L 7/52* (2013.01); *B01L 3/505* (2013.01); *B01L 2200/10* (2013.01); *B01L 2300/0609* (2013.01); *B01L 2300/0636* (2013.01); *B01L 2300/123* (2013.01); *B01L 2300/18* (2013.01); *B01L 2400/0481* (2013.01)

(58) Field of Classification Search
CPC .. B01L 7/52; B01L 3/5027; B01L 3/502715; B01L 3/505; B01L 3/502761; B01L 2300/0609; B01L 2300/0636; B01L 2400/0481; B01L 2200/10; B01L 2300/18
See application file for complete search history.

(56) References Cited

U.S. PATENT DOCUMENTS

| 3,641,909 A | 2/1972 | Baker |
| 3,687,051 A | 8/1972 | Baker et al. |
| 3,776,425 A | 12/1973 | Baker et al. |

(Continued)

FOREIGN PATENT DOCUMENTS

| EP | 0173547 B1 | 6/1990 |
| EP | 0583833 A2 | 2/1994 |

(Continued)

OTHER PUBLICATIONS

Notice of Allowance issued in U.S. Appl. No. 14/206,867, 43 pages (Aug. 7, 2015).

(Continued)

*Primary Examiner* — Brian R Gordon
(74) *Attorney, Agent, or Firm* — Rothwell, Figg, Ernst & Manbeck PC

(57) ABSTRACT

In one embodiment, a multiplex fluid processing cartridge includes a sample well, a deformable fluid chamber, a mixing well with a mixer disposed therein, a lysis chamber including a lysis mixer, an electrowetting grid for microdroplet manipulation, and electrosensor arrays configured to detect analytes of interest. An instrument for processing the cartridge is configured to receive the cartridge and to selectively apply thermal energy, magnetic force, and electrical connections to one or more discrete locations on the cartridge and is further configured to compress the deformable chamber(s) in a specified sequence.

23 Claims, 57 Drawing Sheets

(56) References Cited

U.S. PATENT DOCUMENTS

| | | |
|---|---|---|
| 3,820,149 A | 6/1974 | Baker et al. |
| 4,007,010 A | 2/1977 | Woodbridge, III |
| 4,182,447 A | 1/1980 | Kay |
| 4,469,863 A | 9/1984 | Ts'o et al. |
| 4,769,333 A | 9/1988 | Dole et al. |
| 4,859,603 A | 8/1989 | Dole et al. |
| 4,887,455 A | 12/1989 | Payne et al. |
| 4,978,502 A | 12/1990 | Dole et al. |
| 5,034,506 A | 7/1991 | Summerton et al. |
| 5,089,233 A | 2/1992 | DeVaney, Jr. et al. |
| 5,098,660 A | 3/1992 | DeVaney, Jr. |
| 5,154,888 A | 10/1992 | Zander et al. |
| 5,216,141 A | 6/1993 | Benner |
| 5,229,297 A | 7/1993 | Schnipelsky et al. |
| 5,234,809 A | 8/1993 | Boom et al. |
| 5,235,033 A | 8/1993 | Summerton et al. |
| 5,254,479 A | 10/1993 | Chemelli |
| 5,288,463 A | 2/1994 | Chemelli |
| 5,290,518 A | 3/1994 | Johnson |
| 5,374,395 A | 12/1994 | Robinson et al. |
| 5,386,023 A | 1/1995 | Sanghvi et al. |
| 5,422,271 A | 6/1995 | Chen et al. |
| 5,460,780 A | 10/1995 | DeVaney, Jr. et al. |
| 5,468,366 A | 11/1995 | Wegner et al. |
| 5,512,439 A | 4/1996 | Hornes et al. |
| 5,591,578 A | 1/1997 | Meade et al. |
| 5,593,804 A | 1/1997 | Chemelli et al. |
| 5,602,240 A | 2/1997 | De Mesmaeker et al. |
| 5,637,684 A | 6/1997 | Cook et al. |
| 5,644,048 A | 7/1997 | Yau |
| 5,652,149 A | 7/1997 | Mileaf et al. |
| 5,674,653 A | 10/1997 | Chemelli et al. |
| 5,681,702 A | 10/1997 | Collins et al. |
| 5,692,644 A | 12/1997 | Gueret |
| 5,705,348 A | 1/1998 | Meade et al. |
| 5,705,628 A | 1/1998 | Hawkins |
| 5,714,380 A | 2/1998 | Neri et al. |
| 5,716,852 A | 2/1998 | Yager et al. |
| 5,726,404 A | 3/1998 | Brody |
| 5,726,751 A | 3/1998 | Altendorf et al. |
| 5,747,349 A | 5/1998 | Van Den Engh et al. |
| 5,748,827 A | 5/1998 | Holl et al. |
| 5,770,365 A | 6/1998 | Lane et al. |
| 5,807,701 A | 9/1998 | Payne et al. |
| 5,824,473 A | 10/1998 | Meade et al. |
| 5,851,536 A | 12/1998 | Yager et al. |
| 5,873,990 A | 2/1999 | Wojciechowski et al. |
| 5,876,187 A | 3/1999 | Afromowitz et al. |
| 5,882,497 A | 3/1999 | Persaud et al. |
| 5,898,071 A | 4/1999 | Hawkins |
| 5,932,100 A | 8/1999 | Yager et al. |
| 5,948,684 A | 9/1999 | Weigl et al. |
| 5,955,028 A | 9/1999 | Chow |
| 5,971,158 A | 10/1999 | Yager et al. |
| 5,972,710 A | 10/1999 | Weigl et al. |
| 5,973,138 A | 10/1999 | Collis |
| 5,974,867 A | 11/1999 | Forster et al. |
| 6,007,775 A | 12/1999 | Yager |
| 6,013,170 A | 1/2000 | Meade |
| 6,013,459 A | 1/2000 | Meade |
| 6,033,601 A | 3/2000 | Persaud et al. |
| 6,039,897 A | 3/2000 | Lochhead et al. |
| 6,063,573 A | 5/2000 | Kayyem |
| 6,067,157 A | 5/2000 | Altendorf |
| 6,071,478 A | 6/2000 | Chow |
| 6,090,933 A | 7/2000 | Kayyem et al. |
| 6,091,502 A | 7/2000 | Weigl et al. |
| 6,096,273 A | 8/2000 | Kayyem et al. |
| 6,110,354 A | 8/2000 | Saban et al. |
| 6,134,950 A | 10/2000 | Forster et al. |
| 6,136,272 A | 10/2000 | Weigl et al. |
| 6,159,739 A | 12/2000 | Weigl et al. |
| 6,167,910 B1 | 1/2001 | Chow |
| 6,171,865 B1 | 1/2001 | Weigl et al. |
| 6,180,064 B1 | 1/2001 | Persaud et al. |
| 6,180,114 B1 | 1/2001 | Yager et al. |
| 6,190,858 B1 | 2/2001 | Persaud et al. |
| 6,192,351 B1 | 2/2001 | Persaud |
| 6,221,583 B1 | 4/2001 | Kayyem et al. |
| 6,221,677 B1 | 4/2001 | Wu et al. |
| 6,227,809 B1 | 5/2001 | Forster et al. |
| 6,232,062 B1 | 5/2001 | Kayyem et al. |
| 6,235,501 B1 | 5/2001 | Gautsch et al. |
| 6,236,951 B1 | 5/2001 | Payne et al. |
| 6,248,229 B1 | 6/2001 | Meade |
| 6,255,477 B1 | 7/2001 | Kleiber et al. |
| 6,264,825 B1 | 7/2001 | Blackburn et al. |
| 6,265,155 B1 | 7/2001 | Meade et al. |
| 6,268,136 B1 | 7/2001 | Shuber et al. |
| 6,277,641 B1 | 8/2001 | Yager |
| 6,290,839 B1 | 9/2001 | Kayyem et al. |
| 6,297,061 B1 | 10/2001 | Wu et al. |
| 6,300,138 B1 | 10/2001 | Gleason et al. |
| 6,321,791 B1 | 11/2001 | Chow |
| 6,361,958 B1 | 3/2002 | Shieh et al. |
| 6,366,924 B1 | 4/2002 | Parce |
| 6,376,232 B1 | 4/2002 | Payne et al. |
| 6,387,290 B1 | 5/2002 | Brody et al. |
| 6,391,558 B1 | 5/2002 | Henkens et al. |
| 6,399,023 B1 | 6/2002 | Chow |
| 6,399,025 B1 | 6/2002 | Chow |
| 6,403,338 B1 | 6/2002 | Knapp et al. |
| 6,404,493 B1 | 6/2002 | Altendorf |
| 6,406,857 B1 | 6/2002 | Shuber et al. |
| 6,408,884 B1 | 6/2002 | Kamholz et al. |
| 6,409,832 B2 | 6/2002 | Weigl et al. |
| 6,415,821 B2 | 7/2002 | Kamholz et al. |
| 6,426,230 B1 | 7/2002 | Feistel |
| 6,431,016 B1 | 8/2002 | Payne |
| 6,431,212 B1 | 8/2002 | Hayenga et al. |
| 6,431,476 B1 | 8/2002 | Taylor et al. |
| 6,432,720 B2 | 8/2002 | Chow |
| 6,432,723 B1 | 8/2002 | Plaxco et al. |
| 6,433,160 B1 | 8/2002 | Collis |
| 6,440,725 B1 | 8/2002 | Pourahmadi et al. |
| 6,443,307 B1 | 9/2002 | Burridge |
| 6,451,606 B1 | 9/2002 | Konig et al. |
| 6,454,945 B1 | 9/2002 | Weigl et al. |
| 6,479,240 B1 | 11/2002 | Kayyem et al. |
| 6,482,306 B1 | 11/2002 | Yager et al. |
| 6,488,896 B2 | 12/2002 | Weigl et al. |
| 6,494,230 B2 | 12/2002 | Chow |
| 6,495,104 B1 | 12/2002 | Unno et al. |
| 6,495,323 B1 | 12/2002 | Kayyem et al. |
| 6,503,757 B1 | 1/2003 | Chow |
| 6,518,024 B2 | 2/2003 | Choong et al. |
| 6,524,456 B1 | 2/2003 | Ramsey et al. |
| 6,537,501 B1 | 3/2003 | Holl et al. |
| 6,541,213 B1 | 4/2003 | Weigl et al. |
| 6,541,617 B1 | 4/2003 | Bamdad et al. |
| 6,557,427 B2 | 5/2003 | Weigl et al. |
| 6,562,568 B1 | 5/2003 | Kleiber et al. |
| 6,565,727 B1 | 5/2003 | Shenderov |
| 6,575,188 B2 | 6/2003 | Parunak |
| 6,576,194 B1 | 6/2003 | Holl et al. |
| 6,581,899 B2 | 6/2003 | Williams |
| 6,582,963 B1 | 6/2003 | Weigl et al. |
| 6,596,483 B1 | 7/2003 | Choong et al. |
| 6,600,026 B1 | 7/2003 | Yu |
| 6,602,400 B1 | 8/2003 | Choong et al. |
| 6,627,412 B1 | 9/2003 | Manning et al. |
| 6,642,046 B1 | 11/2003 | McGarry et al. |
| 6,645,758 B1 | 11/2003 | Schnipelsky et al. |
| 6,647,397 B2 | 11/2003 | Parce |
| 6,648,015 B1 | 11/2003 | Chow |
| 6,655,010 B1 | 12/2003 | Hatfield et al. |
| 6,656,431 B2 | 12/2003 | Holl et al. |
| 6,660,480 B2 | 12/2003 | Ramsey et al. |
| 6,664,104 B2 | 12/2003 | Pourahmadi et al. |
| 6,674,525 B2 | 1/2004 | Bardell et al. |
| 6,686,150 B1 | 2/2004 | Blackburn et al. |
| 6,695,147 B1 | 2/2004 | Yager et al. |
| 6,706,498 B2 | 3/2004 | Gautsch et al. |
| 6,712,925 B1 | 3/2004 | Holl et al. |

(56) References Cited

U.S. PATENT DOCUMENTS

| | | |
|---|---|---|
| 6,739,531 B2 | 5/2004 | Taylor |
| 6,740,518 B1 | 5/2004 | Duong et al. |
| 6,742,661 B1 | 6/2004 | Schulte et al. |
| 6,743,399 B1 | 6/2004 | Weigl et al. |
| 6,753,143 B2 | 6/2004 | Tao et al. |
| 6,761,816 B1 | 7/2004 | Blackburn et al. |
| 6,773,566 B2 | 8/2004 | Shenderov |
| 6,783,647 B2 | 8/2004 | Culbertson et al. |
| 6,790,341 B1 | 9/2004 | Saban et al. |
| 6,824,669 B1 | 11/2004 | Li et al. |
| 6,830,729 B1 | 12/2004 | Holl et al. |
| 6,833,267 B1 | 12/2004 | Kayyem |
| 6,852,284 B1 | 2/2005 | Holl et al. |
| 6,857,449 B1 | 2/2005 | Chow |
| 6,875,619 B2 | 4/2005 | Blackburn |
| 6,878,540 B2 | 4/2005 | Pourahmadi et al. |
| 6,881,541 B2 | 4/2005 | Petersen et al. |
| 6,887,693 B2 | 5/2005 | McMillan et al. |
| 6,893,879 B2 | 5/2005 | Petersen et al. |
| 6,914,137 B2 | 7/2005 | Baker |
| 6,919,444 B2 | 7/2005 | Harttig et al. |
| 6,942,771 B1 | 9/2005 | Kayyem |
| 6,951,759 B2 | 10/2005 | Travers et al. |
| 6,960,437 B2 | 11/2005 | Enzelberger et al. |
| 6,960,467 B2 | 11/2005 | Shieh et al. |
| 6,968,978 B1 | 11/2005 | Matthews |
| 6,977,151 B2 | 12/2005 | Kayyem et al. |
| 6,979,424 B2 | 12/2005 | Northrup et al. |
| 7,010,391 B2 | 3/2006 | Handique et al. |
| 7,011,791 B2 | 3/2006 | Weigl et al. |
| 7,014,992 B1 | 3/2006 | Kayyem et al. |
| 7,018,523 B2 | 3/2006 | Meade |
| 7,030,989 B2 | 4/2006 | Yager et al. |
| 7,045,285 B1 | 5/2006 | Kayyem et al. |
| 7,056,475 B2 | 6/2006 | Lum et al. |
| 7,056,669 B2 | 6/2006 | Kayyem et al. |
| 7,087,148 B1 | 8/2006 | Blackburn et al. |
| 7,090,804 B2 | 8/2006 | Kayyem et al. |
| 7,119,194 B2 | 10/2006 | Uematsu et al. |
| 7,125,668 B2 | 10/2006 | Kayyem et al. |
| 7,141,429 B2 | 11/2006 | Munson et al. |
| 7,155,344 B1 | 12/2006 | Parce et al. |
| 7,160,678 B1 | 1/2007 | Kayyem et al. |
| 7,163,612 B2 | 1/2007 | Sterling et al. |
| 7,169,358 B2 | 1/2007 | Henkens et al. |
| 7,172,897 B2 | 2/2007 | Blackburn et al. |
| 7,192,557 B2 | 3/2007 | Wu et al. |
| 7,201,881 B2 | 4/2007 | Cox et al. |
| 7,208,271 B2 | 4/2007 | Bost et al. |
| 7,223,371 B2 | 5/2007 | Hayenga et al. |
| 7,226,562 B2 | 6/2007 | Holl et al. |
| 7,238,268 B2 | 7/2007 | Ramsey et al. |
| 7,255,780 B2 | 8/2007 | Shenderov |
| 7,258,837 B2 | 8/2007 | Yager et al. |
| 7,267,939 B2 | 9/2007 | Meade |
| 7,270,786 B2 | 9/2007 | Parunak et al. |
| 7,271,007 B2 | 9/2007 | Weigl et al. |
| 7,312,087 B2 | 12/2007 | Duong et al. |
| 7,323,140 B2 | 1/2008 | Handique et al. |
| 7,343,248 B2 | 3/2008 | Parce et al. |
| 7,364,886 B2 | 4/2008 | Hasenbank et al. |
| 7,371,830 B2 | 5/2008 | Kleiber et al. |
| 7,381,525 B1 | 6/2008 | Kayyem et al. |
| 7,381,533 B2 | 6/2008 | Kayyem et al. |
| 7,384,749 B2 | 6/2008 | Kayyem et al. |
| 7,393,645 B2 | 7/2008 | Kayyem et al. |
| 7,405,054 B1 | 7/2008 | Hasenbank et al. |
| 7,416,791 B1 | 8/2008 | Carlson et al. |
| 7,416,892 B2 | 8/2008 | Battrell et al. |
| 7,419,575 B2 | 9/2008 | Culbertson et al. |
| 7,419,638 B2 | 9/2008 | Saltsman et al. |
| 7,439,014 B2 | 10/2008 | Pamula et al. |
| 7,473,397 B2 | 1/2009 | Griffin et al. |
| 7,491,495 B2 | 2/2009 | Zielenski et al. |
| 7,514,228 B2 | 4/2009 | Meade |
| 7,534,331 B2 | 5/2009 | Kayyem |
| 7,544,506 B2 | 6/2009 | Breidford et al. |
| 7,550,267 B2 | 6/2009 | Hawkins et al. |
| 7,560,237 B2 | 7/2009 | O'Connor et al. |
| 7,566,534 B2 | 7/2009 | Meade |
| 7,569,346 B2 | 8/2009 | Petersen et al. |
| 7,579,145 B2 | 8/2009 | Meade |
| D599,832 S | 9/2009 | Chapin et al. |
| 7,582,419 B2 | 9/2009 | Meade |
| 7,595,153 B2 | 9/2009 | Meade |
| 7,601,507 B2 | 10/2009 | O'Connor et al. |
| 7,648,835 B2 | 1/2010 | Breidford et al. |
| 7,655,129 B2 | 2/2010 | Blackburn et al. |
| 7,655,190 B2 | 2/2010 | Satou et al. |
| 7,659,089 B2 | 2/2010 | Hasenbank et al. |
| 7,713,711 B2 | 5/2010 | O'Connor et al. |
| 7,727,723 B2 | 6/2010 | Pollack et al. |
| 7,731,906 B2 | 6/2010 | Handique et al. |
| 7,736,891 B2 | 6/2010 | Nelson et al. |
| 7,759,073 B2 | 7/2010 | O'Connor et al. |
| 7,763,453 B2 | 7/2010 | Clemmens et al. |
| 7,763,471 B2 | 7/2010 | Pamula et al. |
| 7,789,270 B2 | 9/2010 | Tanaami et al. |
| 7,794,669 B2 | 9/2010 | Gyonouchi et al. |
| 7,815,871 B2 | 10/2010 | Pamula et al. |
| 7,816,121 B2 | 10/2010 | Pollack et al. |
| 7,820,030 B2 | 10/2010 | Althaus et al. |
| 7,820,391 B2 | 10/2010 | Chunlin |
| 7,822,510 B2 | 10/2010 | Paik et al. |
| 7,833,708 B2 | 11/2010 | Enzelberger et al. |
| 7,851,184 B2 | 12/2010 | Pollack et al. |
| 7,854,897 B2 | 12/2010 | Tanaami et al. |
| 7,858,045 B2 | 12/2010 | Tanaami et al. |
| 7,863,035 B2 | 1/2011 | Clemens et al. |
| 7,867,757 B2 | 1/2011 | Karlsen et al. |
| 7,901,947 B2 | 3/2011 | Pollack et al. |
| 7,910,294 B2 | 3/2011 | Karlsen |
| 7,914,994 B2 | 3/2011 | Petersen et al. |
| 7,919,330 B2 | 4/2011 | De Guzman et al. |
| 7,935,316 B2 | 5/2011 | Gyonouchi et al. |
| 7,935,481 B1 | 5/2011 | Umek et al. |
| 7,935,537 B2 | 5/2011 | Haley |
| 7,939,021 B2 | 5/2011 | Smith et al. |
| 7,943,030 B2 | 5/2011 | Shenderov |
| 7,955,836 B2 | 6/2011 | Clemmens et al. |
| 7,987,022 B2 | 7/2011 | Handique et al. |
| 7,998,436 B2 | 8/2011 | Pollack et al. |
| 7,998,708 B2 | 8/2011 | Handique et al. |
| 8,007,739 B2 | 8/2011 | Pollack et al. |
| 8,012,743 B2 | 9/2011 | Bamdad et al. |
| 8,017,340 B2 | 9/2011 | Collier et al. |
| 8,041,463 B2 | 10/2011 | Pollack et al. |
| 8,048,628 B2 | 11/2011 | Pollack et al. |
| 8,053,239 B2 | 11/2011 | Wheeler et al. |
| 8,088,578 B2 | 1/2012 | Hua et al. |
| 8,093,062 B2 | 1/2012 | Winger |
| 8,101,403 B2 | 1/2012 | Yager et al. |
| 8,101,431 B2 | 1/2012 | McDevitt et al. |
| 8,105,477 B2 | 1/2012 | Althaus et al. |
| 8,105,783 B2 | 1/2012 | Handique |
| 8,105,849 B2 | 1/2012 | McDevitt et al. |
| 8,110,392 B2 | 2/2012 | Battrell et al. |
| 8,114,661 B2 | 2/2012 | O'Connor et al. |
| 8,129,118 B2 | 3/2012 | Weindel et al. |
| 8,133,671 B2 | 3/2012 | Williams et al. |
| 8,133,703 B2 | 3/2012 | Ching et al. |
| 8,137,917 B2 | 3/2012 | Pollack et al. |
| 8,168,442 B2 | 5/2012 | Petersen et al. |
| 8,187,864 B2 | 5/2012 | Wheeler et al. |
| 8,201,765 B2 | 6/2012 | Rajagopal et al. |
| 8,202,686 B2 | 6/2012 | Pamula et al. |
| 8,202,736 B2 | 6/2012 | Mousa et al. |
| 8,208,146 B2 | 6/2012 | Srinivasan et al. |
| 8,216,529 B2 | 7/2012 | Ade et al. |
| 8,216,832 B2 | 7/2012 | Battrell et al. |
| 8,222,023 B2 | 7/2012 | Battrell et al. |
| 8,247,176 B2 | 8/2012 | Petersen et al. |
| 8,247,191 B2 | 8/2012 | Ritzen et al. |
| 8,268,246 B2 | 9/2012 | Srinivasan et al. |

(56) References Cited

U.S. PATENT DOCUMENTS

| | | |
|---|---|---|
| 8,273,308 B2 | 9/2012 | Handique et al. |
| 8,304,253 B2 | 11/2012 | Yi et al. |
| 8,313,698 B2 | 11/2012 | Pollack et al. |
| 8,313,895 B2 | 11/2012 | Pollack et al. |
| 8,317,990 B2 | 11/2012 | Pamula et al. |
| 8,318,109 B2 | 11/2012 | Saltsman et al. |
| 8,318,439 B2 | 11/2012 | Battrell et al. |
| 8,323,900 B2 | 12/2012 | Handique et al. |
| 8,329,453 B2 | 12/2012 | Battrell et al. |
| 8,338,166 B2 * | 12/2012 | Beer .................. B01L 3/502753 435/283.1 |
| 8,343,636 B2 | 1/2013 | Jen et al. |
| 8,349,276 B2 | 1/2013 | Pamula et al. |
| 8,356,763 B2 | 1/2013 | Rajagopal et al. |
| 8,364,315 B2 | 1/2013 | Sturmer et al. |
| 8,367,370 B2 | 2/2013 | Wheeler et al. |
| 8,372,340 B2 | 2/2013 | Bird et al. |
| 8,388,909 B2 | 3/2013 | Pollack et al. |
| 8,389,297 B2 | 3/2013 | Pamula et al. |
| 8,394,608 B2 | 3/2013 | Ririe et al. |
| 8,394,641 B2 | 3/2013 | Winger |
| 8,404,440 B2 | 3/2013 | Solli et al. |
| 8,426,213 B2 | 4/2013 | Eckhardt et al. |
| 8,426,214 B2 | 4/2013 | Stayton et al. |
| 8,431,389 B2 | 4/2013 | Battrell et al. |
| 8,440,392 B2 | 5/2013 | Pamula et al. |
| 8,454,905 B2 | 6/2013 | Pope et al. |
| 8,460,528 B2 | 6/2013 | Pollack et al. |
| 8,470,606 B2 | 6/2013 | Srinivasan et al. |
| 8,481,125 B2 | 7/2013 | Yi et al. |
| 8,492,168 B2 | 7/2013 | Srinivasan et al. |
| 8,506,908 B2 | 8/2013 | Benn et al. |
| 8,518,662 B2 | 8/2013 | Ritzen et al. |
| 8,541,176 B2 | 9/2013 | Pamula et al. |
| 8,551,424 B2 | 10/2013 | Abraham-Fuchs et al. |
| 8,557,198 B2 | 10/2013 | Saltsman et al. |
| 8,562,807 B2 | 10/2013 | Srinivasan et al. |
| 8,580,209 B2 | 11/2013 | Kurowski et al. |
| 8,591,830 B2 | 11/2013 | Sudarsan et al. |
| 8,592,217 B2 | 11/2013 | Eckhardt |
| 8,613,889 B2 | 12/2013 | Pollack et al. |
| 8,637,317 B2 | 1/2014 | Pamula et al. |
| 8,637,324 B2 | 1/2014 | Pollack et al. |
| 8,658,111 B2 | 2/2014 | Srinivasan et al. |
| 8,685,344 B2 | 4/2014 | Sudarsan et al. |
| 8,685,754 B2 | 4/2014 | Pollack et al. |
| 8,951,781 B2 * | 2/2015 | Reed .................. B01L 3/502715 435/287.2 |
| 2002/0006643 A1 | 1/2002 | Kayyem et al. |
| 2003/0025129 A1 | 2/2003 | Hahn et al. |
| 2003/0034271 A1 | 2/2003 | Burridge |
| 2003/0038040 A1 | 2/2003 | Bertl et al. |
| 2003/0048631 A1 | 3/2003 | Ladyjensky |
| 2003/0197139 A1 | 10/2003 | Williams |
| 2004/0037739 A1 | 2/2004 | McNeely et al. |
| 2004/0053290 A1 | 3/2004 | Terbrueggen et al. |
| 2004/0137607 A1 | 7/2004 | Tanaami et al. |
| 2004/0185551 A1 | 9/2004 | Niehaus |
| 2004/0229378 A1 | 11/2004 | Schulte et al. |
| 2004/0254559 A1 | 12/2004 | Tanaami et al. |
| 2005/0003399 A1 | 1/2005 | Blackburn et al. |
| 2005/0064423 A1 | 3/2005 | Higuchi et al. |
| 2005/0164373 A1 | 7/2005 | Oldham et al. |
| 2005/0201903 A1 | 9/2005 | Weigl et al. |
| 2005/0205816 A1 | 9/2005 | Hayenga et al. |
| 2005/0244308 A1 | 11/2005 | Tanaami et al. |
| 2006/0057581 A1 | 3/2006 | Karlsen et al. |
| 2006/0079834 A1 | 4/2006 | Tennican et al. |
| 2006/0166233 A1 | 7/2006 | Wu et al. |
| 2006/0183216 A1 | 8/2006 | Handique et al. |
| 2006/0246575 A1 | 11/2006 | Lancaster et al. |
| 2006/0275813 A1 | 12/2006 | Tanaami et al. |
| 2006/0275852 A1 | 12/2006 | Montagu et al. |
| 2007/0013733 A1 | 1/2007 | Katsurai et al. |
| 2007/0042427 A1 | 2/2007 | Gerdes et al. |
| 2007/0178529 A1 | 8/2007 | Breidford et al. |
| 2007/0184547 A1 | 8/2007 | Handique et al. |
| 2007/0241068 A1 | 10/2007 | Pamula et al. |
| 2007/0242105 A1 | 10/2007 | Srinivasan et al. |
| 2007/0275415 A1 | 11/2007 | Srinivasan et al. |
| 2007/0292941 A1 | 12/2007 | Handique et al. |
| 2008/0038810 A1 | 2/2008 | Pollack et al. |
| 2008/0050287 A1 | 2/2008 | Araragi et al. |
| 2008/0182301 A1 | 7/2008 | Handique et al. |
| 2008/0227185 A1 | 9/2008 | Schonfeld et al. |
| 2008/0230386 A1 | 9/2008 | Srinivasan et al. |
| 2008/0248590 A1 | 10/2008 | Gulliksen et al. |
| 2008/0274513 A1 | 11/2008 | Shenderov et al. |
| 2008/0283439 A1 | 11/2008 | Sullivan et al. |
| 2009/0022624 A1 | 1/2009 | Saltsman et al. |
| 2009/0061450 A1 | 3/2009 | Hunter |
| 2009/0148847 A1 | 6/2009 | Kokoris et al. |
| 2009/0155902 A1 | 6/2009 | Pollack et al. |
| 2009/0197778 A1 * | 8/2009 | Lepschi .................. B01L 7/52 506/32 |
| 2009/0221059 A1 | 9/2009 | Williams et al. |
| 2009/0221091 A1 | 9/2009 | Mogi et al. |
| 2009/0263834 A1 | 10/2009 | Sista et al. |
| 2009/0298059 A1 * | 12/2009 | Gumbrecht ........... B01L 3/5027 435/6.11 |
| 2009/0304944 A1 | 12/2009 | Sudarsan et al. |
| 2009/0325276 A1 | 12/2009 | Battrell et al. |
| 2010/0025250 A1 | 2/2010 | Pamula et al. |
| 2010/0032293 A1 | 2/2010 | Pollack et al. |
| 2010/0048410 A1 | 2/2010 | Shenderov et al. |
| 2010/0068764 A1 | 3/2010 | Sista et al. |
| 2010/0087012 A1 | 4/2010 | Shenderov |
| 2010/0116640 A1 | 5/2010 | Pamula et al. |
| 2010/0120130 A1 | 5/2010 | Srinivasan et al. |
| 2010/0130369 A1 | 5/2010 | Shenderov et al. |
| 2010/0150783 A1 | 6/2010 | Araragi et al. |
| 2010/0151475 A1 | 6/2010 | Tanaami et al. |
| 2010/0178697 A1 | 7/2010 | Doebler et al. |
| 2010/0190263 A1 | 7/2010 | Srinivasan et al. |
| 2010/0194408 A1 | 8/2010 | Sturmer et al. |
| 2010/0206094 A1 | 8/2010 | Shenderov |
| 2010/0224511 A1 | 9/2010 | Boatner |
| 2010/0226199 A1 | 9/2010 | Mogi et al. |
| 2010/0236928 A1 | 9/2010 | Srinivasan et al. |
| 2010/0236929 A1 | 9/2010 | Pollack et al. |
| 2010/0270156 A1 | 10/2010 | Srinivasan et al. |
| 2010/0279374 A1 | 11/2010 | Sista et al. |
| 2010/0282608 A1 | 11/2010 | Srinivasan et al. |
| 2010/0282609 A1 | 11/2010 | Pollack et al. |
| 2010/0288789 A1 | 11/2010 | Tanaami et al. |
| 2010/0291578 A1 | 11/2010 | Pollack et al. |
| 2010/0297754 A1 | 11/2010 | Solli et al. |
| 2010/0307917 A1 | 12/2010 | Srinivasan et al. |
| 2010/0307922 A1 | 12/2010 | Wu |
| 2010/0308051 A1 | 12/2010 | Weber |
| 2010/0311599 A1 | 12/2010 | Wheeler et al. |
| 2010/0317093 A1 | 12/2010 | Turewicz et al. |
| 2010/0323405 A1 | 12/2010 | Pollack et al. |
| 2010/0331522 A1 | 12/2010 | Irvine et al. |
| 2011/0048951 A1 | 3/2011 | Wu |
| 2011/0053289 A1 * | 3/2011 | Lowe .................. B01L 3/5027 436/501 |
| 2011/0076692 A1 | 3/2011 | Sista et al. |
| 2011/0086377 A1 | 4/2011 | Thwar et al. |
| 2011/0091989 A1 | 4/2011 | Sista et al. |
| 2011/0097763 A1 | 4/2011 | Pollack et al. |
| 2011/0104725 A1 | 5/2011 | Pamula et al. |
| 2011/0104747 A1 | 5/2011 | Pollack et al. |
| 2011/0104816 A1 | 5/2011 | Pollack et al. |
| 2011/0114490 A1 | 5/2011 | Pamula et al. |
| 2011/0180571 A1 | 7/2011 | Srinivasan et al. |
| 2011/0186433 A1 | 8/2011 | Pollack et al. |
| 2011/0186466 A1 | 8/2011 | Kurowski et al. |
| 2011/0203930 A1 | 8/2011 | Pamula et al. |
| 2011/0207621 A1 | 8/2011 | Montagu et al. |
| 2011/0209998 A1 | 9/2011 | Shenderov |
| 2011/0240471 A1 | 10/2011 | Wheeler et al. |
| 2011/0303542 A1 | 12/2011 | Srinivasan et al. |
| 2011/0311980 A1 | 12/2011 | Pollack et al. |

(56) References Cited

U.S. PATENT DOCUMENTS

| | | |
|---|---|---|
| 2011/0318824 A1 | 12/2011 | Tanaami et al. |
| 2011/0319279 A1 | 12/2011 | Montagu et al. |
| 2012/0018306 A1 | 1/2012 | Srinivasan et al. |
| 2012/0022695 A1 | 1/2012 | Handique et al. |
| 2012/0044299 A1 | 2/2012 | Winger |
| 2012/0064597 A1 | 3/2012 | Clemmens et al. |
| 2012/0071342 A1 | 3/2012 | Lochhead et al. |
| 2012/0083046 A1 | 4/2012 | Watson et al. |
| 2012/0085645 A1 | 4/2012 | Mousa et al. |
| 2012/0107811 A1 | 5/2012 | Kelso et al. |
| 2012/0122108 A1 | 5/2012 | Handique et al. |
| 2012/0132528 A1 | 5/2012 | Shenderov et al. |
| 2012/0142070 A1 | 6/2012 | Battrell et al. |
| 2012/0156112 A1 | 6/2012 | Sprague et al. |
| 2012/0156750 A1 | 6/2012 | Battrell et al. |
| 2012/0160826 A1 | 6/2012 | Handique |
| 2012/0164627 A1 | 6/2012 | Battrell et al. |
| 2012/0165238 A1 | 6/2012 | Pamula et al. |
| 2012/0171759 A1 | 7/2012 | Williams et al. |
| 2012/0177543 A1 | 7/2012 | Battrell et al. |
| 2012/0187117 A1 | 7/2012 | Weber |
| 2012/0196280 A1 | 8/2012 | Karlsen et al. |
| 2012/0252008 A1 | 10/2012 | Brown et al. |
| 2012/0261264 A1 | 10/2012 | Srinivasan et al. |
| 2012/0270305 A1 | 10/2012 | Reed et al. |
| 2012/0271127 A1 | 10/2012 | Battrell et al. |
| 2012/0329142 A1 | 12/2012 | Battrell et al. |
| 2013/0011912 A1 | 1/2013 | Battrell et al. |
| 2013/0017544 A1 | 1/2013 | Eckhardt et al. |
| 2013/0018611 A1 | 1/2013 | Sturmer |
| 2013/0059366 A1 | 3/2013 | Pollack et al. |
| 2013/0118901 A1 | 5/2013 | Pollack et al. |
| 2013/0130262 A1 | 5/2013 | Battrell et al. |
| 2013/0130936 A1 | 5/2013 | Eckhardt |
| 2013/0142708 A1 | 6/2013 | Battrell et al. |
| 2013/0146461 A1 | 6/2013 | Pamula et al. |
| 2013/0164742 A1 | 6/2013 | Pollack et al. |
| 2013/0178374 A1 | 7/2013 | Eckhardt et al. |
| 2013/0178968 A1 | 7/2013 | Sturmer et al. |
| 2013/0203606 A1 | 8/2013 | Pollack et al. |
| 2013/0217103 A1 | 8/2013 | Bauer |
| 2013/0217113 A1 | 8/2013 | Srinivasan et al. |
| 2013/0225450 A1 | 8/2013 | Pollack et al. |
| 2013/0225452 A1 | 8/2013 | Pollack et al. |
| 2013/0230875 A1 | 9/2013 | Pamula et al. |
| 2013/0233425 A1 | 9/2013 | Srinivasan et al. |
| 2013/0233712 A1 | 9/2013 | Pamula et al. |
| 2013/0252262 A1 | 9/2013 | Srinivasan et al. |
| 2013/0302787 A1 | 11/2013 | Agarwal et al. |
| 2013/0327672 A1 | 12/2013 | Kurowski et al. |
| 2013/0331298 A1 | 12/2013 | Rea |
| 2013/0341231 A1 | 12/2013 | Lange et al. |
| 2014/0000223 A1 | 1/2014 | Osterloh et al. |
| 2014/0000735 A1 | 1/2014 | Weber et al. |
| 2014/0160877 A1 | 6/2014 | Lange et al. |
| 2014/0170641 A1 | 6/2014 | Macemon |
| 2014/0194305 A1 | 7/2014 | Kayyem et al. |
| 2014/0220702 A1 | 8/2014 | Johnson et al. |
| 2014/0255275 A1 | 9/2014 | Barry et al. |
| 2014/0261708 A1 | 9/2014 | Wright et al. |
| 2014/0263439 A1 | 9/2014 | Wright et al. |
| 2014/0322706 A1 | 10/2014 | Kayyem et al. |
| 2015/0024436 A1* | 1/2015 | Eberhart ............ B01L 3/502715 435/91.2 |
| 2015/0132860 A1* | 5/2015 | Cook ................ G01N 35/1079 436/501 |
| 2015/0298118 A1* | 10/2015 | Chard ................ B01L 3/50273 435/7.92 |
| 2015/0323555 A1* | 11/2015 | Kayyem ........... B01L 3/502715 506/39 |
| 2015/0346097 A1* | 12/2015 | Battrell ............. G01N 21/6428 435/6.11 |
| 2016/0129437 A1* | 5/2016 | Kayyem ................ B01L 3/502 204/600 |
| 2016/0130640 A1 | 5/2016 | Wright et al. |
| 2016/0146803 A1* | 5/2016 | Allen ............... G01N 33/54366 435/287.2 |

FOREIGN PATENT DOCUMENTS

| | | |
|---|---|---|
| EP | 0694483 B1 | 1/1996 |
| EP | 0870541 A2 | 10/1998 |
| JP | 2009161187 A | 7/2009 |
| WO | WO 00/62931 | 10/2000 |
| WO | WO 01/10729 A1 | 2/2001 |
| WO | WO 2004/011148 A2 | 2/2004 |
| WO | WO 2004034028 A2 | 4/2004 |
| WO | 2007044917 A2 | 4/2007 |
| WO | 2007112114 A2 | 10/2007 |
| WO | WO 2009/089466 A2 | 7/2009 |
| WO | WO 2009/140373 A2 | 11/2009 |
| WO | WO 2010/025302 A2 | 3/2010 |
| WO | WO 2010069977 A1 | 6/2010 |
| WO | WO 2010/151705 A2 | 12/2010 |
| WO | WO 2012/080190 A1 | 6/2012 |
| WO | WO 2012084615 A1 | 6/2012 |
| WO | WO 2012151192 A2 | 11/2012 |
| WO | 2013059750 A1 | 4/2013 |
| WO | WO 2014066704 A1 | 5/2014 |

OTHER PUBLICATIONS

International Preliminary Report on Patentability issued in International Application No. PCT/US2014/024499, 9 pages (Sep. 24, 2015).

International Search Report and Written Opinion issued in Application No. PCT/US2013/066717, 35 pages (Feb. 3, 2014).

"Mechanisms Information/Worksheets," World Association of Technology Teachers, 2 pages (Mar. 2, 2011). (animated display viewable at https://web.archive.org/web/20110302093447/http://techonologystudent.com/cams/flat1.htm).

Beaucage et al., "Tetrahedron Report No. 329: The Functionalization of Oligonucleotides Via Phosphoramidite Derivatives," *Tetrahedron vol. 49, No. 10*, pp. 1925-2963 (1993).

Bolli et al., "α-Bicyclo-DNA: Synthesis, Characterization, and Pairing Properties of α-DNA-Analogues with Restricted Conformational Flexibility in the Sugar-Phosphate Backbone," *American Chemical Society*, pp. 100-117 (1994).

Brill et. al., "Synthesis of Oligodeoxynucleoside Phosphorodithioates via Thioamidites," *J Am. Chem. Soc.*, pp. 2321-2322 (1989).

Carlsson et al., "Screening for Genetic Mutations" *Letters to Nature, vol. 380*, p. 207 (Mar. 1996).

Dempcy et al., "Synthesis of a Thymidyl Pentamer of Deoxyribonucleic Guanidine and Binding Studies with DNA Homopolynucleotides," *Proc. Natl. Acad. Sci. USA, vol. 92*, pp. 6097-6101 (Jun. 1995).

Egholm et al., "Peptide Nucleic Acids (PNA). Oligonucleotide Analogues with an Achiral Peptide Backbone," *J.Am.Chem.Soc.*, pp. 1895-1897 (1992).

Egholm et al., "PNA hybridizes to complementary oligonucleotides obeying the Watson-Crick hydrogen-bonding rules," *Letters to Nature*, pp. 566-568 (1993).

Herdewijn et al., "Hexopyranosyl-Like Oligonucleotides," *American Chemical Society*, pp. 80-99 (1994).

Horn et al., "Oligonucleotides with Alternating Anionic and Cationic Phosphoramidate Linkages: Synthesis and Hybridization of Stereo-Uniform Isomers," *Tetrahedron Letters, vol. 37, No. 6*, pp. 743-746 (1996).

Jeffs et al., "Unusual Confirmation of a 3-Thioformacetal Linkage in a DNA Duples," *Journal of Biomedecular NMR*, pp. 17-34 (1994).

Jenkins et al., "The Biosynthesis of Carbocyclic Nucleosides," *Chemical Society Reviews*, pp. 169- 176 (Jan. 1995).

Kiedrowski et al., "Parabolic Growth of a Self-Replicating Hexadeoxynucleotide Bearing a 3'-5' Phosphoamidate Linkage," *Angew Chem. Intl. Ed. English 30*, pp. 423-426 (1991).

(56) References Cited

OTHER PUBLICATIONS

Koshkin et al., "LNA (Locked Nucleic Acid): An RNA Mimic Forming Exceedingly Stable LNA: LNA Duplexes," *J. Am. Chem. Soc., vol. 120*, pp. 13252-13253 (1998).
Letsinger et al., "Phosphoramidate Analogues of Oligonucleotides," *J. Org. Chem, vol. 35, No. 1*, pp. 3800-3803 (1970).
Letsinger et al., "Effects of Pendant Groups at Phosphorus on Binding Properties of d-APA Analogues," *Nucleic Acids Research vol. 14, No. 8*, pp. 3487-3499 (1986).
Letsinger et al., "Caionic Oligonucleotides," *J Am. Chem. Soc.*, pp. 4470-4471 (1988).
Letsinger et al., "Hybridization of Alternating Cationic/ Anionic Oligonucleotides to RNA Segments," *Nucleosides & Nucleotides vol. 13, No. 6&7*, pp. 1597-1605 (1994).
Maddry et al., "Synthesis of Nonionic Oligonucleotide Analogues," *American Chemical Society*, pp. 40-51 (1994).
Mag et al., "Synthesis and Selective Clevage of a Oligodeoxynucleotide Containing a Bridged Internucleotide 5 Phosphorothioate Linkage," *Nucleic Acids Research, vol. 19 No. 7*, pp. 1437-1441 (1991).
Meier et al., "Peptide Nucleic Acids (PNA's)-Unusual Properties of Nonionic Oligonucleotide Analogues," *Angew Intl. Ed. English 31, No. 8*, pp. 1008-1010 (1992).
Mesmaeker et al., "Comparison of Rigid and Flexible Backbones in Antisense Oligonucleotides," *Bioorganic & Medicinal Chem. Letters, vol. 4, No. 3*, pp. 395-398 (1994).
Mesmaeker et al., "Novel Backbone Replacements for Oligonucleotides," American Chemical Society, pp. 24-39 (1994).
Pauwels et al., "Biological Activity of New 2-5A Analogues," *Chemica Scripta, vol. 26*, pp. 141-145 (1986).
Rawls "Optomistic About Antisense," *C&EN*, pp. 35-39 (Jun. 1997).
Sawai, "Synthesis and Properties of Oligoadenylic Acids Containing 2'-5' Phosphoramide Linkage," *Chemistry Letters*, pp. 805-808 (1984).
Sprinzl et al., "Enzymatic Incorporation of ATP and CTP Analogues into the 3' end of RNA," *Eur. J. Biochem 81*, pp. 579-589 (1977).
Notice of Allowance issued in U.S. Appl. No. 14/206,867, 52 pages (Jun. 10, 2015).
Supplemental Notice of Allowability issued in U.S. Appl. No. 14/206,867, 5 pages (Jul. 13, 2015).
International Search Report and Written Opinion issued in International Application No. PCT/US2013/06617, 35 pages (Feb. 3, 2014).
International Preliminary Report on Patentability and Written Opinion issued in International Application No. PCT/US2013/06617, 15 pages (Apr. 28, 2015).
Non-final Office Action issued in U.S. Appl. No. 14/206,817, 44 pages (Oct. 8, 2015).
Extended European Search Report issued in European Patent Application No. 138496757, 5 pages (Oct. 12, 2015).
Extended European Search Report issued in European Patent Application No. 15168733.2, 3 pages (Dec. 15, 2015).
Nonfinal Office Action issued in U.S. Appl. No. 14/062,865, 74 pages (Jan. 6, 2016).
Non-final Office Action issued in U.S. Appl. No. 14/062,860, 67 pages (Jul. 23, 2015).
Wolf et al., "Single-Tube Nested PCR with Room-Temperature-Stable Reagents," Cold Spring Harbor Laboratory Press ISSN, 1054-9803/95, vol. 4, pp. 376-379 and source page (1995).

Non-final Office Action issued in U.S. Appl. No. 14/206,903, 47 pages (Jan. 21, 2016).
Final Office Action issued in U.S. Appl. No. 14/062,860, 32 pages (Feb. 11, 2016).
Notice of Allowance issued in U.S. Appl. No. 14/206,817, 20 pages (Feb. 19, 2016).
Invitation to Pay Additional Fees and, Where Applicable, Protest Fee, including partial international search results, issued by the International Searching Authority in International Patent Application No. PCT/US2015/059947, 13 pages (Feb. 23, 2016).
Invitation to Pay Additional Fees and, Where Applicable, Protest Fee, including partial international search results, issued by the International Searching Authority in International Patent Application No. PCT/US2015/059978, 10 pages (Feb. 23, 2016).
European Patent Office Communication Pursuant to Article 94(3) EPC in European Patent Application No. 15168733.2, 3 pages (Feb. 19, 2016).
International Search Report and Written Opinion issued in International Patent Application No. PCT/US2014/024499, 14 pages (Dec. 11, 2014).
Dobson et al., "Emerging Technologies for Point-of-Care Genetic Testing," *Future Drugs Ltd* (www.future-drugs.com), 10.1586/14737159.7.4.359, Expert Rev. Mol. Diagn., pp. 359-370 (2007).
Doebler et al., "Continuous-Flow, Rapid Lysis Devices for Biodefense Nucleic Acid Diagnostic Systems," *The Association for Laboratory Automation* (JALA), pp. 119-125 (Jun. 2009).
Erickson et al., "Integrated Microfluidic Devices," *Elsevier B.V.*, 16 pages (2003).
Findlay et al., "Automated Closed-Vessel System for in Vitro Diagnostics Based on Polymerase Chain Reaction," *Clinical Chemistry*, 39:9, pp. 1927-1933, 1993).
Focke et al., "Lab-on-a-Foil: Microfluidics on Thin and Flexible Films," *The Royal Society of Chemistry*, pp. 1365-1386 (2010).
Malic et al., "Current State of Intellectual Property in Microfluidic Nucleic Acid Analysis," McGill University, *Bentham Science Publishers*, 18 pages (2007).
Vandeventer et al., "Mechanical Disruption of Lysis-Resistant Bacterial Cells by Use of a Miniature, Low-Power, Disposable Device," American Society for Microbiology, *Journal of Clinical Microbiology*, 49:7, pp. 2533-2539 (Jul. 2011).
Office Action issued in U.S. Appl. No. 14/206,867, 22 pages (Nov. 7, 2014).
Extended European Search Report issued in European Patent Application No. 16151365.0, 4 pages (May 23, 2016).
International Search Report and Written Opinion issued in International Patent Application No. PCT/US2015/059978, 23 pages (Jun. 27, 2016).
Notice of Allowance issued in U.S. Appl. No. 14/206,903, 16 pages (May 11, 2016).
Supplemental Notice of Allowance issued in U.S. Appl. No. 14/206,817, 3 pages (Jul. 12, 2016).
Advisory Action issued in U.S. Appl. No. 14/062,860, 7 pages (Jul. 21, 2016).
Final Office Action issued in U.S. Appl. No. 14/062,865, 41 pages (Jul. 21, 2016).
Office Action issued in Chinese Patent Application No. 2016080801483520 (with English translation), 9 pages (Aug. 11, 2016).

* cited by examiner

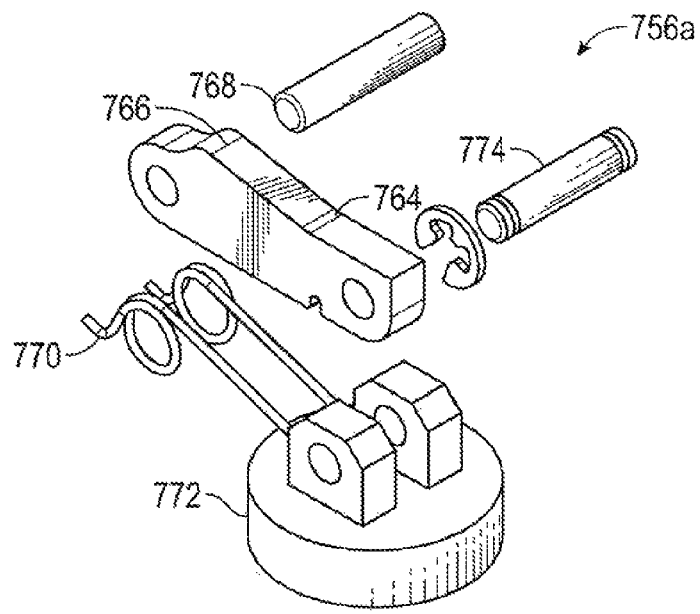
FIG. 55A
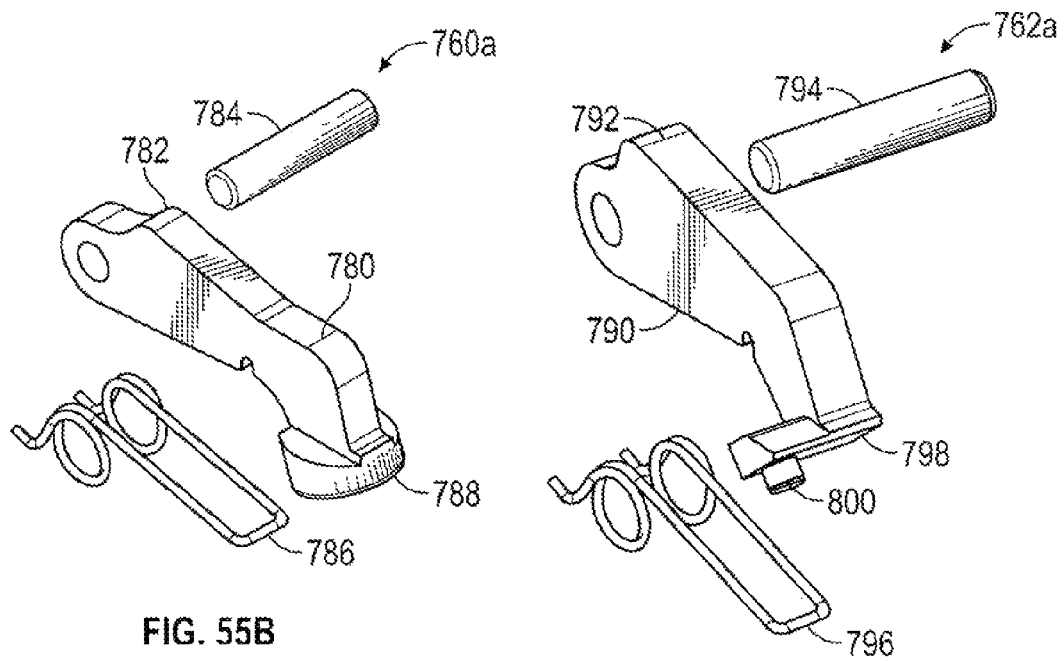
FIG. 55B
FIG. 55C

INSTRUMENT FOR PROCESSING CARTRIDGE FOR PERFORMING ASSAYS IN A CLOSED SAMPLE PREPARATION AND REACTION SYSTEM

RELATED APPLICATIONS

This application is related to U.S. patent application Ser. No. 14/062,860 (U.S. Patent Application Publication No. 2014-0322706) and U.S. patent application Ser. No. 14/062,865 (U.S. Patent Application Publication No. 2014-0194305), the respective disclosures of which are hereby incorporated by reference.

FIELD OF THE INVENTION

This subject matter of this disclosure relates to systems and methods for providing clinical and molecular diagnostics in an integrated, multiplex device that provides sample-to-answer results. In particular, the disclosure relates to a cartridge, to which a sample may be added and which contains reagents, buffers, and other process materials for performing a diagnostic assay or other process on the sample, and an instrument configured to independently process a plurality of such cartridges.

BACKGROUND OF INVENTION

One major challenge in the area of clinical and molecular diagnostics is the ability to have a "sample to answer" system that requires minimal sample handling and preparation and minimal requirements for trained clinical lab personnel. While many systems have been proposed, to date there are virtually no such commercial systems that adequately meet these requirements. Aspects of the present invention provide such an integrated, multiplex system.

SUMMARY OF THE INVENTION

The present invention provides molecular diagnostic methods and compositions based on the detection of target analytes, including nucleic acids. The systems described herein are complete integrated "sample to answer" systems, in contrast with current commercial systems that require some off chip handling of the sample, generally including sample extraction (cell lysis, for example), and sample preparation prior to detection. Thus, in accordance with aspects of the current system, a sample is loaded onto a test platform and the target analyte sample is extracted, amplified as necessary (for example, when the target analyte is a nucleic acid using polymerase chain reaction (PCR) techniques, although isothermal amplification methods can be utilized as well), and then detected using electrochemical detection, all on a microfluidic platform, generally referred to herein as a "multiplex cartridge" or a "fluid sample processing cartridge."

A particular utility of the present system is the ease and rapidity of this integrated system. For example, there are no more than 2 operations required before introduction of the sample to the system, which allows for both ease of use and no requirement for highly trained lab personnel. A significant benefit to the present system is also the speed from sample to answer, which, in some embodiments, is generally no more than about 45-90 minutes from sample introduction to reporting of assay results, with most results being reported in roughly 60-70 minutes or less. This represents a significant advantage to both labs and doctors relying on quick analyses for diagnosis and start of appropriate treatments. In addition, as outlined below, the ability of running not only multiple tests which are highly multiplexed on a single cartridge but the ability to analyze multiple cartridges in a completely random access way is a significant advantage in a clinical lab setting. A further advantage of the present system is that it can be used for point-of-care (POC) diagnostics.

Accordingly, aspects of the present invention are directed to integrated systems that allow for the detection of target analytes from samples.

For example, aspects of the invention are embodied in a fluid sample processing cartridge comprising a substrate, a sample well formed in the substrate, a closure, a deformable fluid chamber supported on the substrate, a mixing well formed in the substrate, and a driven mixing apparatus disposed within the mixing well. The sample well is configured to receive a volume of fluid sample, and the closure is configured to be selectively placed over the sample well. The deformable fluid chamber is configured to hold a fluid therein when in an undeformed state and to collapse upon application of an external compression force to expel at least a portion of the fluid from the fluid chamber. The deformable fluid chamber is in fluid communication with the sample well via a channel formed in the substrate. The mixing well is in fluid communication with the sample well via a channel formed in the substrate and comprises a first peripheral wall and a first floor defining a well and a fluid inlet snorkel extending up a side of the first peripheral wall extending from the channel communicating the mixing well to the sample well and terminating below a top edge of the first peripheral wall. The driven mixing apparatus is constructed and arranged to mix the contents of the mixing well.

According to further aspects of the invention, the fluid inlet snorkel extends up an outer surface of the first peripheral wall and terminates at an opening formed in the first peripheral wall.

According to further aspects of the invention, the sample well comprises a second peripheral wall and a second floor defining a well and a fluid inlet snorkel extending up a side of the second peripheral wall and terminating below a top edge of the second peripheral wall.

According to further aspects of the invention, the mixing well further comprises an exit port comprising one or more openings formed in the floor of the mixing well, wherein the floor tapers downwardly toward the exit port.

According to further aspects of the invention, the driven mixing apparatus comprises a first impeller rotatably disposed within the mixing well and a gear configured to be drivingly engaged by a mating gear of an instrument into which the liquid sample processing cartridge is inserted and to rotate the first impeller when engaged by the mating gear.

According to further aspects of the invention, the sample processing cartridge further comprises a lysis chamber containing a plurality of lysis beads, the lysis chamber being formed in the substrate and disposed along the channel connecting the mixing well and the sample well whereby fluid flowing from the sample well to the mixing well will flow through the lysis chamber, and a bead mixer disposed at least partially within the lysis chamber and constructed and arranged to agitate the lysis beads and fluid flowing through the lysis chamber.

According to further aspects of the invention, the sample processing cartridge further comprises a first optical interface comprising an enlarged portion of the channel connecting the lysis chamber to the sample well and a second optical interface comprising an enlarged portion of the channel connecting the lysis chamber to the mixing well.

According to further aspects of the invention, the bead mixer comprises a motor mounted within the substrate and a second impeller disposed within the lysis chamber and mounted on an output shaft of the motor.

According to further aspects of the invention, the lysis chamber includes a fluid inlet and a fluid outlet and further comprises a mesh filter disposed over each of the fluid inlet and the fluid outlet and configured to retain the lysis beads within the lysis chamber.

According to further aspects of the invention, the sample processing cartridge further comprises a pressure port formed in the substrate and configured to couple the substrate to an external fluid pressure source and a channel formed in the substrate connecting the pressure port to the sample well.

According to further aspects of the invention, the sample processing cartridge further comprises a waste chamber formed in the substrate, the waste chamber being in fluid communication with the mixing well via a channel formed in the substrate, a fluid exit port formed in the substrate, the fluid exit port being in fluid communication with the mixing well via a channel formed in the substrate, a first externally actuatable control valve disposed within the substrate and constructed and arranged to selectively permit or prevent fluid flow from the mixing well to the waste chamber and a second externally actuatable control valve disposed within the substrate and constructed and arranged to selectively permit or prevent fluid flow from the mixing well to the fluid exit port.

According to further aspects of the invention, the sample processing cartridge further comprises a capture chamber disposed along a channel connecting the mixing well and the waste chamber According to further aspects of the invention, the sample processing cartridge further comprises a passive valve assembly disposed within the substrate and a pressure port formed in the substrate and in pressure communication with the passive valve assembly by a pressure conduit formed in the substrate. The passive valve assembly is constructed and arranged to be closed and prevent fluid flow from the mixing well when pressure within the mixing well is not higher than a threshold pressure and to open and permit fluid flow from the mixing well when pressure within the mixing well rises above the threshold pressure. When the pressure port is closed, pressure within the mixing well is allowed to reach the threshold pressure that will open the passive valve assembly and permit fluid flow from the mixing well, and when the pressure port is open, pressure within the mixing cannot not reach the threshold pressure so the passive valve assembly is closed.

According to further aspects of the invention, the sample processing cartridge further comprises a lance blister associated with the deformable fluid chamber. The lance blister is connected or connectable to the associated deformable fluid chamber and contains a bead retained within the lance blister by a breakable septum. The lance blister is configured to collapse upon application of an external compression force to thereby push the bead through the breakable septum.

According to further aspects of the invention, the sample processing cartridge further comprises an external shroud externally enclosing at least a portion of the cartridge.

According to further aspects of the invention, the sample processing cartridge further comprises a plurality of deformable fluid chambers, and each of the fluid chambers contains one or more substances selected from the group consisting of a lysis buffer, a wash buffer, an oil, a rehydration buffer, target capture beads, and a binding buffer.

According to further aspects of the invention, the sample processing cartridge further comprises a first fluid exit port formed in the substrate, the first fluid exit port being in fluid communication with the mixing well via a channel formed in the substrate, a second fluid exit port formed in the substrate, and at least two deformable fluid chambers. One of the two deformable fluid chambers is in fluid communication with the mixing well via a channel formed in the substrate, and the other of the two deformable fluid chambers is in fluid communication with the second fluid exit port via a channel formed in the substrate that is different from the channel communicating the first fluid exit port with the mixing well.

According to further aspects of the invention, the deformable fluid chamber in fluid communication with the mixing well contains a lysis buffer, a wash buffer, target capture beads, or a binding buffer, and the deformable fluid chamber in fluid communication with the second fluid exit contains an oil or a rehydration buffer.

Further aspects of the invention are embodied in a fluid sample processing cartridge comprising a sample preparation module comprising and a reaction module. The sample preparation module comprises a substrate, a sample well formed in the substrate and configured to receive a volume of fluid sample, a closure configured to be selectively placed over the sample well, a first deformable fluid chamber supported on the substrate and configured to hold a fluid therein when in an undeformed state and to collapse upon application of an external compression force to expel at least a portion of the fluid from the first fluid chamber, the first deformable fluid chamber being in fluid communication with the sample well via a channel formed in the substrate, a mixing well formed in the substrate, the mixing well being in fluid communication with the sample well via a channel formed in the substrate, a driven mixing apparatus disposed within the mixing well and constructed and arranged to mix the contents of the mixing well, and a first fluid exit port formed in the substrate, the first fluid exit port being in fluid communication with the mixing well via a channel formed in the substrate. The reaction module is attached to the sample preparation module and is configured to receive a fluid from the sample preparation module via the fluid exit port formed in the sample preparation module. The reaction module comprises a top plate comprising a top surface, a raised wall at least partially circumscribing the top surface and in fluid sealing contact with a surface of the sample preparation module to form an interstitial space between the top surface and the surface of the sample preparation module, a sample chamber fluidly coupled to the first fluid exit port of the sample preparation module, a reagent chamber, and a detection chamber, and a fluidic processing panel coupled to a bottom surface of the top plate and defining a reaction and processing space between the fluidic processing panel and the top plate. The reaction and processing space is open or openable to the sample chamber, the reaction chamber, and the detection chamber.

According to further aspects of the invention, the reaction module includes an inlet port through which fluid sample enters the sample chamber and including a gap between the first fluid exit port of the sample preparation module and the inlet port of the sample chamber, the gap being open to the interstitial space.

According to further aspects of the invention, the first fluid exit port of the sample preparation module comprises an outlet channel formed through a frustoconical nipple.

According to further aspects of the invention, reaction module of the fluid sample processing cartridge further comprising an electrosensor array disposed in each detection chamber.

According to further aspects of the invention, the top plate of the reaction module further comprises one or more bubble traps, each bubble trap comprising a bubble capture hood open to the reaction and processing space and a vent opening open to the interstitial space.

According to further aspects of the invention, the sample preparation module further comprises a second deformable fluid chamber supported on the substrate and configured to hold a fluid therein when in an undeformed state and to collapse upon application of an external compression force to expel at least a portion the fluid from the fluid chamber and a second fluid exit port formed in the substrate. The second fluid exit port is in fluid communication with the second deformable fluid chamber via a channel formed in the substrate, and the reaction and processing space is fluidly coupled to the second fluid exit port of the sample preparation module.

According to further aspects of the invention, the mixing well comprises a peripheral wall and a floor defining a well and a fluid inlet snorkel extending up a side of the peripheral wall extending from the channel communicating the mixing well to the sample well and terminating below a top edge of the peripheral wall.

According to further aspects of the invention, the fluid inlet snorkel extends up an outer surface of the peripheral wall and terminates at an opening formed in the peripheral wall.

According to further aspects of the invention, the mixing well further comprises an exit port comprising one or more openings formed in the floor of the mixing well, and the floor tapers downwardly toward the exit port.

According to further aspects of the invention, the driven mixing apparatus comprises a first impeller rotatably disposed within the mixing well and a gear configured to be drivingly engaged by a mating gear of an instrument into which the liquid sample processing cartridge is inserted and to rotate the first impeller when engaged by the mating gear.

According to further aspects of the invention, the sample preparation module further comprises a lysis chamber comprising a plurality of lysis beads, the lysis chamber being formed in the substrate and disposed along the channel connecting the mixing well and the sample well whereby fluid flowing from the sample well to the mixing well will flow through the lysis chamber, and a bead mixer disposed at least partially within the lysis chamber and constructed and arranged to agitate the lysis beads and fluid flowing through the lysis chamber.

According to further aspects of the invention, the bead mixer comprises a motor mounted within the substrate and a second impeller disposed within the lysis chamber and mounted on an output shaft of the motor.

According to further aspects of the invention, the fluid sample processing cartridge further comprises a first optical interface comprising an enlarged portion of the channel connecting the lysis chamber to the sample well and a second optical interface comprising an enlarged portion of the channel connecting the lysis chamber to the mixing well.

According to further aspects of the invention, the lysis chamber includes a fluid inlet and a fluid outlet and further comprises a mesh filter disposed over each of the fluid inlet and the fluid outlet and configured to retain the lysis beads within the lysis chamber.

According to further aspects of the invention, the sample preparation module further comprises a pressure port formed in the substrate and configured to couple the substrate to an external fluid pressure source and a channel formed in the substrate connecting the pressure port to the sample well.

According to further aspects of the invention, the sample preparation module further comprises a waste chamber formed in the substrate, the waste chamber being in fluid communication with the mixing well via a channel formed in the substrate, a first externally actuatable control valve disposed within the substrate and constructed and arranged to selectively permit or prevent fluid flow from the mixing well to the waste chamber, and a second externally actuatable control valve disposed within the substrate and constructed and arranged to selectively permit or prevent fluid flow from the mixing well to the exit port.

According to further aspects of the invention, the sample preparation module further comprises a capture chamber disposed along a channel connecting the mixing well and the waste chamber.

According to further aspects of the invention, the sample preparation module further comprises a passive valve assembly disposed within the substrate and constructed and arranged to be closed and prevent fluid flow from the mixing well when pressure within the mixing well is not higher than a threshold pressure and to open and permit fluid flow from the mixing well when pressure within the mixing well rises above the threshold pressure and a pressure port formed in the substrate and in pressure communication with the passive valve assembly by a pressure conduit formed in the substrate. When the pressure port is closed, pressure within the mixing well is allowed to reach the threshold pressure that will open the passive valve assembly and permit fluid flow from the mixing well, and when the pressure port is open pressure within the mixing well cannot reach the threshold pressure so the passive valve assembly is closed.

According to further aspects of the invention, the sample preparation module further comprises a lance blister associated with the deformable fluid chamber. The lance blister is connected or connectable to the associated deformable fluid chamber and contains a bead retained within the lance blister by a breakable septum. The lance blister is configured to collapse upon application of an external compression force to thereby push the bead through the breakable septum.

According to further aspects of the invention, an external shroud externally encloses at least a portion of the cartridge.

According to further aspects of the invention, the sample preparation module further comprises a plurality of deformable fluid chambers, and each of the fluid chambers contains a substance selected from the group consisting of a lysis buffer, a wash buffer, an oil, a rehydration buffer, target capture beads, and a binding buffer.

Additional aspects of the invention are embodied in an instrument configured to process a fluid sample processing cartridge including a deformable fluid chamber supported on a planar substrate and configured to hold a fluid therein when in an undeformed state and to collapse upon application of an external compression force to expel at least a portion of the fluid from the fluid chamber. The instrument comprises a cartridge carriage assembly a cartridge carriage assembly configured to receive and hold a fluid sample processing cartridge inserted into the instrument. A heating and control assembly is disposed adjacent the cartridge carriage assembly and is configured for movement with respect to the cartridge carriage assembly between a first position not in operative contact with the cartridge carried within the cartridge carriage assembly and a second position in operative contact with the cartridge carried within the cartridge carriage assembly. One or more movable magnet assemblies are each mounted for movement with respect to the cartridge independently of the heating and control assembly between a first position applying substantially no magnetic force to the cartridge and a second position applying magnetic force to corresponding discrete portions of the cartridge. A cam block assembly is configured for powered movement and is operatively coupled to the heating and control assembly for converting powered movement of the cam block assembly into movement of the heating and control assembly with respect to the cartridge carriage assembly between the first position of the heating and control assembly and the second position of the heating and control assembly. The cam block assembly is operatively coupled to the one or more moveable magnet assemblies for converting powered movement of the cam block assembly into movement of each magnet assembly with respect to cartridge carriage assembly between the first position of the magnet assembly and the second position of the magnet assembly. A deformable chamber compression assembly is configured to selectively apply an external compression force to the deformable fluid chamber to collapse the deformable chamber and expel at least a portion of the fluid from the fluid chamber.

According to further aspects of the invention, the heating and control assembly comprises one or more heater assemblies configured to apply a thermal gradient to corresponding discrete portions of the cartridge when the heating and control assembly is in the second position and a connector board including one or more electrical connector elements configured to effect an electrical connection between the instrument and the cartridge when the heating and control assembly is in the second position.

According to further aspects of the invention, the deformable chamber compression assembly comprises a cam follower plate configured for powered movement in a first direction that is generally parallel to the plane of the substrate and a compression mechanism associated with the deformable chamber of the cartridge and configured to apply a force compressing the chamber against the substrate by movement in a second direction having a component that is generally normal to the plane of the substrate. The cam follower plate is operatively coupled to the compression mechanism to convert movement of the cam follower plate in the first direction into movement of the compression mechanism in the second direction to thereby apply an external compression force to the chamber.

According to further aspects of the invention, the instrument further comprises a pneumatic pump and a pneumatic port connected to the pneumatic pump, wherein the pneumatic port is configured to couple the pneumatic pump to a pressure port of the fluid sample processing cartridge when the cartridge is inserted into the instrument.

According to further aspects of the invention, the instrument further comprises an optical detector configured to detect fluid flow through a part of the fluid sample processing cartridge.

According to further aspects of the invention, the fluid sample processing cartridge includes a driven mixing apparatus including a drive gear, and the instrument further comprises a mixing motor assembly including a powered driving gear. The mixing motor is moveable between a first position in which the driving gear is not engaged with the drive gear of the driven mixing apparatus and a second position in which the driving gear is operatively engaged with the drive gear to actuate the driven mixing apparatus. The cam block assembly is operatively coupled to the mixing motor assembly for converting powered movement of the cam block assembly into movement of the mixing motor assembly between the first position of the mixing motor assembly and the second position of the mixing motor assembly.

According to further aspects of the invention, the instrument further comprises a heater cooling assembly comprising a fan and a cooling duct configured to direct air flow from the fan to a portion of one of the heater assemblies.

According to further aspects of the invention, the cartridge carriage assembly comprises a cartridge holder configured to hold a cartridge inserted therein, a cartridge latch biased into a cartridge-latching position and configured to latch onto a cartridge inserted into the cartridge holder to retain the cartridge within the cartridge holder, and a cartridge eject mechanism configured to automatically push a cartridge at least partially out of the cartridge holder when the cartridge latch is released from a cartridge-latching position.

According to further aspects of the invention, the heating and control assembly comprises a support plate on which the one or more heater assemblies and the connector board are supported. The support plate is mounted in a constrain configuration preventing horizontal movement of the support plate but permitting vertical movement of the support plate to enable movement of the heating and control assembly between its first and second positions.

According to further aspects of the invention, the heater assemblies of the heating and control assembly comprises a resistive heating element attached to the connector board and a heat spreader comprising a thermally-conductive material thermally coupled to the resistive heating element.

According to further aspects of the invention, one of the heater assemblies of the heating and control assembly comprises a thermoelectric element, a heat spreader comprising a thermally-conductive material thermally coupled to the thermoelectric element, and a heat sink including a panel that is in thermal contact with the thermoelectric element and a plurality of heat-dissipating rods.

According to further aspects of the invention, the electrical connector elements of the connector board of the heating and control assembly comprise a plurality of connector pin arrays, each connector pin array comprising a plurality of pogo pins.

According to further aspects of the invention, one of the movable magnet assemblies comprises a magnet holder mounted on a spindle so as to be rotatable about the spindle between the first position and the second position of the magnet assembly, a magnet supported on the magnet holder, an actuator bracket extending from the magnet holder, and a torsion spring configured to bias the magnet holder to a rotational position corresponding to the first position of the magnet assembly.

According to further aspects of the invention, one of the movable magnet assemblies comprises a magnet holder frame mounted on a spindle so as to be rotatable about the spindle between the first position and the second position of the magnet assembly, a magnet array disposed within the magnet holder frame, a focusing magnet disposed within an opening formed in the magnet holder frame and configured to focus magnetic forces of the magnet array, an actuator bracket extending from the magnet holder frame, and a torsion spring configured to bias the magnet holder frame to a rotational position corresponding to the first position of the magnet assembly.

According to further aspects of the invention, the cam block assembly is operatively coupled to each movable magnet assembly by a magnet actuator coupled at one portion thereof to the cam block assembly so as to be moveable by powered movement of the cam block assembly and including a tab configured to be engageable with the actuator bracket of each magnet assembly as the magnet actuator is moved with the cam block assembly to cause corresponding rotation of the magnet assembly from the first position to the second position.

According to further aspects of the invention, the cam block assembly comprises a cam frame, a cam block motor coupled to the cam frame and configured to effect powered movement of the cam frame, and first and second cam rails attached to the cam frame. Each of the cam rails has two cam slots. The cam block assembly is operatively coupled to the heating and control assembly by cam followers extending from the heating and control assembly into the cam slots such that movement of the cam frame and the cam rails with respect to the heating and control assembly causes corresponding relative movement between the cam followers and the cam slots to move the cam followers between respective first segments of the cam slots corresponding to the first position of the heating and control assembly and respective second segments of the cam slots corresponding to the second position of the heating and control assembly.

According to further aspects of the invention, the cam frame comprises a first longitudinal spar extending along one side of the heating and control assembly, a second longitudinal spar extending along an opposite side of the heating and control assembly, and a cross spar extending between the first and second longitudinal spars. Each cam rail is attached to one of the first and second longitudinal spars.

According to further aspects of the invention, the compression mechanism of the deformable chamber compression assembly comprises a cam arm having a cam surface and mounted so as to be pivotable about one end of the cam arm and a compression pad disposed at an opposite end of the cam arm, wherein the cam arm is pivotable between a first position in which the compression pad does not contact the associated deformable chamber and a second position in which the compression pad applies a compressive force to the associated deformable chamber to at least partially collapse the chamber.

According to further aspects of the invention, the deformable chamber compression assembly further comprises a cam arm plate, and the cam arm of the compression mechanism is pivotably mounted within a slot formed in the cam arm plate for pivotable movement of the cam arm with respect to the cam arm plate. The cam surface of the cam arm projects out of the slot above a surface of the cam arm plate. The cam follower plate is operatively coupled to the compression mechanism by a cam follower element of the cam follower plate that is engaged with the cam surface of the compression mechanism during movement of the cam follower plate with respect to the cam arm plate to cause the cam arm to pivot from its first position to its second position.

According to further aspects of the invention, the cam follower plate comprises a cam groove that receives the cam surface of the cam arm projecting above the surface of the cam arm plate, and the cam follower element comprises a follower ridge disposed within the cam groove that contacts the cam surface as the cam follower plate moves with respect to the cam arm plate to cause the cam arm to pivot from its first position to its second position.

According to further aspects of the invention, the instrument further comprises a plurality of compression mechanisms, each comprising a cam arm pivotably mounted within a slot formed in the cam arm plate and a cam arm surface, and the cam follower plate comprises a plurality of cam grooves, each cam groove being associated with at least one of the compression mechanisms and each cam groove including a follower ridge disposed within the cam groove that contacts the cam surface of the associated compression mechanism as the cam follower plate moves with respect to the cam arm plate to cause the cam arm of the associated compression mechanism to pivot from its first position to its second position.

According to further aspects of the invention, the sample processing cartridge includes a plurality of deformable fluid chambers, and the deformable chamber compression assembly comprises a plurality of compression mechanisms. Each compression mechanism is associated with one of the deformable fluid chambers, and the cam follower plate is operatively coupled to the compression mechanisms to convert movement of the cam follower plate in the first direction into movement of each of the compression mechanisms in the second direction to thereby apply an external compression force to each of the associated chambers in a specified sequence According to further aspects of the invention, the fluid sample processing cartridge includes an externally-actuatable control valve configured to selectively control fluid flow by permitting fluid flow through the valve when not externally actuated and preventing fluid flow through the valve when externally actuated. The instrument further comprises a valve actuator compression mechanism associated with the externally-actuatable control valve of the sample processing cartridge and configured to actuate the associated externally-actuatable control valve by movement in a second direction having a component that is generally normal to the plane of the substrate. The cam follower plate is operatively coupled to the valve actuator compression mechanism to convert movement of the cam follower plate in the first direction into movement of the valve actuator compression mechanism in the second direction to thereby actuate the associated externally-actuatable control valve.

Other features and characteristics of the subject matter of this disclosure, as well as the methods of operation, functions of related elements of structure and the combination of parts, and economies of manufacture, will become more apparent upon consideration of the following description and any appended claims with reference to the accompanying drawings, all of which form a part of this specification.

BRIEF DESCRIPTION OF THE DRAWINGS

The accompanying drawings, which are incorporated herein and form part of the specification, illustrate various embodiments of the subject matter of this disclosure. In the drawings, like reference numbers indicate identical or functionally similar elements.

FIG. 55A is an exploded perspective view of a single fluid blister compression mechanism.

FIG. 55B is an exploded prospective view of a single lance blister compression mechanism.

FIG. 55C is an exploded perspective view a single valve actuator compression mechanism.

DETAILED DESCRIPTION OF THE INVENTION

Figure 1:
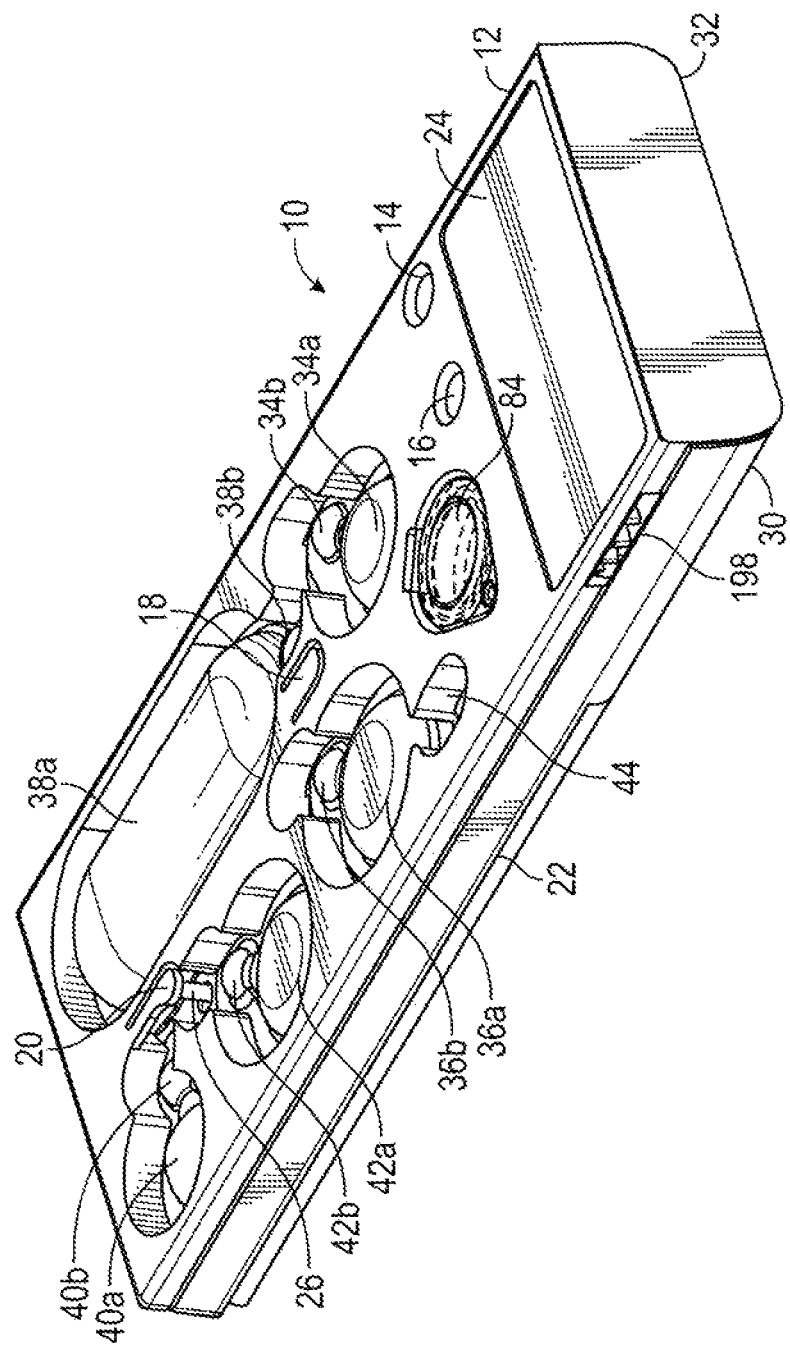
FIG. 1 is a top perspective view of a multiplex cartridge embodying aspects of the present invention.
Figure 2:
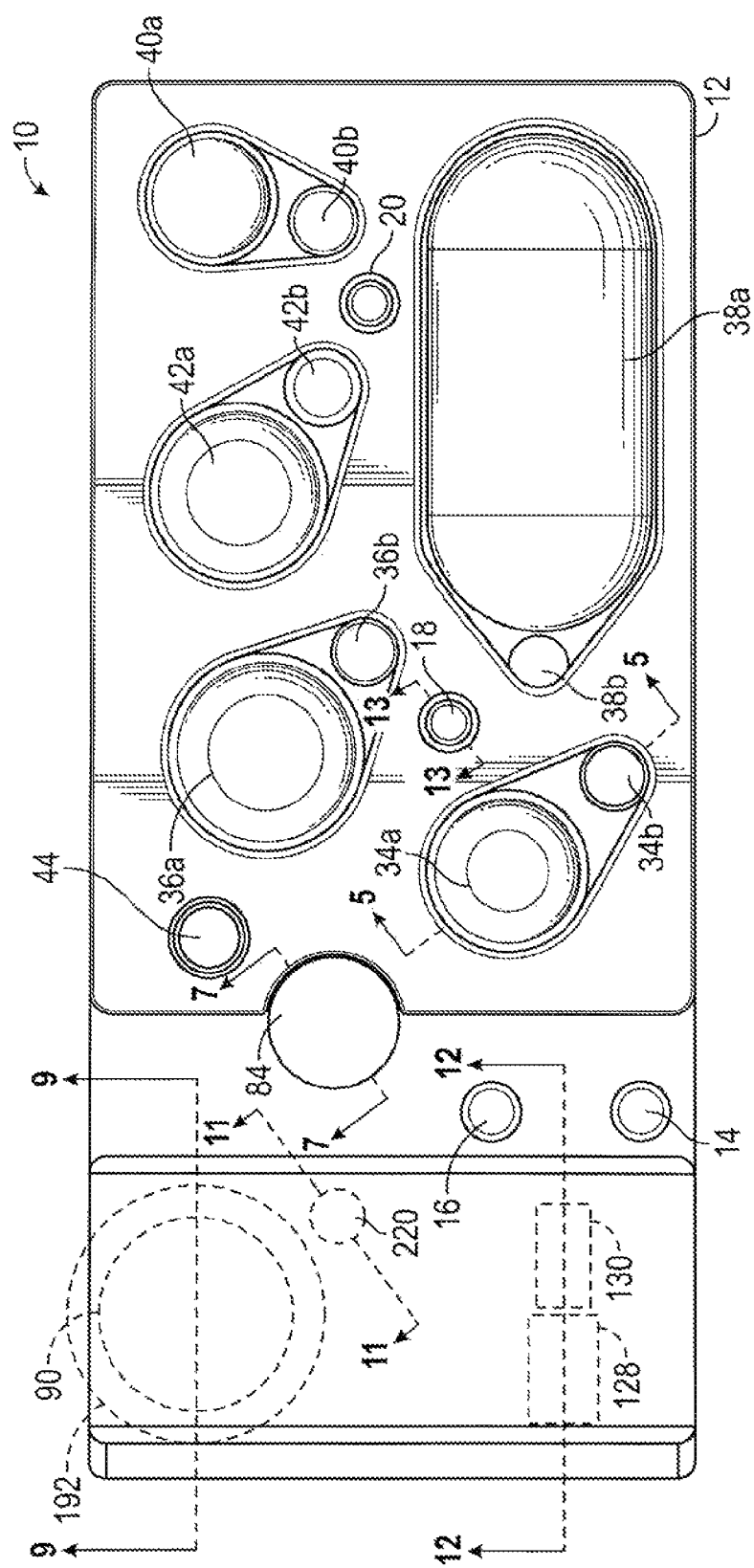
FIG. 2 is a top plan view of the multiplex cartridge.
Figure 3:
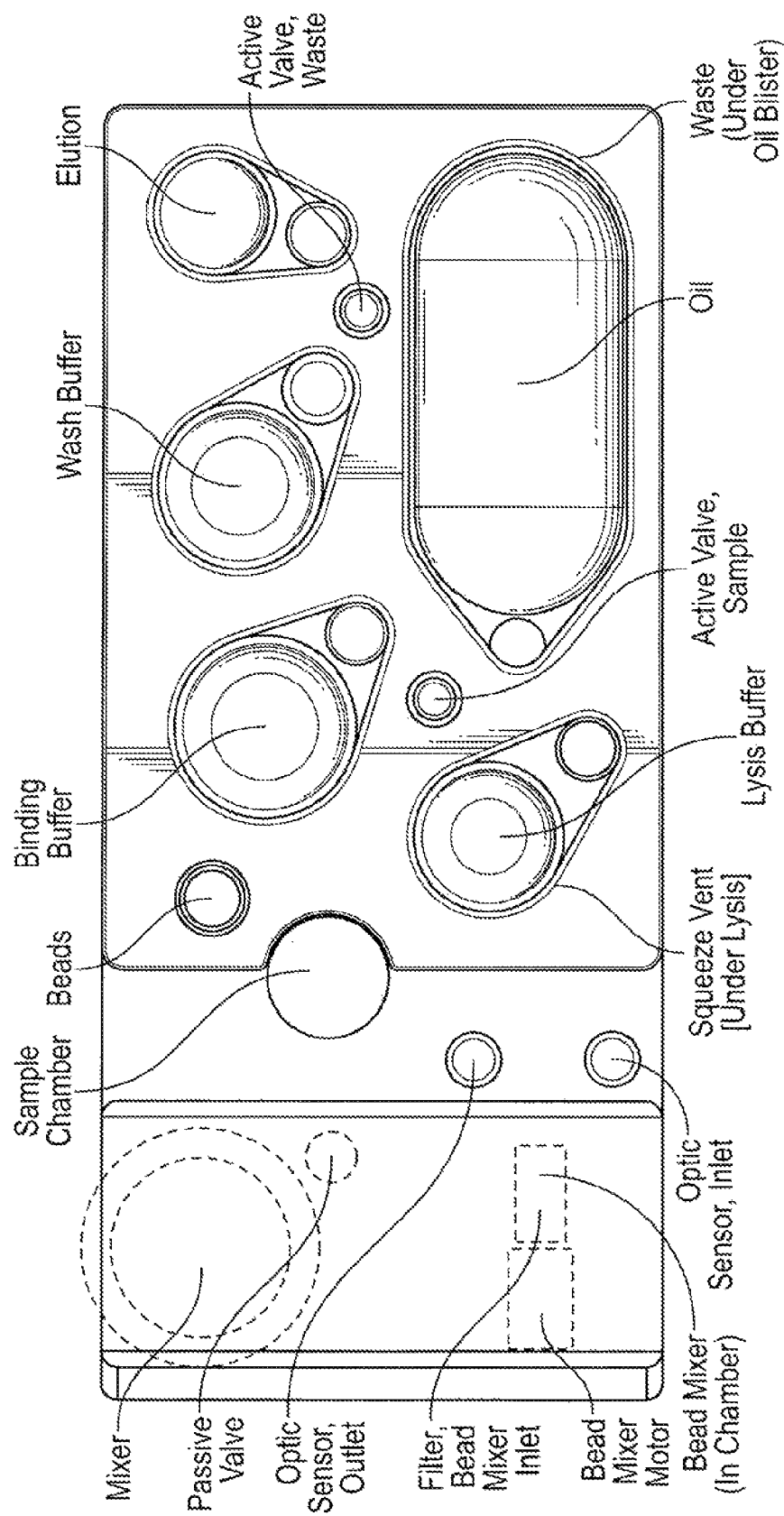
FIG. 3 is a top plan view of the multiplex cartridge annotated with identifying labels.

While aspects of the subject matter of the present disclosure may be embodied in a variety of forms, the following description and accompanying drawings are merely intended to disclose some of these forms as specific examples of the subject matter. Accordingly, the subject matter of this disclosure is not intended to be limited to the forms or embodiments so described and illustrated.

Unless defined otherwise, all terms of art, notations and other technical terms or terminology used herein have the same meaning as is commonly understood by one of ordinary skill in the art to which this disclosure belongs. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

Unless otherwise indicated or the context suggests otherwise, as used herein, "a" or "an" means "at least one" or "one or more."

This description may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of, right of, in front of, behind, next to, adjacent, between, horizontal, vertical, diagonal, longitudinal, transverse, radial, axial, etc., are used for convenience in referring to such component, apparatus, location, feature, or a portion thereof in the drawings and are not intended to be limiting.

Furthermore, unless otherwise stated, any specific dimensions mentioned in this description are merely representative of an exemplary implementation of a device embodying aspects of the invention and are not intended to be limiting.

INTRODUCTION

In general, the system includes two components: the multiplex cartridge, into which the sample is loaded and which contains various reagents, buffers, and other processing materials for performing the desired assay or other procedure, and the processing instrument into which the cartridge is inserted to perform the sample processing and final detection of the target analytes.

In various embodiments, the microfluidic platform relies on the formation of microdroplets and the ability to independently transport, merge, mix and/or process the droplets. In various embodiments, such microdroplet operations are performed using electrical control of surface tension (i.e., electrowetting). In general, liquid samples are contained within a microfluidic device, known as a processing module, between two parallel plates. One plate—referred to as the fluidic processing panel—contains etched drive electrodes on its surface while the other plate contains either etched electrodes or a single, continuous plane electrode that is grounded or set to a reference potential ("biplanar electrowetting"). Hydrophobic insulation covers the electrodes and an electric field is generated between electrodes on opposing plates. This electric field creates a surface-tension gradient that causes a droplet overlapping the energized electrode to move towards that electrode. In some embodiments, the active electrowetting electrodes may be adjacent and on the same plane as the neighboring ground reference electrode, which is referred to as "coplanar electrowetting". Through proper arrangement and control of the electrodes, a droplet can be transported by successively transferring it between adjacent electrodes. The patterned electrodes can be arranged in a two dimensional array so as to allow transport of a droplet to any location covered by that array. The space surrounding the droplets may be filled with a gas such as air or an immiscible fluid such as oil, with immiscible oils being preferred in many embodiments of the present invention.

As the droplets containing the target analytes move across the surface, they can pick up reagents and buffers. For example, when dried reagents are placed on the surface (generally described herein as printed circuit board, although as will be appreciated by those in the art, additional surfaces can be used), a droplet moving through that zone will pick up and dissolve the reagent for use in a biological process, such as PCR amplification. In addition, as more fully described below, addition from a sample preparation module positioned above the substrate, allows for specific addition of buffers and other reagents such as wash buffers, etc., as well as preparation, e.g., lysis, purification, dissolution, etc., of the sample prior to transferring the sample to the microfluidic platform.

Aspects of the present invention also involve the use of electrochemical detection of analytes of interest. Suitable electrochemical detection systems are described in U.S. Pat. Nos. 4,887,455; 5,591,578; 5,705,348; 5,770,365; 5,807,701; 5,824,473; 5,882,497; 6,013,170; 6,013,459; 6,033,601; 6,063,573; 6,090,933; 6,096,273; 6,180,064; 6,190,858; 6,192,351; 6,221,583; 6,232,062; 6,236,951; 6,248,229; 6,264,825; 6,265,155; 6,290,839; 6,361,958; 6,376,232; 6,431,016; 6,432,723; 6,479,240; 6,495,323; 6,518,024; 6,541,617; 6,596,483; 6,600,026; 6,602,400; 6,627,412; 6,642,046; 6,655,010; 6,686,150; 6,740,518; 6,753,143; 6,761,816; 6,824,669; 6,833,267; 6,875,619; 6,942,771; 6,951,759; 6,960,467; 6,977,151; 7,014,992; 7,018,523; 7,045,285; 7,056,669; 7,087,148; 7,090,804; 7,125,668; 7,160,678; 7,172,897; 7,267,939; 7,312,087; 7,381,525; 7,381,533; 7,384,749; 7,393,645; 7,514,228; 7,534,331; 7,560,237; 7,566,534; 7,579,145; 7,582,419; 7,595,153; 7,601,507; 7,655,129; 7,713,711; 7,759,073; 7,820,391; 7,863,035; 7,935,481; 8,012,743; 8,114,661 and U.S. Pub. No. 2012/0181186, the respective disclosures of which are expressly incorporated herein by reference.

In various embodiments processed target analyte droplets are transported to a detection zone on the fluidic processing panel, where they are specifically captured on individual detection electrodes, using systems described in numerous patents above with specific reference to U.S. Pat. Nos. 7,160,678, 7,393,645, and 7,935,481. This detection system relies on the use of label probes (in the case of nucleic acids) containing electrochemically active labels, such that the presence of the target analyte results in a positive signal, allowing detection of the pathogen, disease state, etc.

Samples

Aspects of the invention provide systems and methods for the detection of target analytes in samples to diagnose disease or infection by pathogens (e.g. bacteria, virus, fungi, etc.). As will be appreciated by those in the art, the sample solution may comprise any number of things, including, but not limited to, bodily fluids (including, but not limited to, blood, urine, serum, plasma, cerebrospinal fluid, lymph, saliva, nasopharyngeal samples, anal and vaginal secretions, feces, tissue samples including tissues suspected of containing cancerous cells, perspiration and semen of virtually any organism, with mammalian samples being preferred and human samples being particularly preferred); environmental samples (including, but not limited to, air, agricultural, water and soil samples, environmental swabs and other collection kits); biological warfare agent samples; food and beverage samples, research samples (i.e., in the case of nucleic acids, the sample may be the products of an amplification reaction, including both target and signal amplification as is generally described in WO/1999/037819, the disclosure of which is hereby incorporated by reference, such as PCR amplification reaction); purified samples, such as purified genomic DNA, RNA, proteins, etc.; raw samples (bacteria, virus, genomic DNA, etc.); as will be appreciated by those in the art, virtually any experimental manipulation may have been done on the sample.

The multiplex cartridge may be used to detect target analytes in patient samples. By "target analyte" or "analyte" or grammatical equivalents herein is meant any molecule or compound to be detected and that can bind to a binding species, defined below. Suitable analytes include, but are not limited to, small chemical molecules such as environmental or clinical chemical or pollutant or biomolecule, including, but not limited to, pesticides, insecticides, toxins, therapeutic and abused drugs, hormones, antibiotics, antibodies, organic materials, etc. Suitable biomolecules include, but are not limited to, proteins (including enzymes, immunoglobulins and glycoproteins), nucleic acids, lipids, lectins, carbohydrates, hormones, whole cells (including prokaryotic (such as pathogenic bacteria) and eukaryotic cells, including mammalian tumor cells), viruses, spores, etc.

In one embodiment, the target analyte is a protein ("target protein"). As will be appreciated by those in the art, there are a large number of possible proteinaceous target analytes that may be detected using the present invention. By "proteins" or grammatical equivalents herein is meant proteins, oligopeptides and peptides, derivatives and analogs, including proteins containing non-naturally occurring amino acids and amino acid analogs, and peptidomimetic structures. The side chains may be in either the (R) or the (S) configuration. In a preferred embodiment, the amino acids are in the (S) or L-configuration. As discussed below, when the protein is used as a binding ligand, it may be desirable to utilize protein analogs to retard degradation by sample contaminants. Particularly preferred target proteins include enzymes; drugs, cells; antibodies; antigens; cellular membrane antigens and receptors (neural, hormonal, nutrient, and cell surface receptors) or their ligands.

In a preferred embodiment, the target analyte is a nucleic acid ("target nucleic acid"). The present system finds use in the diagnosis of specific pathogens exogenous to a patient such as bacteria and viruses, as well as the diagnosis of genetic disease, such as single nucleotide polymorphisms (SNPs) that cause disease (e.g. cystic fibrosis) or are present in disease (e.g. tumor mutations).

As will be appreciated by those in the art, the present invention relies on both target nucleic acids and other nucleic acid components like capture probes and label probes used in the detection of the target nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs can be included as primers or probes that may have alternate backbones, comprising, for example, phosphoramide (Beaucage et al., Tetrahedron 49(10). T 925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Left. 805 (1984), Letsinger et al., J. Am. Chem. Soc. 1 10:4470 (1988); and Pauwels et al., Chemica Scripta 26: 141 91986)), phosphorothioate (Mag et al., Nucleic Acids Res. 19: 1437 (1991); and U.S. Pat. No. 5,644,048), phosphorodithioate (Briu et al, J. Am. Chem. Soc. 1 1 1:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 1 14: 1895 (1992); Meier et al., Chem. Int. Ed. Engl. 31: 1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); those with bicyclic structures including locked nucleic acids, Koshkin et al., J. Am. Chem. Soc. 120: 13252-3 (1998); non-ionic backbones (U.S. Pat. Nos. 5,386,023, 5,637,684, 5,602,240, 5,216, 141 and 4,469,863; Kiedrowshi et al., Angew. Chem. Intl. Ed. English 30:423 (1991); Letsinger et al., J. Am. Chem. Soc. 1 10:4470 (1988); Letsinger et al, Nucleoside & Nucleotide 13: 1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al, J. Biomolecular NMR 34: 17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) ppl 69-176). Several nucleic acid analogs are described in Rawls, C & E News Jun. 2, 1997 page 35. All of these references are hereby expressly incorporated by reference. These modifications of the ribose-phosphate backbone may be done to facilitate the addition of ETMs, or to increase the stability and half-life of such molecules in physiological environments.

As will be appreciated by those in the art, all of these nucleic acid analogs may find use in the present invention, in general for use as capture and label probes. In addition, mixtures of naturally occurring nucleic acids and analogs can be made (e.g. in general, the label probes contain a mixture of naturally occurring and synthetic nucleotides).

The nucleic acids may be single stranded or double stranded, as specified, or contain portions of both double stranded or single stranded sequence. The nucleic acids (particularly in the case of the target nucleic acids) may be DNA, both genomic and cDNA, RNA or a hybrid, where the nucleic acid contains any combination of deoxyribo- and ribonucleotides, and any combination of bases, including uracil, adenine, thymine, cytosine, guanine, inosine, xathanine hypoxathanine, isocytosine, isoguanine, etc. One embodiment utilizes isocytosine and isoguanine in nucleic acids designed to be complementary to other probes, rather than target sequences, as this reduces non-specific hybridization, as is generally described in U.S. Pat. No. 5,681,702, disclosure of which is hereby incorporated by reference. As used herein, the term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

As will be appreciated by those in the art, a large number of analytes may be detected using the present methods; basically, any target analyte for which a binding ligand, described below, may be made may be detected using the methods of the invention.

Thus, the systems of the invention are used in assays of target analytes that then allow the diagnosis, prognosis or treatment options of disease based on the presence or absence of the target analytes. For example, the systems of the invention find use in the diagnosis or characterization of pathogen infection (including bacteria (both gram positive and gram negative bacteria, and/or the ability to distinguish between them), viruses (including the presence or absence of viral nucleic acid as well as the isotypes of the virus, for example in the case of hepatitis C virus (HCV) or respiratory viruses), fungal infection, antibiotic drug resistance, genetic diseases (including cystic fibrosis, sickle cell anemia, etc.). Included in the definition of genetic disease for the purposes of this invention are genetic conditions that do not necessarily cause disease but can result in an alternative treatment options. For example, single nucleotide polymorphisms (SNPs) in many cytochrome p450 enzymes cause different therapeutic drug processing, such as in the case of warfarin testing, where a patient may be diagnosed as a "slow", "normal" or "fast" processor, leading to different dosage regimes, or where a drug may be contraindicated for a particular patient based on the patient's genetics, or where selection between two or more drugs is aided by the knowledge of patient's genetics.

Multiplex Cartridge

Figure 4:
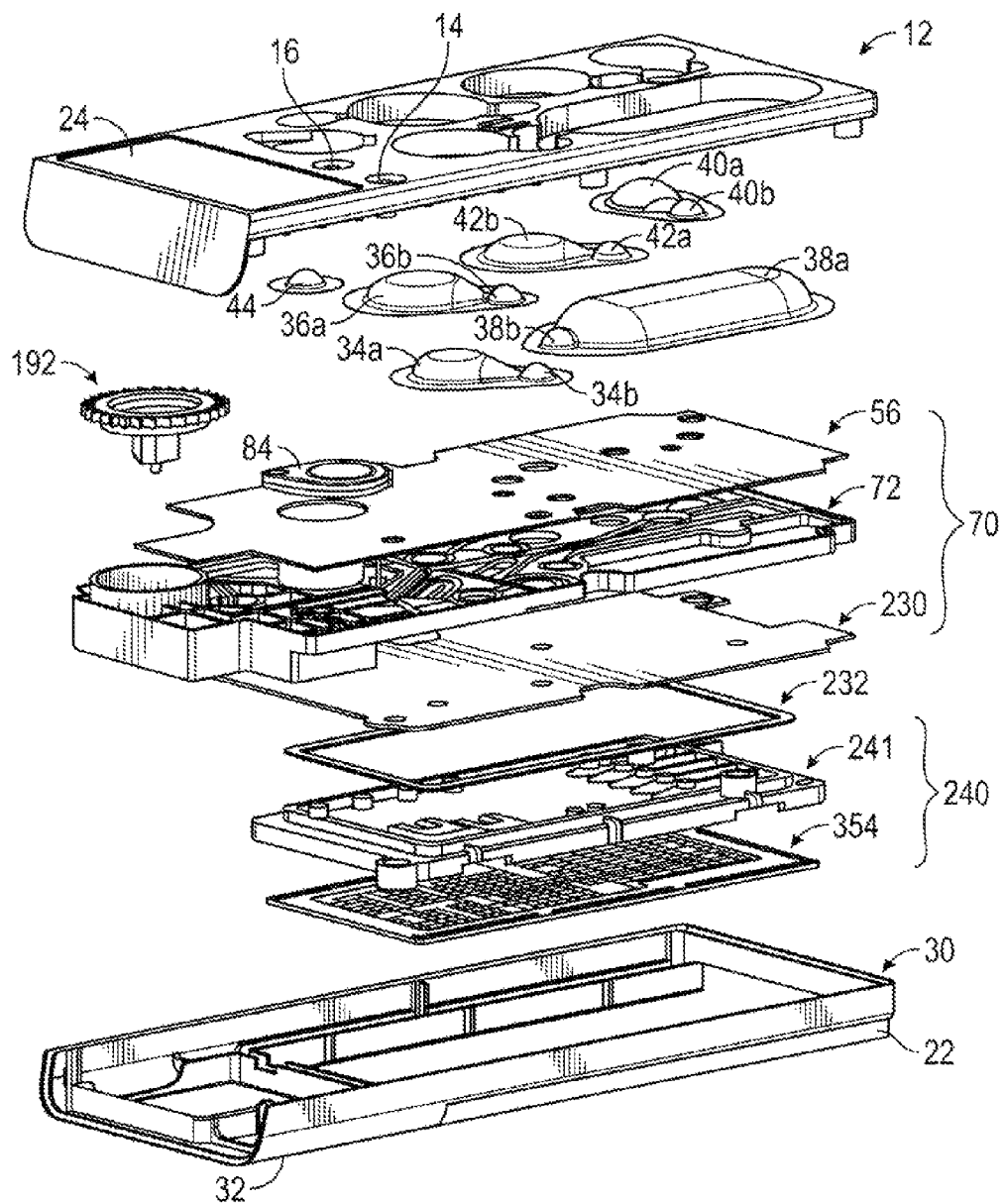
FIG. 4 is an exploded perspective view of the multiplex cartridge.

A multiplex cartridge embodying aspects of the present invention is shown in FIGS. 1-4. As shown in FIG. 4, the multiplex cartridge comprises an assembly that includes a sample preparation module 70. The sample preparation module 70 includes various wells, inlet and outlet ports, fluid channels, mixing mechanisms, valves, and other components for receiving, transporting, intermingling, mixing, and performing other processes on fluid sample materials and process fluids, such as reagents and buffers, in a manner that will be described in further detail below. The sample preparation module 70 comprises a substrate 72, with a top seal 56 secured to a top surface thereof and a bottom seal 230 secured to a bottom surface thereof. The substrate 72 includes a number of grooves or open channels formed on the top and bottom surfaces thereof. Each of the grooves may connect to one or more inlet ports comprising a blind hole formed in the top surface of the substrate 72 and/or to one or more outlet ports comprising a blind hole formed in the bottom surface of the substrate 72. The top seal 56 and bottom seal 230 cover the top and bottom, respectively, of the substrate 72 and having openings that align with the inlets and outlets formed in the substrate 72, thereby forming a network of conduits, or enclosed channels, through which a fluid—e.g., liquid, gas, solution, emulsion, liquid-solid suspension, etc.—may flow from one part of the sample preparation module 70 to another and inlet ports and outlet ports through which fluids may flow into and out of, respectively, the sample preparation module 70. In various embodiments, the sample preparation module 70 is transparent or translucent and is made from, for example, polycarbonate, polypropylene, acrylic, Mylar, acrylonitrile butadiene styrene ("ABS"), or other suitable polymers A rotary mixer 192 is operatively disposed within a mixing well 90 (described below) formed in the substrate 72. In various embodiments, the rotary mixer 192 can be used, for example, to grind up solid samples, maximize exposure of sample to capture beads, mix sample with chemical lysis buffer, mix magnetic beads with binding buffer (typically magnetic beads cannot be stored in their binding buffer and thus must be combined only at the time of use), etc.

A sample cap 84 is provided to enclose a sample well 78 (described below) formed in the substrate 72. A plurality of deformable compartments (or blisters) 34a, 36a, 38a, 40a, 42a, and 44 are supported on top of the substrate sample preparation module 70. Each deformable compartment may contain a fluid and may be connected to a fluid channel within the sample preparation module 70, via one of the inlet ports, by an openable connection that is initially closed to prevent fluid from flowing from the blister into the channel. Upon application of a compressive force to the exterior of the blister, increased pressure within the blister ruptures or otherwise opens or alters the openable connection to permit fluid flow from the blister into an associated inlet port and channel of the sample preparation module 70.

An upper shroud 12 is disposed over a top portion of the cartridge above the sample preparation module 70 and includes openings corresponding in number, size, and shape to the various deformable compartments supported on the sample preparation module 70. As can be appreciated from FIG. 1, the deformable compartments are recessed within the openings formed in the upper shroud 12, thereby providing some protection for the deformable compartments while allowing each compartment to be compressed from above by an actuator. In various embodiments, the upper shroud 12 further includes an inlet optical port 14 and an outlet optical port 16 to enable monitoring of fluid movement through a particular portion of the sample preparation module 70, as will be described in further detail below. The upper shroud 12 may further include a label panel 24 on which identifying information may be placed, such as, human and/or machine-readable indicia (e.g., a barcode).

The upper shroud 12 may further include valve actuator tabs, such as a sample valve actuator tab 18 and a waste valve actuator tab 20. The valve actuator tabs 18 and 20 are resilient, flexible tabs formed in the shroud that will deflect upon application of an external compressive force onto the tab. Each tab further includes a downwardly-extending actuator post—see, e.g., actuator post 26 in FIG. 1—to thereby actuate an active valve within the sample preparation module 70 and located below the respective tab 18 or 20, as will be described in further detail below.

Referring to FIG. 4, a reaction module 240 is disposed below the sample processing module 70 and, in various embodiments, may be configured to receive a processed sample from the sample processing module 70. In various embodiments, the reaction module 240 includes process fluid compartments (containing, for example, reagents, buffers, etc.), means for moving fluid droplets in a specified directed manner throughout the module, means for incubating reaction mixtures, and means for detecting target analytes (e.g., nucleic acids), The reaction module 240 may be secured to the bottom of the sample preparation module 70 by means of an adhesive gasket 232 that preferably provides a fluid-tight seal between the reaction module 240 and the sample preparation module 70. In various embodiments, the reaction module 240 comprises a top plate 241 and a bottom, a fluidic processing panel 354 secured to the bottom of the top plate 241 and which together define a gap between the bottom surface of the top plate 241 and a top surface of the fluidic processing panel 354. This gap defines fluid processing and reaction spaces within which various steps of the assay or other process are performed.

A lower shroud 30 partially encloses a bottom portion of the cartridge assembly and cooperates with the upper shroud 12 to define a relatively hard and ridged outer shell for the cartridge 10. The upper and lower shrouds may provide the cartridge 10 with an asymmetric shape so as to ensure that the cartridge 10 is inserted into a processing instrument in only one orientation. In the illustrated embodiment, the lower shroud 30 has rounded edges 32 whereas the upper shroud 12 has relatively square edges. Thus, a receiving slot of a processing instrument configured to receive the multiplex cartridge 10 and having a shape conforming to that of the shroud will ensure that the shroud is always inserted right side up into the instrument. In addition, the lower shroud 30 may include contour features, such as longitudinal side grooves 22 that extend only partially along the length of the lower shroud 30. Such grooves cooperate with corresponding features in a receiving slot of a processing instrument to ensure that the cartridge is inserted into the instrument in the proper direction.

Deformable Fluid Compartments (Blisters)

In general, the blisters are made of a deformable material that preferably collapses upon the application of suitable pressure; that is, the materials used to form blisters do not return to their starting shape when the pressure is removed, as this could cause backflow of the applied reagents. In addition, the blisters may be used once (a single application of pressure is done during the assay) or a number of times (e.g. multiple aliquots of reagent are delivered to either a single location or multiple locations during the assay run). Each blister may contain a unique process material (e.g., buffer, reagent, immiscible liquid, etc.), or two or more blisters may contain the same process material. This redundancy may be used to deliver the same process material to multiple locations in the rest of the disposable.

Although the size, number, arrangement, and contents of the compartments is largely dictated by the assay or other process that is intended to be performed in the multiplex cartridge 10, the illustrated embodiment includes six deformable fluid compartments, or blisters: 34a, 36a, 38a, 40a, 42a, and 44. A deformable blister may have an associated lance blister. In the illustrated embodiment, each of deformable fluid blisters 34a, 36a, 38a, 40a, and 42a has an associated deformable lance cartridge, or lance blister, 34b, 36b, 38b, 40b, and 42b.

Figure 5:
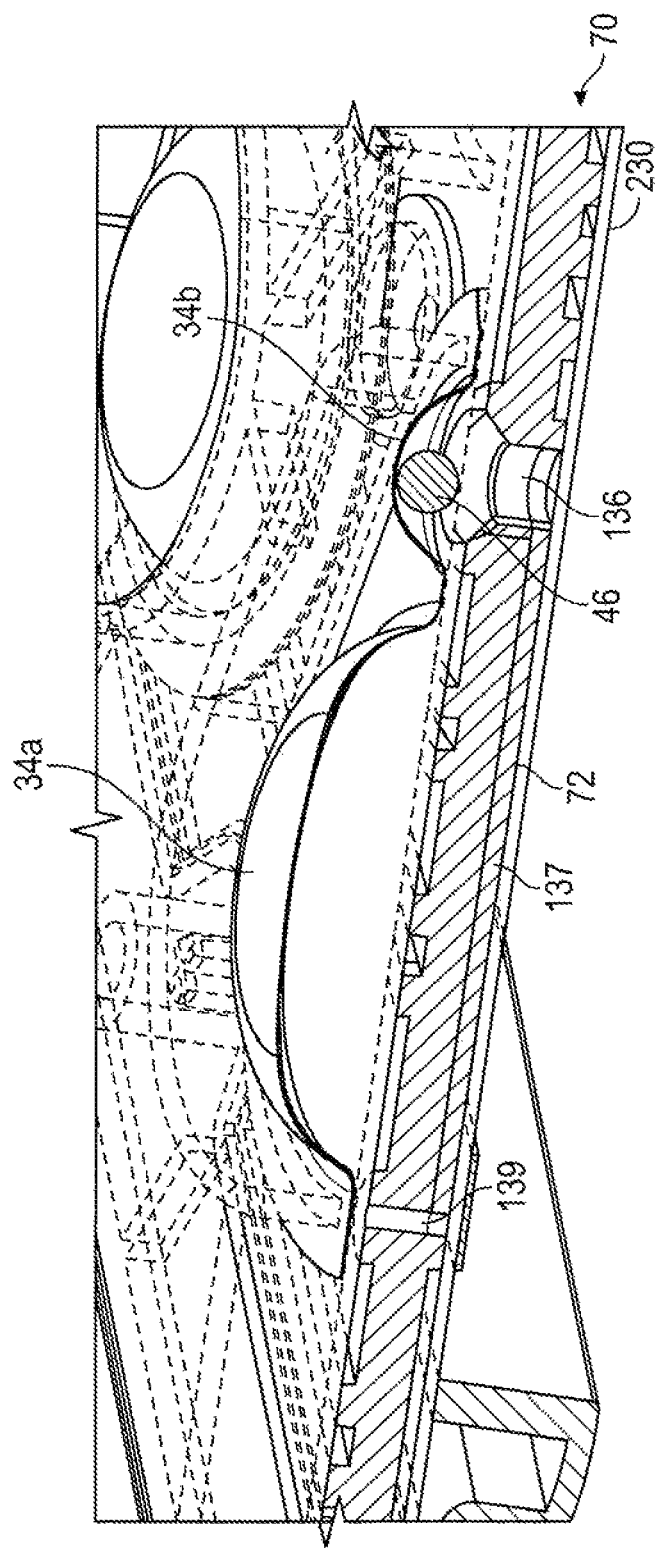
FIG. 5 is a partial perspective view in cross-section of a deformable fluid compartment (or blister) of the multiplex cartridge.

Operation of an embodiment of a deformable compartment is described with reference to FIG. 5, which shows a cross section of the deformable compartment 34a. In various embodiments, the deformable compartments of the multiplex cartridge 10 incorporate features described in commonly-owned U.S. patent application Ser. No. 14/206,867 entitled "Devices and Methods for Manipulating Deformable Fluid Vessels" the contents of which are hereby incorporated by reference.

When compressing a deformable compartment to displace the fluid contents thereof, sufficient compressive force must be applied to the blister to break, or otherwise open, a breakable seal that is holding the fluid within the compartment. The amount of force required to break the seal and displace the fluid contents of a compartment typically increases as the volume of the compartment increases. To limit the amount of compressive force that must be applied to a deformable compartment or blister to break or otherwise open a breakable seal that is holding the fluid within the compartment, a lance blister 34b is provided in association with the deformable compartment 34a. The deformable compartment 34a and the lance blister 34b may be connected by means of a channel, which may be initially blocked by a breakable seal. The lance blister 34b contains an opening device, e.g., a bead 46 (such as a steel ball bearing), enclosed within the lance blister 34b and supported above a fluid port 136 formed in the sample preparation module 70 by means of a breakable foil partition, or septum, that retains the bead 46 and the fluid contents within the lance blister 34b and the deformable compartment 34a. Thus, to open the deformable compartment 34a, a compressive force is first applied externally to the lance blister 34b to compress the lance blister 34b and force the bead 46 through the foil partition blocking the fluid port 136. After the fluid port 136 is opened, the fluid contents of the deformable compartment 34a can be dispensed into the fluid port 136 relatively easily by application of an external compressive force to the deformable compartment 34a. The amount of pressure required to compress the lance blister 34b and force the bead 46 through the foil partition is much less than that required to compress the primary compartment 34a and create sufficient pressure to open a burstable seal. Fluid flowing into the fluid port 136 will next flow through a horizontal channel 137, defined by a groove formed in a bottom surface of the substrate 72 and covered by the bottom seal 230, to a vertical channel transition 139 and from there to one or more other points within the sample preparation module 70.

Sample Preparation Module

Various details of a sample preparation module 70 are shown in FIGS. 6-15.

Figure 6:
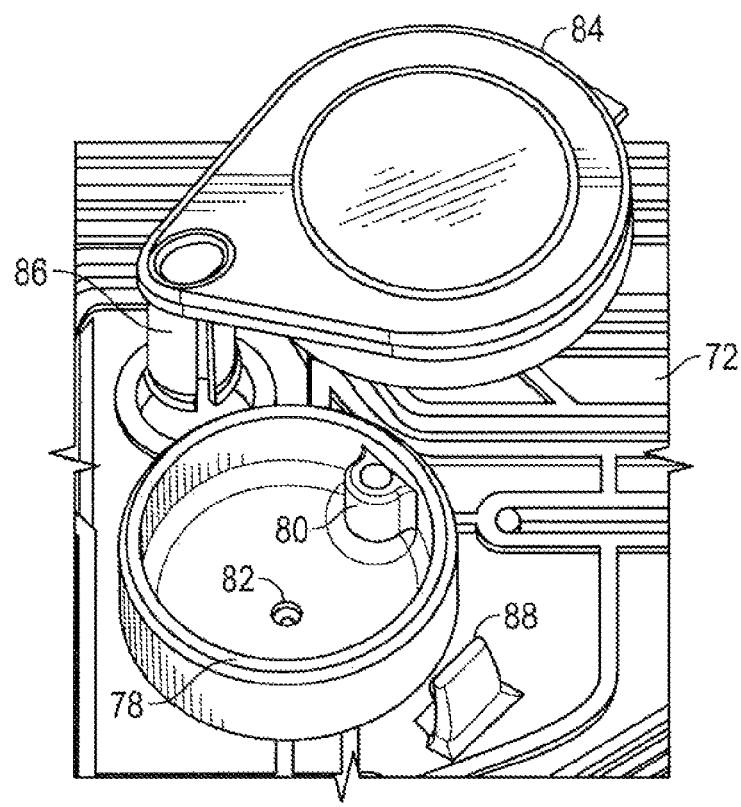
FIG. 6 is a perspective detail of a sample well and a sample cap of the multiplex cartridge.
Figure 7:
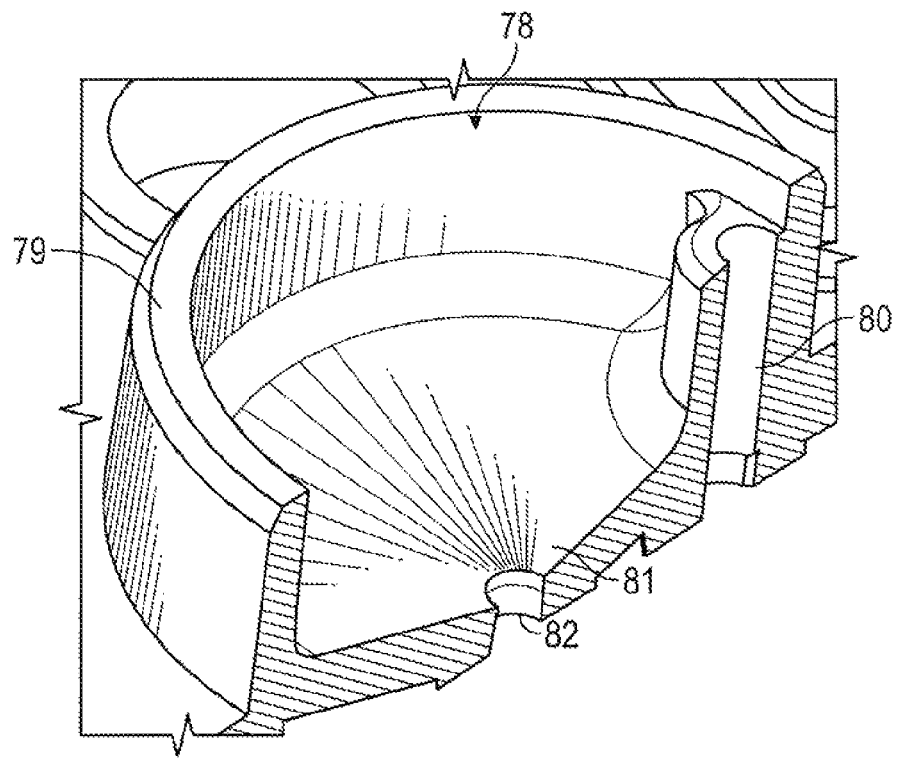
FIG. 7 is a perspective, cross sectional view of the sample well along the line 7-7 in FIG. 2.

The sample well 78 is configured to receive a fluid sample material that is to be assayed or otherwise processed in the multiplex cartridge 10. As shown in FIGS. 6 and 7, the sample well 78 may be defined by an upright peripheral wall 79 (which is circular in the illustrated embodiment) and a bottom wall, or floor 81. The sample well 78 further includes an inlet snorkel 80 extending up along the peripheral wall 79 of the sample well 78 and terminating at a position below the top of the peripheral wall. An exit port 82 is provided in the floor 81 of the well 78, and the floor 81 is preferably conical so as to taper downward toward the exit port 82.

The sample cap 84 may be provided for closing the sample well 78 after a sample material has been deposited into the sample well 78. In one embodiment, the sample cap 84 comprises a circular cover with an outer peripheral wall that fits over the upright peripheral wall 79 of the sample well 78. The sample cap 84 may include a pivot post 86 defined by radially-resilient locking tabs extending through an opening in the substrate 72 and permitting the cap 84 to be pivoted about an axis defined by the pivot post 86 relative to the sample well 78. After a sample material is deposited into the sample well 78, the sample cap 84 may be pivoted over the top of the sample well 78 and pushed down over the sample well 78. A clip, or other detent, 88, extending upwardly may be provided to catch on and securely lock the sample cap 84 when pushed down into the clip 88 and to also provide a tactile confirmation that cap 84 has been securely closed. In some embodiments, the sample cap 84 may have a bottom surface that tapers downwardly when the sample cap 84 is placed over the sample well 78 (not shown). The conical configuration helps to reduce the amount of fluid condensate retained on the inside surface of the sample cap 84 during sample processing in the sample well 78.

Figure 8A:
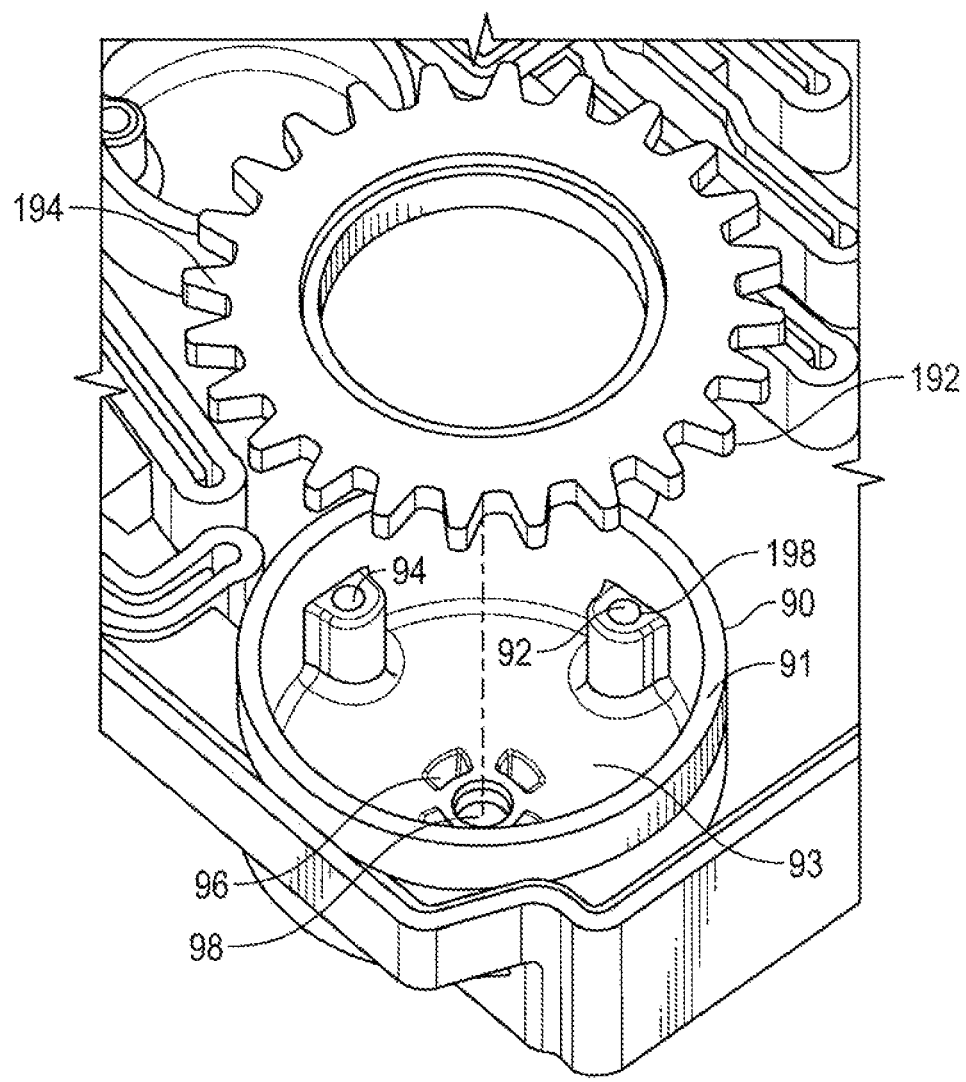
FIG. 8A is a perspective detail of a mixing well and mixer of the multiplex cartridge.
Figure 9A:
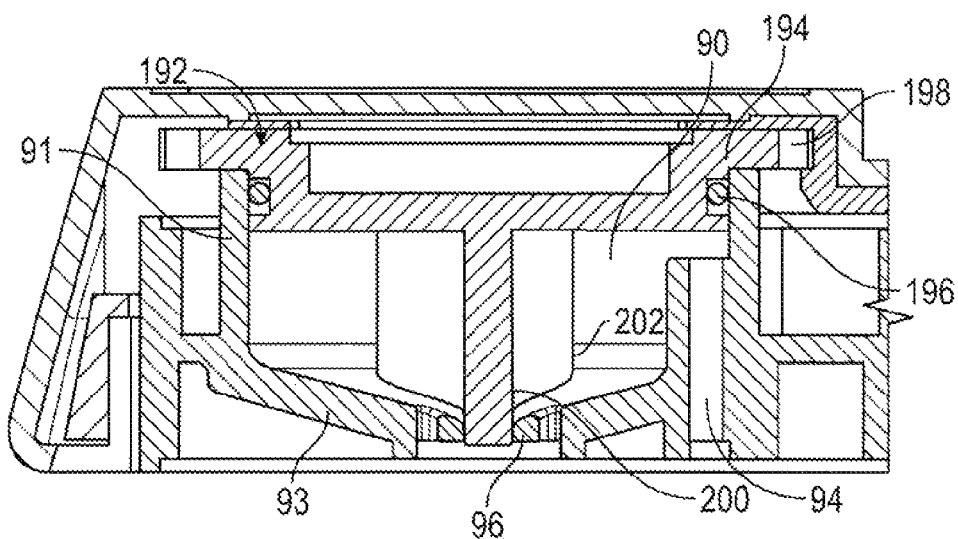
FIG. 9A is a cross sectional view of the mixing well and mixer along the line 9-9 in FIG. 2.

The sample preparation module 70 also includes a mixing well 90 formed in the substrate 72. As shown in FIGS. 8A and 9A, the mixing well 90 may be defined by an upright peripheral wall 91 (which is circular in the illustrated embodiment) and a bottom wall, or floor 93. In various embodiments, a fluid inlet snorkel 92 extends up the peripheral wall 91 of the mixing well 90 and terminates below the top of the wall 91. In various embodiments, a pressure snorkel 94 extends up another portion of the peripheral wall 91 of the mixing well 90 and terminates at a position below the top of the wall 91. An exit port 96 allows fluid to exit the mixing well 90 and may comprise a plurality of openings located near the center of a downwardly tapered portion of the floor 93 of the well 90 and surrounding a spindle seat 98 formed at the bottom center of the floor 93.

The rotary mixer 192 is disposed within the mixing well 90 and includes an upper circular disk 194 supported on an upper edge of the peripheral wall 91 of the well 90. Peripheral gear teeth 198 are formed about the periphery of the disk 194, and a portion of the teeth 198 project from an outer edge of the upper and lower shrouds 12, 30 of the multiplex cartridge 10 so as to be engageable by an external drive mechanism of a processing instrument to effect powered rotation of the rotary mixer 192. An O ring 196 is disposed within a peripheral O ring groove about the upper disk 194 below the peripheral gear teeth 198. The O ring 196 provides a seal between the rotary mixer 192 and the peripheral wall 91 of the well 90. A spindle 200 extends downwardly from the upper disk 194 and is seated within the center spindle seat 98 of the mixing well 90. A plurality of impeller blades 202 extend radially from the spindle 200.

Figure 8B:
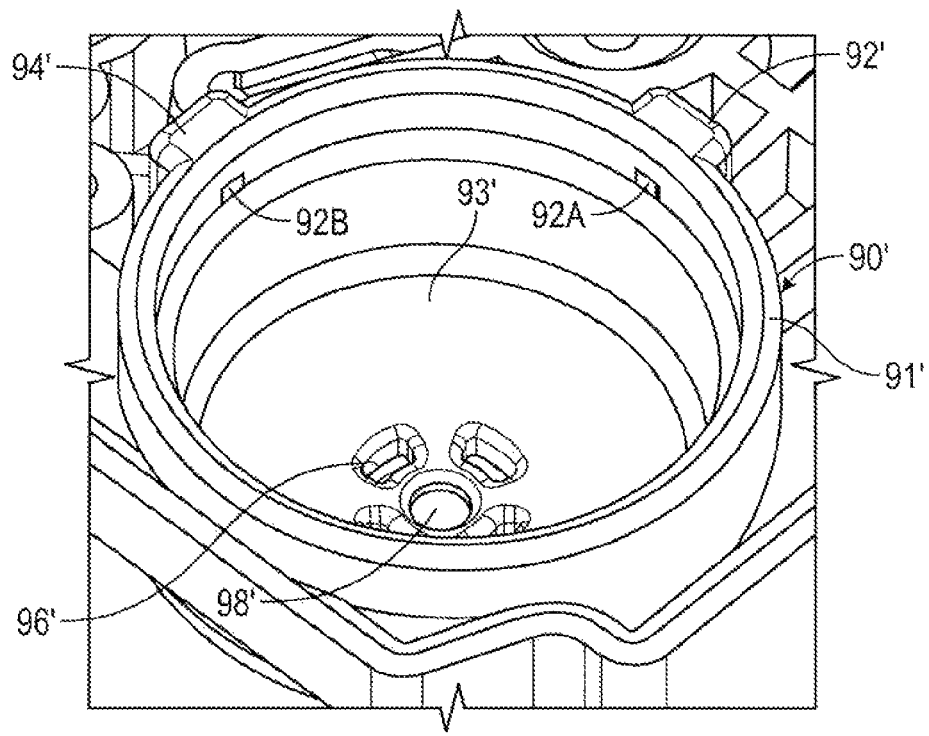
FIG. 8B is a perspective detail of an alternate mixing well of the multiplex cartridge.
Figure 8C:
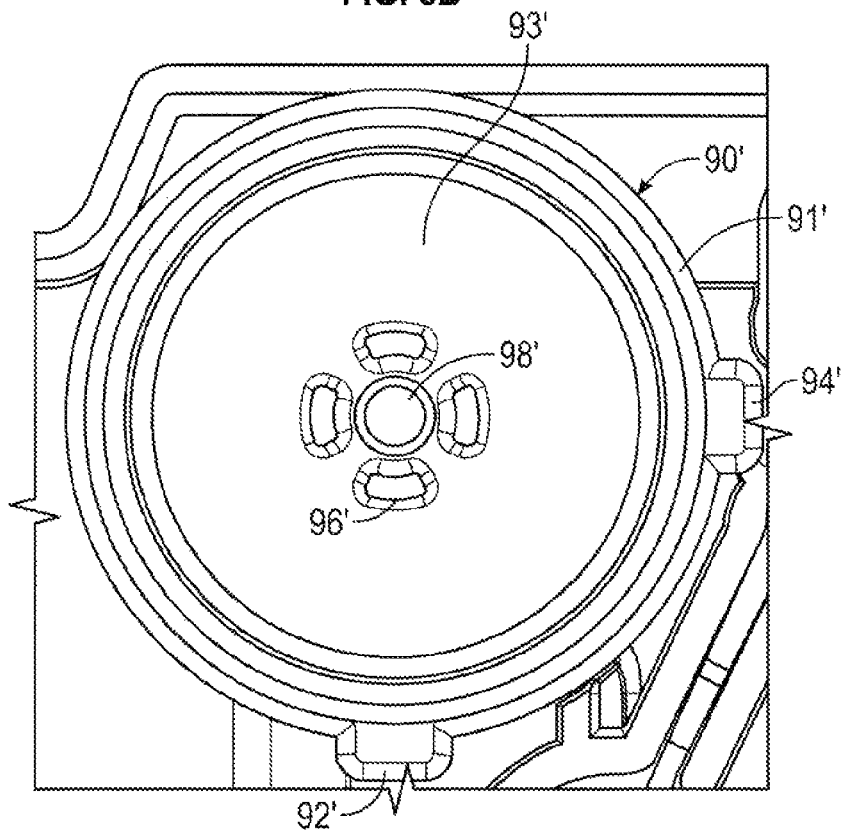
FIG. 8C is a top plan view of the mixing well of FIG. 8C.

An alternate embodiment of a mixing well 90' is shown in FIGS. 8B and 8C. As shown, mixing well 90' may be defined by an upright peripheral wall 91' (which is circular in the illustrated embodiment) and a bottom wall, or floor 93'. A fluid inlet snorkel 92' extends up an outer surface of the peripheral wall 91' of the mixing well 90' and includes an opening 92a below the top of the wall 91'. A pressure snorkel 94' extends up outer surface of the peripheral wall 91' of the mixing well 90' and includes an opening 94a below the top of the wall 91'. An exit port 96' allows fluid to exit the mixing well 90' and may comprise a plurality of openings located near the center of a downwardly tapered portion of the floor 93' of the well 90' and surrounding a spindle seat 98' formed at the bottom center of the floor 93'. The exit port 96' and spindle seat 98' may be substantially identical to the exit port 96 and spindle seat 98, respectively, of the mixing well 90.

With the alternate mixing well 90' of FIGS. 8B and 8C, a rotary mixer disposed within the mixing well 90' may be configured with impeller blades extending radially from a spindle of the mixer substantially to the inner surface of the peripheral wall 91'. This is opposed to the configuration of the rotary mixer 192 configured for operation in the mixing well 90, in which the radial impeller blades 202 cannot extend substantially to the inner surface of the peripheral wall 91 so as to provide clearance for the snorkels 92, 94 formed on the inner surface of the peripheral wall 91. Having a mixer with impeller blades extending to the inner surface of the peripheral wall 91' may, in some circumstances, provide more complete and/or efficient mixing of the contents of the mixing well 90'.

Figure 9B:
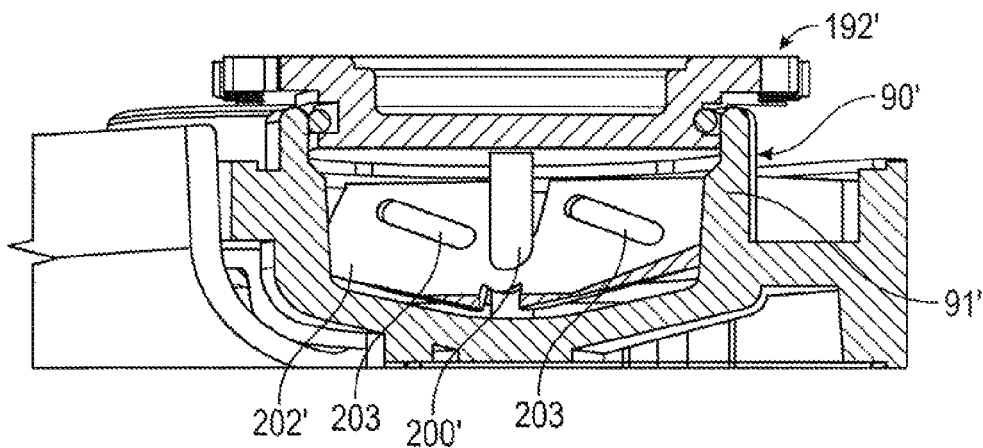
FIG. 9B is cross sectional view of the alternate mixing well of FIGS. 8B and 8C and an alternate mixer disposed therein.

Referring to FIG. 9B, the rotary mixer 192' disposed within the mixing well 90' includes an upper circular disk 194', peripheral gear teeth 198', and an O ring 196' that may be substantially identical to the circular disk 194, peripheral gear teeth 198, and an O ring 196 of the rotary mixer 192 shown in FIG. 9A. A spindle 200' extends downwardly from the upper disk 194'. Two or more impeller blades 202' extend radially from the spindle 200'. The impeller blades 202' extend substantially to the inner surface of the peripheral wall 91'. In various embodiments the impeller blades 202' may be skewed with respect to the spindle 200' and may further include openings 203 formed therein to improve the mixing efficiency of the rotary mixer 192'.

Referring again to FIG. 15, which shows a top plan view of the sample preparation module 70, the sample preparation module 70 may include alignment holes 74 and 76, or other alignment features may be provided in the sample preparation module 70, or some other portion of the multiplex cartridge 10 to facilitate alignment of the multiplex cartridge 10 with a processing instrument, for example, by means of a pin or other structure within the instrument extending into each alignment hole.

The sample preparation module 70 includes a first inlet port 136 formed in a top surface of the module by which a process fluid from the deformable compartment 34a may be introduced into the sample preparation module 70. In one embodiment, the deformable compartment 34a contains a lysis buffer, such as water for hypotonic lysis, or a commercially available lysis buffer, such as those containing chiatropic salts such as guanidinium salts, and or high/low pH, and/or surfactants such as sodium dodecyl sulfate (SDS), TWEEN® 20 (polysorbate 20), TRITON™ X-100 (polyoxyethylene octyl phenyl ether), etc. In some cases, the lysis buffer optionally comprises reagents to disrupt undesired enzymatic activity, such as DNase and RNase activity, which are then removed during the bead capture/elution process (although these can be separate reagents, either dried or liquid, that can be added as needed depending on the target analytes and the assay).

After cells of the sample material are lysed, it is often desirable to perform an at least partial purification, to remove other cellular and sample debris from the sample to facilitate the downstream handling and processing. Research samples in buffer do not necessarily require purification, but even there purification is typically performed. A well-known technique relies on the use of target capture beads (e.g., magnetic capture beads) that capture and immobilize the desired target analyte(s) away from the cellular and sample debris. In various implementations, capture beads and binding buffer are mixed with the sample in lysis buffer after the cells or viruses are disrupted by mechanical and/or chemical means. The capture beads may be magnetic to facilitate subsequent immobilization of the beads and the target analyte bound thereto by selective application of magnetic forces, although as will be appreciated by those in the art, other implementations may employ non-magnetic beads, such as polystyrene or silica beads (for example, beads may be captured in a zone by size or on an affinity column).

Thus, in various embodiments, the sample preparation module 70 includes a second inlet port 138 by which a process fluid from the deformable compartment 36a may be introduced into the sample preparation module 70. In one embodiment, the deformable compartment 36a contains a binding buffer to facilitate the binding of target capture beads, such as magnetic beads, to one or more target analytes of interest.

In various embodiments, the sample preparation module 70 includes a third inlet port 140 by which a process material from the deformable compartment 44 may be introduced into the sample preparation module 70. In one embodiment, the deformable compartment 44 contains target capture beads which may comprise magnetic particles, which, in combination with a binding buffer from the deformable compartment 36a, binds to an analyte or analytes of interests within the sample material to thereby isolate and enable the magnetic separation of the analyte(s) of interest from the remainder of the sample material.

The capture beads may be coated with a material that facilitates capture of the target analyte(s). For example, for the capture of nucleic acids, the beads can be coated with a negatively charged coating to facilitate the adsorption of positively charged nucleic acids to the surface, which are then washed with buffer and then treated with elution buffer to remove the purified nucleic acids from the beads for further processing. As will be appreciated by those in the art, there are a number of suitable, commercially available bead systems, including, for example, MagaZorb® Beads from Promega, MagMax from Life Tech, or beads from Qiagen, MoBio, BioRad, etc.

Thus, the target capture beads that may be contained in the deformable compartment 44 facilitate the purification of the desired target analyte with fluid access to a binding buffer, such as the bind buffer that may be contained in the deformable compartment 36*a*, used in conjunction with the capture beads.

In an alternate embodiment, target capture beads may be provided directly within the sample preparation module 70, for example, in the form of a lyophilized pellet placed into the mixing well 90 during assembly of the multiplex cartridge 10 and stored in the mixing well in pellet form until reconstituted by a fluid added to the mixing well 90 during use of the multiplex cartridge 10. In this alternate embodiment, the deformable blister 44 may be omitted.

In alternate implementations, capture beads may be functionalized with capture nucleic acid probes in order to either specifically or non-specifically pull out nucleic acids. For example, the beads may be functionalized with random 6-mers, to generally pull out nucleic acids, or with capture probes specific to the desired target nucleic acids. In some cases, for example when mRNA is the target, beads coated with poly-T capture probes can be used.

In various embodiments, the sample preparation module 70 further includes a fourth inlet port 142 by which process material from the deformable compartment 38*a* may be introduced into the sample preparation module 70. In one embodiment, the deformable compartment 38*a* contains an immiscible fluid (e.g., an oil, such as mineral oil, silicone oil, etc., as discussed in detail below).

In various embodiments, the sample preparation module 70 further includes a fifth inlet port 144 by which a process material from the deformable compartment 40*a* may be introduced into the substrate 72. In one embodiment, the deformable compartment 40*a* contains an elution buffer.

In various embodiments, the sample preparation module 70 further includes a sixth inlet port 146 by which process material from the deformable compartment 42*a* may be introduced into the sample preparation module 70. In one embodiment, the deformable compartment 42*a* contains a wash buffer.

In various embodiments, the sample preparation module 70 includes a first outlet port 182, a second outlet port 188, and a third outlet port 190 formed in a bottom surface of the sample preparation module 70 by which fluid can exit the module 70 and flow into the reaction module 240.

It should be noted here that the designation of inlet ports or outlet ports as the first, second, third, fourth, fifth, or sixth ports is merely to provide a convenient means for distinguishing one port from another and is not meant to be limiting, such as, for example, by specifying a particular order or sequence by which the ports may be used.

A first fluid channel 150 extends from the first inlet port 136 to the sample well 78. In the diagrams, the fluid channels are represented by parallel lines extending from point to point across the sample preparation module 70. Each channel may include one or more channel transition points, represented by a circle in the channel, one of which is indicated by reference number 151. The channel transition point represents a vertically extending section of channel extending up, from a channel section formed on the bottom of the substrate 72 to a channel section formed on the top of the substrate 72, or down, from a channel section formed on the top of the substrate 72 to a channel section formed on the bottom of the substrate 72, so that the channel may pass over or under another channel within the substrate 72.

A second fluid channel 152 extends from the sample well 78 to the lysis chamber inlet 122. A third fluid channel 156 extends from the lysis chamber outlet 124 to a fifth fluid channel 162 that extends from the third inlet port 140 to the mixing well inlet snorkel 92. A fourth fluid channel 160 extends from the second inlet port 138 to the third inlet port 140. A sixth fluid channel 164 extends from the fourth inlet port 142 to the first outlet port 182. A seventh fluid channel 166 extends from the fifth inlet port 144 to the second outlet port 188. An eighth fluid channel 168 extends from the mixing well exit port 96 to a passive valve assembly 220 (described below). A ninth fluid channel 170 extends from a passive valve cavity of the passive valve assembly 220 to a capture compartment 100. A tenth fluid channel 172 extends from an active valve assembly 204 to an active valve assembly 219. An eleventh fluid channel 174 extends from the active valve assembly 219 to a waste chamber 102. A twelfth fluid channel 176 extends from the sixth inlet port 146 to the capture compartment 100. A thirteenth fluid channel 178 extends from the capture compartment 100 to the active valve assembly 204. A fourteenth fluid channel 180 extends from the active valve assembly 204 to the third outlet 190.

It should be noted here that the designation of the various fluid channels as the first, second, third, fourth, fifth, etc. fluid channels is merely to provide a convenient means for distinguishing one port from another and is not meant to be limiting, such as, for example, by specifying a particular order or sequence in which the fluid channels may be used or a particular direction in which fluids flow through the channels.

In various embodiments, the sample preparation module 70 further includes a passive valve assembly 220 adjacent the mixing well 90. In one embodiment, the passive valve assembly 220 is configured such that the passive valve assembly 220 is closed if pressure within the mixing well 90 is below a threshold pressure and thus fluid within the mixing well 90 is retained. On the other hand, if pressure is allowed to increase within the mixing well 90, at a sufficient pressure level, above the threshold pressure, the passive valve assembly 220 will be opened, thereby permitting fluid within the mixing well to escape via the exit port 96 and the eighth fluid channel 168 connecting the mixing well exit port 96 to the passive valve assembly 220.

Figure 10:
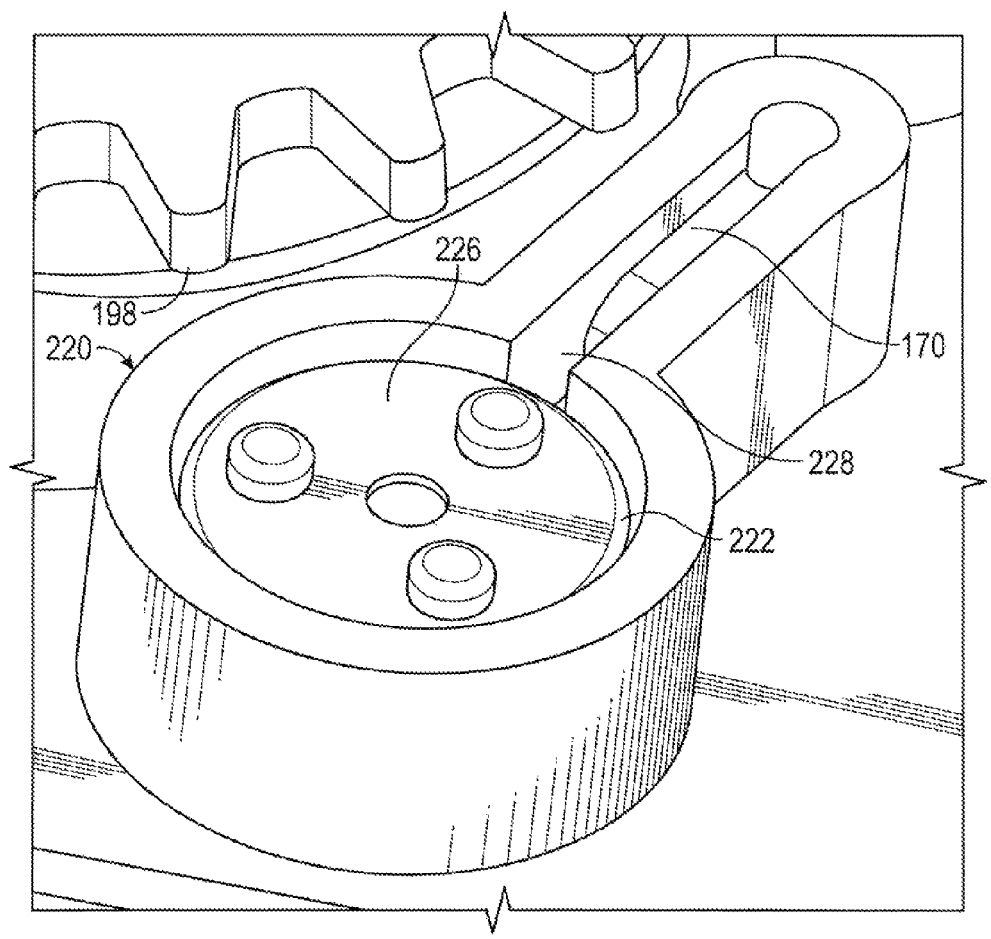
FIG. 10 is a perspective detail of a passive valve of the multiplex cartridge.
Figure 11:
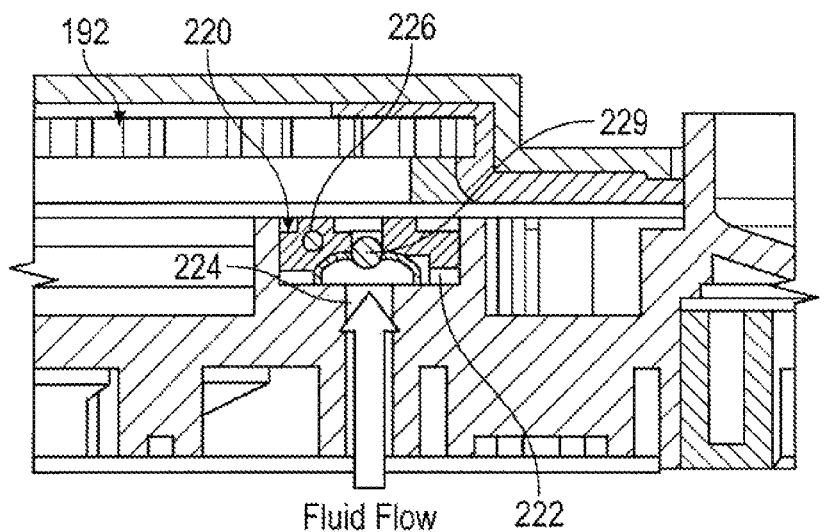
FIG. 11 is a perspective, cross sectional view of the passive valve along the line 11-11 in FIG. 2.
Figure 12:
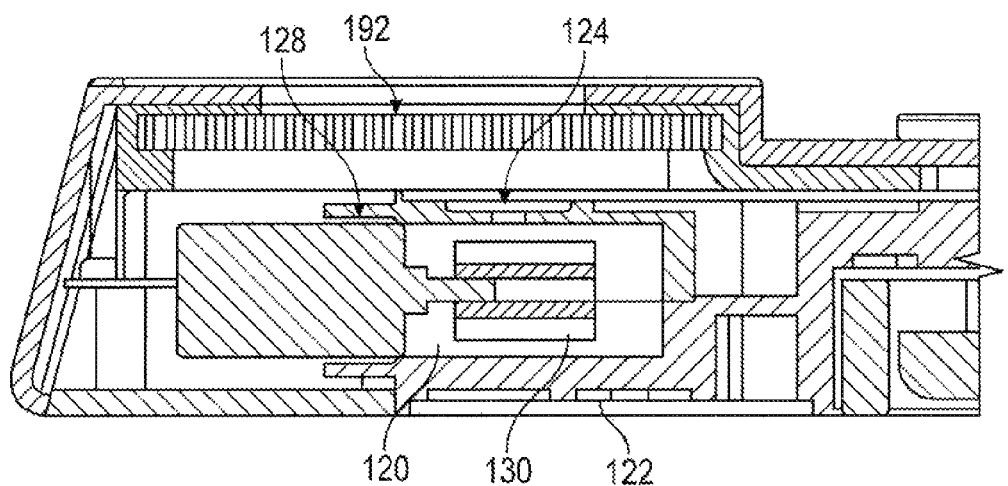
FIG. 12 is a perspective, cross sectional view of a lysis chamber and bead mixer along the line 12-12 in FIG. 2.

Details of the passive valve assembly 220 are shown in FIGS. 10 and 11. The valve assembly 220 comprises a valve cavity 222 formed in the substrate 72 and an inlet 224 formed in the substrate 72 and extending upwardly into the valve cavity 222. A valve 229, which may comprise a Belleville valve, is disposed within the valve cavity 222 over the inlet 224. A retainer 226 is disposed over the valve 229. An outlet 228 extends radially from the valve cavity 222.

In an unpressurized condition, the valve 229 and the retainer 226 are at rest at the bottom of the valve cavity 222, with the valve 229 covering the inlet 224. The retainer 226 may be biased in a down position, e.g., by a suitable spring or the like. Accordingly, fluid flowing from the inlet 224 is not able to pass into and through the valve cavity 222, and thus, fluid is not able to escape the mixing well 90. On the other hand, if fluid in the inlet 224 is sufficiently pressurized to overcome any force (e.g., spring bias) holding the retainer 226 in a down position (e.g., about 3 to 5 psi), the valve 229 and the retainer 226 will be lifted off the bottom of the valve cavity 222 thereby opening the inlet 224 and allowing fluid to flow into the valve cavity 222 and out of the outlet 228.

The sample preparation module 70 may further include a pump port 104 by which an external source of pressure may be coupled to the sample preparation module 70. The pump port 104 is connected, via a pressure conduit 106 to the sample well 78 so that pressure applied at the pump port 104 will pressurize the sample well 78 to motivate the contents of the sample well 78 out of the well.

The sample preparation module 70 may further include a passive valve port 108 is connected, via a valve conduit 110 to the pressure snorkel 94 of the mixing well 90. If the passive valve port 108 is open, pressure will not build up within the mixing well 90, and the passive valve assembly 220 will remain closed. If the passive valve port 108 is closed, pressure will build up within the mixing well 90 and the passive valve assembly 220 will open so that the contents of the mixing well 90 can flow from the well.

Some organisms, such as viruses and many bacteria, can be lysed chemically by the addition of a lysis buffer with or without elevated temperature or proteolytic enzymes. Some organisms are difficult to lyse by chemical and/or enzymatic methods and require mechanical disruption or shearing of the cell membranes. As such, an optional component of the multiplex cartridge 10 is an impeller component, wherein the impeller is activated to grind or break up solid components such that individual cells are more accessible to lysis buffer and so that more target analytes are released. The impeller imparts turbulent action to the fluid in which lysis beads are contained. The primary lysis action is due to bead collisions with target organisms, which are thereby lysed, breaking them open and exposing the target nucleic acids. The presence of the lysis buffer inhibits the DNases or RNases which may destroy the RNA or DNA targets once the cells are disrupted. In various embodiments, the impeller is like a paddle wheel that rotates very fast.

Thus, in various embodiments, the sample preparation module 70 further includes a lysis chamber 120 with a driven agitator, such as a motorized bead mixer mechanism, disposed therein. The driven agitator is disposed at least partially within the lysis chamber 120 and is constructed and arranged to agitate fluid flowing through the processing chamber. The fluid flowing through the lysis chamber may comprise a mixture of sample material, lysis buffer, and lysis beads. The lysis beads may comprise silica (ceramic) beads (of, e.g., 100 μm diameter) that are dispensed into the lysis chamber 120 during assembly of the multiplex cartridge 10. The bead mixer comprises a motor 128 with an impeller 130 mounted on an output shaft of the motor (see FIG. 2). Fluid flows into the lysis chamber 120 through an inlet 122 and flows out of the lysis chamber 120 through an outlet 124. A mesh filter may be provided in front of the inlet 122 and/or the outlet 124. The mesh filter(s) have a pore size configured to retain the lysis beads within the lysis chamber 120 while allowing sample fluid to flow into and out of the lysis chamber 120. In operation, the motor 128 rotates the impeller 130 at a high rate of rotation (e.g., about 5,000 to about 100,000 rpm, preferably about 10,000 to about 50,000 rpm, more preferably about 20,000 to about 30,000 rpm), so that fluid within the lysis chamber 120, which may include sample material and lysis beads, is vigorously agitated by the rotating impellor, thereby assisting the lysis beads in disrupting the molecular structure of the sample material. Thus, the sample mixture flowing out of the lysis chamber 120 is more completely lysed than it would be without the bead mixer.

A suitable motor 128 of the bead mixer includes Feiying, Model FY0610-Q-04170Y from Jinlong Machinery. The motor may be powered by a temporary connection of the multiplex cartridge 10 to an external power source of an instrument in which the cartridge 10 is being processed. Control of the motor 128 may be implemented by means of logic elements provided externally and/or internally of the cartridge 10. In one embodiment, a mixer printed circuit board ("PCB") is provided within the lower shroud 30 that controls operation of the bead mixer motor 128. The mixer motor 128 is ideally only operated when fluid is flowing through the lysis chamber 120. Fluid flowing into the lysis chamber 120 can be detected by an optical sensor through the inlet optical port 14 formed in the upper shroud 12 (see FIG. 2), which is aligned with an inlet optical sensing chamber 154 (see, e.g., FIG. 15), so that the bead mixer motor 128 can be activated, for example, upon detection of the forward end of a fluid stream flowing through the inlet optical sensing chamber 154 toward the lysis chamber 120. Similarly, fluid flowing out of the lysis chamber 120 can be detected by an optical sensor through the outlet optical port 16 (see FIG. 2), which is aligned with the outlet optical sensing chamber 158 (see FIG. 15), so that the bead mixer motor 128 can be deactivated, for example, upon detection of the trailing end of a fluid stream flowing through the outlet optical sensing chamber 158.

The sample preparation module 70 further includes two active valve assemblies 204, 219. The valve assembly 204 is known as the sample valve assembly and is positioned at the junction of the tenth fluid channel 172, the thirteenth fluid channel 178, and the fourteenth fluid channel 180 and controls flow from the thirteenth fluid channel 178 into the fourteenth fluid channel 180. Valve assembly 219 is known as the waste valve assembly and is positioned at the junction of the tenth fluid channel 172 and the eleventh fluid channel 174 and controls flow from the tenth fluid channel 172 to the eleventh fluid channel 174 and the waste chamber 102.

Figure 13:
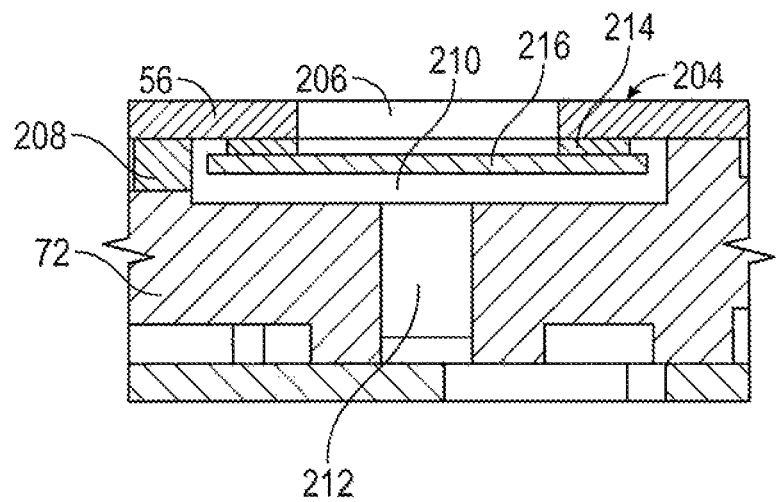
FIG. 13 is a perspective, cross sectional view of an active valve assembly along the line 13-13 in FIG. 2.
Figure 14:
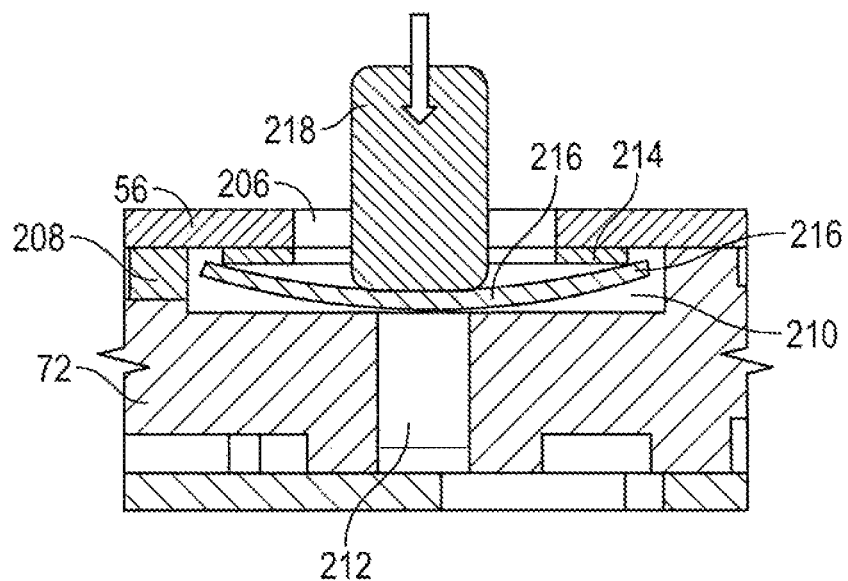
FIG. 14 is a perspective, cross sectional view of the active valve, wherein the valve is actuated by an external valve actuator.

Details of an active valve assembly, e.g., the valve assembly 204, are shown in FIGS. 13 and 14. The valve assembly 204 comprises a valve cavity 210 formed in the substrate 72. An inlet conduit 208 leads into the valve cavity 210, and an outlet channel 212 extends out of the cavity 210. An access opening 206 is formed in the top seal 56 disposed atop the substrate 72. A flexible valve membrane 216 is secured to an underside of the top seal 56 beneath the access opening 206 by means of an adhesive 214 surrounding the access opening 206. In the undeflected, or unactuated, position, as shown in FIG. 13, fluid may flow into the valve cavity 210 through the inlet 208 and flow out of the valve cavity 210 through the outlet 212. Accordingly, fluid flow through the valve assembly 204 is unimpeded. As shown in FIG. 14, when an external valve actuator 218 presses down through the access opening 206 to deflect the valve membrane 216 over the outlet 212, fluid flow through the valve assembly 204 is blocked. The valve actuator 218 may comprise an actuator post 26 of the actuator tab 20 formed in the upper shroud 12 (see FIG. 1). Specifically, valve actuator tab 18 is aligned with the active valve assembly 204, and valve actuator tab 20 is aligned with the active valve assembly 219.

In various embodiments, the sample preparation module 70 further includes a waste chamber 102 (or more than one waste chamber) configured to receive and container excess or used fluids.

Reaction Module—Top Plate

Figure 24:
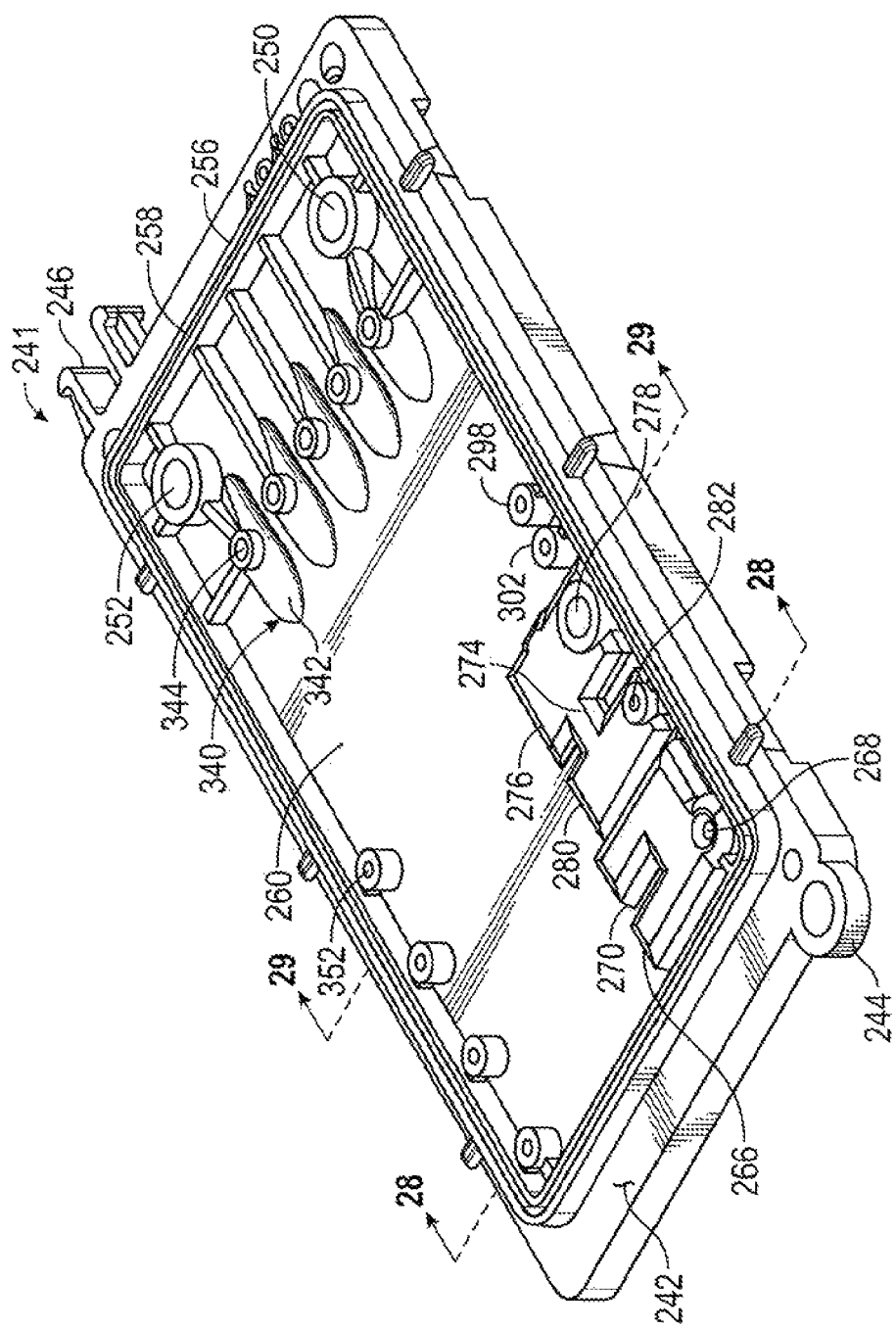
FIG. 24 is a top perspective view of a top plate of a reaction module of the multiplex cartridge.
Figure 25:
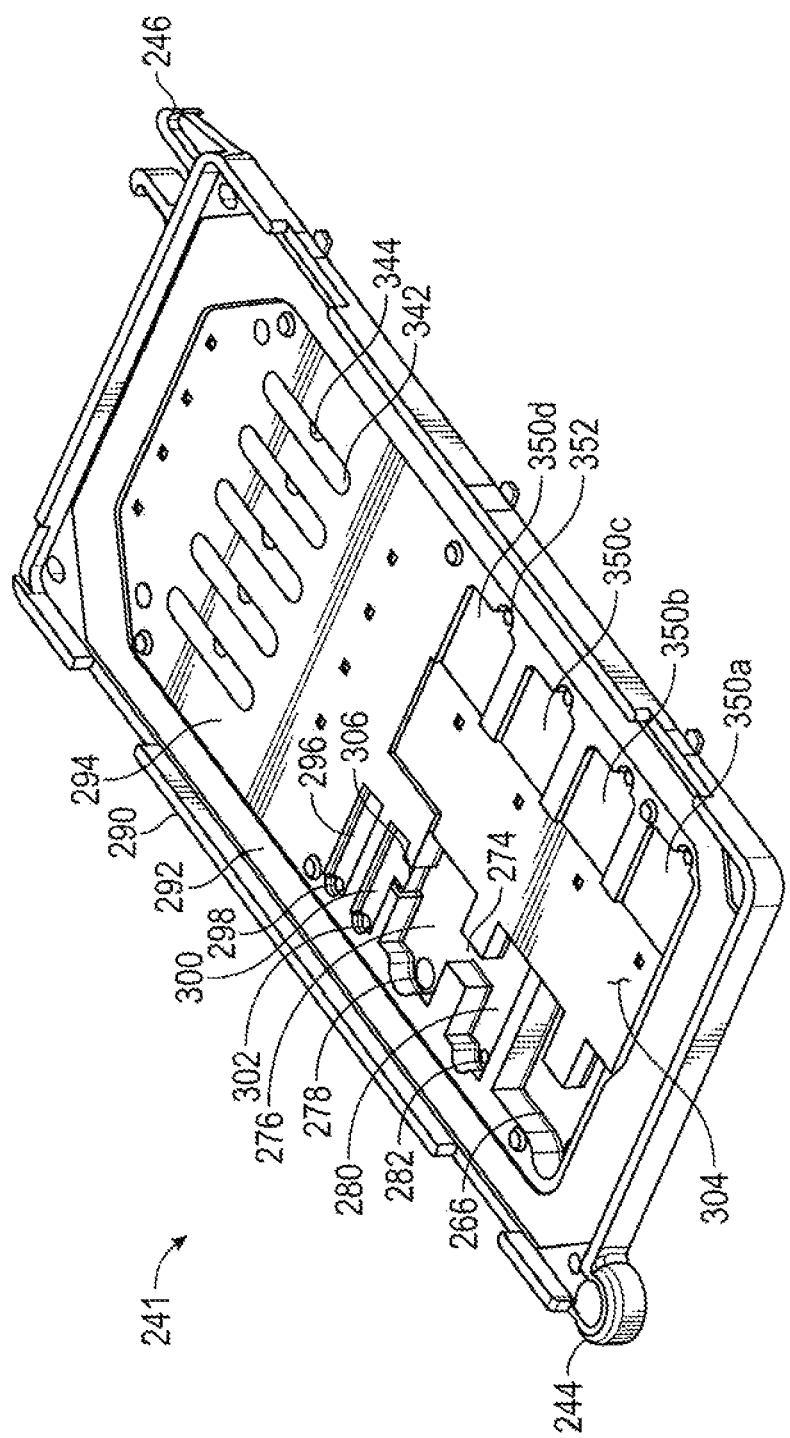
FIG. 25 is a bottom perspective view of the top plate.
Figure 26:
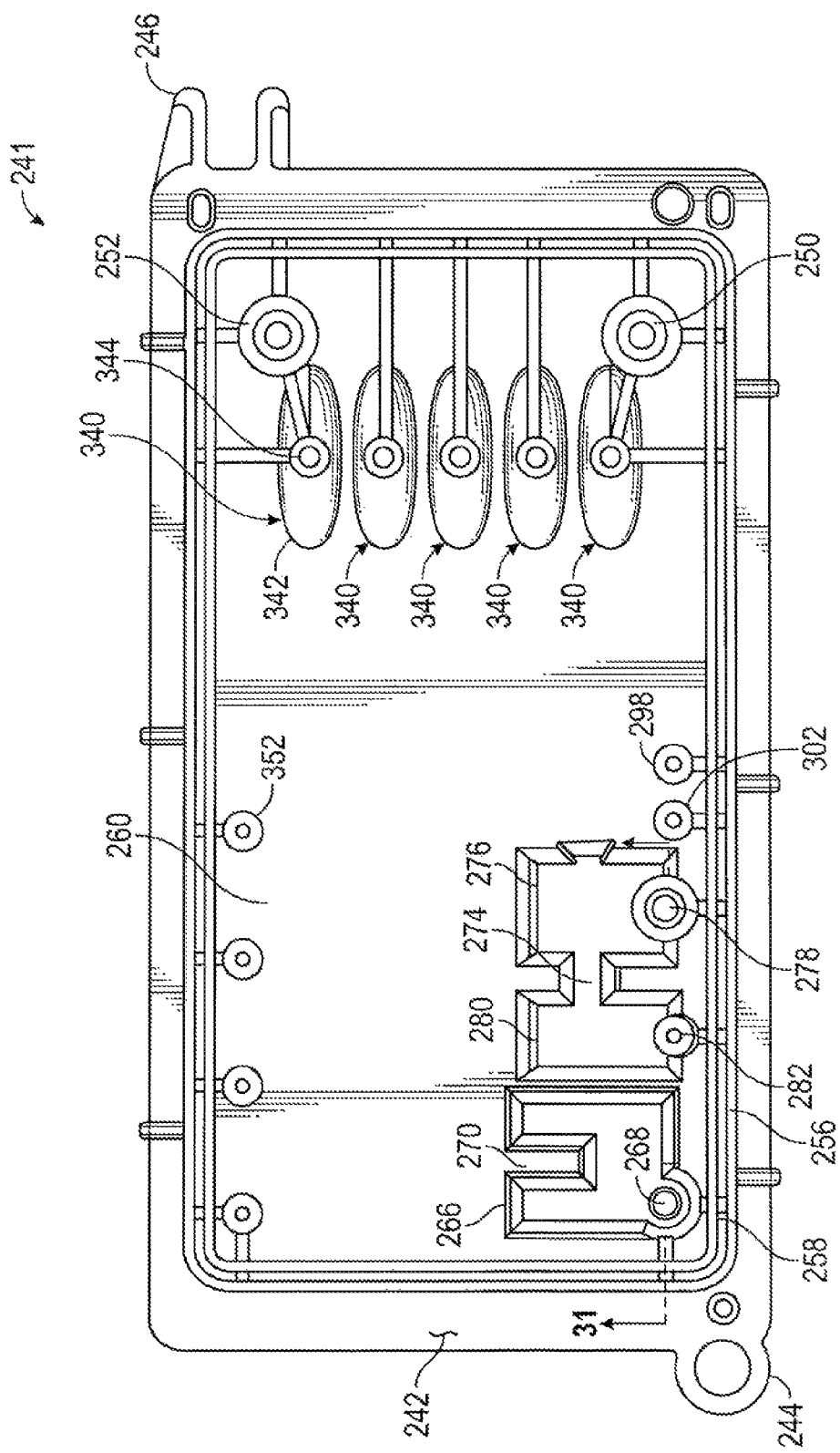
FIG. 26 is a top plan view of the top plate.

Details of the reaction module 240, and the top plate 241 in particular, are shown in FIGS. 24-31. Referring to FIGS. 24 and 26, which show a top perspective view and a top plan view, respectively, of the top plate 241, the top plate 241 includes an upper perimeter wall 256 projecting above a top surface 242 of the top plate 241 and at least partially circumscribing the top surface 240 at a location offset inwardly from the outer edges of the top plate 241. The upper perimeter wall 256 has a continuous open channel or groove 258 formed along its top edge which provides a seat for the adhesive gasket 232 securing the reaction module 240 to the sample preparation module 70. See FIG. 4. The upper perimeter wall 256 forms a recessed area 260 surrounded by the upper perimeter wall 256 on the top surface 242. See also FIGS. 28 and 29.

Top plate 241 can take on a number of configurations and can be made of a variety of materials. Suitable materials include, but are not limited to, fiberglass, TEFLON®, ceramics, glass, silicon, mica, plastic (including acrylics, polystyrene and copolymers of styrene and other materials, polypropylene, polyethylene, polybutylene, polycarbonate, polyurethanes, and derivatives thereof, etc.), etc. A particularly preferred top plate material is polycarbonate.

An alignment fork 246 extends from one end of the top plate 241, and an alignment loop 244 extends from an opposite end of the top plate 241. The alignment fork 246 and alignment loop 244 are configured to receive alignment pins in an instrument for processing the multiplex cartridge 10 to ensure proper alignment of the cartridge 10, as described in more detail below.

The top plate 241 further includes a sample compartment 266 with an inlet port 268 that is in fluid communication with the third outlet port 190 of the sample preparation module 70.

The top plate 241 further includes a rehydration (elution) buffer compartment 276 having an inlet port 278 that is in fluid communication with the second outlet port 188 of the sample preparation module 70. A detection buffer compartment 280 contains an initially-dried detection buffer (applied to a portion of the top plate 241 forming the detection buffer compartment 280 or a portion of the fluidic processing panel 354 covering the detection buffer compartment 280) that is reconstituted with an amount of the reconstitution buffer dispensed into the rehydration buffer compartment 276 and transferred to the detection buffer compartment 280. In one embodiment, the detection buffer compartment 280 has a capacity of 120-160 µl. In various embodiments, top plate 241 includes a connecting passage 274 between the detection buffer compartment 280 and the rehydration buffer compartment 276. The detection buffer compartment 280 may further include a port 282 for injecting a buffer into the compartment 280 during a manufacturing process and/or for venting the compartment 280.

Figure 27:
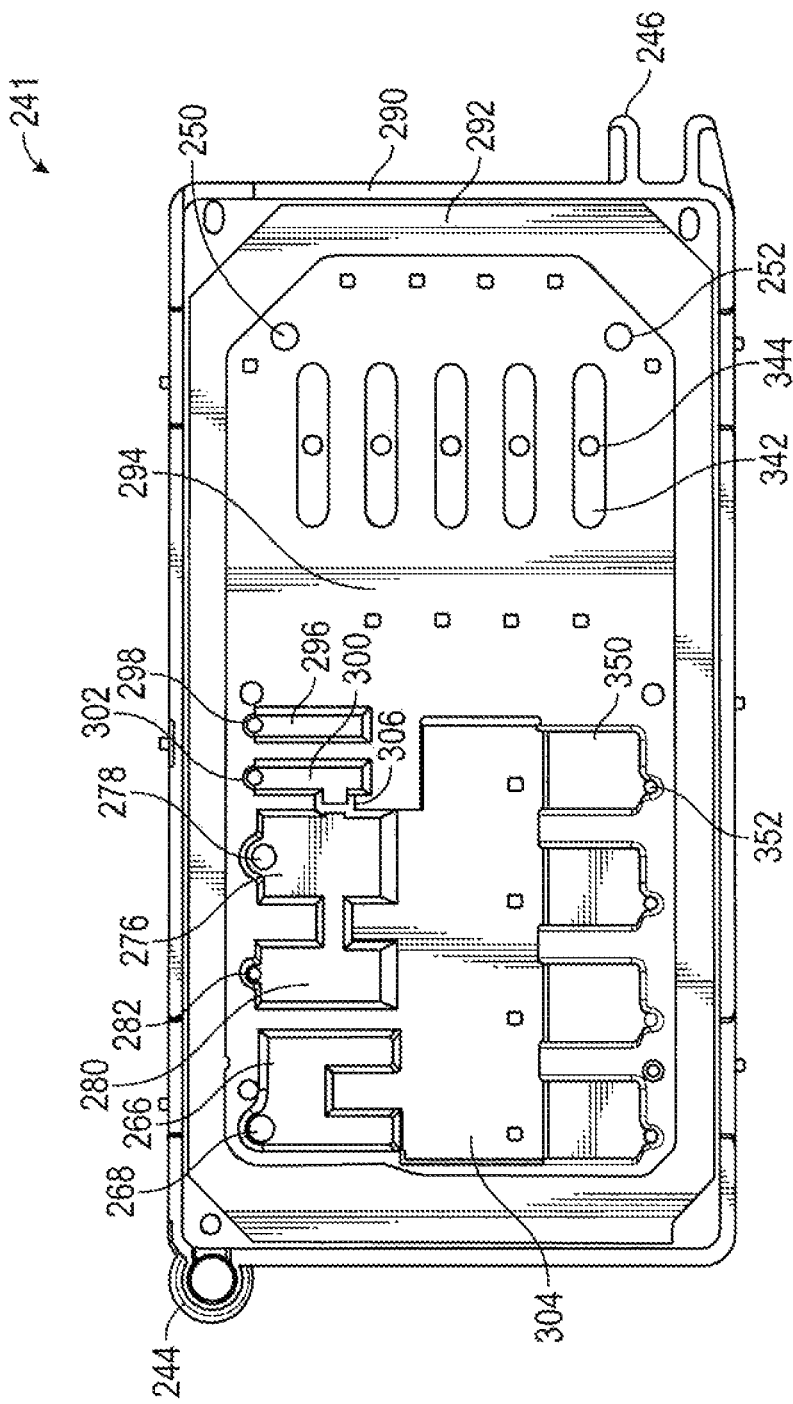
FIG. 27 is a bottom plan view of the top plate.
Figure 28:
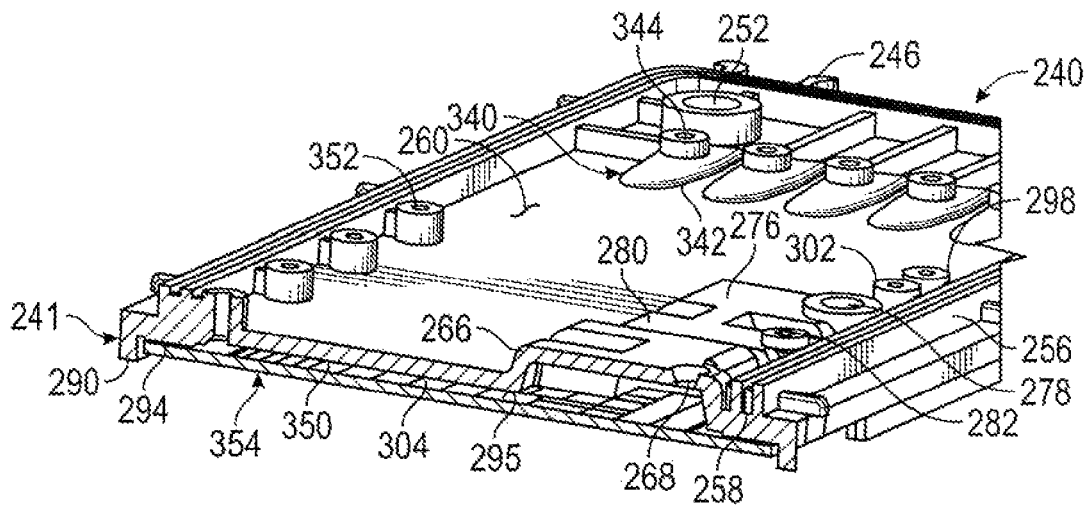
FIG. 28 is perspective, cross sectional view of the reaction module along the line 28-28 in FIG. 24.
Figure 29:
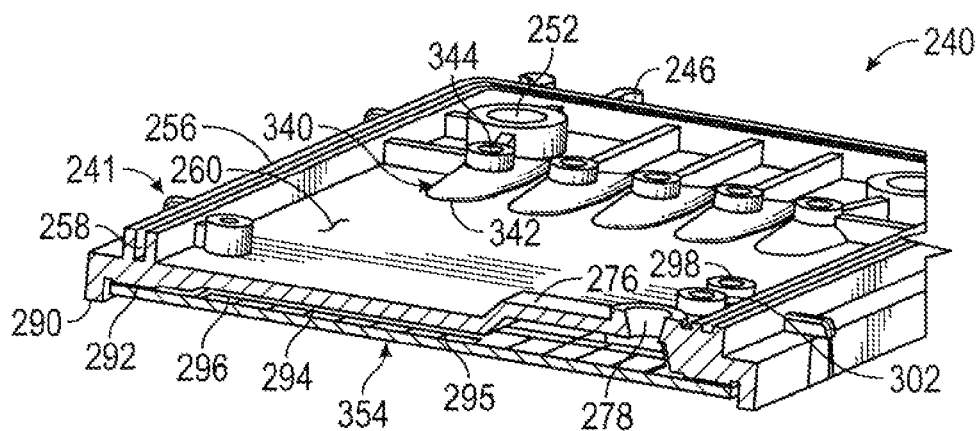
FIG. 29 perspective, cross sectional view of the reaction module along the line 29-29 in FIG. 24.

FIGS. 25 and 27 show a bottom perspective view and a bottom plan view, respectively, of the top plate 241. Referring to FIGS. 25 and 27, in addition to FIGS. 24 and 26, the top plate 241 further includes a buffer compartment 296, which, in one embodiment, contains a PCR buffer/enzyme in a dried form (applied to a portion of the top plate 241 forming the buffer compartment 296 or to a portion of the fluidic processing panel 354 (see FIGS. 4 and 58) covering the buffer compartment 296), to be later reconstituted (rehydrated) by an amount of rehydration buffer from the rehydration buffer compartment 276. In one embodiment, the buffer compartment 296 has a capacity of about 20 µl. A port 298 is provided for injecting the PCR buffer/enzyme into the compartment during the manufacturing process and/or for venting the buffer compartment 296.

The top plate 241 further includes a second buffer compartment 300 which may contain an exonuclease reagent in a dried form (applied to a portion of the top plate 241 forming the second buffer compartment 300 or to a portion of the fluidic processing panel 354 covering the second buffer compartment 300), to be later reconstituted by an amount of rehydration buffer from the rehydration buffer compartment 276. In one embodiment, the second buffer compartment 300 has a capacity of about 20 µl. A port 302 may be provided for injecting buffer into the second buffer compartment 300 during a manufacturing process and/or for venting the compartment 300. A weir 306 may be provided between the rehydration buffer compartment 276 and the second buffer compartment 300 to permit fluid flow from the rehydration buffer compartment 276 into the compartment 300.

The top plate 241 further includes a lower perimeter wall 290 circumscribing the bottom of the top plate 241. The lower perimeter wall 290 defines a recess surrounded by the perimeter wall 290 configured to receive a panel, such as the fluidic processing panel 354, to enclose the lower half of the top plate 241. A raised panel support 290 surrounds the outer periphery of the lower surface of the top plate 241 just inside the perimeter wall 290. Area 294 inside the panel support 292 is slightly recessed with respect to the panel support 292, so that a panel inserted within the perimeter wall 290 is supported on the panel support surface 292, and the recess 294 defines a gap 295 (see FIGS. 28, 29) between the panel and the top plate 241.

The top plate 241 may further include fluid inlet ports 250, 252, at least one of which is in fluid communication with the first outlet port 182 of the sample preparation module 70. The inlet ports 250, 252 provide a fluid communication with the gap 295 between the bottom surface of the reaction top plate 241, e.g., at the area 294, and the fluidic processing panel 354 enclosing the bottom surface of the top plate 241.

The top plate 241 further includes detection compartments 350a, 350b, 350c, and 350d, each with an inlet port or venting port 352. The illustrated embodiment includes four detection compartments 350a-d, though one can easily envision alternative configurations of the top plate 241 comprising a smaller or larger number of the detection compartments 350.

Area 304 on the lower surface comprises a processing area that is slightly recessed relative to the area 294, thereby forming a larger gap between the top plate 241 and a lower panel in the area 304 than in the area 294.

The reaction module 240 may further include one or more bubble traps 340 that are formed in the top plate 241. Each bubble trap 340 includes a bubble capture hood 342 formed in the top plate 241 which slopes upwardly toward a vent opening 344. In one embodiment, rising air bubbles generated by fluid movement beneath the bubble trap are captured in the capture hood 344 and released through the vent opening 344. The capture hood may be shaped as to conform to a fluid movement path beneath or adjacent to the bubble trap. In the illustrated embodiment, five bubble traps 340 having elongated capture hoods 342 are positioned above four fluid movement paths, each located below and between two adjacent bubble traps 340, as will be described in further detail below.

Figure 30:
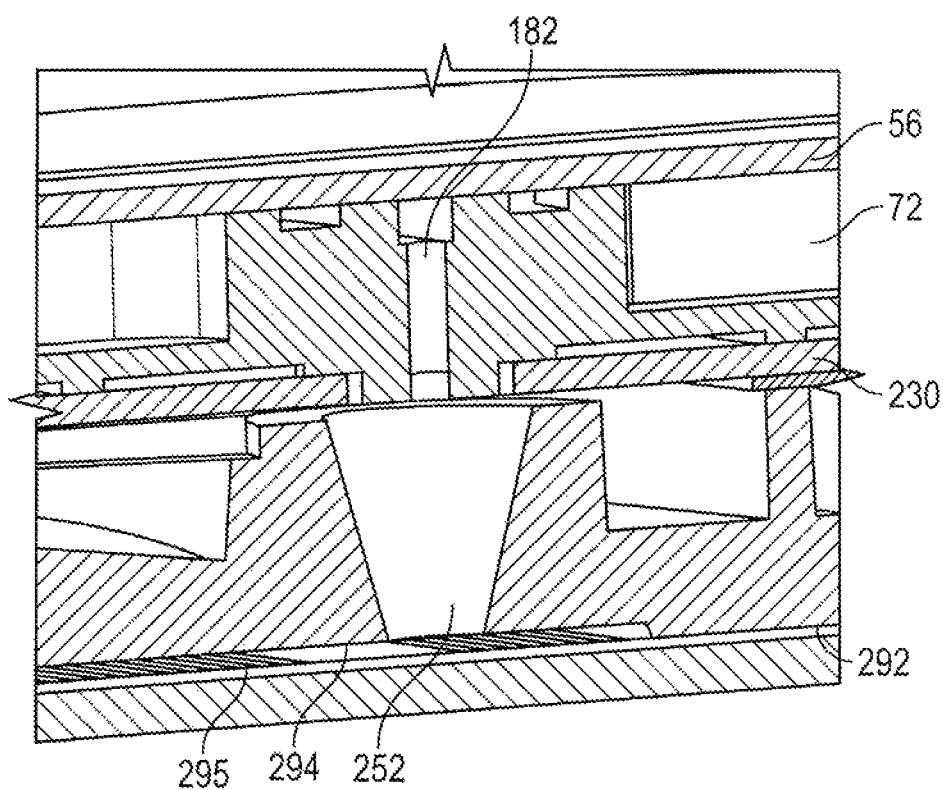
FIG. 30 is a perspective detail of a fluid inlet of the reaction module.

Details of the fluid inlet 252 are shown in FIG. 30. As noted, the fluid inlet 252 may be aligned with first fluid outlet 182 of the sample preparation module 70. The fluid inlet 252 may have an inwardly tapered, frustoconical shape, wherein the size of the outlet 182 above the inlet 252 is narrower than the upper end of the inlet 252. This helps ensure that fluid dispensed through the outlet 182 is captured by the inlet 252.

Figure 31:
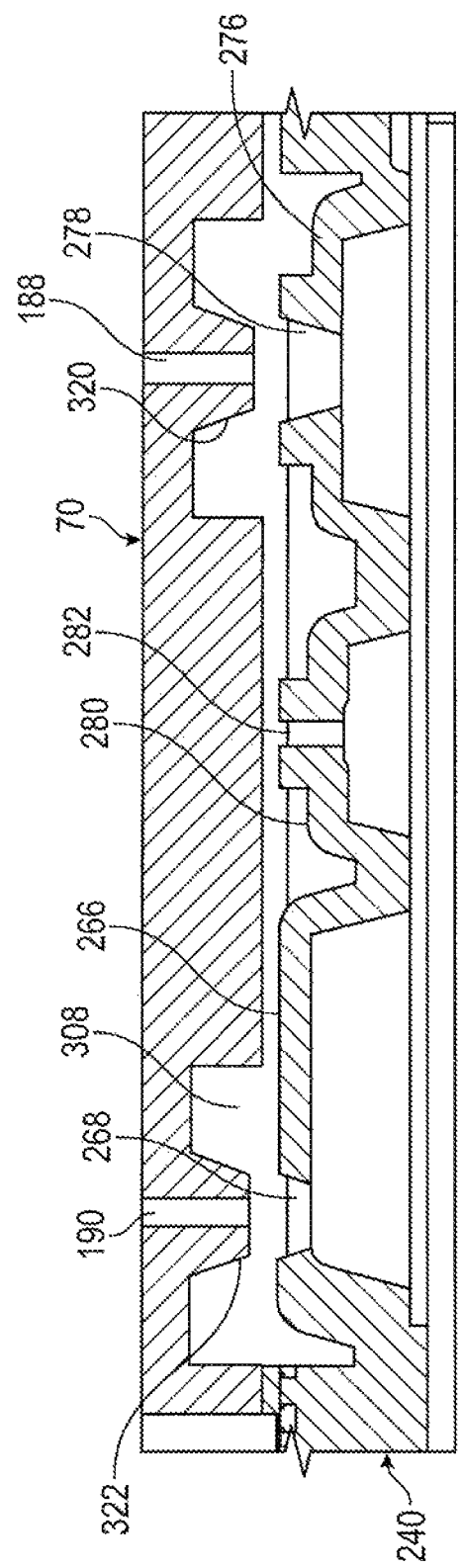
FIG. 31 is a partial cross sectional view along the line 31-31 in FIG. 26.

Details of the sample compartment 266, the rehydration buffer compartment 276, and the detection buffer compartment 280 are shown in FIG. 31. The sample compartment 266 is configured to receive an amount (e.g., 200 µl) of magnetic beads with bound target analyte (e.g., DNA, nucleic acid) from the sample preparation module 270 through the inlet port 268. The inlet port 268 of the sample compartment 266 preferably has a conical shape and is aligned with the third outlet 190 of the sample preparation module 70. In various embodiments, the third outlet 190 passes through a tapered nipple 322 to minimize hanging droplets from the end the outlet 190. The inlet port 268 is also preferably tapered with its widest end at the top to thereby ensure that fluid dispensed through the outlet 190 is captured in the inlet port 268. The outlet 190 and the inlet port 268 are configured such that there is a small gap therebetween. This gap comprises part of an interstitial space 308 between the top of the top plate 241 of the reaction module 240 and the bottom of the sample preparation module 70. This gap provides a trap for collecting any air bubbles contained in fluids within the reaction module 240, especially air bubbles that may be generated when dispensing fluid from the outlet 190 into the inlet port 268.

The rehydration buffer compartment 276 is configured to receive an amount (e.g., 200 µl) of a buffer solution that is suitable for rehydration of dried reagents and elution of nucleic acid from beads from the sample preparation module 270 through the inlet port 278. The inlet port 278 of the rehydration buffer compartment 276 is aligned with the second outlet 188 of the sample preparation module 70. Again, the outlet 188 preferably flows through a tapered nipple 320, the end of which is spaced apart from the inlet port 278, which is also tapered. Again, the space between the end of the nipple 320 and the inlet port 278 allows gas bubbles within the fluid flowing between the outlet 188 and the inlet port 278 to escape into the interstitial space 308.

Reaction Module—Fluidic Processing Panel

Figure 58:
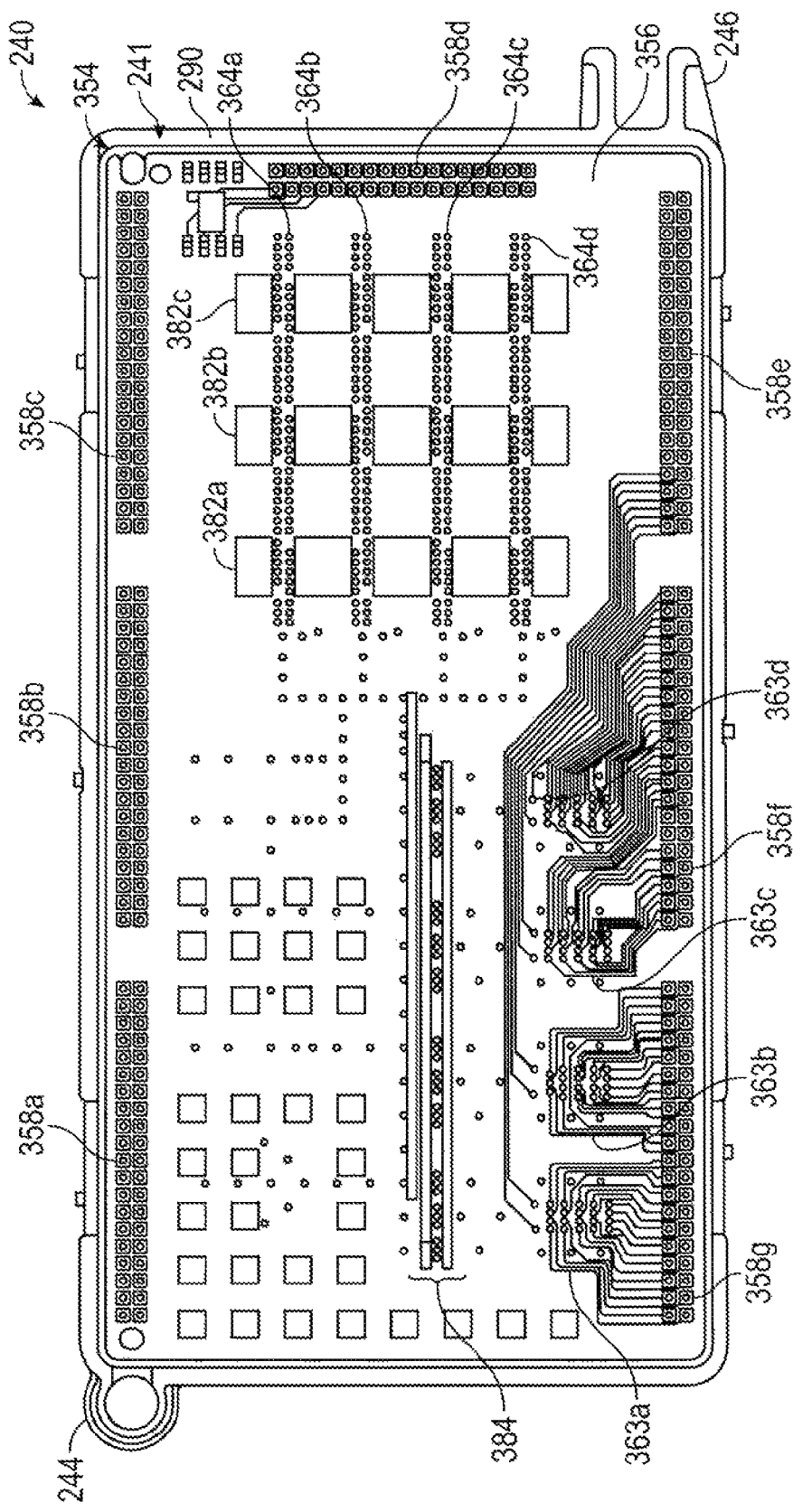
FIG. 58 is a bottom plan view of a fluidic processing panel of the reaction module.
Figure 59:
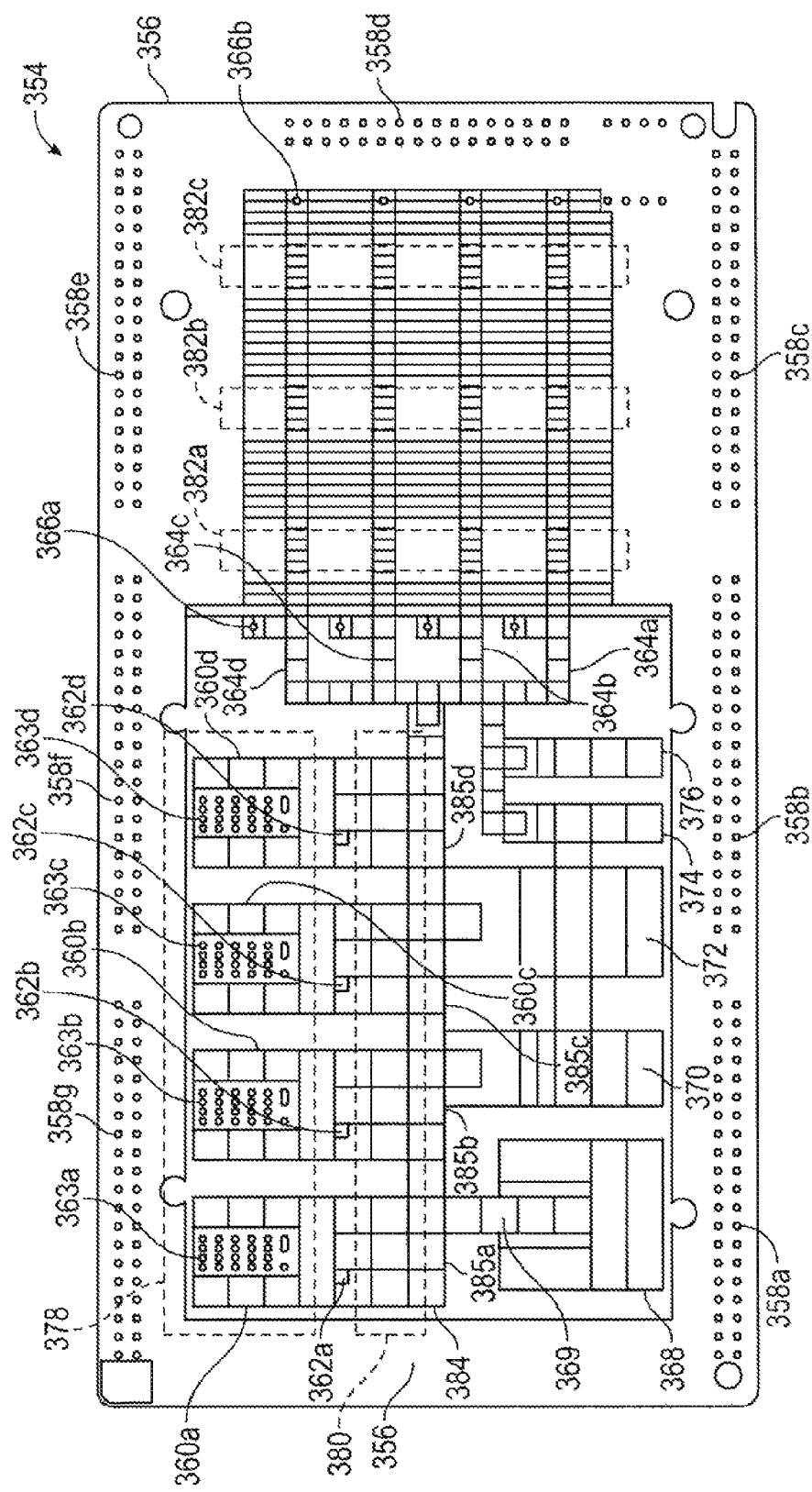
FIG. 59 is a top plan view of the fluidic processing panel.

Referring to FIGS. 58, 59, in various embodiments, the reaction module 240 of the multiplex cartridge 10 includes a fluidic processing panel 354, secured to the bottom of the top plate 241. The fluidic processing panel 354 is surrounded peripherally by the perimeter wall 290 and is support on and secured to the panel support 292, for example by an oil and temperature-resistant adhesive. The fluidic processing panel 354 facilitates a number of functionalities of the multiplex cartridge 10, such as fluid movement and analyte detection. Such fluid movements may include transporting one or more droplets of fluid along fluid transport pathways, mixing fluids by moving one or more droplets in an oscillatory fashion (e.g., linearly back and forth or in a continuous (e.g., circular, oval, rectangular) path), combining fluid droplets that may contain different materials, splitting droplets into two or more smaller droplets, etc.

The fluidic processing panel 354 includes a substrate 356. Suitable substrates include metal surfaces such as gold, electrodes as defined below, glass and modified or functionalized glass, fiberglass, ceramics, mica, plastic (including acrylics, polystyrene and copolymers of styrene and other materials, polypropylene, polyethylene, polybutylene, polyimide, polycarbonate, polyurethanes, TEFLON®, and derivatives thereof, etc.), GETEK® (a blend of polypropylene oxide and fiberglass), etc., polysaccharides, nylon or nitrocellulose, resins, silica or silica-based materials including silicon and modified silicon, carbon, metals, inorganic glasses and a variety of other polymers, with printed circuit board (PCB) materials being particularly preferred.

In various embodiments, the fluidic processing panel 354 may divided into a number of distinct functional areas or processing zones, which can be spatially overlapping or spatially distinct or partially spatially separate and partially spatially distinct.

In various embodiments, fluid reaction processing within the reaction module 240 is at least partially based on microfluidic fluid manipulation using so-called electrowetting techniques to form microdroplets that can be manipulated both spatially and biochemically.

In general, electrowetting is the modification of the wetting properties of a hydrophobic surface (such as PCB) with an applied electric field. In an electrowetting system, the change in the substrate-electrolyte contact angle due to an applied potential difference results in the ability to move the electrolyte on a surface. Essentially, as described in U.S. Pat. No. 6,565,727, the disclosure of which is hereby expressly incorporated by reference, by applying an electric potential to an electrode (or group of electrodes) adjacent to a drop of polar liquid (e.g., one containing a target analyte), the surface on these electrodes becomes more hydrophilic and the drop is pulled by a surface tension gradient to increase the area overlap with the charged electrodes. This causes the drop to spread on the surface, and, by subsequently removing the potential or activating different electrodes, the substrate returns to a hydrophobic state, resulting in the drop moving to a new hydrophilic area on the substrate. In this way, the drops can be physically and discretely moved on the planar surface of the substrate to different processing zones, for processing, handling, and detection. The drops can be moved at varied speeds, split (e.g. a single drop can be split into two or more drops), pulsed and/or mixed (two or more drops merged onto the same location and then either split or moved as one). In addition, electrowetting can instigate mixing within a single droplet. As described in more detail below, drops can also be used to rehydrate dry reagents stored at different locations on the PCB substrate. One typical characteristic of electrowetting is precise manipulation of very small fluid volumes. For example, isolated target nucleic acid can be eluted at a very high concentration in less than 10 µl prior to PCR amplification, compared to 100 µl elution volumes and much lower target analyte concentrations featured in other systems. In addition, electrowetting allows fluid paths to be altered in development and in the product via software, without the need to make any changes to the physical interface (e.g., new valves, fluid paths, etc.).

Exemplary microfluidic systems utilizing electrowetting techniques are described in U.S. Patent Pub. Nos. 2013/0252262, 2013/0233712, 2013/0233425, 2013/0230875, 2013/0225452, 2013/0225450, 2013/0217113, 2013/0217103, 2013/0203606, 2013/0178968, 2013/0178374, 2013/0164742, 2013/0146461, 2013/0130936, 2013/0118901, 2013/0059366, 2013/0018611, 2013/0017544, 2012/0261264, 2012/0165238, 2012/0132528, 2012/0044299, 2012/0018306, 2011/0311980, 2011/0303542, 2011/0209998, 2011/0203930, 2011/0186433, 2011/0180571, 2011/0114490, 2011/0104816, 2011/0104747, 2011/0104725, 2011/0097763, 2011/0091989, 2011/0086377, 2011/0076692, 2010/0323405, 2010/0307917, 2010/0291578, 2010/0282608, 2010/0279374, 2010/0270156, 2010/0236929, 2010/0236928, 2010/0206094, 2010/0194408, 2010/0190263, 2010/0130369, 2010/0120130, 2010/0116640, 2010/0087012, 2010/0068764, 2010/0048410, 2010/0032293, 2010/0025250, 2009/0304944, 2009/0263834, 2009/0155902, 2008/0274513, 2008/0230386, 2007/0275415, 2007/0242105, 2007/0241068, U.S. Pat. Nos. 8,541,176, 8,492,168, 8,481,125, 8,470,606, 8,460,528, 8,454,905, 8,440,392, 8,426,213, 8,394,641, 8,389,297, 8,388,909, 8,364,315, 8,349,276, 8,317,990, 8,313,895, 8,313,698, 8,304,253, 8,268,246, 8,208,146, 8,202,686, 8,137,917, 8,093,062, 8,088,578, 8,048,628, 8,041,463, 8,007,739, 7,998,436, 7,943,030, 7,939,021, 7,919,330, 7,901,947, 7,851,184, 7,822,510, 7,816,121, 7,815,871, 7,763,471, 7,727,723, 7,439,014, 7,255,780, 6,773,566, and 6,565,727, the respective disclosures of which are hereby incorporated by reference.

Thus, in various embodiments, the fluidic processing panel 354 comprises a grid of electrodes which form and define discrete processing zones, including pathways, for fluid droplets as appropriate for the assays or other process(es) being performed in the reaction module 240. In general, a "spot" or "location" or "pad" (sometimes referred to as an "electrowetting pad" or "EWP") is generally depicted in the figures as a rectangle wherein the lines forming the sides of the rectangle represent electrodes, such that a droplet moves along a path in discrete steps, from pad to pad. By manipulating the electrode grid, the droplets can be selectively moved in any of four directions as needed: forward, backward, left, or right, relative to a current position. Thus, in various embodiments the fluidic processing panel 354 includes a grid of etched electrodes forming a network of pads for moving sample droplets from sample preparation through detection of target analytes.

In the illustrated embodiment, the electrodes formed on the substrate 356 of the fluidic processing panel 354 define a number of discrete, functional regions that provide for movement and/or collection of fluid droplets. As shown in FIGS. 26, 27, and 59, these zones include a sample bead zone 368 spatially corresponding to the sample compartment 266 of the top plate 241, a hybridization zone 370 spatially corresponding to the detection buffer compartment 280 of the top plate 241, a rehydration buffer zone 372 spatially corresponding to the rehydration (elution) buffer compartment 276 of the top plate 241, an exonuclease reagent zone 374 spatially corresponding to the second buffer compartment 300 of the top plate 241, and a PCR reagent zone 376 spatially corresponding to the buffer compartment 296 of the top plate 241. Other zones defined on the fluidic processing panel 354 include electrosensor zones 360a, 360b, 360c, and 360d corresponding spatially to detection compartments 350a, 350b, 350c, and 350d, respectively, and which further include electrosensor arrays 363a, 363b, 363c, and 363d, respectively. Still other pathways defined on the fluidic processing panel 354 include thermocycling, or PCR, pathways 364a, 364b, 364c, and 364d, each being located spatially below and between two adjacent bubble traps 340 of the top plate 241.

Electrodes of the fluidic processing panel 354 may further define an exonuclease zone 384.

Electrodes of the fluidic processing panel 354 may further define detection mixing zones, which, in the illustrated embodiment comprise four groups of nine electrode pads indicated by reference numbers 385a, 385b, 385c, and 385d.

The fluidic processing panel may further include a number of connector pad arrays configured to contact and make electrical connections with connector pins (e.g., pogo pins) located within the processing instrument, as will be described in further detail below. The illustrated embodiment includes seven connector pad arrays: 358a, 358b, 358c, 358d, 358e, 358f, and 358g.

As will be appreciated by those in the art, there are a wide number of electrode grid configurations that can be employed in the multiplex cartridge 10, including, without limitation, configurations described herein. Exemplary electrowetting electrode configurations for different utilities are shown in previously-incorporated U.S. Pat. No. 8,541,176.

In general, preferred materials for the fluidic processing panel 354 include printed circuit board materials. In various embodiments, circuit board materials are those that comprise an insulating substrate (e.g., the substrate 356) that is coated with a conducting layer and processed using lithography techniques, particularly photolithography techniques, to form the patterns of electrodes and interconnects (sometimes referred to in the art as interconnections or leads). The insulating substrate is generally, but not always, a polymer. As is known in the art, one or a plurality of layers may be used, to make either "two dimensional" boards (e.g., all electrodes and interconnections in a plane, "edge card connectors") or "three dimensional" boards (wherein the electrodes are on one surface and the interconnects may go through the board to the other side or wherein electrodes are on a plurality of surfaces). Three dimensional systems frequently rely on the use of drilling or etching to form holes, or vias, through the substrate, followed by electroplating with a metal such as copper, such that the "through board" interconnections are made. Circuit board materials are often provided with a foil already attached to the substrate, such as a copper foil, with additional copper added as needed (for example for interconnections), for example by electroplating. The copper surface may then need to be roughened, for example through etching, to allow attachment of the adhesion layer.

In one embodiment, electrical connections from both the electrowetting electrode grids and detection electrodes, i.e., the connector pad arrays 360a-g, extend through the panel to produce a so-called land grid array that can interface to a pogo pin or like connector to make connections from the chip to a processing instrument. In various embodiments, the surface of the fluidic processing panel 354 (e.g., the PCB with the electrode grids) is coated with a film of a substance to facilitate the electrowetting mechanism and clean transport from pad to pad. In various embodiments, the surface is coated with a polyimide film, such as KAPTON® from DuPont (e.g., black or yellow KAPTON®), which forms a dielectric layer. The surface properties of the dielectric layer are important to facilitate electrowetting and to attenuate the voltage being used in order to prevent electrolysis in the aqueous droplet. In addition, the Kapton® or similar surface, such as a solder mask, must be coated with a hydrophobic coating, such as Paralyene, TEFLON® (polytetrafluoroethylene), CYTOP® fluoropolymers, to name a few, to render the surface hydrophobic, which is required for electrowetting to function.

As will be appreciated by those in the art, the form of the reagent provided in the reaction module 240 will depend on the reagent. Some reagents can be dried or in solid form (for example, when particular buffers are to be used), others can be lyophilized, etc. Particularly useful embodiments utilize dried reagents with added stabilizers, such as salts, sugars, polysaccharides, polymers or proteins such as gelatins, etc. as will be appreciated by those in the art. For example, Biomatrica produces commercial stabilizers for use in the present system.

As will be appreciated by those in the art, if used, the dried reagents can be rehydrated in one of two general ways. Either liquid from the sample preparation module 70 is introduced at the appropriate pad (or zone) or the sample itself serves as an aqueous solvent to put the solid reagents into solution. For example, the appropriate resuspension buffer (which can be water, in some cases) can be added through the top plate 241 from the sample preparation module 70 to a particular pad to rehydrate the reagent(s), and then the reagent droplet can be merged with the sample droplet.

Alternatively, the drops containing the target analyte (for example, in elution buffer used to liberate the target analytes from the capture beads) may be transported to a pad containing the dried reagent(s), which are then suspended in the drop itself. One benefit of this embodiment is that the ultimate volume of a droplet does not increase significantly, as it does when a drop of reagent is merged with a drop of sample. This may be particularly useful in situations where multiple reagent additions are required.

The number, type and quantity of the different reagents will depend on sample, the target analyte and the desired reaction. For example, for nucleic acid target sequences in a standard PCR reaction, when the starting sample is DNA, the on-board dried reagents include RT-PCR buffer, PCR enzyme (e.g. a Taq polymerase), dNTPs, PCR primers, exonuclease, signal probes, signal buffer and detection buffers (with the lysis buffer, the binding buffer, the elution buffer, the (optional) reconstitution buffer(s), and magnetic bead suspension all being contained in the sample preparation module 70, rather than dried on the fluidic processing panel 354). Exemplary embodiments are outlined herein. However, as will be appreciated by those in the art, any number of configurations of dried reagents and liquid reagents in the sample preparation module 70 can be used.

The compartment within the reactor module 240 formed between the fluidic processing panel 354 and top plate 241 described above, is generally filled with a fluid in which the target analyte droplets (usually aqueous solutions) are immiscible, and this immiscible fluid is generally less polar than the solution of the drop. As described in U.S. Pat. No. 8,541,177, the disclosure of which is hereby incorporated by reference, there are two general ways of isolating drops on pads including filling the compartment with an immiscible fluid including immiscible liquids and immiscible gases, or by using the immiscible liquid as a droplet encapsulant, for example giving the droplet a shell of oil by passing the droplet through an air/oil interface.

Particularly suitable immiscible fluids for use in the nucleic acid detection assays described herein include, but are not limited to, silicone oils, mineral oil, fluorosilicone oils; hydrocarbons, including for example, alkanes, such as decane, undecane, dodecane, tridecane, tetradecane, pentadecane, hexadecane; aliphatic and aromatic alkanes such as dodecane, hexadecane, and cyclohexane, hydrocarbon oils, mineral oils, paraffin oils; halogenated oils, such as fluorocarbons and perfluorocarbons (e.g. 3M Fluorinert liquids) as well as mixtures of the above. Examples of suitable gas filler fluids include, without limitation, air, argon, nitrogen, carbon dioxide, oxygen, humidified air, any inert gases. In one embodiment, the primary phase is an aqueous solution, and the secondary phase is air or oil, which is relatively immiscible with water. In another embodiment, the filler fluid includes a gas that fills the space between the plates surrounding the droplets. A preferred filler fluid is low-viscosity oil, such as silicone oil. Other suitable fluids are described in U.S. Patent Application No. 60/736,399, entitled "Filler Fluids for Droplet-Based Microfluidics" filed on Nov. 14, 2005, the entire disclosure of which is incorporated herein by reference. The fluid may be selected to prevent any significant evaporation of the droplets.

As will be understood by those in the art, the movement of droplets from pad to pad, with the addition of reagents as needed, can be used for any number of sample manipulations. In the case of the nucleic acid manipulations for nucleic acid detection, these manipulations generally include the addition of reagents, such as PCR enzymes, PCR buffer, primers, exonuclease, reverse transcriptase (RT) enzymes, RT-PCR buffers, signal buffers, signal probes, etc.

In various embodiments, one or more portions, or sections, of the electrode grid pathway of pads is/are exposed to heat within discrete thermal zones for, e.g., amplification, exonuclease digestion, reverse transcription, target elution, and electrochemical detection. Such thermal zones may comprise a detection region 378, an exonuclease region 380, and a thermocycling (PCR) regions (also referred to as thermal zones) 382a, 382b, 382c.

As will be appreciated by those in the art, some manipulations, such as PCR amplification, require the thermocycling between 2 to 3 different temperatures (primer binding, extension and denaturation), while others require a uniform temperature for best results, e.g., enzymatic processes such as the use of exonuclease and reverse transcriptase, specific temperature(s) for improved elution and/or reagent resuspension, or binding/assay temperatures in the case of the electrochemical detection. Isothermal amplification techniques and other PCR alternatives typically require precise temperature control.

In various embodiments, heat applied to different portions of the fluidic processing panel 354 is generated by thermal components, such as resistive heaters or thermoelectric (Peltier) chips and are found off-cartridge in the processing bays of the instrument into which the cartridge 10 is placed. Examples of such thermal components are described below.

In one embodiment, the sample manipulation zones on the reactor panel 354 can optionally include sensors, for example, to monitor and control thermal zone temperatures, particularly in the case where specific temperatures are desirable. These sensors can include, but are not limited to, thermocouples and resistance temperature detectors (RTDs). Alternatively, such sensors can also be "off cartridge" in the bays.

In various embodiments for detecting nucleic acid targets, the fluidic processing panel 354 comprises one or more thermocycling, or PCR or amplification, pathways 364a, 364b, 364c, and 364d. The fluidic processing panel 354 can contain 1, 2, 3 or more thermocycling pathways of pads. These can be used for individual PCR reactions (e.g., one droplet is moved up and down a pathway or up one pathway and down another, etc.) or for multiplexing (e.g. for multiple pathways, multiple different droplets can be moved up and down each pathway).

As will be appreciated by those in the art, each PCR reaction can additionally be multiplexed. That is, for target-specific amplification, the use of multiple primer sets in a single PCR reaction can be unwieldy, and thus the present invention allows multiple reactions to achieve higher levels of multiplexing. For example, for the evaluation of 21 different target sequences (for example, in screening of respiratory viruses), it may be desirable to run 3 different reactions of seven primer sets; e.g. a first PCR sample droplet in a first pathway picks up a first set of 7 primer pairs (e.g., "Primer Mix A"), a second droplet picks in a second pathway up a second set of 7 primer pairs ("Primer Mix B"), and a third droplet in a third pathway pick up a third set ("Primer Mix C"). In some embodiments, more than one droplet can be processed in each pathway, so each pathway may include more than one primer set. In some embodiments, the primers will be completely different in each set; in others, redundancy and/or internal controls are built into the system by adding the same primer sets to different pathways. The number of multiplexes can vary easily through software without the need to modify any physical components of the system.

In general, amplification reactions suitable for use in the present systems use sets of primers wherein one primer of each set has a blocked end that is impervious to standard exonucleases. That is, it is desirable to remove one strand of the double stranded amplicons that are generated in the PCR reaction, so as to simplify the detection reactions and remove background signal. Thus, by running a first PCR reaction and then adding exonuclease, one strand of the double stranded amplicon is digested, leaving only the detection strand.

The use of multiple heating zones along the thermocycling pathways 364a-d, as generally depicted in FIG. 59, allows the droplets to travel through the appropriate thermal zones. As shown in FIG. 59, the four thermocycling pathways 364a, 364b, 364c, and 364d are shown that extend through the three thermal zones 382a, 382b, and 382c. Thermal elements, e.g., resistive heaters, corresponding to the thermal zones, 382a, 382b, and 382c zones are off-cartridge heater elements and may be maintained at temperatures of 95° C., 72° C., and 64° C. for use in PCR thermocycling. In some embodiments, two different temperature zones (e.g., about 95° C. for denaturation and about 60° C. for annealing and extension) can be used for a two-step PCR reaction. In other embodiments, a three-zone, two-temperature configuration may be employed, wherein a middle heater corresponding to middle thermal zone 382b controls the denaturation temperature (e.g., about 95° C.), and additional heaters corresponding to the thermal zones 382a, 382c on each side of the denaturation heater provide substantially the same annealing and extension temperature (e.g., about 60° C.). In this configuration, two-step amplification cycles can be performed with more than one droplet in each thermocycling pathway 364a-d. For example, two droplets may be positioned in each thermocycling pathway and spaced in such a way that when one droplet is in the denaturation zone 382b, the other is in one of the combined annealing and extension zones 382a or 382b, and vice versa. Each droplet may pick up amplification reagents (e.g., a primer cocktail) at locations, for example, at each end of a thermocycling pathway, such as locations 366a, 366b of each of the thermocycling pathways 364a-d. By shuttling the droplets in tandem back and forth between the denaturation and annealing/extension zones, one can amplify both of them in the same amount of time it would normally take to amplify a single droplet. In a four pathway configuration as shown, this means that eight droplet can be amplified simultaneously instead of three.

In various embodiments, the multiplex cartridge 10 of the present invention relies on the use of electrodes and electrochemical labels for the detection of target analytes. Generally, the surface of electrodes within each electrosensor array 363a, 363b, 363c, and 363d (optionally coated with a self-assembled monolayer (SAM)) has capture ligands which bind the target. A second label ligand, which also binds to the target, is included, such that in the presence of the target, the label ligand is bound near the surface of the electrode, and can be detected electronically.

Thus, the detection zone of the fluidic processing panel 354 comprises one or more separate arrays of detection electrodes 363a, 363b, 363c, and 363d within the respective electrosensor zones 360a, 360b, 360c and 360d. By "electrode" herein is meant a composition, which, when connected to an electronic device, is able to sense a current or charge and convert it to a signal. Alternatively, an electrode can be defined as a composition which can apply a potential to and/or pass electrons to or from species in the solution. Preferred electrodes are known in the art and include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide ($Mo_2O_6$), tungsten oxide ($WO_3$) and ruthenium oxides; and carbon (including glassy carbon electrodes, graphite and carbon paste). Preferred electrodes include gold, silicon, carbon and metal oxide electrodes, with gold being particularly preferred. In a particularly useful embodiment, both the electrowetting electrode grid and the detection electrodes are gold, and are fabricated simultaneously on the fluidic processing panel 354.

The present system finds particular utility in array formats, i.e., wherein there is a matrix of addressable detection electrodes. By "array" herein is meant a plurality of capture ligands on electrodes in an array format; the size of the array will depend on the composition and end use of the array. Arrays containing from about two different capture ligands to about 50 to 100 can be made. In some preferred embodiments, 80 or 100 working detection electrodes are split into four or five distinct zones of twenty, with each zone having up to sixty capture probes (three different capture probes per electrode).

The detection zone of the fluidic processing panel 354 comprises one or more arrays of detection electrodes 363a-d, each of which is within an electrosensor zone 360a-d that is in fluid communication with the droplet pathway of an associated one of the detection mixing zones 385a-d. That is, the droplets containing the amplicons will pick up necessary detection reagent such as label probe (e.g., a signal probe cocktail which may be in dry form, e.g., at locations 362a, 362b, 362c, and 362d) adjacent to the electrosensor detection zones 360a, 360b, 360c, and 360d, respectively, and then be dispersed on the associated electrosensor detection zones 360a, 360b, 360c, and 360d. The signal probe cocktails may be applied to a portion of the top plate 241 forming the locations 362a, 362b, 362c, and 362d or a portion of the fluidic processing panel 354 covering the locations 362a, 362b, 362c, and 362d. In general, each detection zone receives one or more sample droplets which are generally dispersed on the array of electrodes, which is considered one larger "pad".

In one embodiment, the reaction module 240 includes four (4) electrosensor detection zones, and each electrosensor array includes 20 working electrodes (which may include one reference electrode and one auxiliary electrode). Each detection electrode of each electrosensor array 363a-d comprises an independent lead (interconnect) to transmit input and electronic response signals for each electrode of the array such that both input and electronic response signals are independently monitorable for each electrode. That is, each electrode is independently addressable. Moreover, the reaction module is preferably configured for independent control of electrowetting pads surrounding each electrode of each electrosensor array 363a, 363b, 363c, and 363d.

In addition to the components of the fluidic processing panel 354 described above, the fluidic processing panel 354 can also optionally comprise an EPROM, EEPROM or RFID to identify the cartridge, for example containing information about the batch, treatment or contents of the multiplex cartridge 10. This can include information about the identification of the assay, for example.

Instrument Overview

Figure 32:
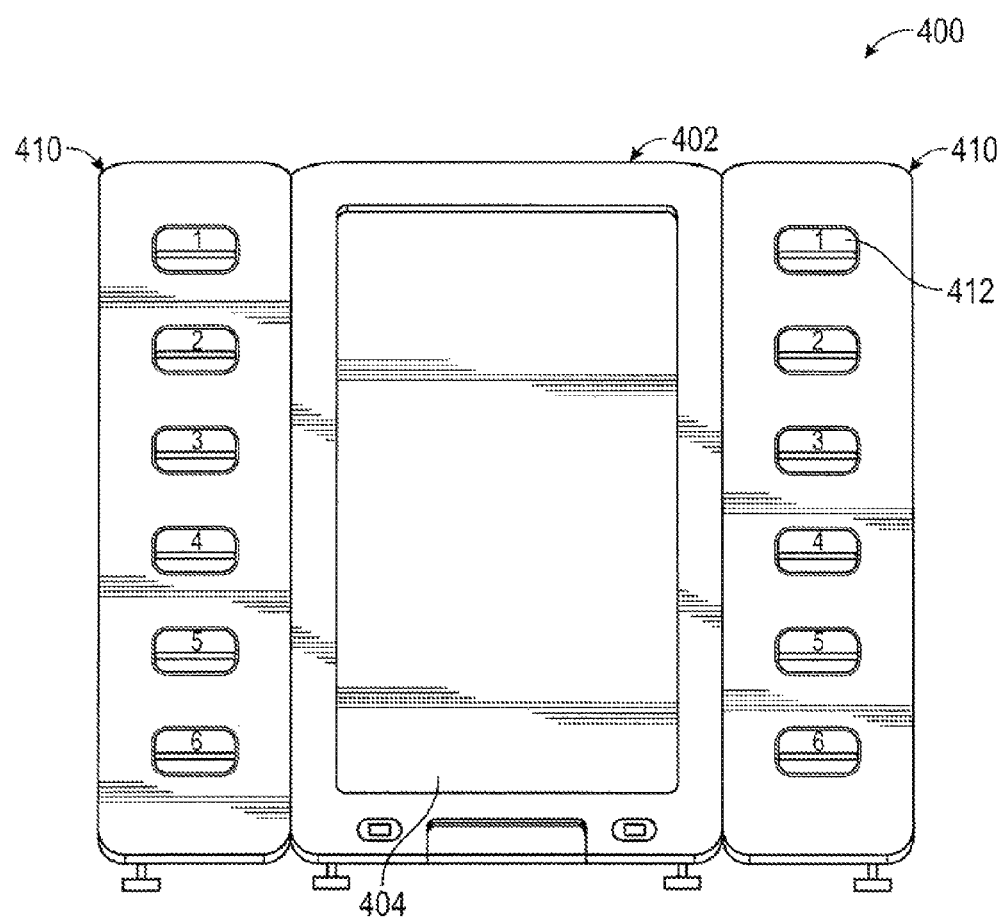
FIG. 32. is a front view of an instrument embodying aspects of the invention.
Figure 33:
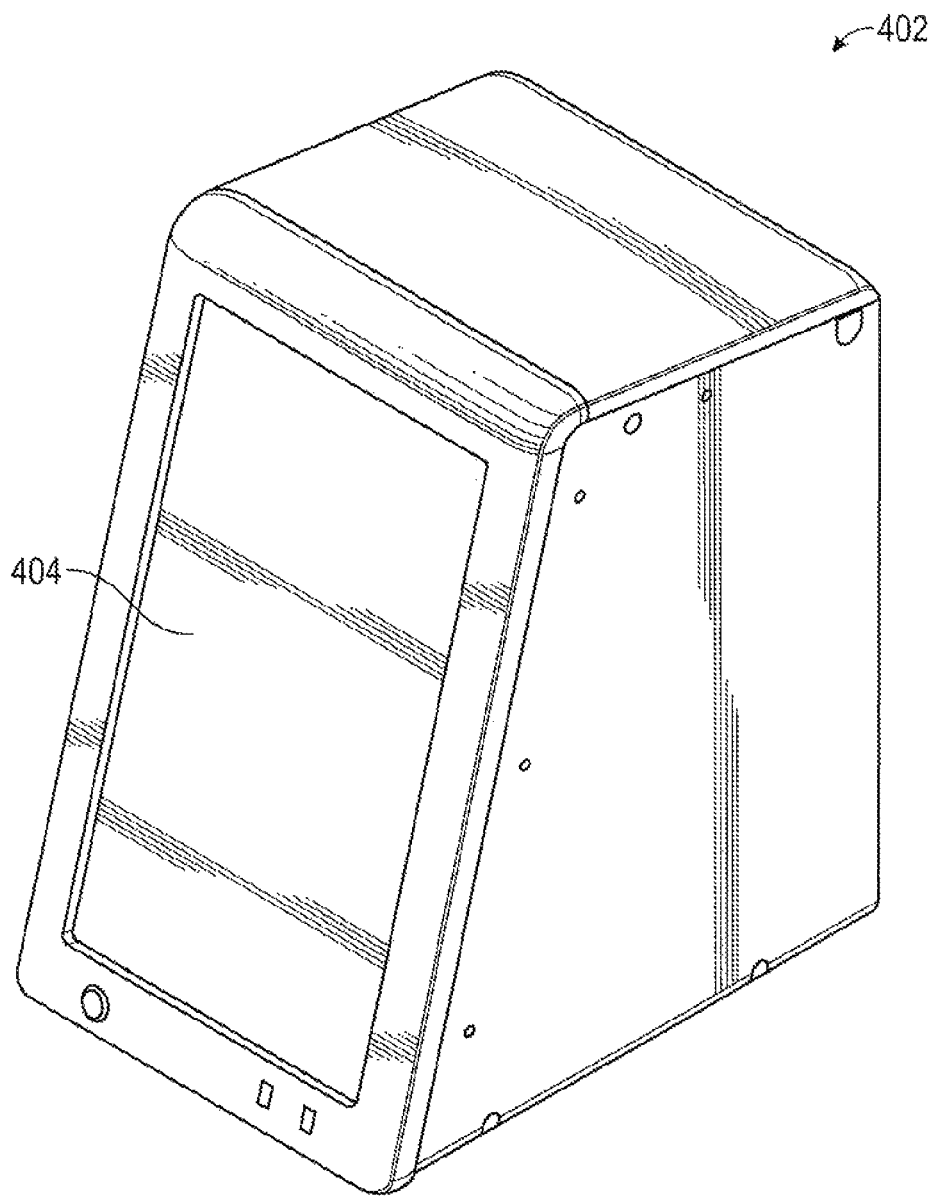
FIG. 33 is a front perspective view of a control console of the instrument.

An instrument configured for processing the multiplex cartridge 10 and embodying aspects of the present invention is indicated by reference number 400 in FIG. 32. The instrument comprises a control console 402, one or more processing modules 410 operatively coupled to the control console 402, processing bays within each processing module 410, each of which is configured to receive a multiplex cartridge and process the multiplex cartridge independently of the other bays, and instrument software (ISW). In various embodiments, the instrument comprises one control console 402 and up to four processing modules 410, with each processing module including six processing bays. Each processing module 410 is operatively coupled to the control console 402, e.g., to exchange power, input and output data, and control signal transmissions with the control console 402 and may be physically connected to the control console 402 as well. Each processing bay with the processing module 410 is configured to accept one multiplex cartridge 10 at a time and to process the cartridge independently of other processing bays processing other multiplex cartridges. In various embodiments, the instrument is configured for each processing bay to complete processing of a cartridge in 60 minutes or less.

The ISW provides the graphical user interface for the user to start runs, receive results, and provide inputs that at least partially control operation of the instrument. In various embodiments, the ISW is configured to run on a Windows® computer with a touchscreen 404 located on the control console 402 providing the primary functionality for user input. In various embodiments, the instrument is configured to provide connectivity to a local area network ("LAN") and a laboratory information system ("LIS"). The instrument may also include a barcode scanner (not shown) that facilitates logging in to the ISW, tracking samples, and positive ID features of the instrument.

The control console 402 of the instrument includes a touchscreen panel 404, a system computer, a power supply, connectivity to external data systems, and connectivity for the processing module(s) and processing bay(s). In various embodiments, a power supply in the control console powers the entire instrument. Cabling from the control console provides power transmission and provides for data flow to and from the processing bays. In various embodiments, the control console also has provision for physically attaching the one or more processing modules to the control console Each processing bay includes hardware, firmware, and electronics that run an assay on a multiplex cartridge 10. Each processing bay may include a bay PCB. In various embodiments, the bay PCB includes the electronics and firmware of the processing bay (such as, microprocessors and firmware on the microprocessors), circuitry that supplies power (e.g., up to 300 V to the electrowetting pads) in the multiplex cartridge, circuitry that performs electronic sensing of reaction products on the multiplex cartridge, circuitry that controls heaters in the processing bay that interact with the multiplex cartridge, circuitry that measures and controls temperatures in the multiplex cartridge, circuitry that controls motion of various moving components of the processing bay, and circuitry that controls a pump of the processing bay.

Each processing bay may also include a connector PCB. In various embodiments, the connector PCB includes pogo pins configured to make contact with the multiplex cartridge and transmit data, control signals, and power between the multiplex cartridge and the processing bay PCB and pogo pins configured to make electrical contact with heater elements within the processing bay.

Each processing bay further includes stepper motors. In various embodiments, the processing bay comprises two stepper motors: one stepper motor that controls positioning of magnets, heaters, and pogo pins, or other connector elements, relative to the multiplex cartridge, and one stepper motor controls a cam follower plate within the processing bay that compresses blisters on the multiplex cartridge and causes the blisters to dispense their contents in a predefined sequence.

Each processing bay also includes a blister compression assembly configured to compress the blisters of the multiplex cartridge 10 in a specified sequence and actuate the active valves of the multiplex cartridge 10, thereby dispensing the contents of the cartridge's blisters in the specified sequence. In various embodiments, the blister compression mechanism assembly comprises an array of blister-compressing actuators, or compression mechanisms, each comprising a cam arm configured to push a compression pad onto a blister. The blister compression mechanism assembly further includes a cam arm plate within which the cam arms and compression pads of the compression mechanisms are operatively mounted above the blisters for movement between a retracted position and an extended, blister-compressing position, a cam follower plate that is movable with respect to the cam arm plate and includes grooves with ridges (or other cam follow elements) located and sequenced to engage cam arms of the actuator array as the cam follower plate moves with respect to the cam arm plate to actuate the cam arms to compress the blisters in a sequence determined by the relative locations of the compression mechanisms in the cam arm plate and the grooves and ridges of the cam follower plate.

Each processing bay may also include a pump coupled to the multiplex cartridge 10 via pump port 104 and configured to provide a motivating force for reagents and sample in sample preparation module of the multiplex cartridge.

Each processing bay may also include an LED PCB 466 (see FIGS. 38-41) that provides LED indicators of the processing bay status and optical sensors that detect conditions within the multiplex cartridge, for example, through inlet optical port 14 and outlet optical port 16.

Each processing bay may also include mounting hardware configured to attach the processing bay into the processing module and electrical connectors configured to transmit power and data between the processing bay and the processing module.

Each processing bay may also include a multiplex cartridge carrier configured to provide a physical connection and alignment between the top bay, comprising the blister compression mechanism assembly, and a multiplex cartridge processing assembly, or bottom bay, comprising a cartridge carriage assembly, a heating and control assembly, and a cam frame assembly configured to effect movement of the heating and control assembly with respect to a multiplex cartridge held in the cartridge carriage assembly.

Control Console

A processing instrument embodying aspects of the present invention and configured to process the multiplex cartridge 10 described above is indicated by reference number 400 in FIG. 32. As noted above, the instrument 400 includes the control console 402 and one or more processing modules 410 operatively associated with the control console 402. The control console 402, in one embodiment, includes a display panel 404 presenting a graphical user interface and comprising a touchscreen by which a user may input information to the control console 402 and/or by which information can be presented to the user. In various embodiments, the control console 402 may comprise additional or alternate means for inputting data, such as keyboards, microphones, switches, manually-operated scanners, voice-activated input, etc. As further noted above, the instrument may include a barcode scanner for reading barcodes, for example, one-dimensional or two-dimensional barcodes, or other types of scanners for reading machine-readable code, such as an RFID scanner. In various embodiments, the control console 402 may comprise additional or alternate means for outputting data (i.e., information and/or results), including hard drives or other storage media, monitors, printers, indicator lights, or audible signal elements (e.g., buzzer, horn, bell, etc.), email, text message, etc.

Processing Module

Figure 34:
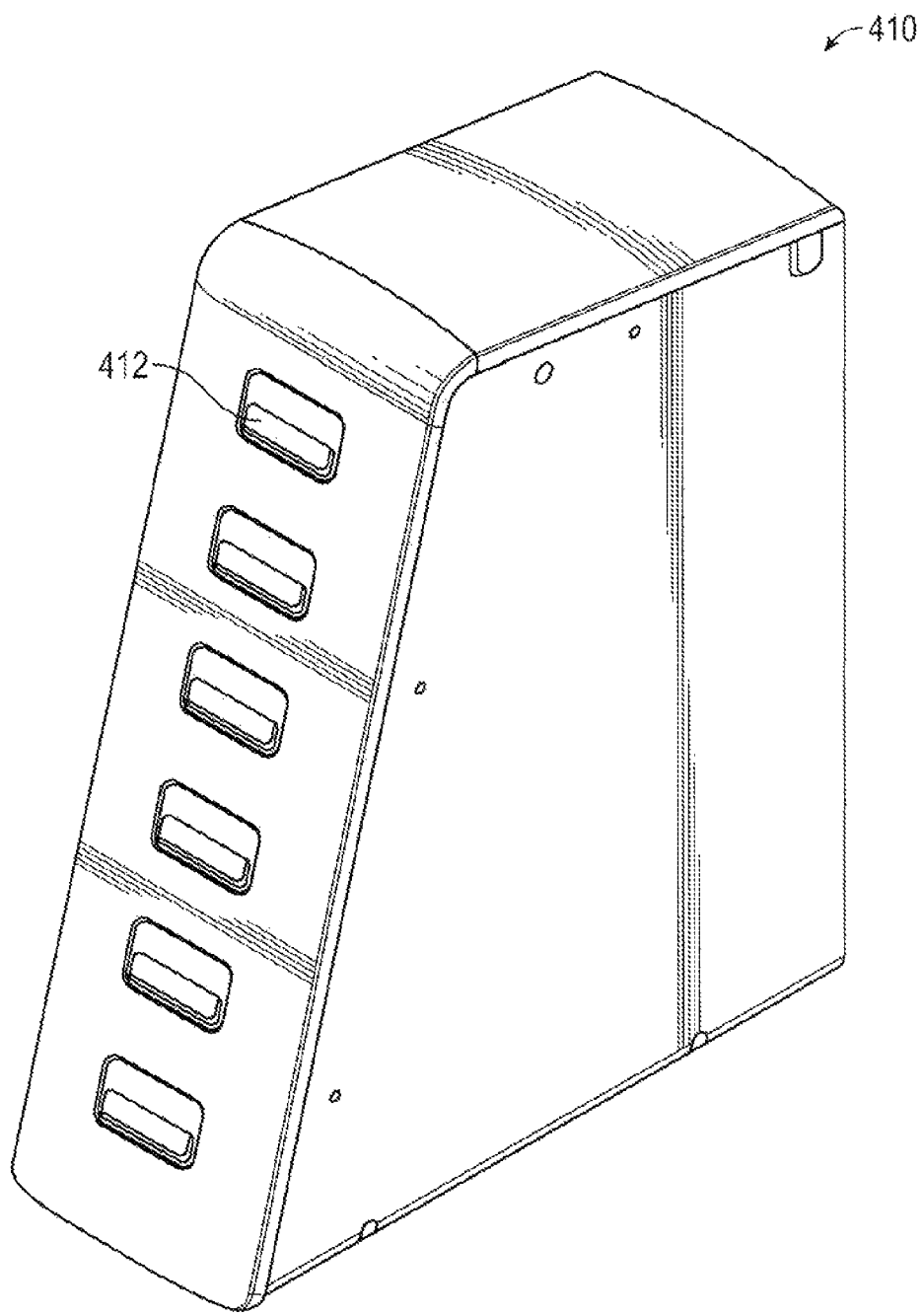
FIG. 34 is a front perspective view of a processing module of the instrument.

As shown in FIGS. 32 and 34, each processing module 410 includes one or more cartridge doors 412, each cartridge door 412 being associated with a processing bay (described below) within which a cartridge 10 may be processed. In the illustrated embodiment, each processing module 410 includes six (6) cartridge doors 412 and associated processing bays. Each cartridge door 412 is configured to accept a multiplex cartridge 10, preferably in a single, preferred orientation. Each cartridge door also preferably includes a closeable door (e.g., a pivoting door panel) that is biased, e.g., by a spring or the like, in a closed position but can be pushed open when a cartridge is inserted therein.

In various embodiments, each processing module 410 is operatively coupled to the control console 402. The processing module 410 may be electronically coupled to the control console 402 so as to enable electronic transmissions between the control console 402 and the processing module 410. Such electronic transmissions may comprise power transmissions from the control console to the processing module for powering various electronic components within the processing module, control signals, input data, output data, etc.

Each processing module 410 may also be physically connected, e.g., in a side-by-side relationship as shown in FIG. 32, with the control console 402. As in the illustrated embodiment, the instrument 400 may include one or more processing modules 410 secured to one or both sides of the control console 402. Additional processing modules maybe secured to other processing modules in a side-by-side relationship on one or both sides of the control console 402. In one preferred arrangement, the instrument 400 includes up to 2 processing modules 410 secured to each side of the control console 402, each processing module 410 comprising six (6) cartridge doors 412 and associated processing bays for processing up to six multiplex cartridges 10 per processing module.

It is preferred that the control console 402 and the processing module 410 be provided in a modular manner as shown so as to facilitate scalability of the instrument, e.g., by adding one or more processing modules 410 to or subtracting one or more processing modules 410 from a single control console 402, and also to facilitate instrument trouble-shooting whereby a processing module 410 having one or more malfunctioning processing bays can be removed from the instrument for repair or replacement, and the instrument may still be useable with the remaining, operative processing modules 410.

In an alternate embodiment, however, a control console and associated input screen—and/or other input means—and one or more—preferably a plurality of—cartridge doors and associate processing bays may be provided in a single, integral instrument having a single housing.

Figure 35:
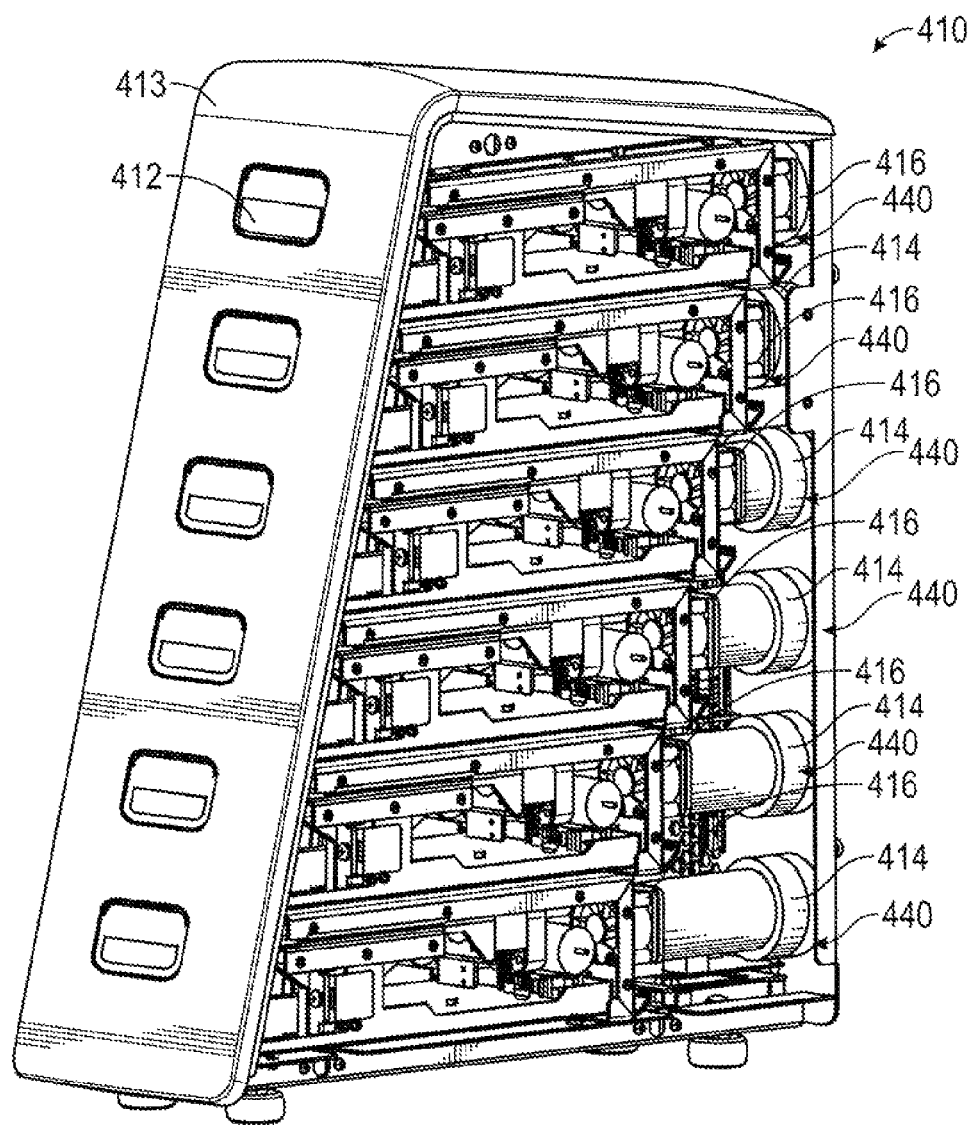
FIG. 35 is a front perspective view of the processing module with one side wall of the module removed to show internal components of the processing module.
Figure 36:
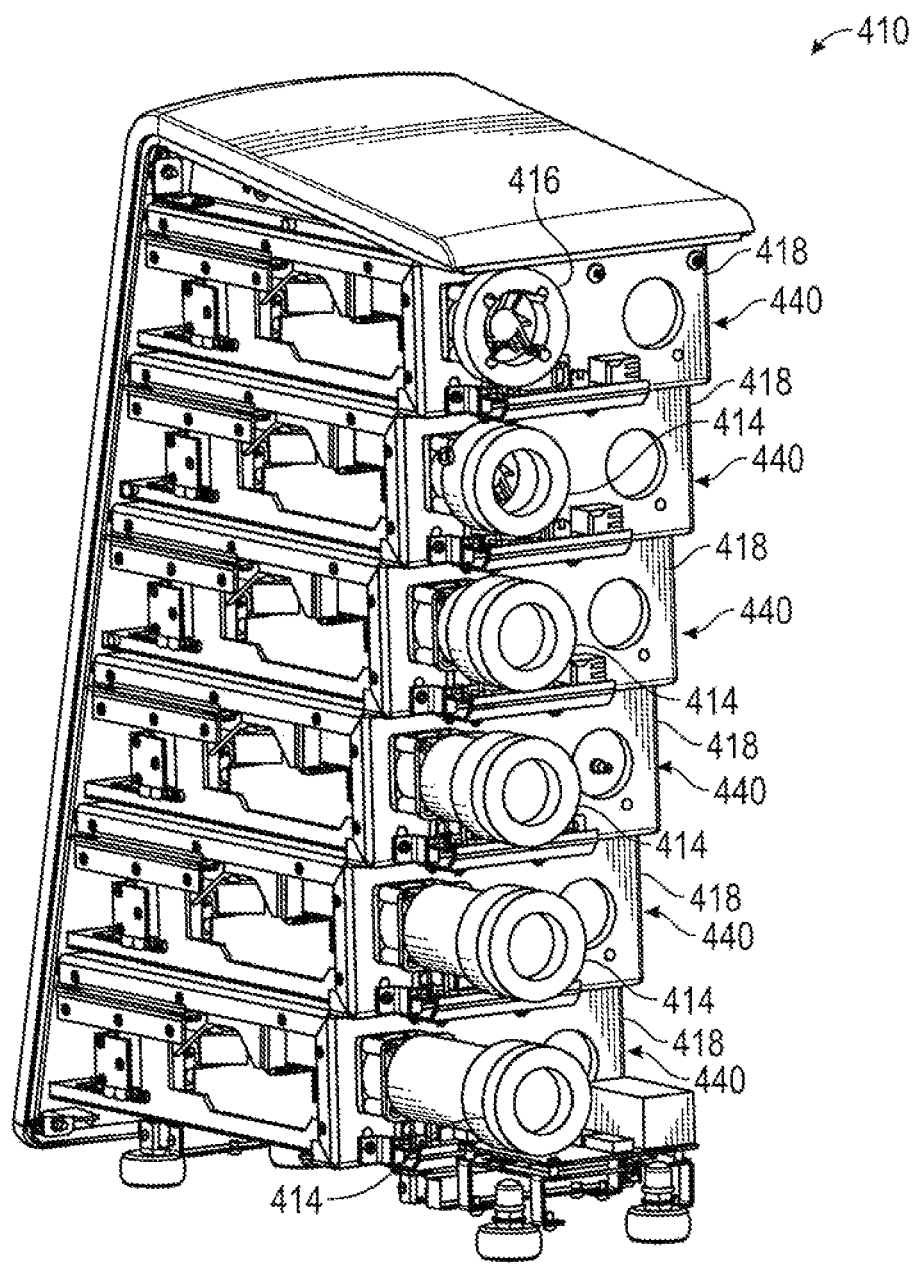
FIG. 36 is a rear perspective view of the processing module with one side wall and the rear wall of the module removed to show internal components of the processing module.
Figure 37:
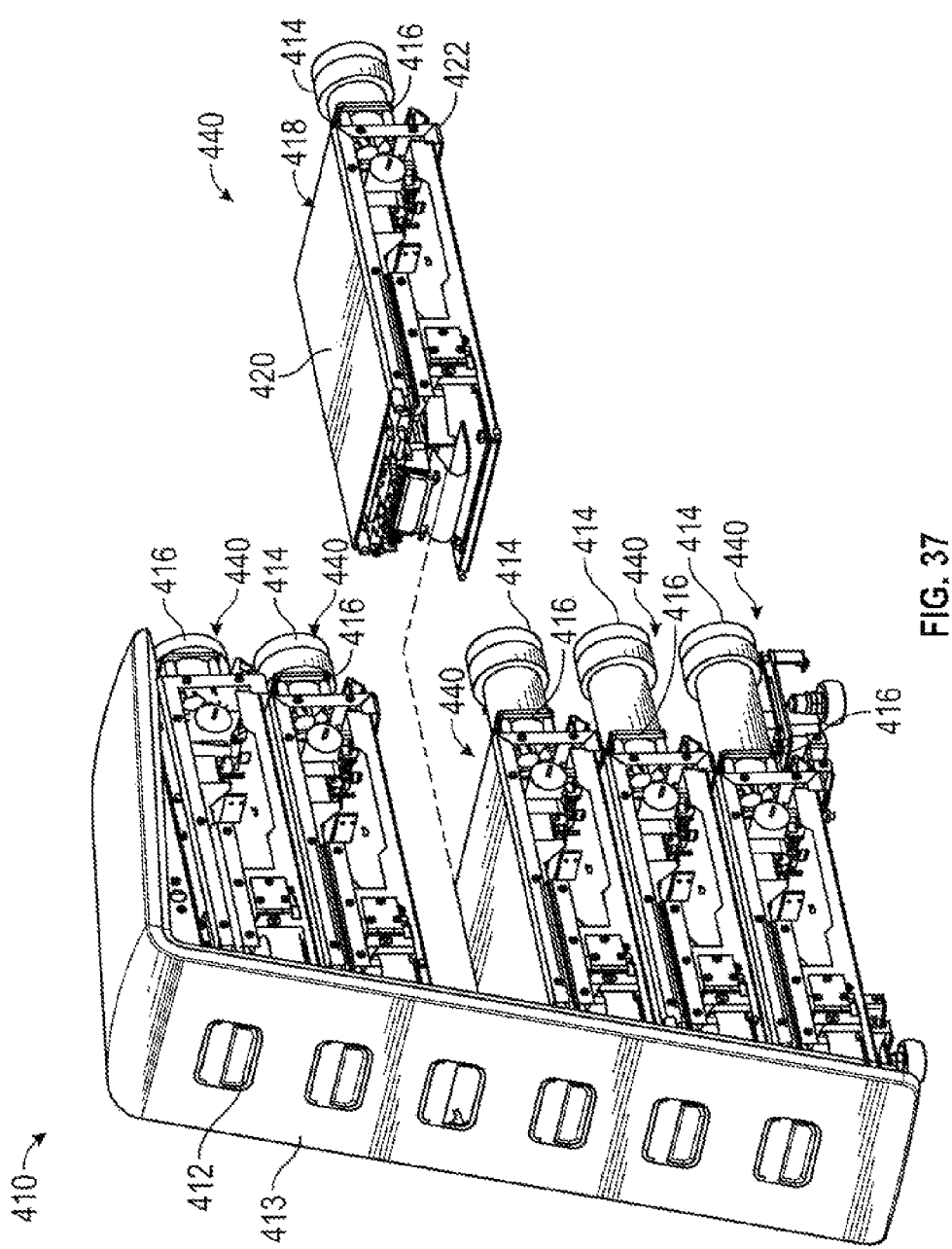
FIG. 37 is a front perspective view of the processing module with one side wall and one rear wall of the module removed and with one processing bay of the processing module exploded from the module.

Further details of the processing module 410 are shown in FIGS. 35, 36, and 37. Each processing module 410 includes a plurality of cartridge doors 412 and associated processing bays 440. The illustrated embodiment includes six (6) processing bays 440. The processing bays 440 are arranged in a stacked arrangement within a housing of the processing module 410. Each processing bay 440 has associated therewith a frame 418 partially surrounding the processing bay with a horizontal top panel 420 and a vertical rear panel 422 (See FIG. 37). As shown in the figures, a front panel 413 of the processing module 410 within which the cartridge doors 412 are positioned is oriented at an angle tilted back from the bottom of the processing module 410 to the top of the processing module 410. This may be for ergonomic and/or esthetic reasons. In other embodiments, a front panel of the processing module may be vertical. Because of the angle of the front panel 413 of the processing module 410, each processing bay 440 is offset horizontally (i.e., rearwardly) relative to the processing bay immediately below it.

In various embodiments, each processing bay 440 has associated therewith a ventilation fan 416 secured to the vertical panel 422 of the housing 418 and a ventilation duct 414 extending from the fan 416 to a rear wall of the housing of the processing module 410. As shown in the figures, due to the tilt of the front panel 413 and the horizontal offset of the processing bays 440, the ventilation ducts 414 have decreasing lengths progressing from the bottom-most processing bay 440 to the top-most processing bay.

The processing module 410 may further include additional structural elements for securing each of the processing bays 440 within the housing of the processing module. The processing bays 440 and processing module 410 are preferably configured so that each bay 440 may be independently removed from the processing module 410 and replaced to facilitate instrument repair if one or more processing bays 440 malfunctions or is otherwise in need of maintenance or repair.

Processing Bay

Figure 38:
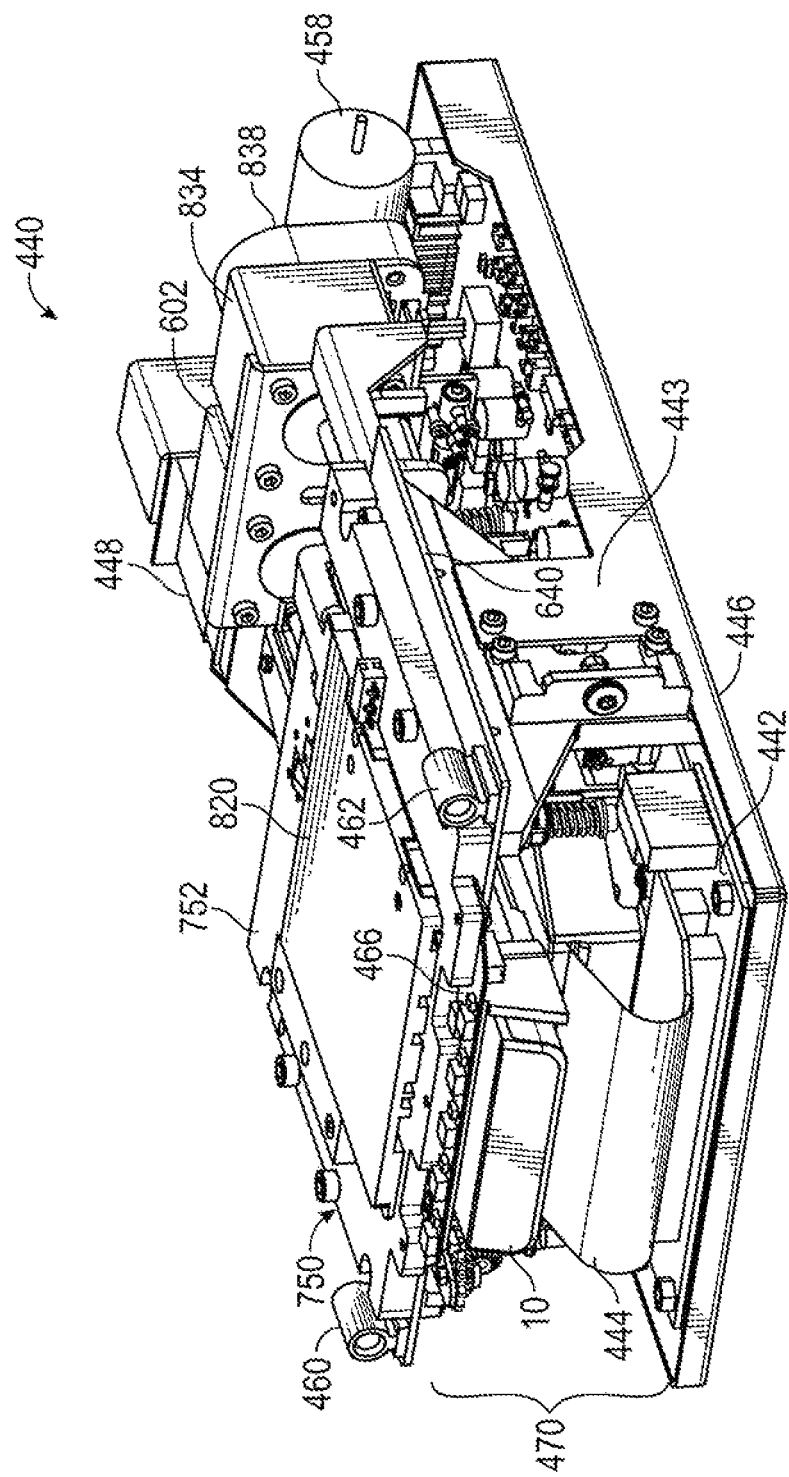
FIG. 38 is a front, right-side perspective view of a processing bay embodying aspects of the present invention.
Figure 39:
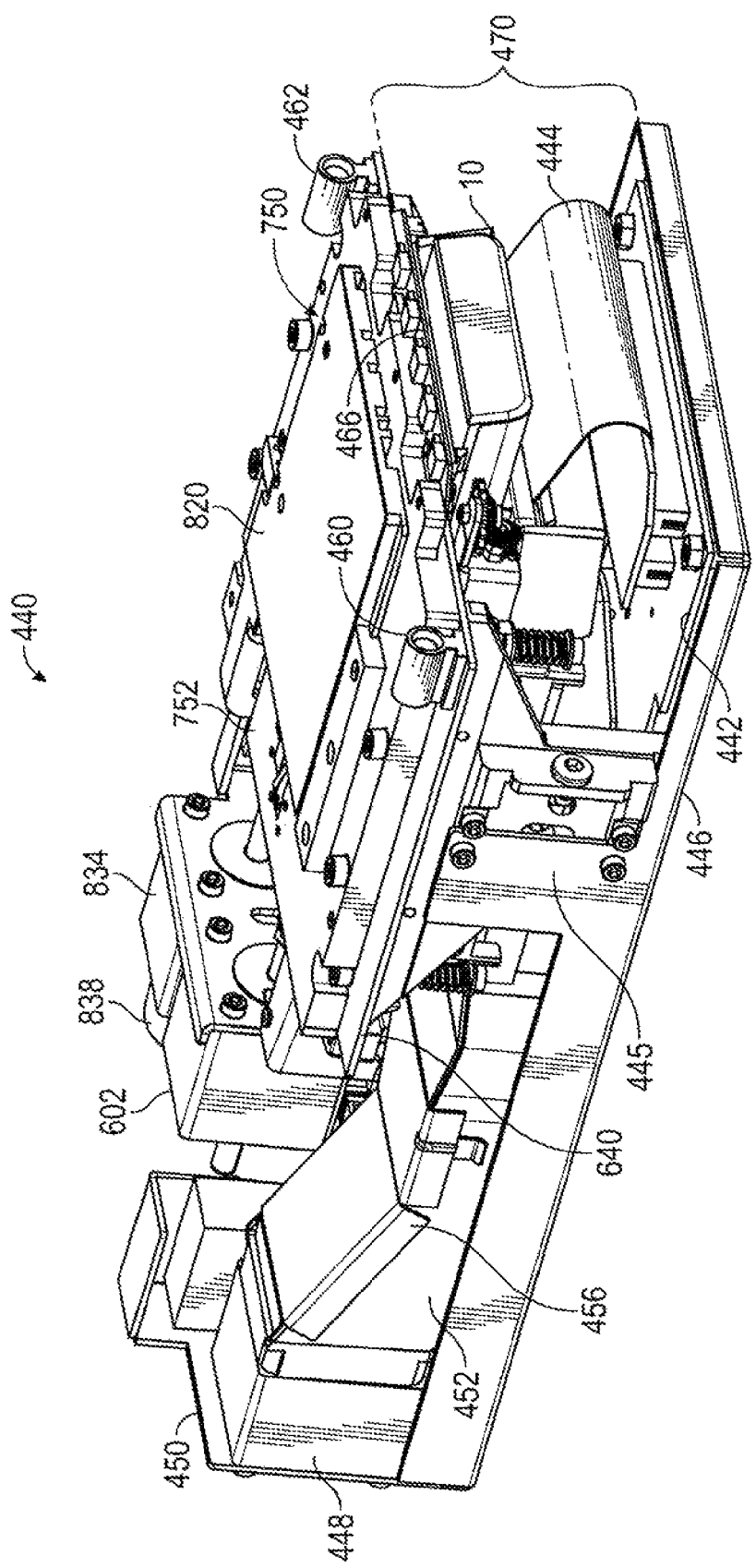
FIG. 39 is a front, left-side perspective view of the processing bay.
Figure 40:
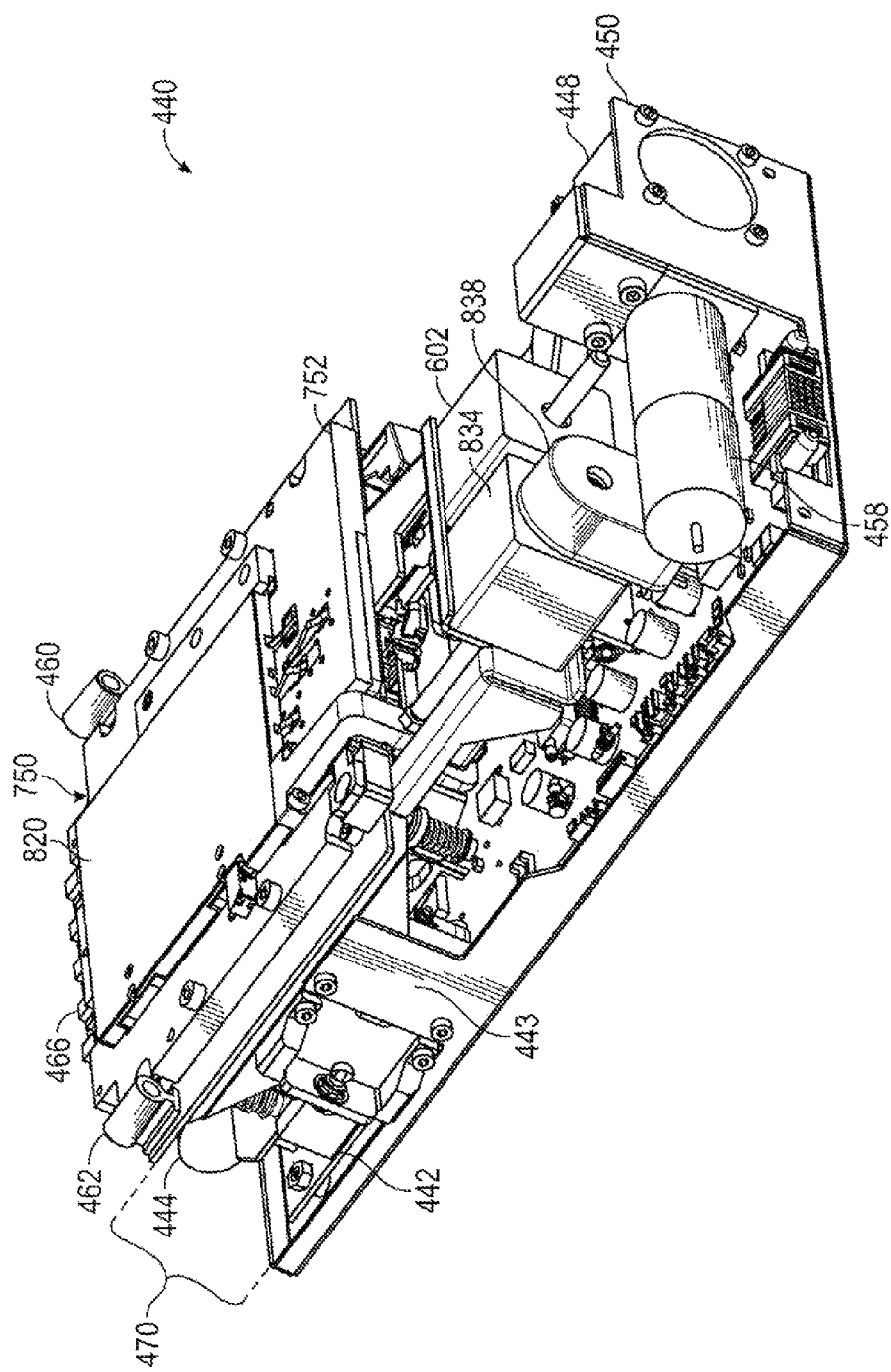
FIG. 40 is a rear, right-side perspective view of the processing bay.
Figure 41:
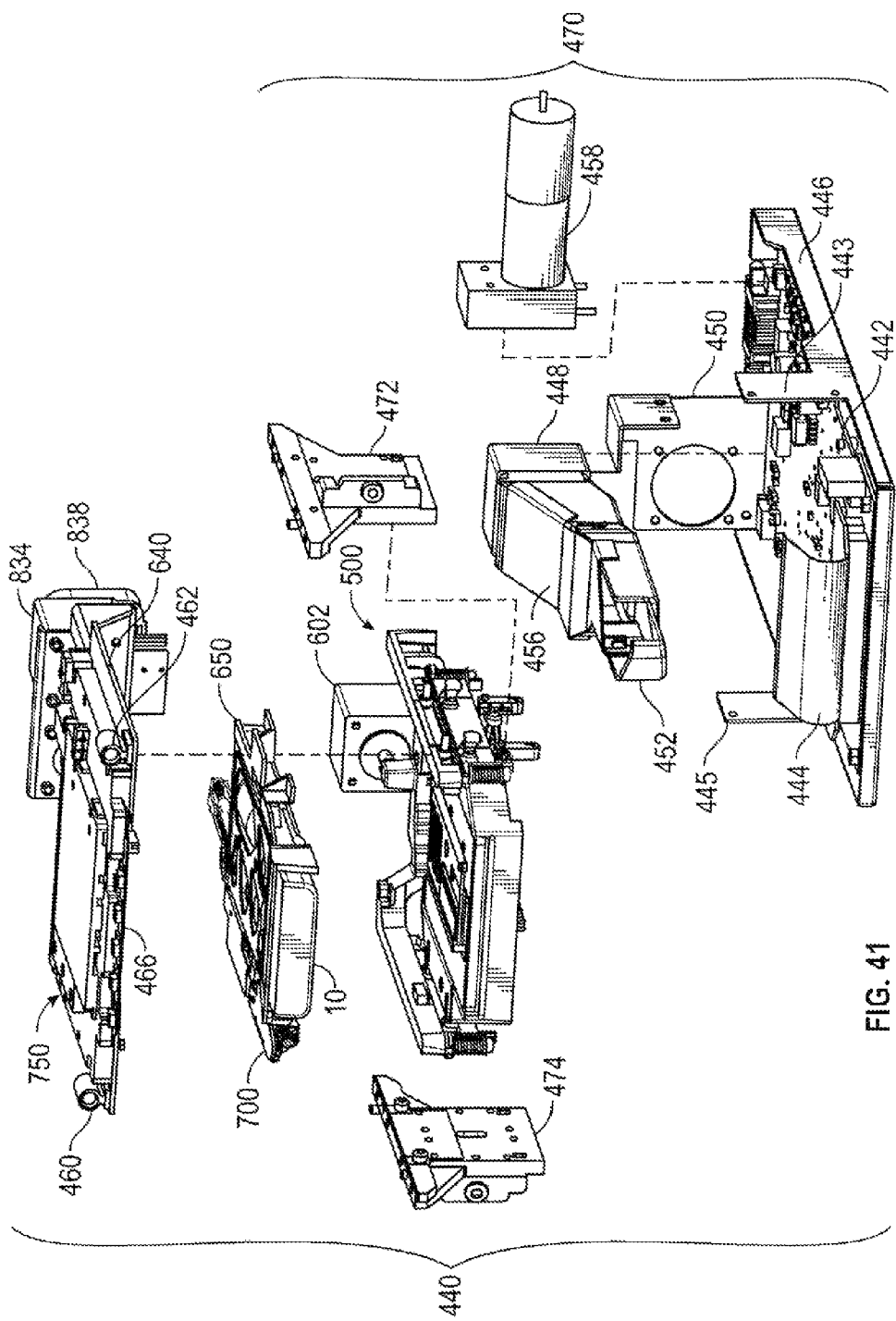
FIG. 41 is a front, right-side, exploded perspective view of the processing bay.

A processing bay 440 is shown in various views in FIGS. 38, 39, 40, and 41. In each of FIGS. 38-41, the frame 418 of the processing bay 440 is omitted from the figure. FIG. 38 is a front, right-side perspective view of the processing module 440 with a multiplex cartridge 10 inserted therein. FIG. 39 is a front, left-side perspective view of the processing module 440 with a multiplex cartridge 10 inserted therein. FIG. 40 is a rear, right-side perspective view of the processing module 440. FIG. 41 is a front, right-side, exploded perspective view of the processing module 440 with a multiplex cartridge 10 inserted therein.

Each processing bay 440 has a drip tray 446 forming a lower floor of the processing bay 440 and constructed and arranged to contain fluid leaks that may occur from the multiplex cartridge 10 and to provide a support and mounting structure for various components of the processing bay 440. A main PCB (printed circuit board) 442, also referred to as the bay PCB, provides primary control of the processing bay 440 as well as data and power distribution and transmission. A flexible connector 444 connects the bay PCB 442 with a connector PCB (described below, not visible in FIGS. 38-41) within the processing bay 440, as will be described in further detail below. The processing bay 440 may further include alignment elements, such as two (2) tubular female alignment elements 460, 462, that receive male alignment elements disposed within the processing module 410 for properly aligning and positioning the processing bay 440 in a bay mounting location within the processing module 410.

The processing bay 440 may be conceptually divided along functional lines between a cartridge processing assembly 470 (also known as the lower bay) and a blister (or deformable chamber) compression mechanism assembly 750 (also known as the upper bay). The primary function of the cartridge processing assembly 470 is to receive the cartridge 10, secure the cartridge within the bay 440, apply heat and magnetic forces to the processing module 240 of the multiplex cartridge 10, apply controlled power to the multiplex cartridge 10, engage the rotary mixer 192 of the cartridge 10 and effect powered rotation of the rotary mixer 192, and eject the cartridge 10 from the processing bay 440 at the conclusion of an assay or other process performed within the bay 440. The primary function of the blister compression mechanism assembly 750 is to collapse the various deformable chambers of the multiplex cartridge 10 in a proper sequence. Each of these various components will be discussed in further detail below.

Processing bay 440 further includes an LED PCB 466 for controlling one or more LEDs that provide information to a user, such as indicating the status of the processing bay 440 and/or whether a cartridge is located within the processing bay 440. The status LEDs may be visible via a light pipe or other optical transmitter that provides an optical indication signal adjacent to the cartridge door 412 associated with the bay 440 on the front panel 413 of the processing module 410. The LED PCB 466 may also control optical sensors constructed and arranged to detect (e.g., generate a signal), through the inlet and outlet optical ports 14, 16, fluid flow through the inlet optical sensing chamber 154 and the outlet optical sensing chamber 158 of the sample preparation module 70.

Sidewalls 472, 474 extend upwardly along opposite sides of the processing bay 440 and may be secured to upwardly extending elements 443 445 of the drip tray 446. A mounting plate 640 includes a generally horizontal blister plate 644 (see FIG. 42) secured to the top edges of the sidewalls 472, 474 and which generally separates the cartridge processing assembly 470 from the blister compression assembly 750.

In various embodiments, each processing bay 440 further includes a cam follower motor 834 and an associated encoder 838 and a cam frame motor 602. The cam plate motor 834 and the cam frame motor 602 are secured to a motor mount 642 of the mounting plate 640 (see FIG. 42).

A pump 458 provides the pressure that is applied to the multiplex cartridge 10 via the pump port 104.

As will be described in further detail below, the cartridge processing assembly 470 includes a Peltier heater assembly for effecting thermal processes within the processing bay 440. To ventilate the processing bay 440 and dissipate excess heat generated at the Peltier heater, the processing bay 440 may include a peltier ventilation assembly. The ventilation assembly comprises a cooling fan 448 attached to a fan mount 450 of the drip tray 446 and positioned in front of an airflow duct extending between the cooling fan 448 and the Peltier heating assembly within the processing bay 440. In various embodiments, the airflow duct may comprise a cooling duct 452 and a duct cover 456 extending between the cooling fan 448 and the beginning of the cooling duct 452. (See FIGS. 39 and 41).

Cartridge Processing Assembly (Lower Bay)

Figure 42:
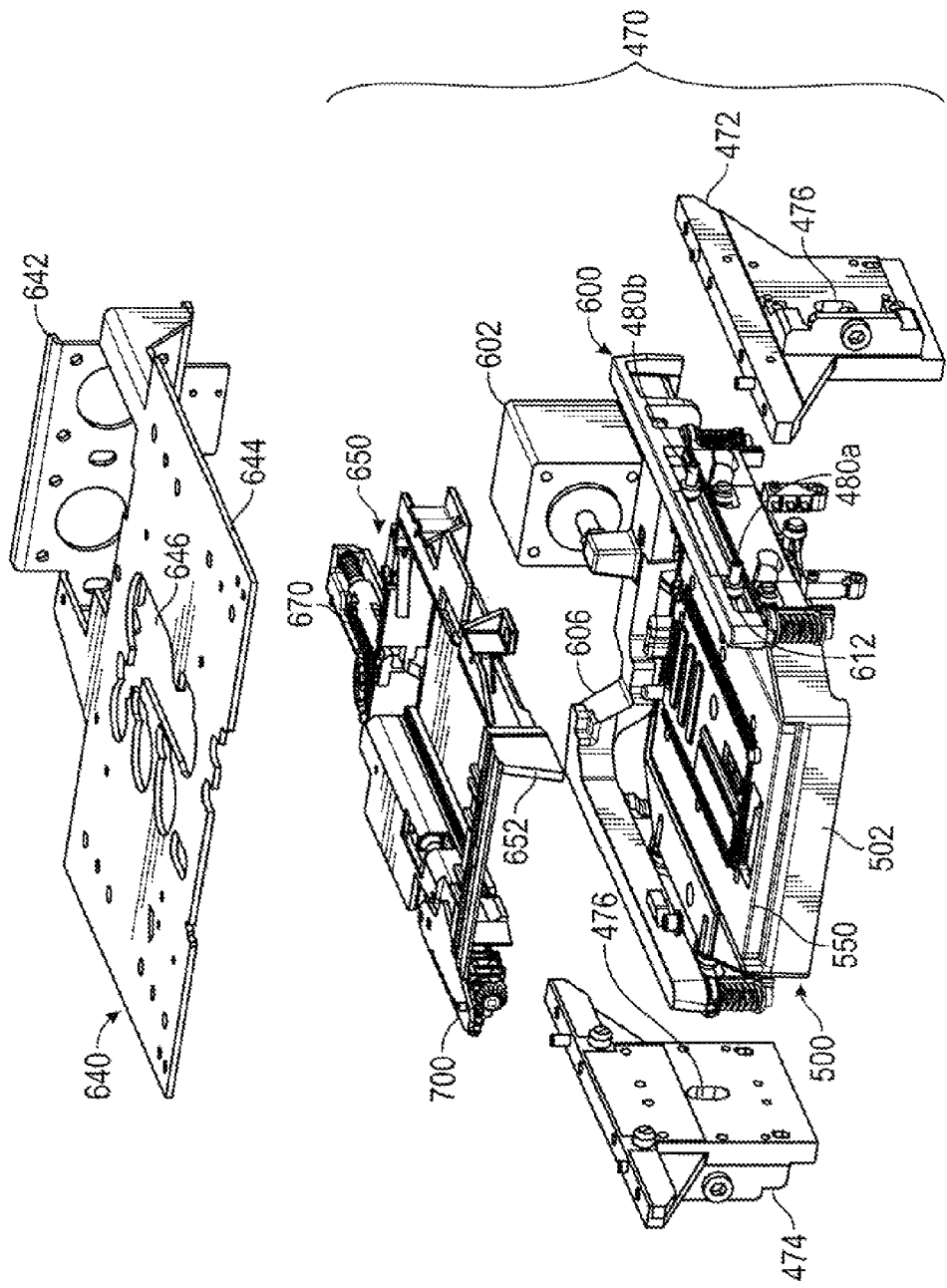
FIG. 42 is an exploded perspective view of the cartridge processing assembly of the processing bay.

Aspects of the cartridge processing assembly 470 are shown in FIGS. 41 and 42. As noted above, most features of the cartridge processing assembly 470 are located beneath the blister plate 644 of the motor mount 642. The cartridge processing assembly 470 includes a cartridge carriage assembly 650 configured to receive and hold, and later eject, a multiplex cartridge 10. The cartridge carriage assembly 650 is secured to a bottom surface of the blister plate 644 of the mounting plate 640.

A cam block assembly 600 includes a cam frame 606 that surrounds the cartridge carriage assembly 650 on three sides and is mounted for linear fore and aft movement within the processing bay 440 where it is supported on linear cam followers 480a, 480b extending from each of the sidewalls 472, 474 into a follower slot 612 formed on each side of the cam frame 606.

A mixing motor assembly 700 is pivotally connected to the blister plate 644 beneath the blister plate and is configured to pivot into and out of an operative engagement with the rotary mixer 192 of the multiplex cartridge 10 disposed within the cartridge carriage assembly 650.

A heating and control assembly 500 is positioned beneath the cartridge carriage assembly 650 and is operatively coupled to the cam frame 606 and the cam block assembly 600 for converting the longitudinal, fore and aft movement of the cam frame 606 into vertical movement of the heating and control assembly 500 for selectively bringing the heating and control assembly 500 into contact with a bottom surface of the multiplex cartridge 10 when a cartridge is inserted into the cartridge carriage assembly 650.

Cartridge Carriage Assembly

Figure 46:
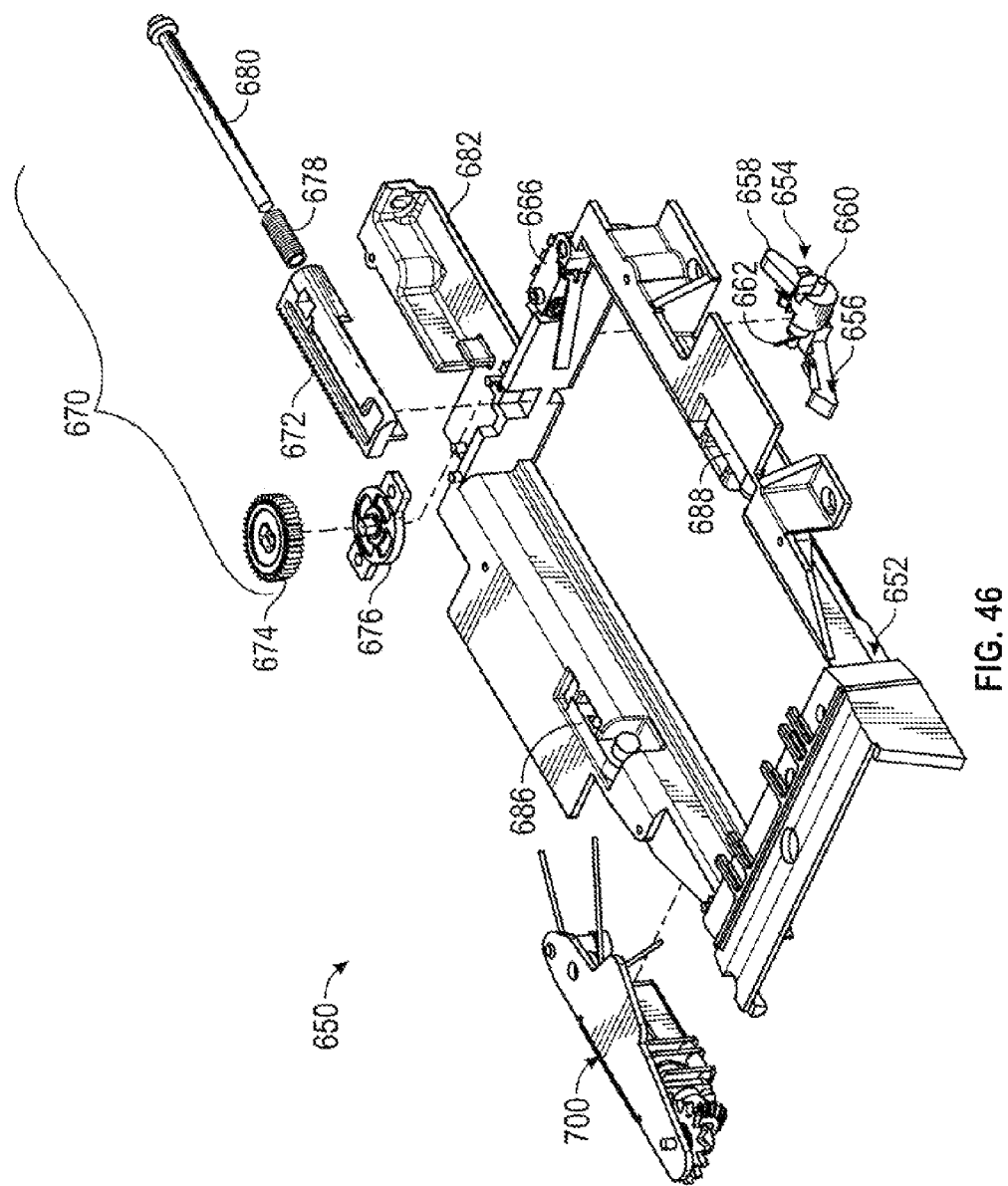
FIG. 46 is an exploded perspective view of a cartridge carriage assembly of the cartridge processing assembly.

Further details of the cartridge carriage assembly 650 are shown in FIG. 46, which is an exploded perspective view of the cartridge carriage assembly 650 with other components of the cartridge processing assembly 470 omitted. The cartridge carriage assembly 650 includes a carriage holder 652 comprising a generally rectangular frame which is secured to the underside of the blister plate 644 of the mounting plate 640. A detector may be provided for detecting when a multiplex cartridge 10 (not shown in FIG. 46) is inserted into the cartridge holder 652. In various embodiments, the detector comprises an optical detector comprising an emitter 686 and detector 688 each disposed within a respective pocket on opposite sides of the cartridge holder 652. An optical beam from the emitter 686 to the detector 688 is broken when a multiplex cartridge is inserted into the cartridge holder 652, thereby generating a signal indicating the presence of the cartridge.

A cartridge latch 654 is mounted for pivotal movement at a closed end of the cartridge holder 652. The cartridge latch 654 is pivotally mounted on a latch pin 660 for rotation about a horizontal axis of rotation. The cartridge latch 654 further includes a forward hook 656 and a trailing lever 658. A torsion spring 662 rotationally biases the latch 654 so that the hook 656 is in an upward position. When a cartridge 10 is inserted into the cartridge holder 652, the cartridge pushes the hook down until the hook 656 of the cartridge latch 654 engages a recess in a bottom portion of the lower shroud 30 of the cartridge 10. The bias of the torsion spring 662 holds the hook 656 into that recess to retain the cartridge within the cartridge holder 652.

A cartridge ejector assembly 670 includes an ejector rack 672 that is positioned within an ejector bracket 682 extending off a rear end of the cartridge holder 652. The linear gear-teeth of the ejector rack 672 engage a damper pinion gear 674 that is coupled to a rotary damper 676 and is mounted for rotation on the ejector bracket 682 adjacent the ejector rack 672. A spring capture pin 680 extends through the ejector rack 672 and is supported at an end thereof by an end wall of the ejector bracket 682. A compression spring 678 is disposed between an end of the ejector rack 672 and the end of the spring capture pin 680. Accordingly, the ejector rack 672 is biased longitudinally toward the open end of the cartridge holder 652. A limit stop element may be provided to prevent the cartridge rack 672 from being pushed too far by the spring 678. The ejector rack 672 initially extends into the cartridge holder 652 and is contacted by the end of a multiplex cartridge 10 inserted into the cartridge holder 652. As the cartridge is further inserted into the cartridge holder 652, the ejector rack 672 is pushed back, thereby compressing the spring 678 and generating a bias force urging the cartridge 10 longitudinally toward the open end of the cartridge holder 652 and out of the processing bay 440. Because the cartridge latch 654 captures the fully-inserted multiplex cartridge, the ejector assembly 670 is prevented from pushing the cartridge back out of the cartridge holder 652.

A cartridge latch switch 666 is positioned at the closed end of the cartridge holder 652 and is configured to signal when the multiplex cartridge has been inserted to a position within the cartridge holder 652, such that the cartridge will be engaged by the cartridge latch 654. At the conclusion of an assay or other process performed within the processing bay 440 the cartridge latch 654 is pivoted (counterclockwise in the illustrated embodiment) against the bias of the torsion spring 662, in a manner that will be described below, to thereby release the multiplex cartridge held within the cartridge holder 652. Upon release of the cartridge, the cartridge is ejected by the stored energy in the compress spring 678 bearing against the ejector rack 672. The damper pinion 674 and the operatively-associated rotary damper 676 with which the ejector rack 672 is engaged ensures a controlled release of the ejector rack 672 so that the multiplex cartridge 10 is not ejected too abruptly from the cartridge holder 652.

Heating and Control Assembly

Figure 43:
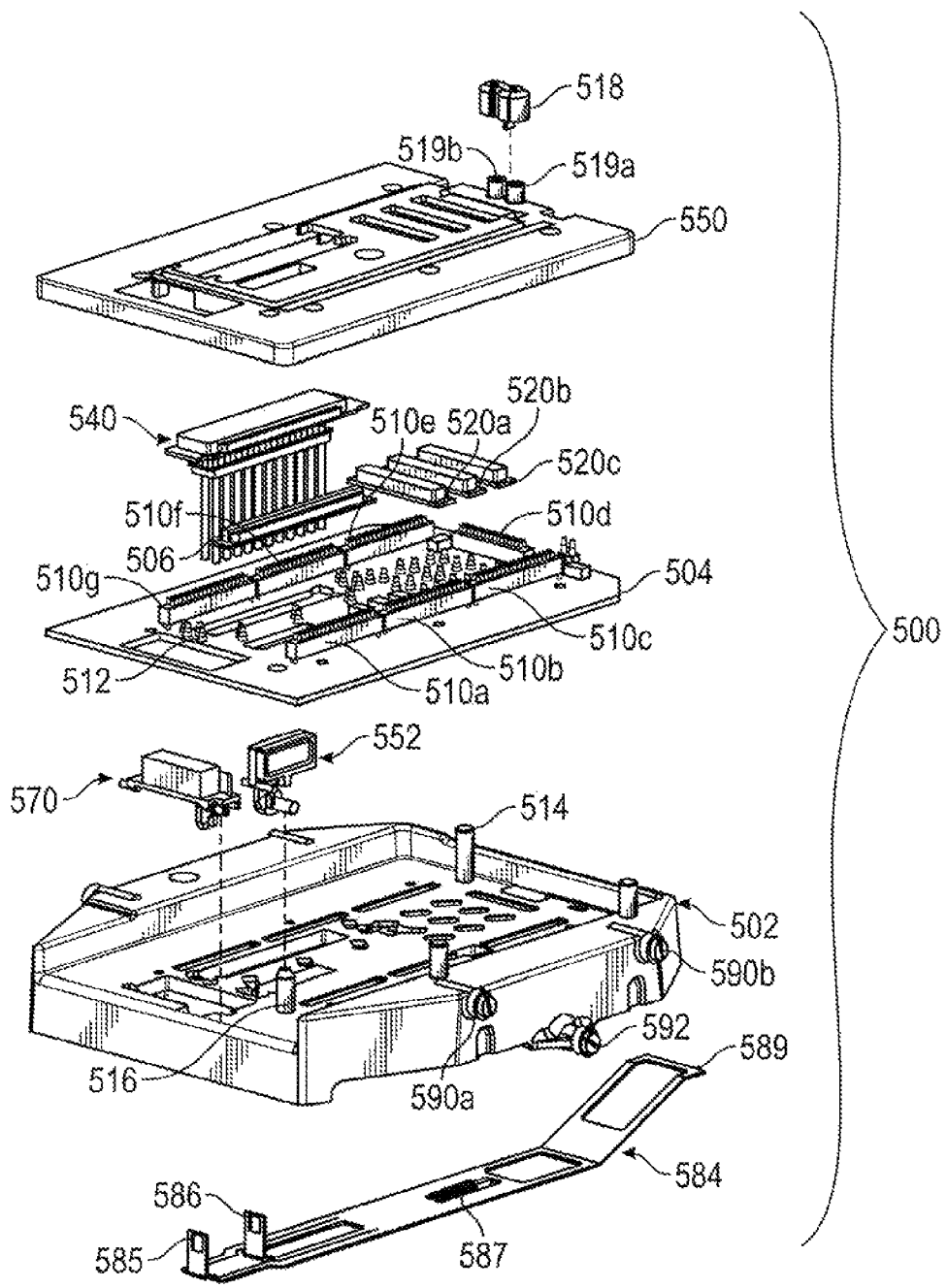
FIG. 43 is an exploded perspective view of a heating and control assembly of the cartridge processing assembly.

Details of the heating and control assembly 500 are shown in FIG. 43, which is an exploded perspective view of the heating and control assembly 500 with other components of the cartridge processing assembly 470 omitted.

The heating and control assembly 500 includes a support plate 502, a connector PCB 504 supported on the support plate 502, a cover plate 550 partially covering the connector PCB 504, a cartridge magnet assembly 552, a sample preparation magnet assembly 570, and a magnet actuator 584 located beneath the support plate 502. A front alignment pin 416 and a rear alignment pin 414 extend upwardly from the support plate 502.

A pneumatic connector 518 is attached to pneumatic ports 519a, 519b of the cover plate 550. The pneumatic connector 518 provides a connection between the pressure source, e.g., pump 458, and the cartridge 10 via pump port 104 and provides a connection between an external valve within the processing bay 440 and the passive valve assembly 220 of the cartridge 10 via the passive valve port 108 (see FIG. 15).

Figure 44:
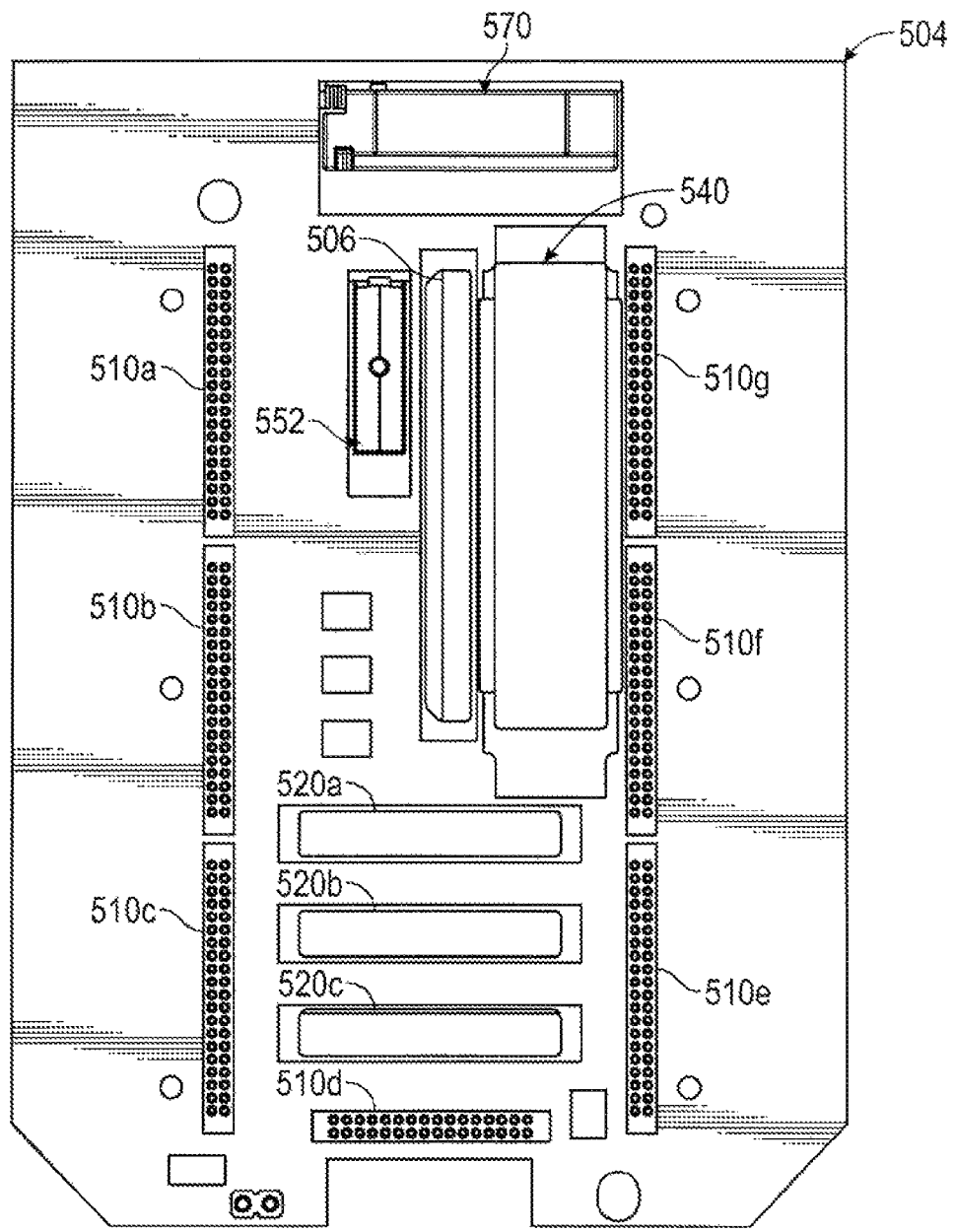
FIG. 44 is a top plan view of a connector PCB and magnets of the heating and control assembly of the cartridge processing assembly.

Referring to FIGS. 43 and 44, which is a top plan view of the connector PCB 504, the connector PCB 504 includes an elution heater assembly 506, a detection Peltier assembly 540, and PCR heater assembly 520a, 520b, and 520c. In various embodiments, the elution heater assembly 506 comprises a resistive heating element attached to a dedicated PCB and a heat spreader comprised of a thermally-conductive material attached or otherwise thermally coupled to the resistive heating element. Similarly, in various embodiments, each element 520a, 520b, and 520c of the PCR heater assembly comprises a resistive heating element attached to a dedicated PCB and a heat spreader comprised of a thermally-conductive material attached or otherwise thermally coupled to the resistive heating element.

Figure 45:
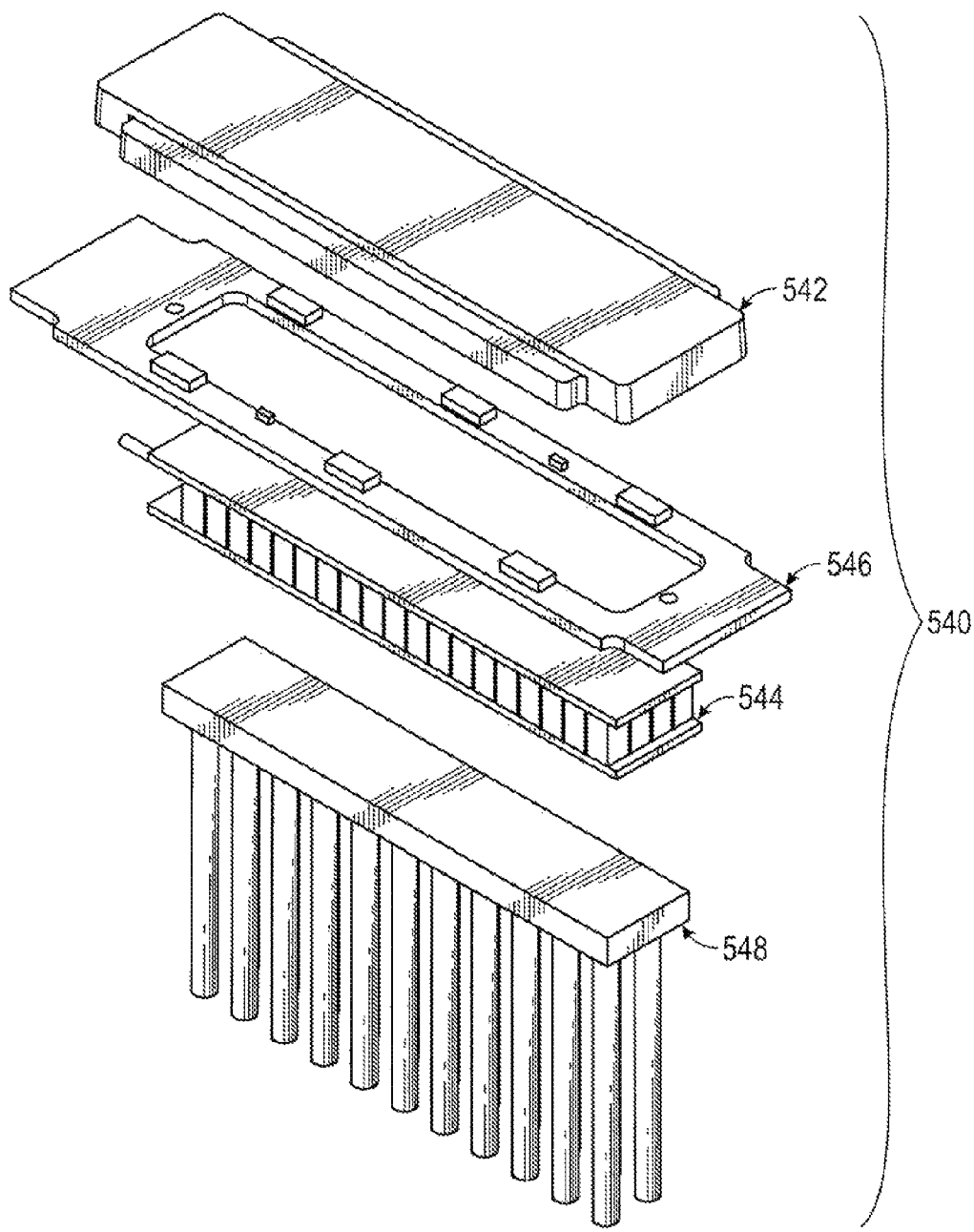
FIG. 45 is an exploded perspective view of a detection Peltier heater assembly of the heating and control assembly.

Details of the detection Peltier assembly 540 are show in FIG. 45, which is an exploded, perspective view of the Peltier assembly 540. The assembly 540 includes a Peltier device 544 (i.e., a thermoelectric element) coupled to a power and control printed circuit board 546. A heat spreader 542, preferably comprised of a thermally conductive material, is disposed above the Peltier device 544. A heat sink 548 is disposed beneath the peltier chip 544. The heat sink 548 may comprise a panel that is in surface-to-surface contact with a surface of the Peltier device 544 with a plurality of heat-dissipating rods (or fins) extending therefrom and formed from a thermally conductive material. The detection Peltier assembly 540 is mounted within, and at least a portion of the heat sink 548 extends through, an associated opening formed in the support plate 542. The heat dissipating rods of the heat sink 548 extend beneath the support plate 502 and are disposed at a terminal end of the Peltier cooling duct 452 (See FIGS. 39 and 41). In one embodiment, the detection Peltier is configured to apply a thermal gradient to, e.g., reduce the temperature of, a detection area, e.g., the detection region 378, of the multiplex cartridge 10.

A plurality of connector pin arrays 510a, 510b, 510c, 510d, 510d, 510e, 510f, and 510g are disposed around the connector PCB 504 and comprise arrays of connector pogo pins that contact and effect electrical connection between connection pads of associated connector pad arrays 358a-358g of the fluidic processing panel 354 of the multiplex cartridge 10 (See FIG. 58). Connections between the connector pin arrays 510a-510g and the connector pad arrays 358a-358g provides connections between the instrument 400 and the multiplex cartridge 10 for, e.g., power, control signals, and data. For example, the connections between the connector pin arrays 510a-510g and the connector pad arrays 358a-358g provides provide power and control from the instrument to the electrowetting grid (e.g., the thermal cycling tracks 364a-364d, the sample bead zone 368, the hybridization zone 370, the elution buffer zone 372, the exonuclease reagent zone 374, the PCR reagent zone 376, the detection mixing zones 385a-385d, and the exonuclease zone 384). In addition, connections between the connector pin arrays 510a-510g and the connector pad arrays 358a-358g provides power to and receives date from the electrosensor arrays 363a-363d.

As shown in FIG. 43, the connector PCB 504 further includes a number of heater pins 512—which may comprise pogo pins—that connect to the various heater assemblies 540, 506, and 520a, b, c.

The heating and control assembly 500 further includes a cartridge magnet assembly 552 and a sample preparation magnet assembly 570.

Figure 49A:
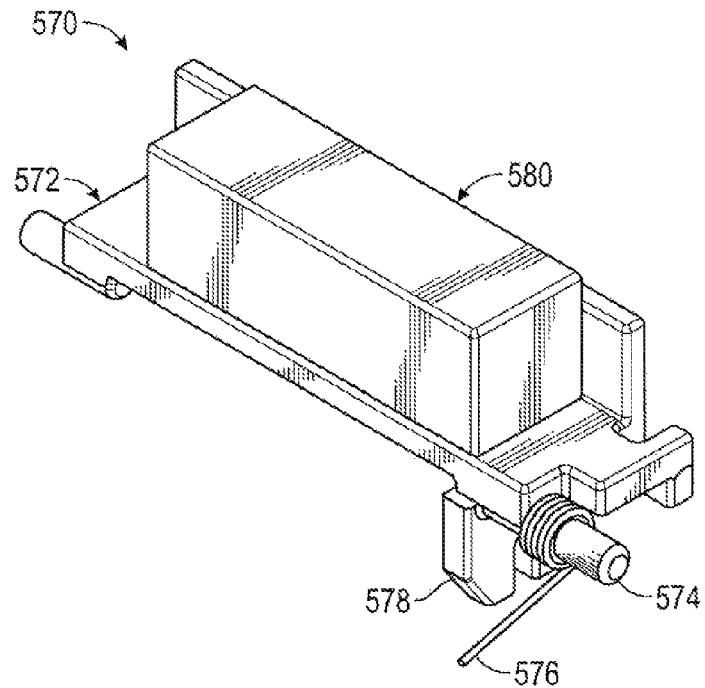
FIG. 49A is a top perspective view of a sample preparation magnet assembly of the cartridge processing assembly.

Details of the sample preparation magnet assembly 570 are shown in FIG. 49A, which is a top perspective view of the sample preparation magnet assembly. The sample preparation magnet assembly 570 comprises a magnet holder 572 mounted on a horizontal spindle 574 so as to be rotatable about the spindle 574 relative to the support plate 502. A torsion spring 576 biases the sample preparation magnet assembly 570 downwardly. An actuator bracket 578 extends beneath the magnet holder 572, and a magnet 580 is supported on top of the magnet holder 572 and is secured thereto, e.g., by a suitable adhesive. When deployed and rotated upwardly against the bias of the torsion spring 576, the magnet 580 extends through aligned openings formed in the support plate 502, the connector PCB 504, and the cover plate 550.

The sample preparation magnet assembly 570, when deployed, is positioned adjacent the capture chamber 100 of the sample preparation module 70 of the multiplex cartridge 10 to thereby apply a magnetic force to fluids contained within and flowing through the capture chamber.

Figure 49B:
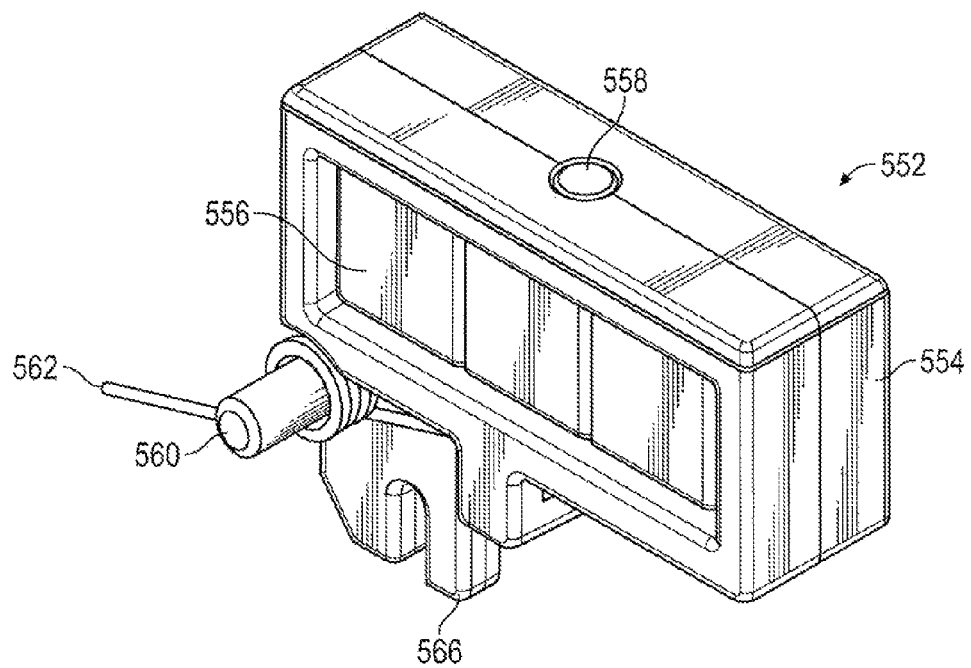
FIG. 49B is a top perspective view of a cartridge magnet assembly of the cartridge processing assembly.

Details of the cartridge magnet assembly 552 are shown in FIG. 49B, which is a top perspective view of the cartridge magnet assembly. The cartridge magnet assembly 552 comprises a magnet holder frame 554 and a magnet array 556 disposed within the magnet holder frame 554. The magnet array 556 may comprise individual magnets (e.g., three), and may be surrounded on four sides by the magnet holder frame 554 to form a frame surrounding the magnet array 556. The magnet array 556 may be secured within the magnet holder frame 554 by, for example, a suitable adhesive. A focusing magnet 558 is disposed within an opening in a top part of the frame of the magnet holder 554. In one embodiment, the focusing magnet 558 is cylindrical and may comprise neodymium N52. The focusing magnet 558 focuses the magnetic forces of the magnet array 556 to a relatively small area for attracting magnetic target capture beads to that small area. The magnet holder 554 is mounted on a horizontal spindle 560 connected to the support plate 502 so that the magnet holder 554 and the magnet array 556 are rotatable about the spindle 560. A torsion spring 562 biases the cartridge magnet assembly 552 downwardly. An actuator bracket 566 extends beneath the magnet holder 554. When the magnet holder 554 is rotated upwardly against the bias of the torsion spring 562, the upper portion of the magnet assembly 552 extends through aligned openings formed in the support plate 502, the connector PCB 504, and the cover plate 550.

The cartridge magnet assembly 552, when deployed, is positioned adjacent to the sample chamber 266 of the reaction module 240, adjacent to a position indicated by reference number 270 (see FIG. 26).

Returning now to FIG. 43, cam followers 590a and 590b extend from opposite sides of the support plate 502 and a slot follower 592 extends from opposite sides of the support plate 502. The slot followers 592 extend into and are vertically movable within a slot 476 formed in each of the side walls 472, 474 (see FIG. 42) and are configured to enable vertical movement of the support plate 502 relative to the side walls 472, 474 while preventing horizontal movement of the support plate 502 relative to the side walls 472, 474.

Cam Frame Assembly

Figure 47:
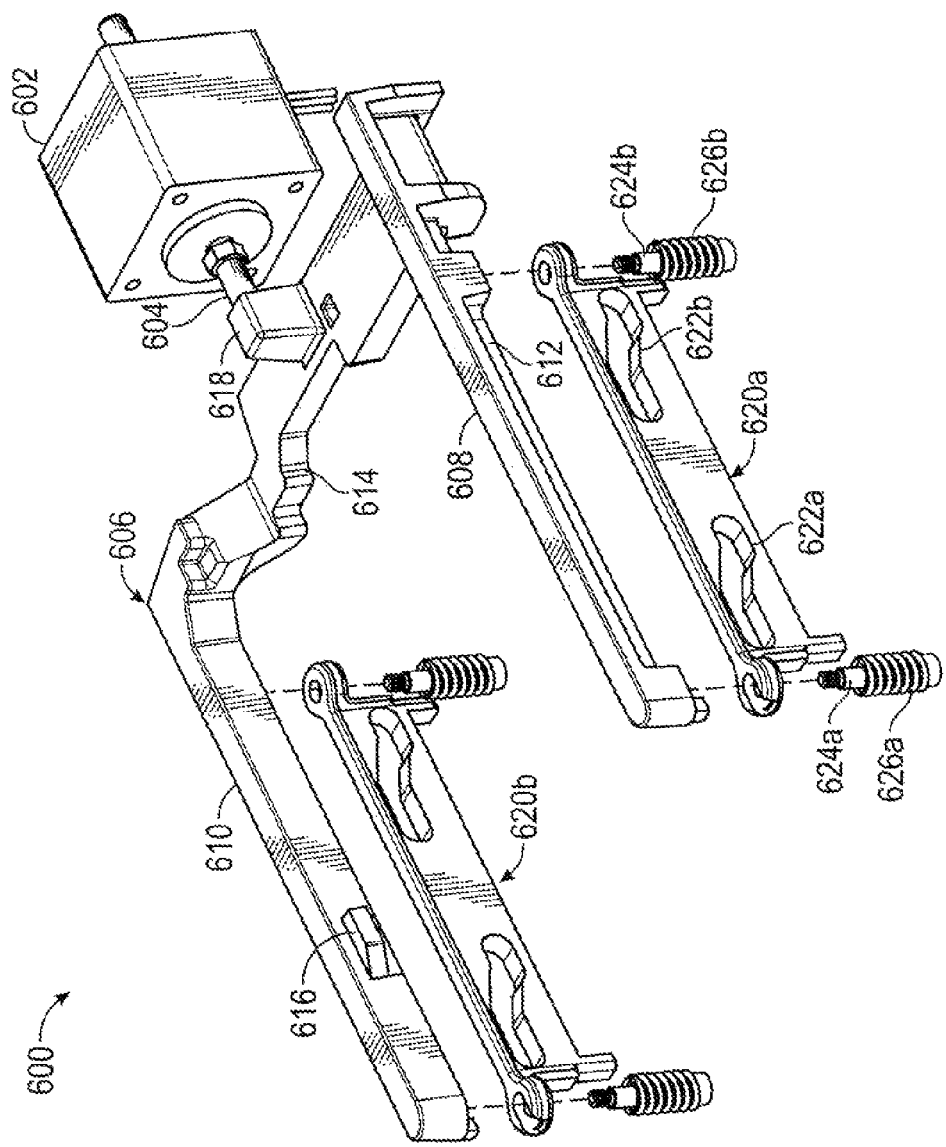
FIG. 47 is an exploded perspective view of the cam frame assembly of the cartridge processing assembly.

Details of a cam frame assembly 600 are shown in FIG. 47, which is an exploded perspective view of the cam frame assembly 600 with other components of the cartridge processing assembly 470 omitted. The cam frame assembly 600 includes the cam frame motor 602 that drives a linear actuator 604. A cam frame 606 includes opposed, generally parallel, longitudinal spars 608, 610 and a cross spar 614 extending between corresponding ends of each of the longitudinal spars 608, 610. The linear actuator 604 is coupled to the cam frame 606 at a motor connector 618 projecting upwardly from the cross spar 614. A follower slot, or channel, 612 is formed along the outer side beneath a top surface of the each of the longitudinal spars 608, 610. Follower elements 480a, 480b extending from each of the side walls 472, 474 (See FIG. 42) extend into the follower slot 612.

A cam rail 620a is secured to the longitudinal spar 608, and a cam rail 620b is secured to the longitudinal spar 610. A top edge of the cam rail 620a cooperates with the follower slot 612 formed in lower outer edge of the longitudinal spar 608 to form a channel that receives the cam followers 480a, 480b, which permit longitudinal movement of the cam frame 606 and the cam rails 620a, 620b with respect to the side walls 472, 474, while preventing vertical movement of the cam frame 606 relative to the side walls 472, 474.

Each cam rail 620a and 620b includes a forward cam slot 622a and a rear cam slot 622b. The cam followers 590a, 590b projecting from the side of the support plate 502 of the heating and control assembly 500 (See FIG. 43) extend into the cam slots 622a, 622b, respectively. Each cam slot 622a, 622b has a lower horizontal segment (the right-side segment in FIG. 47), an upper horizontal segment (the left-side segment in FIG. 47), and an angled transition between the lower horizontal segment and the upper horizontal segment.

Before a multiplex cartridge 10 is inserted into the cartridge carriage assembly 650, the cam frame 606 is in a relatively forward position relative to the heating and control assembly 500 so that the cam followers 590a, 590b extending from the support plate 502 are at the lower horizontal segment (the right side segment as shown in FIG. 47) of each of the cam slots 622a, 622b. Thus, the support plate 502 and the entire heating and control assembly 500 is in a down position with respect to the cartridge carriage assembly 650. When a multiplex cartridge 10 is inserted into the cartridge carriage assembly 650, the alignment fork 246 of the top plate 241 (see FIG. 24) engages the rear alignment pin 514—which is longer than the front alignment pin 516 and extends up into the cartridge carriage assembly 650 even with the support plate 502 in the down position—to properly position the cartridge within the carriage assembly 650.

After the multiplex cartridge is inserted into the cartridge carriage assembly 650, as indicated, for example, when the cartridge latch switch 666 is triggered by the end of a fully-inserted cartridge, the cam frame motor 602 is activated to retract the linear actuator 604 and the cam frame 606 attached thereto. This causes movement of cam rails 620a, 620b relative to the support plate 502, thereby moving the cam followers 590a, 590b from the lower, right side horizontal segments of the cam slots 622a, 622b, up the angled transitions, and to the upper, left side horizontal segments of the cam slots 622a, 622b, thereby raising the support plate 502 and the heating and control assembly 500 into contact with the multiplex cartridge that has been placed into the cartridge carriage assembly 650.

Raising the support plate 502 relative to the cartridge held in the cartridge carriage assembly 650, causes the front alignment pin 516 of the support plate 502 to extend into the alignment loop 244 extending from the top plate 241 (See FIG. 24). With the rear alignment pin 514 engaged by the alignment fork 246 and the front alignment pin 516 extending into the alignment loop 244, the cartridge is substantially immobilized within the cartridge carriage assembly 650.

Raising the heating and control assembly 500 with respect to the cartridge 10 held in the cartridge carriage assembly 650 places the connector pin arrays 510a-510g of the connector PCB 504 into contact with the respective connector pad arrays 358a-358g of the fluidic processing panel 354 of the multiplex cartridge 10. In addition, the elution heater assembly 506 of the connector PCB 504 is brought into contact or close proximity (i.e., so as to enable the transfer of thermal energy) with a portion of the fluidic processing panel 354 corresponding to the exonuclease region 380. Similarly, the components of the PCR heater assembly 520a, 520b, 520c of the connector PCB 504 are brought into contact or close proximity (i.e., so as to enable the transfer of thermal energy) with portions of the fluidic processing panel 354 corresponding to the thermocycling regions 382a, 382b, and 382c. The detection Peltier assembly 540 of the connector PCB 504 is brought into contact or close proximity (i.e., so as to enable the transfer of thermal energy) with portions of the fluidic processing panel 354 corresponding to the detection region 378. Also, the pneumatic connector 518 is brought into contact with the pump port 104 and the passive valve port 108 of the sample preparation module 70 of the multiplex cartridge 10.

Each cam rail 620a, 620b is secured to the respective longitudinal spar 608, 610 of the cam frame 606 by means of two threaded spring capture posts 624a, 624b with a compression spring 626a, 626b disposed between the cam rail 620a and a head of each of the posts 624a, 624b. This "shock absorber" configuration permits a certain amount of movement of the cam rails 620a, 620b relative to the longitudinal spars 608, 610 to thereby prevent the heating and control assembly 500 from being pushed against the bottom of the multiplex cartridge 10 with too great a force. Accordingly, the heating and control assembly 500 will be pushed against the bottom of the multiplex cartridge with a force that is no greater than the compressive force of the springs 626a, 626b.

Figure 48:
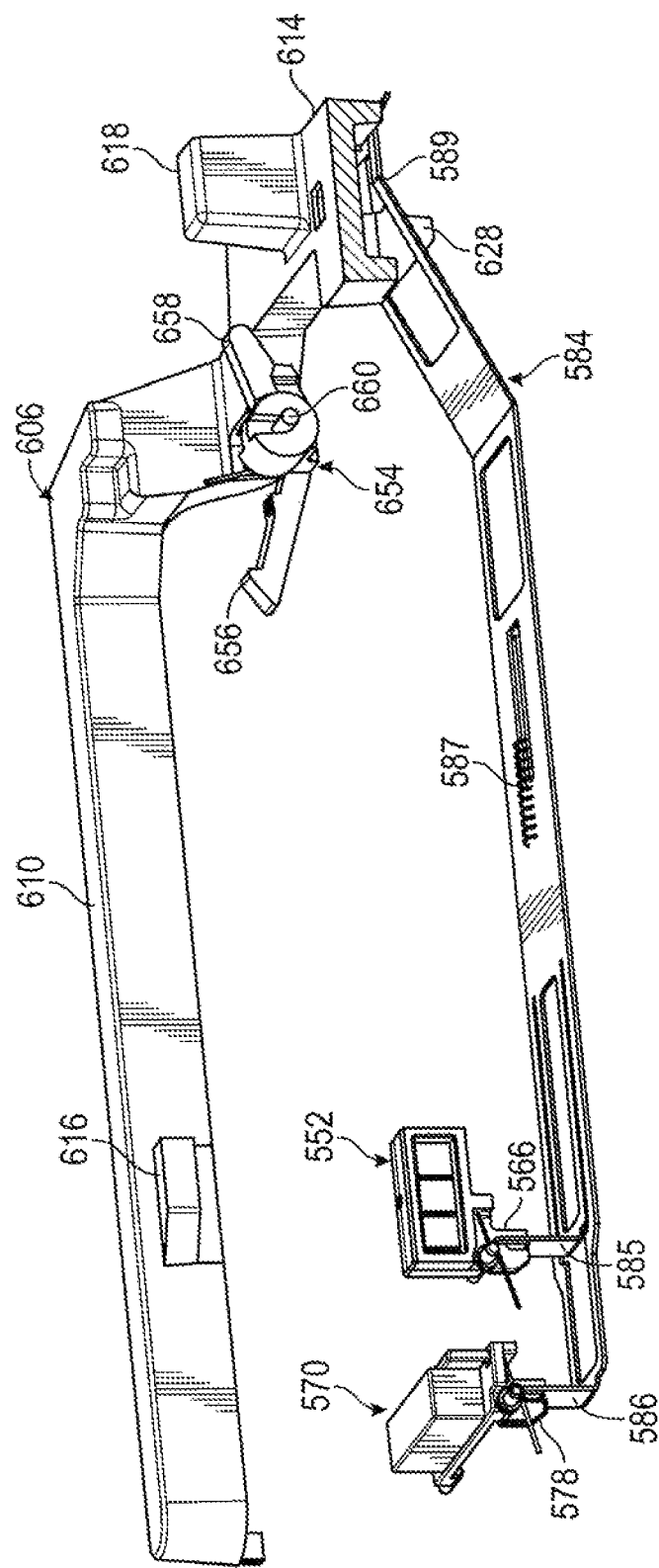
FIG. 48 is a perspective, cross-sectional view of the cam frame and a magnet actuator of the cartridge processing assembly.

Referring to FIGS. 43 and 48, which is a perspective cross-sectional view of the cam frame and a magnet actuator 584 of the cartridge processing assembly 470, a magnet actuator 584 is coupled to the cam frame 606 and is configured to rotate the cartridge magnet assembly 552 and the sample preparation magnet assembly 570 into their respective operative positions with respect to a multiplex cartridge when the cartridge is inserted in the cartridge carriage assembly. The magnet actuator 584 includes a spring 587 that biases the actuator to the left in FIG. 48. The magnet actuator 584 includes a vertical tab 585 configured to engage the actuator bracket 566 of the cartridge magnet assembly 552 and a vertical tab 586 configured to engage the actuator bracket 578 of the sample preparation magnet assembly 570. The magnet actuator 584 is coupled to the cam frame 606 by means of a magnet actuator hook 628 extending below the cross bar 614 and engaging a hook loop 589 formed in an end of the magnet actuator 584.

As noted above, before a multiplex cartridge 10 is inserted into the cartridge carriage assembly 650, the cam frame 606 is in a forward position. The magnet actuator 584 is biased forward (to the left) by the spring 587 so that the cartridge magnet assembly 552 and the sample preparation magnet assembly 570 are rotated clockwise to their retracted positions due to the force of their respective torsion springs 562, 576, respectively. In the present context, the retracted positions of the cartridge magnet assembly 552 and the sample preparation magnet assembly 570 positions in which the cartridge magnet assembly 552 and the sample preparation magnet assembly 570 do not apply a significant magnetic force to any portion of the multiplex cartridge 10. After the multiplex cartridge is inserted into the cartridge carriage assembly 650, the cam frame 606 is retracted by the cam frame motor 602 and the linear actuator 604 (to the right in FIG. 48) as described above. Retraction of the cam frame 606 causes the heating and control assembly 500 to be raised into contact with the multiplex cartridge 10, as the cam followers 590a, 590b of the support plate 502 move from the lower, right side horizontal segments of the cam slots 622a, 622b, up the angled transitions, and to the upper, left side horizontal segments of the cam slots 622a, 622b.

The magnet actuator 584 coupled to the cam frame 606 by the magnet actuator hook 628 also moves with the cam frame 606 to pull the magnet actuator 584 to the right in FIG. 48 against the bias of the spring 587. As the actuator bracket 584 is pulled by the moving cam frame 606, the vertical tab 585 engaging the actuator bracket 566 of the cartridge magnet assembly 552 rotates the magnet assembly 552 counterclockwise toward its upward, deployed position as shown in FIG. 48. Similarly, the vertical tab 586 of the actuator bracket 584 engaging the actuator bracket 578 of the cartridge magnet assembly 570 rotates the magnet assembly 570 counterclockwise toward its upward, deployed position as shown in FIG. 48. Due to the longitudinal extent of the upper horizontal segment of each of the cam slots 622a, 622b, the cam frame 606 and the cam rails 620a, 620b can move longitudinally with respect to the support plate 502, while the cam followers 590a, 590b are positioned in the upper horizontal segments, without changing the height position of the support plate 502 and the heating and control assembly 500 with respect to the multiplex cartridge that has been placed into the cartridge carriage assembly 650. In various embodiments, the magnet actuator bracket 584 is configured with respect to the cartridge magnet assembly 552 and the sample preparation magnet assembly 570 so that as the cam frame 606 moves (to the right) to raise the support plate 502 and the heating and control assembly 500, the magnet assemblies 552, 570 are not initially deployed (or are not fully deployed) when the support plate 502 and the heating and control assembly 500 are first raised into contact with the multiplex cartridge (i.e., when the cam followers 590a, 590b of the support plate 502 first reach the upper horizontal segments of the cam slots 622a, 622b). Further movement (to the right) of the cam frame 606 (which, due to the longitudinal extent of the upper horizontal segments of the cam slots 622a, 622b, will not change the position of the support plate 502 and the heating and control assembly 500 with respect to the cartridge carriage assembly 650 and the multiplex cartridge held therein) will further pull the magnet actuator bracket 584 to fully rotate the magnet assemblies 552, 570 (counterclockwise) into their fully deployed positions in contact or close proximity to the multiplex cartridge. Thus, with the support plate 502 and the heating and control assembly 500 maintained at the up position in contact with the multiplex cartridge, the magnet assemblies are configured for movement independently of the rest of the heating and control assembly 500 and the cam frame 606 can move longitudinally to effect selective deployment of the magnet assemblies 552, 570 in support of requirements to selectively apply or remove magnetic forces with respect to the multiplex cartridge held within the cartridge carriage assembly 650.

Also, as can be best seen in FIG. 48, when the cam frame 606 is advanced (to the left in FIG. 48) to lower the heating and control assembly 500 relative to the cartridge, the linear actuator connector 618 extending above the cross bar 614 contacts the lever 658 of the cartridge latch 654, thereby rotating the cartridge latch 654 counterclockwise to lower the hook 656 and disengage the hook 656 from the multiplex cartridge so that the multiplex cartridge can be ejected from the cartridge holder 652 by the cartridge ejector assembly 670.

Mixing Motor Assembly

Figure 50A:
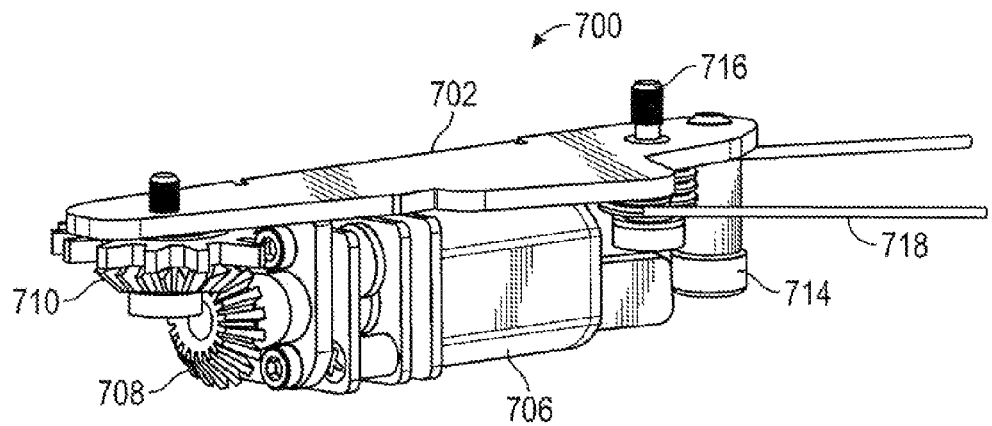
FIG. 50A is a perspective view of a mixing motor assembly of the cartridge processing assembly.
Figure 50B:
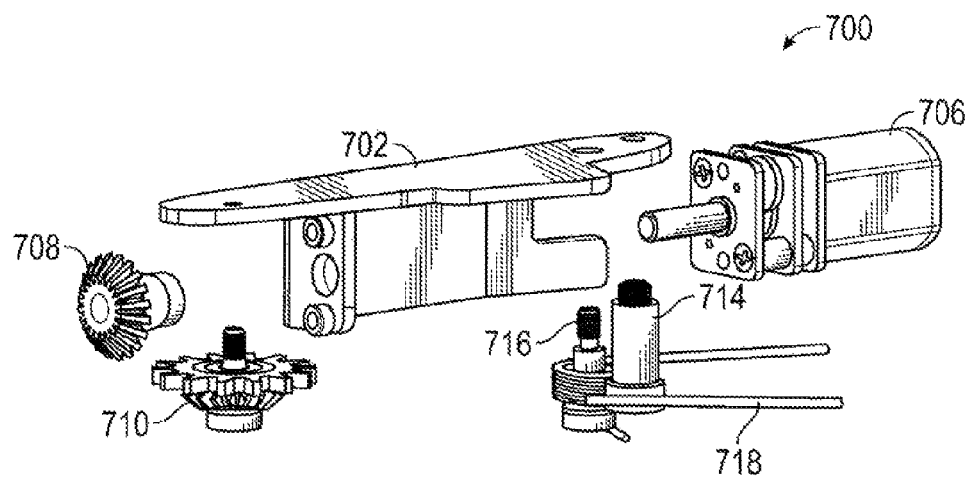
FIG. 50B is an exploded perspective view of the mixing motor assembly.

Details of the mixing motor assembly 700 are shown in FIGS. 50A and 50B. FIG. 50A is a perspective view of the mixing motor assembly 700, and FIG. 50B is an exploded perspective view of the mixing motor assembly 700.

The mixing motor assembly 700 includes a mixing motor bracket 702 to which is mounted a mixing motor 706. Suitable motors include the Pololu Micro Metal Gearmotor with a 150:1 gearbox and the Maxon, model DCX10L EB SL 4.5V with a 64:1 gearbox. Preferred characteristics of the motor include 100 rep at 12 oz-in torque, 3000 hrs. life at 45° C. operating environment and compact size (e.g., 10 mm width (diameter) and less than 25 mm long).

A beveled gear 708 is fixed to an output shaft of the motor 706. A bevel-spur gear 710 rotatably mounted to the mixing motor mounting bracket 702 is operatively coupled to the beveled gear 708 with the beveled gear teeth of the bevel-spur gear 706 engaged with the beveled gear teeth of the beveled gear 708. Thus, powered rotation of the beveled gear 708 about a horizontal axis of rotation corresponding to the output shaft of the motor 706 is converted to a rotation of the bevel-spur gear 710 about a vertical axis of rotation.

The mixing motor assembly 700 is pivotally connected to an underside of the blister plate 644 of the mounting plate 640 by means of a pivot screw 716 extending through the mixing motor bracket 702. A standoff 714 (comprising a threaded screw and a cylindrical sleeve disposed over a portion of the screw shaft) is attached to one end of the mounting bracket 702. A torsion spring 718 is coupled to the pivot screw 716 and biases the mixing motor assembly 700 inwardly relative to the sidewall 474 (see FIG. 42) so that the bevel-spur gear 710 engages the peripheral gear teeth 198 of the rotary mixer 192 (see FIG. 8) of the multiplex cartridge 10.

As shown in FIG. 48, the longitudinal spar 610 of the cam frame 606 includes a beveled block 616 extending inwardly from the longitudinal spar 610. As noted above, the mixing motor assembly 700 is biased to pivot inwardly relative to the side wall 474 and the longitudinal spar 610 due to the torsion spring 718. The beveled block 616 is positioned so as to engage the mixing motor assembly 700 when the cam frame 606 is in the forward position. Thus, when the cam frame 606 is in the retracted position to raise the heating and control assembly 500 into engagement with the multiplex cartridge 10 held in the cartridge carriage assembly 650, the mixing motor assembly 700 pivots inwardly under the force of the torsion spring 718 into engagement with the multiplex cartridge. As the cam frame 606 moves forwardly (to the left in FIG. 48) to lower the heating and control assembly 500 away from the multiplex cartridge held in the cartridge carriage assembly 650, the beveled block 616 contacts the standoff 714 of the mixing motor assembly 700 and pivots the mixing motor assembly outwardly (toward the longitudinal spar 610) against the bias of the torsion spring 718 to disengage the bevel spur gear 710 from the rotary mixer 192 of the multiplex cartridge 10. In one embodiment, the beveled block 616 contacts the standoff 714 to pivot the mixing motor assembly 700 out of engagement with the rotary mixer 192 before the actuator connector 618 of the cam frame 606 contacts the lever 658 of the cartridge latch 654 to lower the hook 656 and release the cartridge to be ejected by the cartridge ejector assembly 670.

Thus, when the cam frame 606 is in the forward position, the heating and control panel 500 is in the lowered position out of contact with the multiplex cartridge, the magnet assemblies 552, 570 rotate downwardly to their retracted positions away from the multiplex cartridge, the mixing motor assembly 700 is pivoted outwardly out of an engagement with the multiplex cartridge, and the multiplex cartridge latch 654 is pivoted so that the hook 656 disengages from the multiplex cartridge. Therefore, the multiplex cartridge is not contacted or otherwise engaged by any of the components of the multiplex cartridge processing assembly 470, and the multiplex cartridge 10 can be ejected by the cartridge ejector assembly 670.

Blister Compression Mechanism Assembly (Top Bay)

Figure 51:
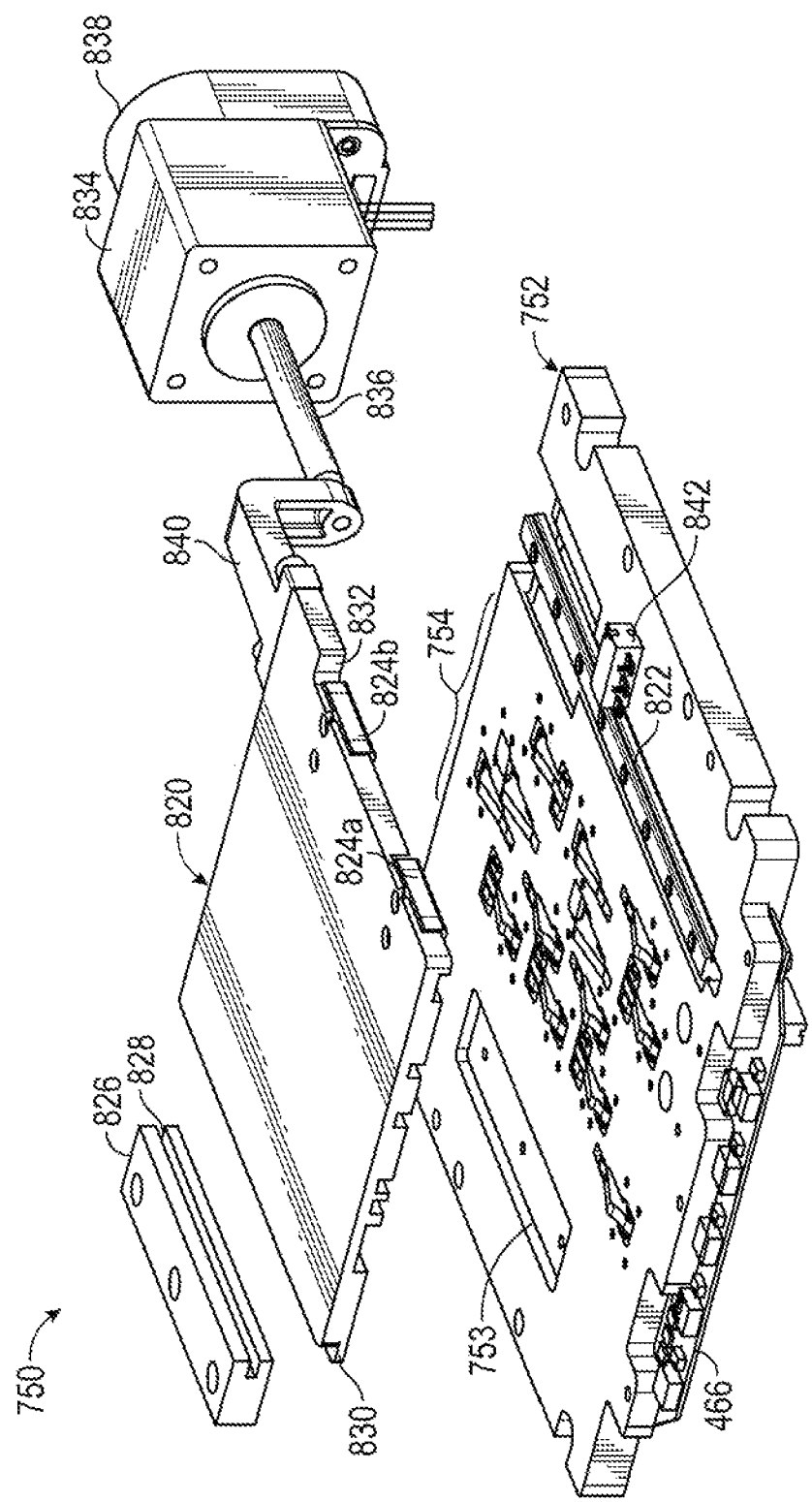
FIG. 51 is an exploded prospective view of a blister compression mechanism assembly of the processing bay.

Details of a blister compression mechanism assembly 750 are shown in FIG. 51; which is an exploded prospective view of the blister compression mechanism assembly 750. The assembly 750 comprises a cam arm plate 752 and an array 754 of cam arm-operative compression mechanisms operatively mounted within the cam arm plate 752. The cam arm plate 752 is mounted on top of the blister plate 644 of the mounting plate 640. The compression mechanisms of the array 754 comprise compression mechanisms configured to compress collapsible fluid compartments or blisters of the multiplex cartridge 10, compression mechanisms configured to compress lance blisters of the cartridge, and compression mechanisms configured to press down on and close active valve assemblies of the cartridge. The various compression mechanisms of the array 754 are aligned with blister holes 646 formed in the blister plate 644 so that the compression mechanisms of the array 754 can access the blisters and active valves of the multiplex cartridge 10 positioned below the blister plate 644 within the processing bay 440.

In various embodiments, the LED PCB 466 is attached to the cam arm plate 752.

The blister compression mechanism assembly 750 further includes a cam follower plate 820 mounted to the cam arm plate 752 for linear movement with respect to the cam arm plate. In various embodiments, one edge of the cam follower plate 820 is secured to a linear guide rail 822 attached to a top surface of the cam arm plate 752 by means of linear guide carriages 824*a* and 824*b* attached to the cam follower plate 820. An opposite edge of the cam follower plate 820 is secured against vertical movement by a hold down element 826 (or Z-axis constraint) mounted within a recess 753 formed in the cam arm plate 752, e.g., by suitable fasteners, and including a longitudinal slot 828 along one edge thereof which receives a stepped edge 830 of the cam follower plate 820. Suitable materials for construction of the hold down element include Delrin and brass. Accordingly, the cam follower plate 820 is fixed in the Z, or vertical direction or normal direction with respect to the plane of the cam arm plate 752, at a given space from the cam arm plate 752 and is allowed movement in a longitudinal direction corresponding to the longitudinal direction of the linear guide rail 822 and generally parallel to the plane of the cam arm plate 752 but is restricted from movement in any direction transverse to the linear guide rail 822.

Powered movement of the cam follower plate 820 with respect of the cam arm plate 752 is effected by a cam follower plate motor 834 attached by means of a linear actuator 836 to a drive bracket 840 that is attached to an edge of the cam follower plate 820. In various embodiments, the motor 834 further includes a rotary encoder 838 for providing precise control of and feedback from the motor 834. In various embodiments, the drive bracket 840 has an "L" shape with a first portion extending away from an attachment point to the cam follower plate 820 in a plane generally corresponding to the plane of the cam follower plate and a second portion extending downwardly in a direction that is generally normal to the plane of the cam follower plate. The linear actuator 836 is attached to the drive bracket 840 at a lower end of the second, downwardly-extending portion of the drive bracket 840. This configuration of the drive bracket 840 limits the amount by which the cam follower plate motor 834 extends above the cam follower plate 820, to thus maintain a slim profile of the processing bay 440.

In various embodiments, a sensor mechanism is provided for indicating when the cam follower plate 820 is in a particular, pre-defined position with respect to the cam arm plate 752. In one embodiment, the sensor mechanism may comprise a home switch 842 that is mounted to the cam arm plate 752 and is contacted by a home switch contact surface 832 of the cam follower plate 820 when the cam follower plate 820 has been moved to a home position relative to the cam arm plate 752.

In various embodiments, cam arm plate 752 includes two optical sensors 810, 812 positioned so as to correspond spatially to the locations of the inlet and outlet optical ports 14, 16, respectively (see FIG. 1). Sensors 810, 812 are constructed and arranged to detect (e.g., generate a signal) fluid flow through inlet optical sensing chamber 154 and outlet optical sensing chamber 158 of the sample preparation module 70 (see, e.g., FIG. 15). Optical sensors 810, 812 may be connected to and at least partially controlled by the LED PCB 466.

Compression Mechanism

Figure 52:
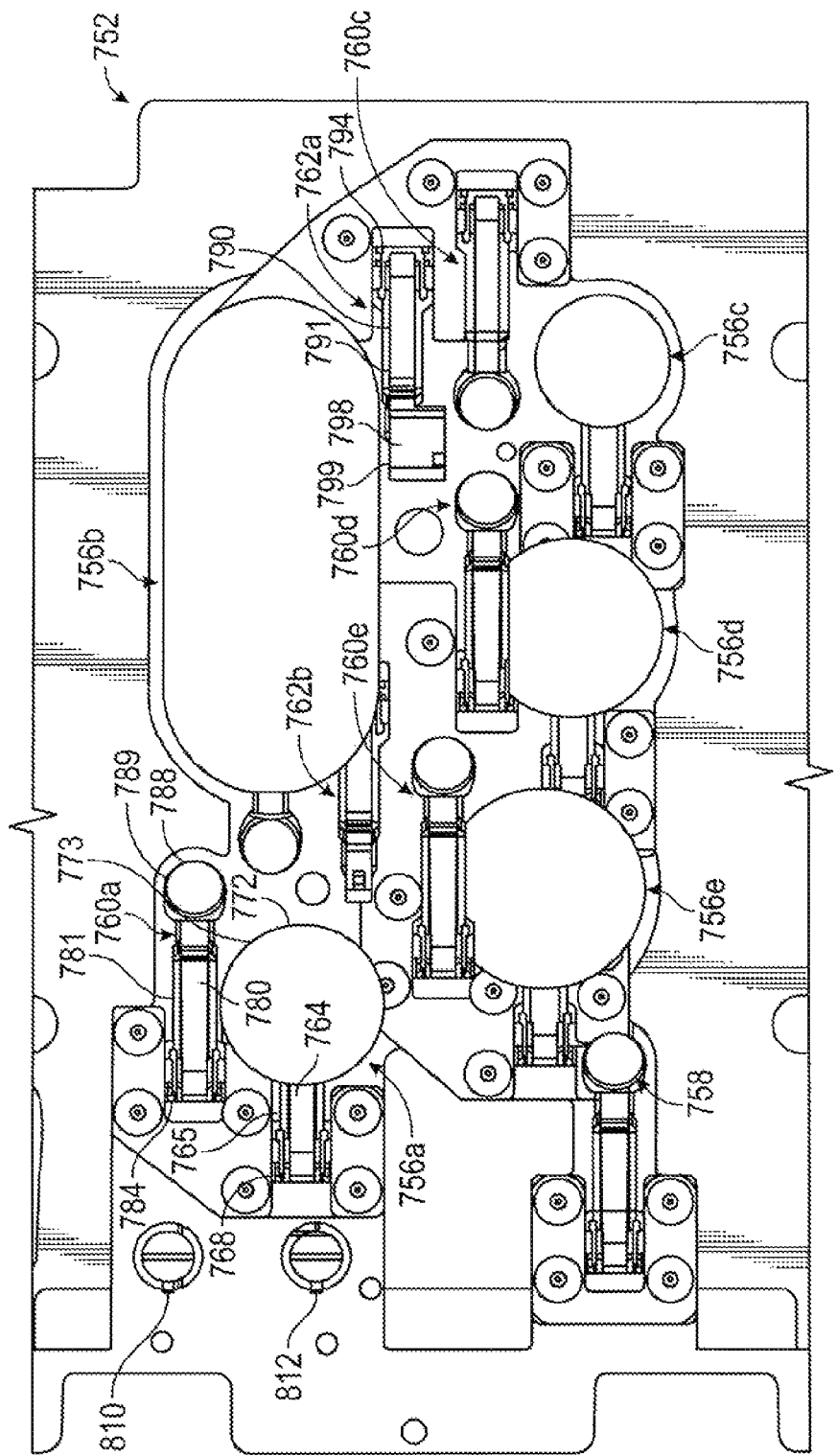
FIG. 52 is a partial bottom plan view of a cam arm plate showing compression pads of an array of compression mechanisms.
Figure 53:
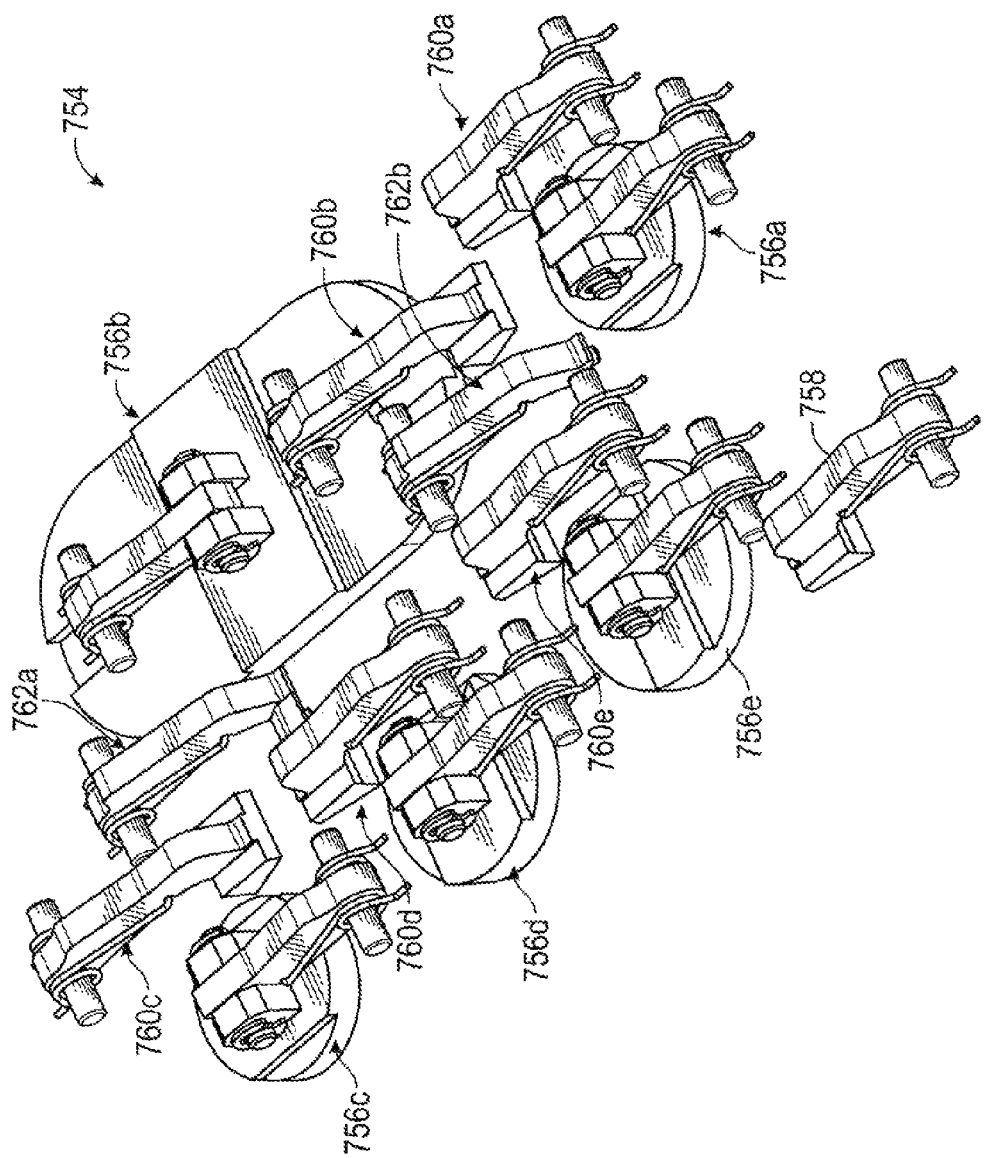
FIG. 53 is a top perspective view of the compression mechanisms of the array isolated from the cam arm plate.
Figure 54:
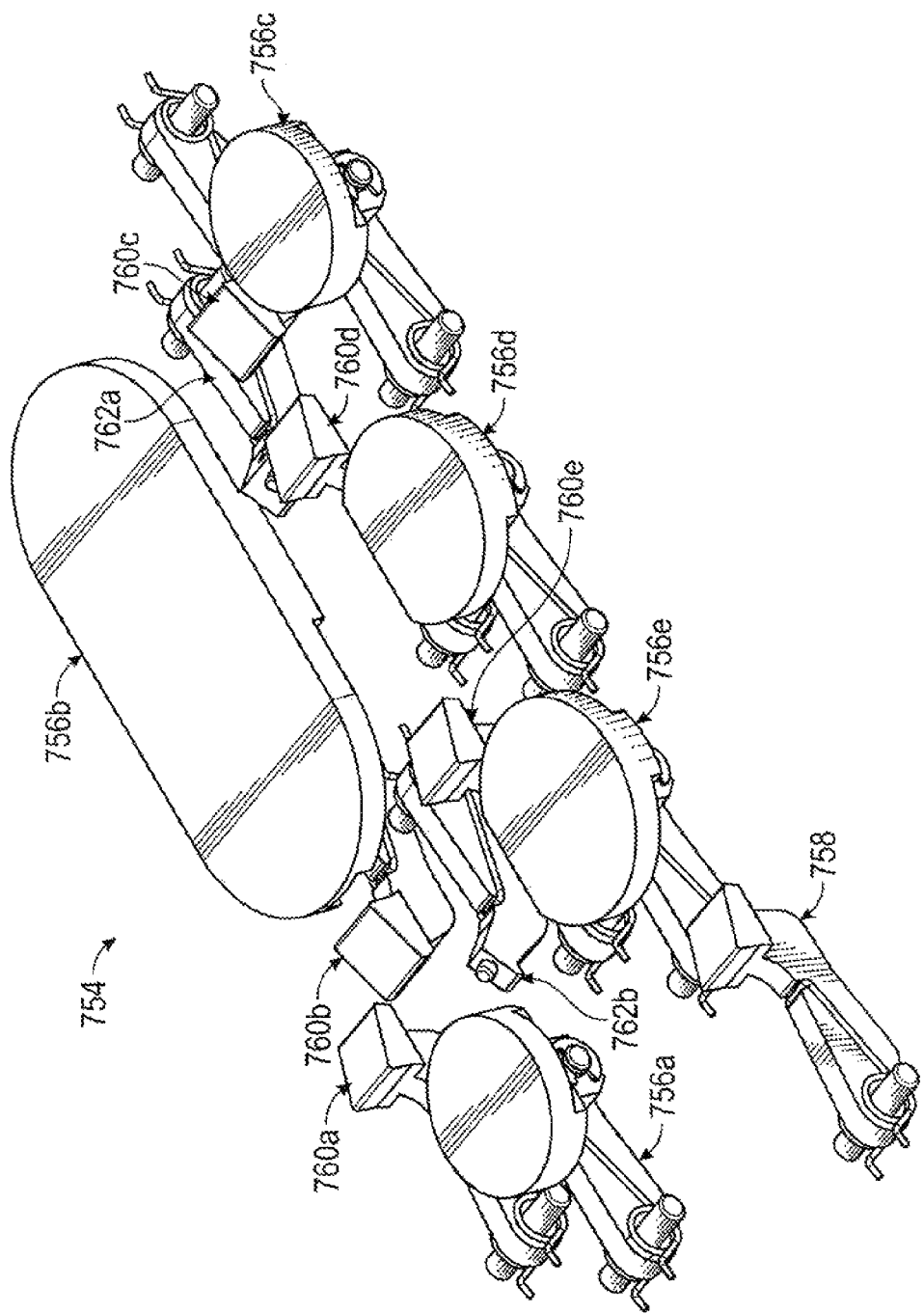
FIG. 54 is a bottom perspective view of the compression mechanisms of the array isolated from the cam arm plate.

Details of the compression mechanisms are shown in FIGS. 52, 53 and 54. FIG. 52 is a bottom partial plan view of the cam arm plate 752 showing compression pads of the array 754 of compression mechanisms. FIG. 53 is a top perspective view of the compression mechanisms of the array 754 isolated from the cam arm plate 752. FIG. 54 is a bottom perspective view of the compression mechanisms of the array 754 isolated from the cam arm plate 752.

The array 754 comprises a plurality of fluid blister compression mechanisms, each configured to, when actuated, apply a compressive force onto an associated deformable fluid blister and thereby compress the deformable blister. In the illustrated embodiment, there are five fluid blister compression mechanisms 756a, 756b, 756c, 756d, and 756e corresponding to the deformable fluid chambers 34a, 36a, 38a, 40a, and 42a, respectively, of the multiplex cartridge.

The array 754 further includes a plurality of lance blister compression mechanisms, each configured to, when actuated, apply a compressive force onto an associated lance blister that is associated with one of the deformable fluid blister and thereby compress the lance blister and lance the fluid seal within the lance blister. In the illustrated embodiment, there are five lance blister compression mechanisms 760a, 760b, 760c, 760d, and 760e corresponding to the lance blisters 34b, 36b, 38b, 40b, and 42b, respectively, of the multiplex cartridge.

The array 754 further includes a compression mechanism 758 having substantially the same configuration as a lance blister compression mechanism 760a-e and corresponding to blister 44 of the multiplex cartridge.

Figure 15:
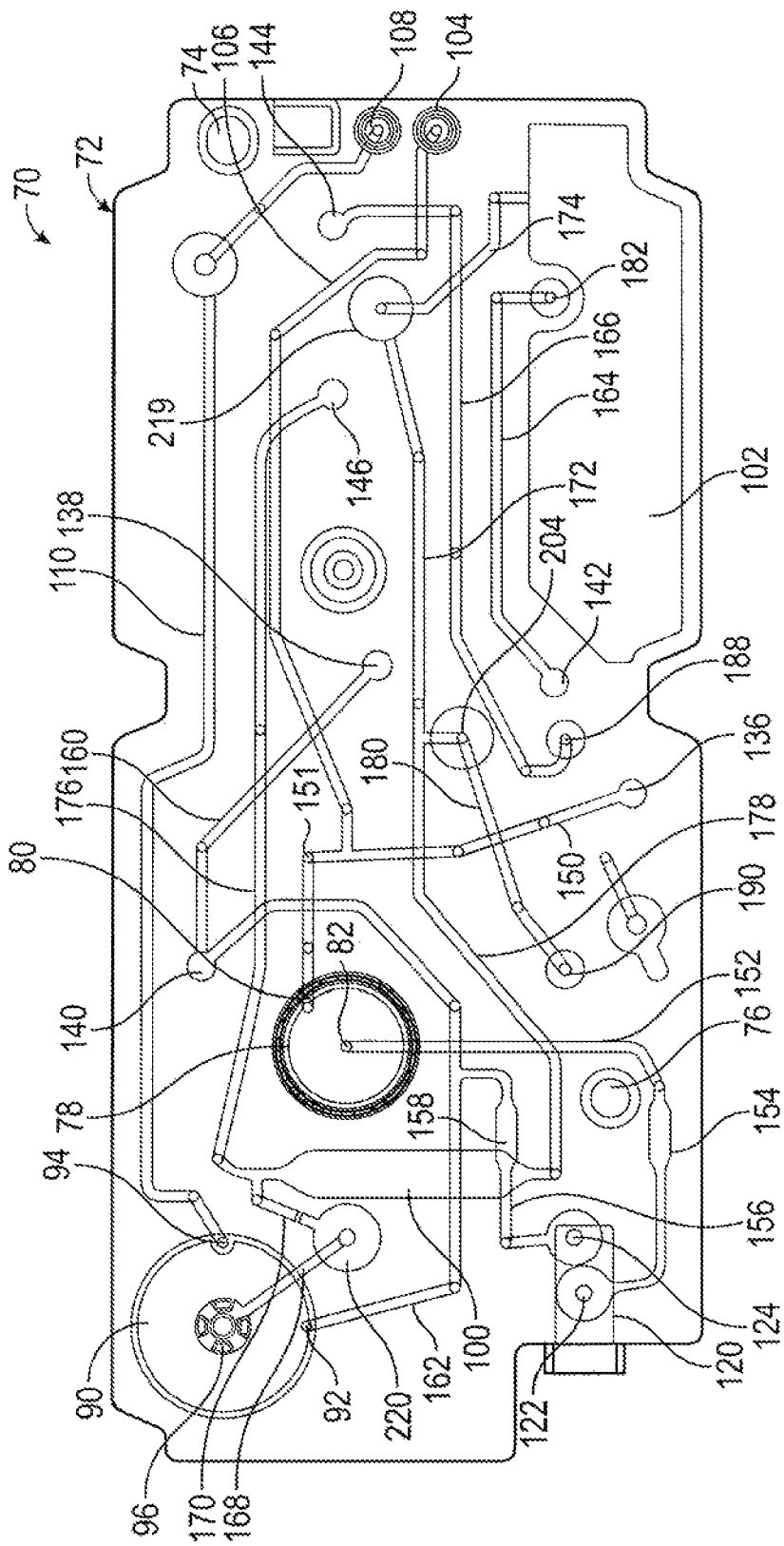
FIG. 15 is a top plan view of a sample preparation module of the multiplex cartridge.

The array 754 includes two valve actuator compression mechanisms 762a, 762b associated with sample valve assembly 204 and waste valve assembly 219, respectively (see FIG. 15). Each of the valve actuator compression mechanisms 762a, 762b is configured to, when actuated, apply a compressive force on the valve actuator tabs 20, 18 (see FIG. 1), respectively, and thus to actuate, and close, the active valves 219 and 204.

Details of the constructions of each of the various compression mechanisms are shown in FIGS. 53 and 54, as well as in FIGS. 55A, 55B, and 55C. FIG. 55A is an exploded perspective view of a single fluid blister compression mechanism. FIG. 55B is an exploded prospective view of a single lance blister compression mechanism. FIG. 55C is an exploded perspective view a valve actuator compression mechanism.

The blister compression mechanism assembly employs principles and concepts described in U.S. patent application Ser. No. 14/206,817 entitled "Apparatus and Methods for manipulating deformable fluid vessels" the contents of which are hereby incorporated by reference. In particular, the blister compression mechanism assembly is constructed and arranged to convert the horizontal movement of cam follower pate 820 into vertical, or partially vertical, movement of the compression mechanisms to compress a fluid blister, a lance blister, and a valve assembly without requiring pneumatic, electromechanical, or other components at larger distances above and/or below the multiplex cartridge 10 to thus maintain a slim profile of the processing bay 440.

Referring to FIG. 55A, each fluid blister compression mechanism, such as the fluid blister compression mechanism 756a, includes a cam arm 764 with a cam surface 766 formed along a top edge thereof. The cam arm 764 is mounted within the cam arm plate 752 for pivoting movement about an arm pivot pin 768 extending through a hole formed in one end of the cam arm 764. The cam arm 764 is disposed within a slot 765 formed in the cam arm plate 752, and the arm pivot pin 768 is mounted within the cam arm plate 752 transversely to that slot (see FIG. 52). A compression pad 772 is pivotally mounted to an opposite end of the cam arm 764 for pivoting movement about a pad pivot pin 774 extending through a hole formed in the opposite end of the cam arm 764. In various embodiments, the compression pad 772 is disposed within a blind recess 773 formed in a bottom surface of the cam arm plate 752 in a shape generally conforming to the shape of the compression pad 772 (see FIG. 52).

The fluid blister compression mechanism 756a is configured to pivot with respect to the cam arm plate 752 about the arm pivot pin 768 between a retracted position in which the compression mechanism is not applying pressure to the associated fluid blister and an extended, or deployed, position in which the compression mechanism is applying a compressive force onto the fluid blister. A torsion spring 770 biases the compression mechanism 756a into the retracted position. In the retracted position, the cam arm 764 is substantially disposed within the corresponding slot 765 formed in the cam arm plate 752 and the compression pad 772 is disposed within the pad recess 773 formed in the cam arm plate 752 so that the blister-contacting surface of the compression pad 772 is substantially flush with a surface of the cam arm plate 752. In the extended position, the cam arm 756 is rotated about the cam arm pivot pin 768 so that the compression pad 772 is extended beneath the cam arm plate 752 to compress and collapse the reagent blister disposed beneath the compression pad 772.

The cam surface 766 may include a convex bulge, or other feature, that, in various embodiments, extends above a top surface of the cam arm plate 752 (see FIG. 51, showing cam features of the cam arms of the array 754 of compression mechanisms extending above cam arm plate 752). When the cam surface 766 is engaged by a cam follower element moving relative to the cam arm 764 over the cam surface 766, the cam arm 764 is caused to pivot from the retracted position to the extended position as the cam follower moves over the convex bulge of the cam surface 766. As the cam follower element moves off the cam surface 766, the cam arm 764 returns to the retracted position under the force of the torsion spring 770.

The cam arm 764 is preferably made from a material having sufficient strength to withstand forces applied to it by a cam follower element pushing the cam arm 764 against a collapsible fluid blister and having suitable machinability. Suitable materials include steel for applications in which the cam follower element comprises a roller that rolls over the cam surface 766. For applications in which the cam follower element comprises a sliding (i.e., non-rolling) element that slides over the cam surface 766, suitable materials include low friction, low abrasion materials, such as nylon or a lubricant-impregnated material, such as oil-impregnated bronze.

In various embodiments, the construction and operation of the other fluid blister compression mechanisms, 756b, 756c, 756d, and 756e are substantially the same as that of the fluid blister compression mechanism 756a, although the size and shape of the compression pads (e.g., compression pad 772) may vary from one fluid blister compression mechanism to the next according to the size and shape of the fluid blister that is to be compressed by the compression mechanism.

Referring to FIG. 55B, each lance blister compression mechanism, such as the lance blister compression mechanism 760*a*, includes a cam arm 780 with a cam surface 782 formed along a top edge thereof. The cam arm 780 is mounted within the cam arm plate 752 for pivoting movement about an arm pivot pin 784 extending through a hole formed in one end of the cam arm 780. The cam arm 780 is disposed within a slot 781 formed in the cam arm plate 752, and the arm pivot pin 784 is mounted within the cam arm plate 752 transversely to that slot (see FIG. 52). A compression pad 788 is formed or positioned on an opposite end of the cam arm 780. In various embodiments, the compression pad 788 is disposed within a blind recess 789 formed in a bottom surface of the cam arm plate 752 in a shape generally conforming to the shape of the compression pad 788 (see FIG. 52).

The lance blister compression mechanism 760*a* is configured to pivot with respect to the cam arm plate 752 about the arm pivot pin 784 between a retracted position in which the compression mechanism is not applying pressure to the associated lance blister and an extended, or deployed, position in which the compression mechanism is applying a compressive force onto the lance blister. A torsion spring 786 biases the compression mechanism 760*a* into the retracted position. In the retracted position, the cam arm 780 is substantially disposed within the corresponding slot 781 formed in the cam arm plate 752 and the compression pad 788 is disposed within the pad recess 789 formed in the cam arm plate 752 so that the blister-contacting surface of the compression pad 788 is substantially flush with a surface of the cam arm plate 752. In the extended position, the cam arm 780 is rotated about the cam arm pivot pin 784 so that the compression pad 788 is extended beneath the cam arm plate 752 to compress and collapse the lance blister disposed beneath the compression pad 788.

The cam surface 782 may include a convex bulge, or other feature, that, in various embodiments, extends above a top surface of the cam arm plate 752 (see FIG. 51, showing cam features of the cam arms of the array 754 of compression mechanisms extending above the cam arm plate 752). When the cam surface 782 is engaged by a cam follower element moving relative to the cam arm 780 over the cam surface 782, the cam arm 780 is caused to pivot from the retracted position to the extended position as the cam follower moves over the convex bulge of the cam surface 782. As the cam follower element moves off the cam surface 782, the cam arm 780 returns to the retracted position under the force of the torsional spring 786.

The cam arm 780 is preferably made from a material having sufficient strength to withstand forces applied to it by a cam follower element pushing the cam arm 780 against a collapsible lance blister and having suitable machinability. Suitable materials include steel for applications in which the cam follower element comprises a roller that rolls over the cam surface 782. For applications in which the cam follower element comprises a sliding (i.e., non-rolling) element that slides over the cam surface 782, suitable materials include low friction, low abrasion materials, such as nylon or a lubricant-impregnated material, such as oil-impregnated bronze.

In various embodiments, the construction and operation of the other lance blister compression mechanisms, 760*b*, 760*c*, 760*d*, and 760*e*, and the compression mechanism 758, are substantially the same as that of the lance blister compression mechanism 760*a*.

Referring to FIG. 55C, each valve actuator compression mechanism, such as valve actuator compression mechanism 762*a*, includes a cam arm 790 with a cam surface 792 formed along a top edge thereof. The cam arm 790 is mounted within the cam arm plate 752 for pivoting movement about an arm pivot pin 794 extending through a hole formed in one end of the cam arm 790. The cam arm 790 is disposed within a slot 791 formed in the cam arm plate 752, and the arm pivot pin 794 is mounted within the cam arm plate 752 transversely to that slot (See FIG. 52). A contact pad 798 is formed or positioned on an opposite end of the cam arm 790. In various embodiments, the contact pad 798 is disposed within a blind recess 799 formed in a bottom surface of the cam arm plate 752 in a shape generally conforming to the shape of the contact pad 798 (see FIG. 52).

In various embodiments, the contact pad 798 may further include a contact pin, or point, 800 projecting from the contact pad 798. The contact point is configured to engage a small dimple or depression formed in the top surface of the valve actuator tab 18 or 20 when the valve actuator compression mechanism is pressing against the tab to prevent the compression mechanism from slipping off the valve actuator tab. Also, in various embodiments, a portion of the contact pad 798, and the contact pin 800, may be offset from the cam arm 690 to accommodate space and orientation limitations within the array 754 of compression mechanisms.

The valve actuator compression mechanism 762*a* is configured to pivot with respect to the cam arm plate 752 about the arm pivot pin 794 between a retracted position in which the compression mechanism is not applying pressure to the associated valve actuator tab and active valve assembly and an extended, or deployed, position in which the compression mechanism is applying a compressive force onto the actuator tab and valve assembly. A torsion spring 796 biases the compression mechanism 762*a* into the retracted position. In the retracted position, the cam arm 790 is substantially disposed within the corresponding slot 791 formed in the cam arm plate 752 and the contact pad 798 is disposed within the pad recess 799 formed in the cam arm plate 752 so that the contact surface of the contact pad 798 is substantially flush with a surface of the cam arm plate 752. In the extended position, the cam arm 790 is rotated about the cam arm pivot pin 794 so that the contact pad 798 is extended beneath the cam arm plate 752 to deflect the valve actuator tab downwardly and close the associated valve assembly disposed beneath the valve actuator tab.

The cam surface 792 may include a convex bulge, or other feature, that, in various embodiments, extends above a top surface of the cam arm plate 752 (see FIG. 51, showing cam features of the cam arms of the array 754 of compression mechanisms extending above the cam arm plate 752). When the cam surface 792 is engaged by a cam follower element moving relative to the cam arm 790 over the cam surface 792, the cam arm 790 is caused to pivot from the retracted position to the extended position as the cam follower moves over the convex bulge of the cam surface 792. As the cam follower element moves off the cam surface 982, the cam arm 790 returns to the retracted position under the force of the torsion spring 796.

The cam arm 790 is preferably made from a material having sufficient strength to withstand forces applied to it by a cam follower element pushing the cam arm 790 against a valve assembly and having suitable machinability. Suitable materials include steel for applications in which the cam follower element comprises a roller that rolls over the cam surface 792. For applications in which the cam follower element comprises a sliding (i.e., non-rolling) element that slides over the cam surface 792, suitable materials include low friction, low abrasion materials, such as nylon or a lubricant-impregnated material, such as oil-impregnated bronze.

In various embodiments, the construction and operation of the other valve actuator compression mechanism 762b are substantially the same as that of the valve actuator compression mechanism 762a.

Figure 56:
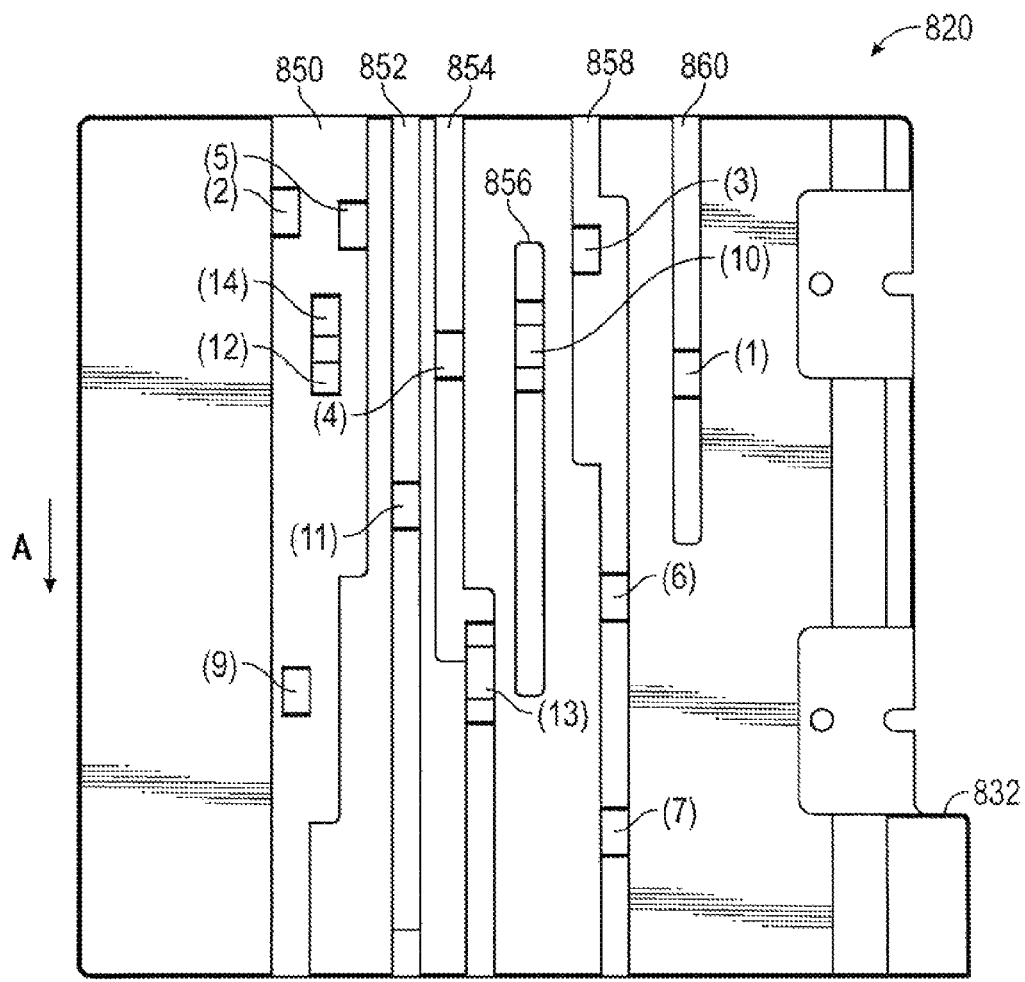
FIG. 56 is a bottom plan view of a cam follower plate of the blister compression mechanism assembly.
Figure 57:
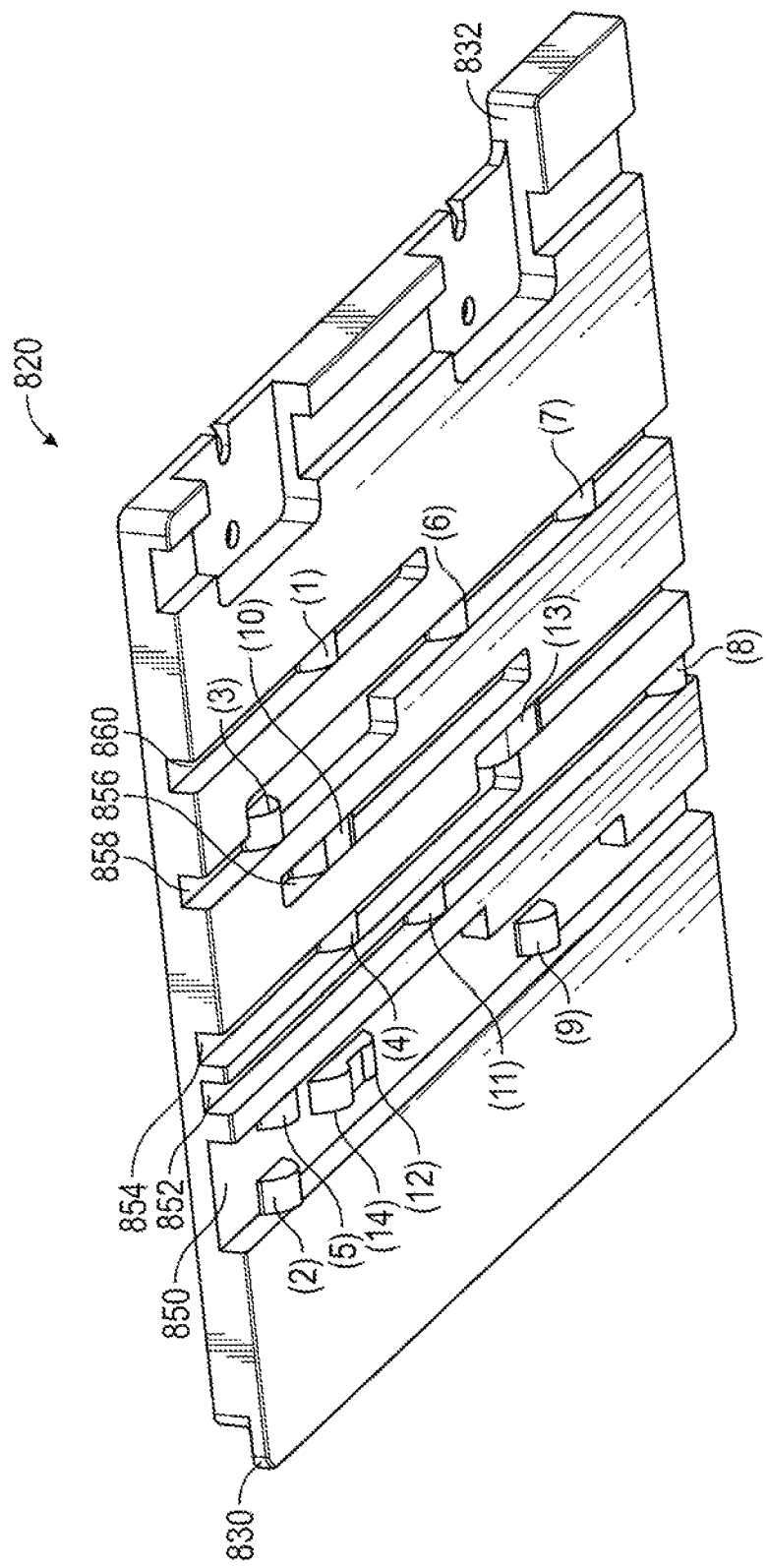
FIG. 57 is a bottom perspective view of the cam follower plate.

Details of the cam follower plate 820 are shown in FIGS. 56 and 57. FIG. 56 is a bottom plain view of the cam follower plate 820, and FIG. 57 is a bottom perspective view of the cam follower plate 820.

The cam follower plate 820 includes a number of generally parallel, longitudinal cam grooves 850, 852, 854, 856, 858 and 860. Each of the grooves 850-860 of the cam follower plate 820 receives a portion of one or more the cam arms 764, 780, 790 of the compression mechanisms of the array 754. In addition, each groove 850-860 includes one or more cam follower elements, e.g., in the form of ribs or rollers formed or positioned at discreet positions along the corresponding groove.

The cam follower plate 820, as noted above, is configured for linear movement relative to the cam arm plate 752 in a plane that is parallel to the cam arm plate 752. As the cam follower plate 820 moves relative to the cam arm plate 752, when a cam follower element within a cam groove encounters the cam surface of the cam arm of the compression mechanism (e.g., cam surface 766, 782, or 792 of cam arms 764, 780, or 790, respectively), the cam arm is pushed downwardly, pivoting about its respective arm pivot pin (e.g., pivot pin 768, 784, or 794) to cause the compression mechanism to compress the blister (e.g., compressible fluid blister or lance blister) or press the active valve assembly disposed beneath that compression mechanism.

During movement of the cam follower plate 820 with respect to the cam arm plate 852, the relative locations of the compression mechanisms of the array 754 of compression mechanisms and the cam follower ribs formed in the grooves 850, 852, 854, 856, 858, and 860 define the sequence in which the compression mechanisms are actuated.

Software and Hardware

As generally and specifically describe above, aspects of the disclosure are implemented via control and computing hardware components, user-created software, data input components, and data output components. Hardware components include computing and control modules (e.g., system controller(s)), such as microprocessors and computers, configured to effect computational and/or control steps by receiving one or more input values, executing one or more algorithms stored on non-transitory machine-readable media (e.g., software) that provide instruction for manipulating or otherwise acting on the input values, and output one or more output values. Such outputs may be displayed or otherwise indicated to a user for providing information to the user, for example information as to the status of the instrument or a process being performed thereby, or such outputs may comprise inputs to other processes and/or control algorithms. Data input components comprise elements by which data is input for use by the control and computing hardware components. Such data inputs may comprise positions sensors, motor encoders, as well as manual input elements, such as graphic user interfaces, keyboards, touch screens, microphones, switches, manually-operated scanners, voice-activated input, etc. Data output components may comprise hard drives or other storage media, graphic user interfaces, monitors, printers, indicator lights, or audible signal elements (e.g., buzzer, horn, bell, etc.).

Software comprises instructions stored on non-transitory computer-readable media which, when executed by the control and computing hardware, cause the control and computing hardware to perform one or more automated or semi-automated processes.

Sample Preparation Process

An exemplary sample preparation process that may be performed in the sample preparation module 70 is described and illustrated in FIGS. 16-23. Persons of ordinary skill will recognize that sample preparation processes other than that described herein—e.g., reordering of the steps from what is described herein, the omission of certain steps described herein, and/or addition of certain steps—may be performed with the sample preparation module or a modified version of the sample preparation module.

Figure 16:
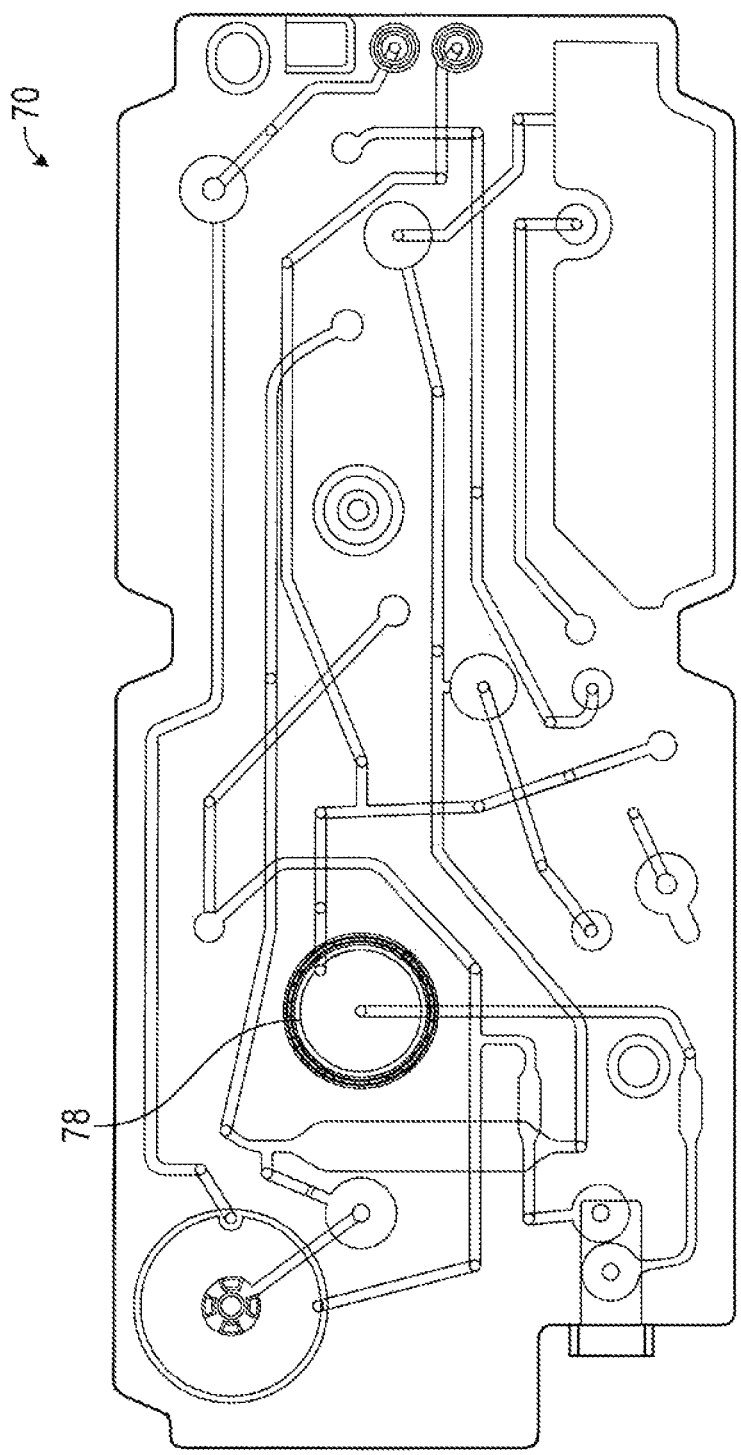
FIGS. 16-23 show top plan views of the sample preparation module, each showing a different step of a sample preparation process performed within the module.

In a first step, illustrated in FIG. 16, a fluid sample specimen is dispensed into the sample well 78. In general, the multiplex cartridge 10 is designed to process liquid or solid samples. Liquid samples may include blood, serum, plasma, urine, saliva, cerebral spinal fluid, lymph, perspiration, semen or epithelial samples such as cheek, nasopharyngeal, anal or vaginal swabs to which lysis buffer has been added to resuspend the cells. Solid samples, such as feces or tissue samples (e.g. tumor biopsies), generally need to be resuspended and diluted in a buffer, e.g., the Cary Blair transport medium. The sample well 78 may then be closed using the sample cap 84 (see FIG. 6), and the multiplex cartridge 10 is then placed in a processing instrument (e.g., into the processing bay 440 of the processing module 410 of the instrument 400).

Figure 17:
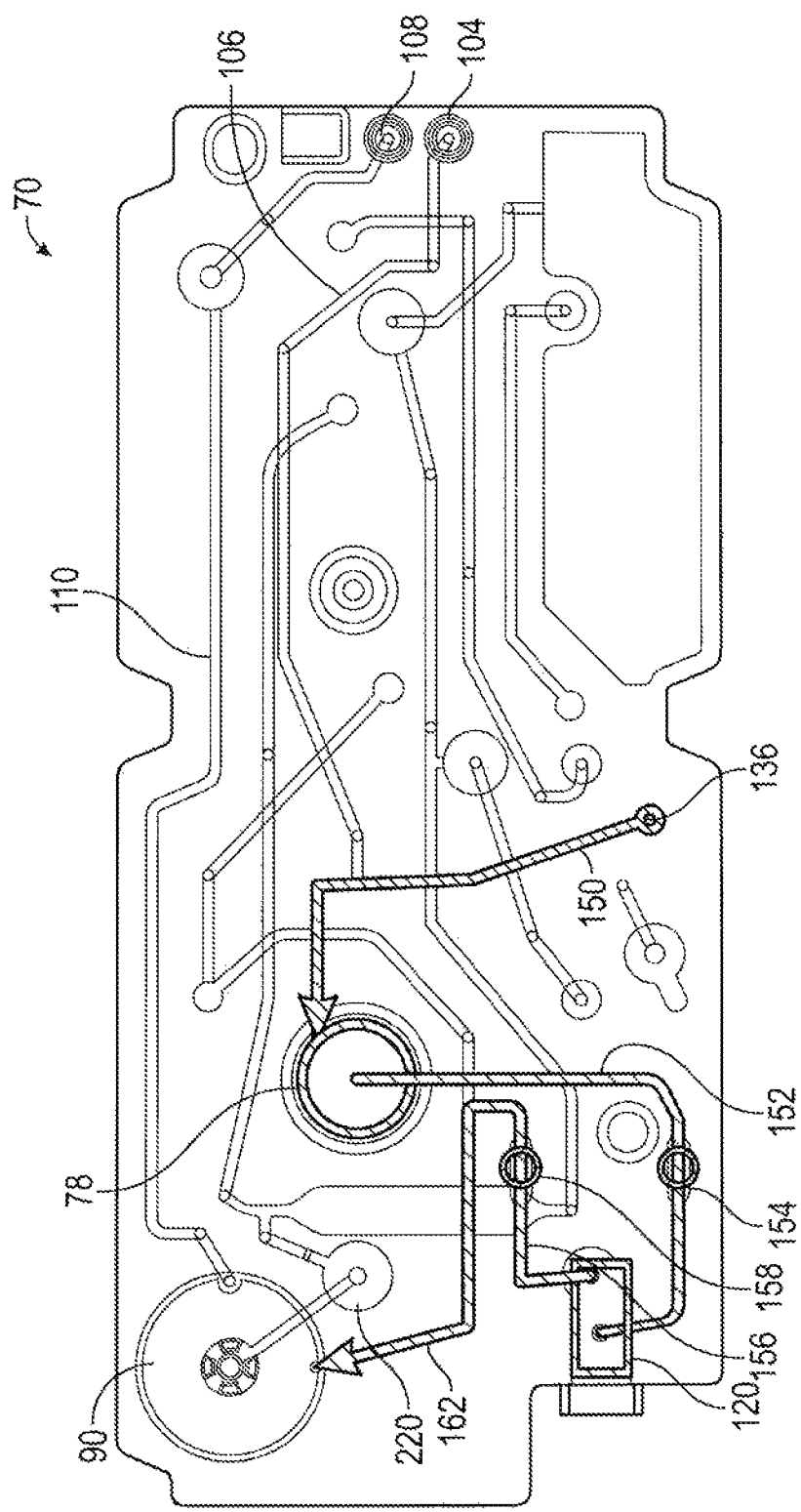

In a first step performed within the instrument, as illustrated in FIG. 17, the lance blister 34b associated with the deformable compartment 34a is compressed by an external actuator (e.g., the compression mechanism 760a) to press a bead or other opening device through a closing seal (i.e., lance the seal with the bead or other device), and then the deformable compartment 34a is compressed by an external actuator (e.g., the compression mechanism 756a) to force a process fluid contained therein into the first inlet port 136 formed in the substrate 72. In one embodiment, the process fluid contained in the deformable compartment 34a is a lysis buffer. The fluid is directed by the first fluid channel 150 from the inlet port 136 to the sample well 78, where the fluid enters the sample well 78 through the inlet snorkel 80. In addition, an external pump (e.g., pump 458) connected to the sample preparation module 70 at the pump port 104 generates pressure that is applied to the contents of the sample well 78 via the pressure conduit 106.

The pressure generated by compressing the deformable compartment 34a and the pressure applied at pressure conduit 106 pushes the fluid contents—comprising the fluid sample and the contents of the deformable compartment 34a—from the sample well 78 through the second fluid channel 152 to the lysis chamber inlet 122. The fluid continues to flow through the lysis chamber, exiting the outlet 124, where it is directed by the third fluid channel 156 and a portion of the fifth fluid channel 162 into the mixing well 90. As the fluid stream first enters or exits the lysis chamber 120 and passes through the inlet optical sensing chamber 154 or the outlet optical sensor chamber 158, it is detected through the associated optical port 14 or 16 formed in the upper shroud 12 (see FIG. 1) by an optical detector (e.g., optical detector(s) mounted in LED PCB 466). A signal from the optical detector indicating fluid flow (e.g., an air-fluid interface) through the inlet or outlet optical sensing chamber 154 or 158 activates the motor 128 of the lysis chamber mixer to disrupt the fluid flowing through the lysis chamber 120 with lysis beads contained within the lysis chamber 120. The motor 128 continues to operate until a signal from an optical detector indicating the end fluid flow through the inlet or outlet optical sensing chamber 154 or 158—and thus the end of flow through the lysis chamber 120, deactivates the motor 128.

As the fluid mixture is flowing into the mix compartment 90, the passive valve port 108 remains open so that pressure within the mixing well 90 does not rise to a level that will open the passive valve assembly 220. Thus, at the conclusion of the step illustrated in FIG. 17, the mixing well 90 will contain a mixture of fluid sample and the contents of the deformable compartment 34*a* (e.g., a lysis buffer) which has been physically lysed by the lysis mixer and lysis beads contained in the lysis chamber 120.

Figure 18:
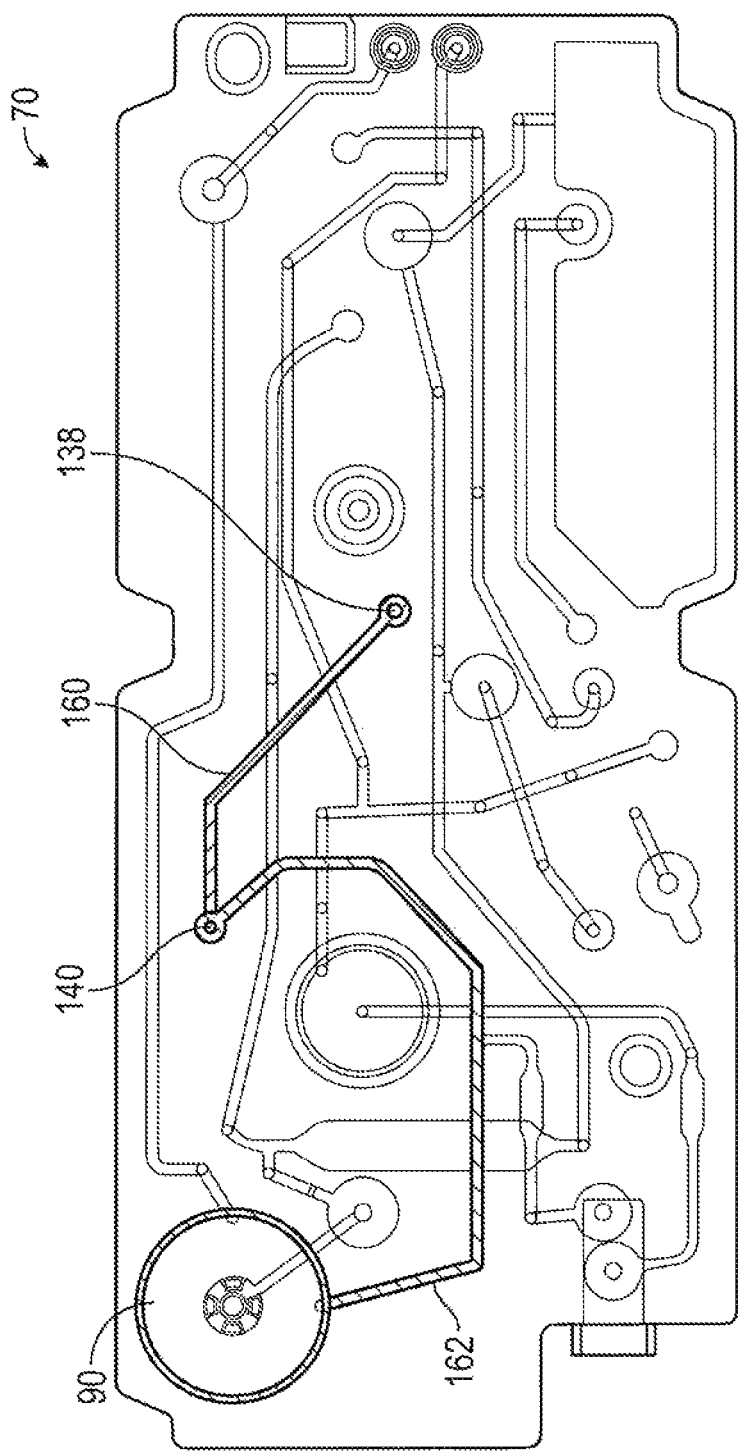

Referring now to FIG. 18, after the step shown in FIG. 17, the pneumatic pump applying pressure at pressure port 104 is turned off, e.g., after a prescribed period of operation, and the third deformable compartment 44 is compressed by an external actuator (e.g., the compression mechanism 758) to force the contents of the deformable compartment 44 into the third inlet port 140. In one embodiment, the contents of the deformable compartment 44 comprise magnetic target capture beads.

Next, the lance blister 36*b* associated with the deformable compartment 36*a* is compressed by an external actuator (e.g., the compression mechanism 760*e*) to press a bead or other opening device through a closing seal (i.e., lance the seal with the bead or other device), and then the deformable compartment 36*a* is compressed by an external actuator (e.g., the compression mechanism 756*e*) to force a process fluid contained therein into the second inlet port 138 formed in the substrate 72. The process fluid then flows through the fourth fluid channel 160 and the fifth fluid channel 162 to the mixing well 90. The contents of the deformable compartment 36*a* may comprise a binding buffer for facilitating the binding of the target capture beads to the target analyte(s). The flowing fluid past the third inlet port 140, under the pressure generated by the compression of the deformable compartment 36*a*, transports the fluid contents of the deformable compartment 36*a* and the contents of the deformable compartment 44 through the fifth fluid channel 162 to the mixing well 90.

As noted above, in an alternate embodiment, the magnetic beads may be provided in the form of a lyophilized pellet contained within the mixing well 90, and the deformable compartment 44, the associated external actuator (e.g., the compression mechanism 758), and the step of bursting the deformable compartment 44 may be omitted.

After the step illustrated in FIG. 18 is completed, the rotary mixer 192 within the mixing well 90 may be activated (e.g., by the mixing motor assembly 700) to stir the contents of the mixing well 90. In various embodiments, a lyophilized or other dried reagent form may be pre-positioned in the mixing well 90 and is dissolved or reconstituted by the fluids transported into the mixing well 90. The rotary mixer 192 helps facilitate the dissolution or reconstitution of the dried reagent and mixes all the materials contained in the mixing well to form a homogeneous fluid mixture.

Figure 19:
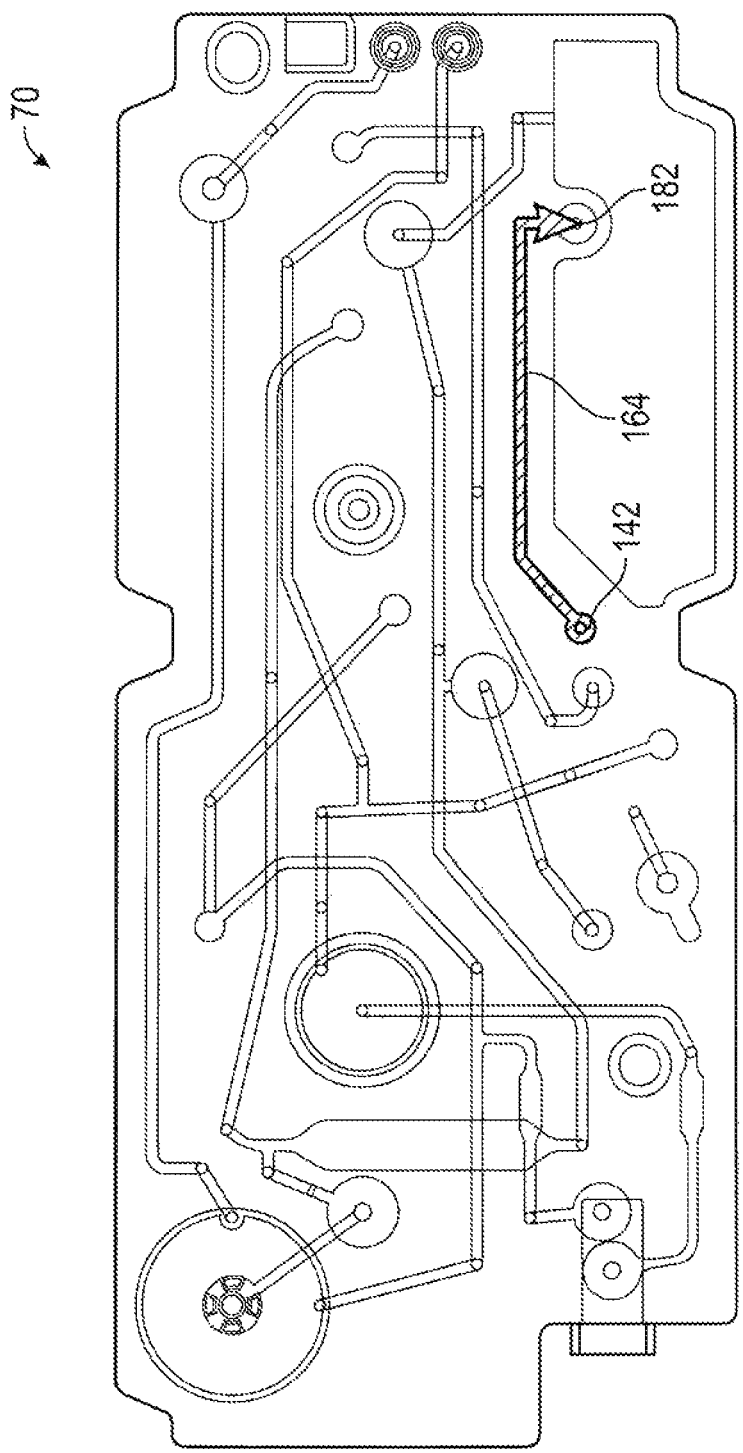

Referring to FIG. 19, a next step comprises collapsing the lance blister 38*b* (e.g., with the compression mechanism 760*b*) associated with the deformable compartment 38*a* to thereby open the compartment to the fourth inlet port 142. The deformable compartment 38*a* is then collapsed (e.g., with the compression mechanism 756*b*) to direct the fluid contents thereof into the fourth inlet port 142, through the sixth fluid channel 164 and to the first outlet port 182, where the fluid exits the sample preparation module 70. The first outlet port 182 is in communication with the inlet port 252 of the reaction module 240 as explained above. The fluid contained in the deformable compartment 38*a* may comprise an immiscible fluid, e.g., an oil, which is used to fill a reaction space 295 within the reaction module 240 between the top plate 241 and the fluidic processing panel 354, as shown in FIG. 30.

Figure 20:
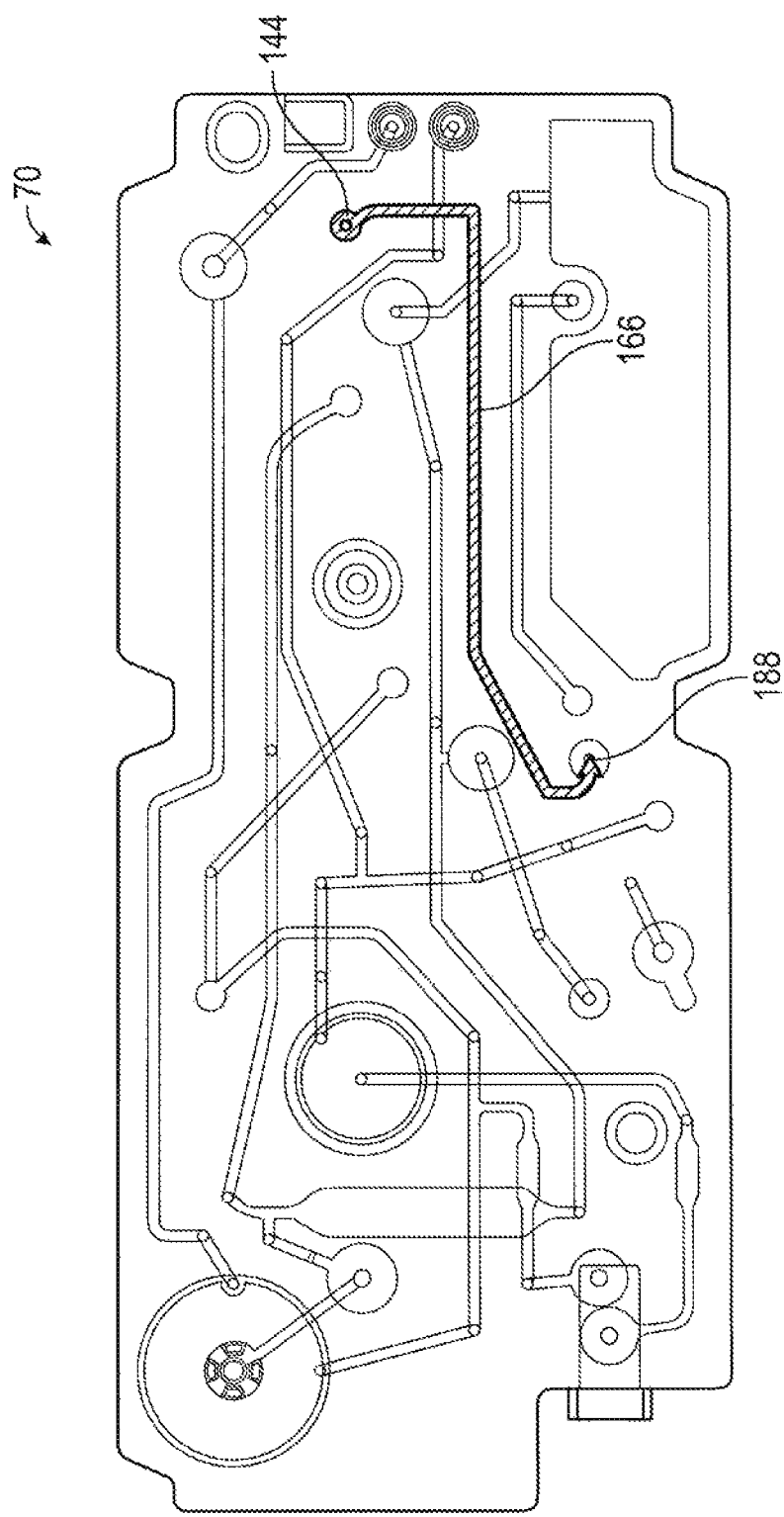

Referring now to FIG. 20, the lance blister 40*b* associated with the deformable compartment 40*a* is collapsed by an external actuator (e.g., the compression mechanism 760*c*) to open the compartment to the fifth inlet port 144, and then the deformable compartment 40*a* is collapsed by an external actuator (e.g., the compression mechanism 756*c*) to force the fluid contents thereof into the fifth inlet port 144. The fluid contents flow from the fifth inlet port 144 to a second outlet 188 via a seventh channel fluid 166. In one embodiment, the fluid content of the deformable compartment 40*a* comprises a rehydration or elution buffer that flows from the second exit port 188 into the rehydration buffer compartment 276 of the reaction module 240 via inlet 278, as shown in FIG. 31 and described above. The same buffer solution contained in the deformable compartment 40*a* may be used for both rehydration of dried or lyophilized reagents or other substances or for elution of nucleic acid or other target analyte from a substrate with which it is bound.

Figure 21:
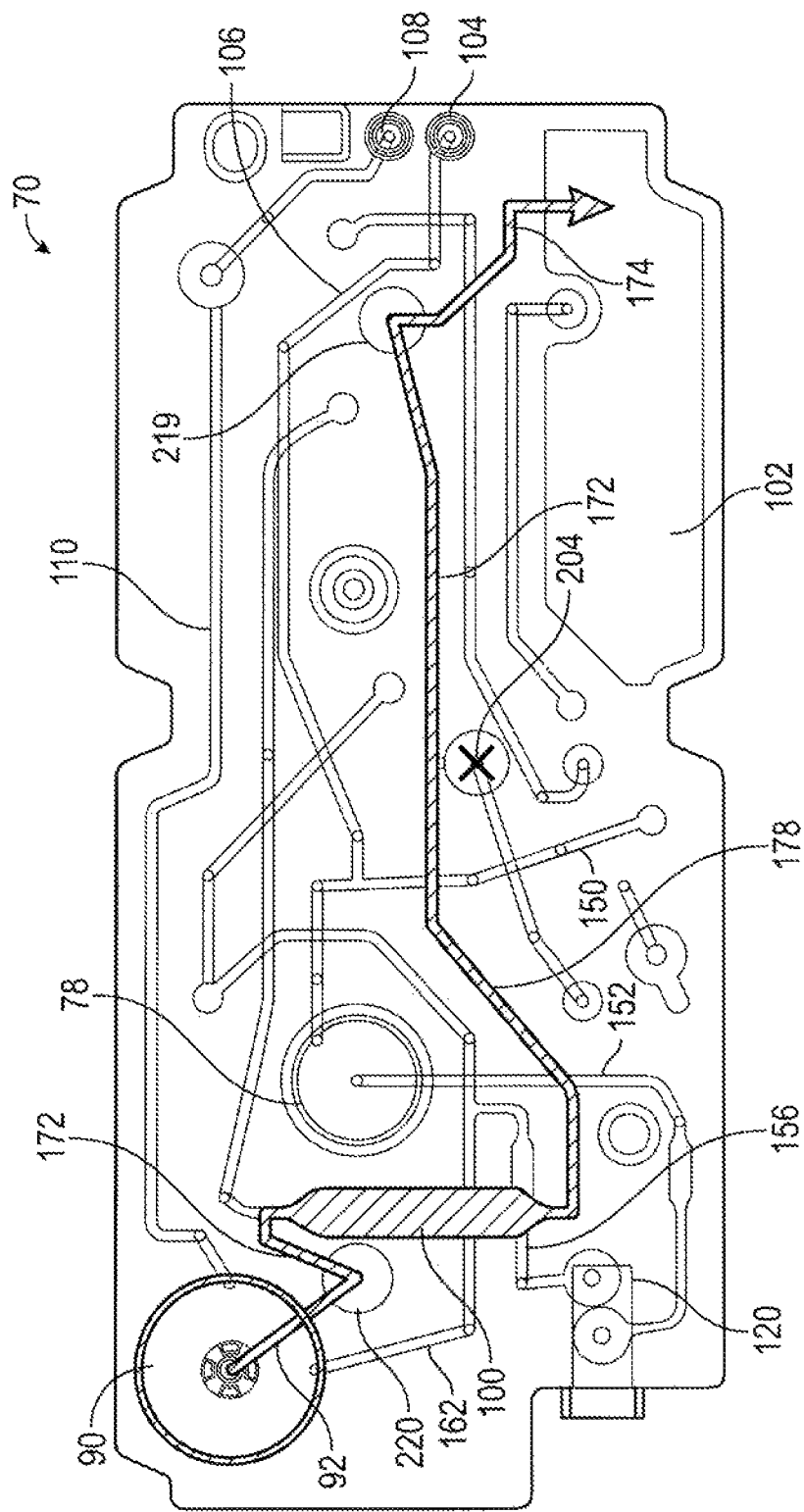

Referring now to FIG. 21, in a next step, the active valve assembly 204 is closed by an external actuator (e.g., the valve actuator 762*b*) pressing down on the valve. The pneumatic pump coupled to the pump port 104 is activated to pressurize the mixing well 90 via the pressure conduit 106, a portion of the first fluid channel 150, the second fluid channel 152, the third fluid channel 156, and a portion of the fifth fluid channel 162. At the same time, the passive valve port 108 is closed to allow a pressure buildup in the mixing well 90 that will actuate the passive valve assembly 220, thereby opening the passive valve 220 to allow fluid contents of the mixing well 90 to flow, via the channels 92 and 172, through the capture compartment 100. Fluid flowing through the capture compartment 100 flows through the thirteenth fluid channel 178, but is prevented by the closed active valve assembly 204 from flowing into the fourteenth fluid channel 180. The active valve assembly 219 remains open so that fluid within the thirteenth fluid channel 178 flows into the tenth fluid channel 172 and into the waste chamber 102. While the fluid is flowing through the capture compartment 100, the contents are subjected to a magnetic force, for example, by placement of an external magnet (e.g., by deploying the sample preparation magnet assembly 570) in proximity to the capture compartment 100. The magnetic force retains magnetic target capture beads and target analyte(s) (e.g., nucleic acid(s)) bound thereto within the capture compartment 100 while the remainder of the contents of the mixing well 90 flows through the capture compartment 100 and into the waste chamber 102.

Figure 22:
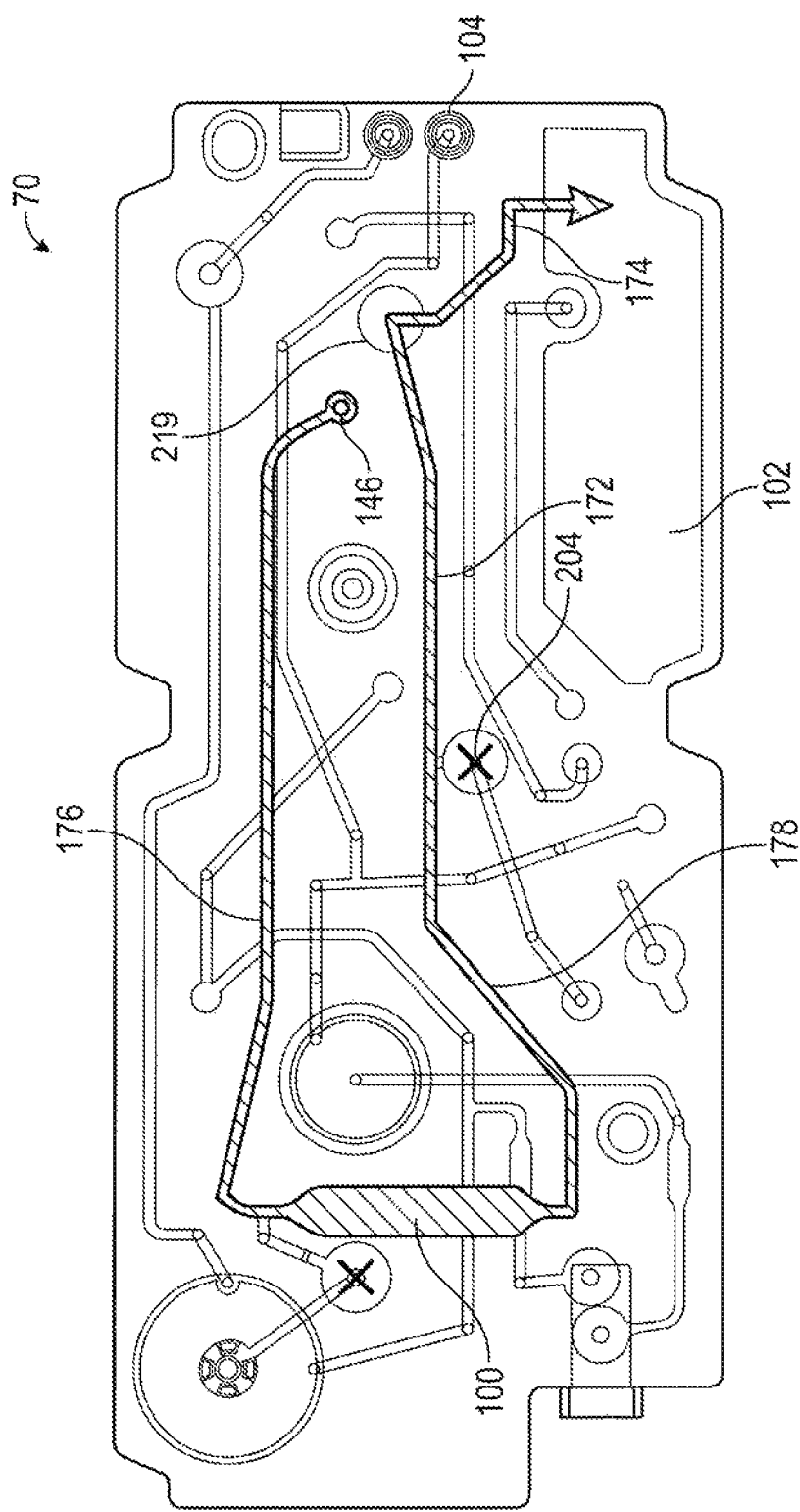

Referring now to FIG. 22, in a next step, the valve assembly 204 remains closed and the valve assembly 219 remains open, and the lance blister 42*b* associated with the deformable compartment 42*a* is collapsed (e.g., with compression mechanism 760*d*) to thereby open the compartment to the sixth inlet port 146. The deformable compartment 42*a* is then partially collapsed (e.g., with the compression mechanism 756d) to dispense a portion (e.g., approximately 50%) of its contents into the sixth inlet port 146. In one embodiment, the fluid contents of the deformable compartment 42a comprise a wash buffer which flows from the sixth inlet port 146 via the twelfth fluid channel 176 to the capture compartment 100. The wash fluid flows over the capture beads that are immobilized (e.g., by a magnet) within the capture compartment 100 and flows through the channels 178, 172, and 174 to the waste chamber 102 to thereby carry unbound material and other debris into the waste chamber 102.

Figure 23:
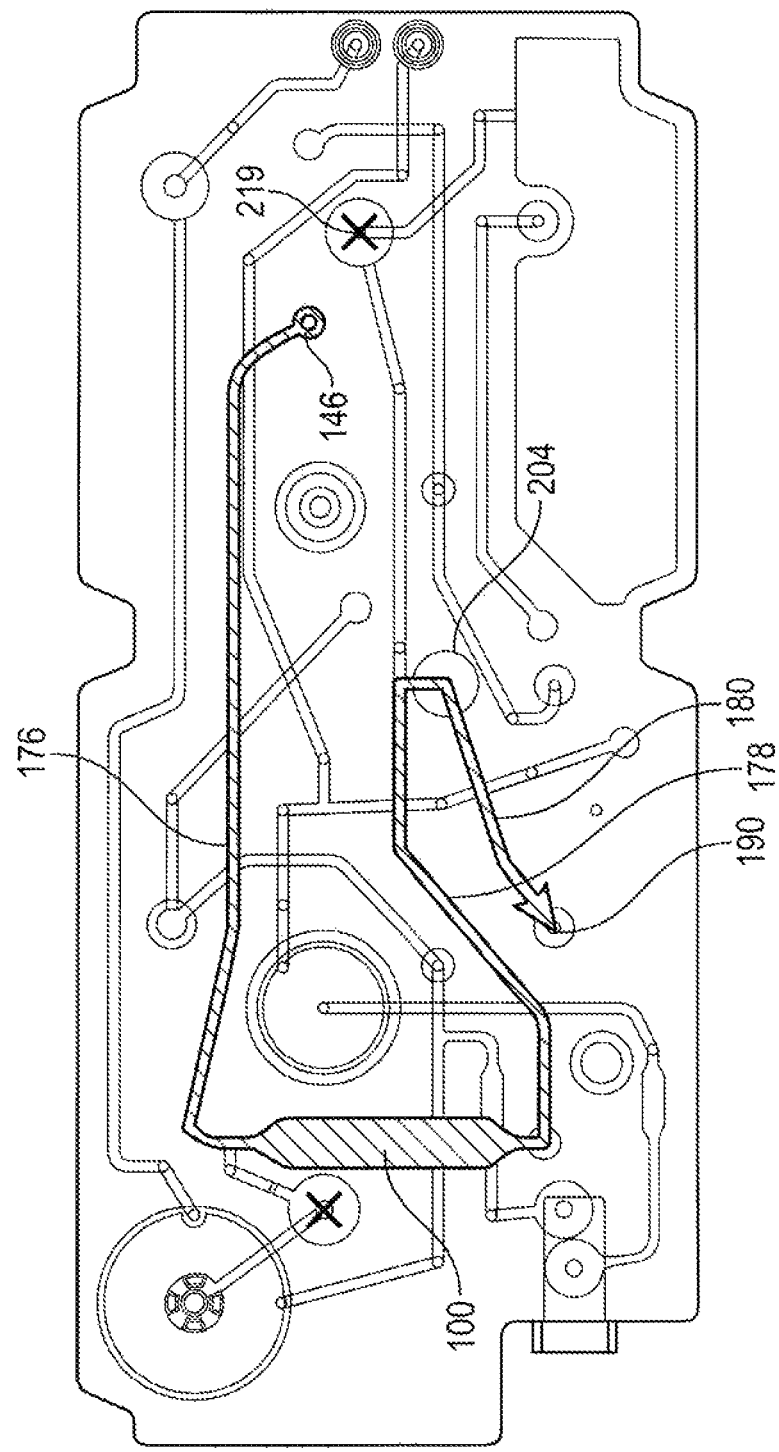

Referring now to FIG. 23, in a next step, the waste valve assembly 219 is closed by an external actuator (e.g., the valve actuator 762a), and the sample valve assembly 204 is opened by removing the external actuator. Next, the remainder of the deformable compartment 42a is collapsed by the external actuator (e.g., the compression mechanism 756d), thereby forcing the remainder of the fluid (e.g., a wash buffer) through the twelfth fluid channel 176 into the capture compartment 100. The magnetic force is removed from the capture compartment 100 (e.g., by retracting the sample preparation magnet assembly 570) so that the magnetic beads within the capture compartment 100 are released and can be carried by the fluid flowing through the capture compartment 100 through the thirteenth fluid channel 178 through the sample valve assembly 204 and the fourteenth fluid channel 180 to a third outlet 190. The fluid flowing from the third outlet 190, which now comprises an at least partially purified target analyte carried on the magnetic beads, is dispensed into the sample compartment 266 of the reaction module 240 via the inlet 268, as shown in FIG. 31 and described above.

In FIGS. 56 and 57, each of the cam follower ribs formed in the cam grooves 850-860 of the cam follower plate 820 is indicated by a unique parenthetical number (1)-(14). As the cam follower plate 820 is moved relative to the cam arm plate 852 in the direction "A," the cam follower ribs formed in various cam grooves 850-860 contact the compression mechanisms of the actuator array 754 in a predetermined sequence so as to open the various reagent chambers and dispense their contents and actuate the various active values in a specified sequence. The parenthetical numbers assigned to the cam follower ribs in FIGS. 56, 57 indicates the sequence in which each rib contacts an associated cam arm of the compression mechanisms of the array 754 to actuate the compression mechanisms in a sequence corresponding to the sample preparation process performed in the sample preparation module 70 as described above and shown in FIGS. 16-23. Table 1 below shows correspondence between each cam follower rib of the cam follower plate 820, the process step, the corresponding compression mechanism, and compressing collapsible chamber or active valve of the multiplex cartridge 10 for the process shown in FIGS. 16-23.

TABLE 1

| Follower Element | Process Step | Compression Mechanism/Valve Actuator | Compressible Chamber/Active Valve |
|---|---|---|---|
| (1) | Open Lysis Lance Blister | 760a | 34b |
| (2)* | Open and dispense magnetic beads | 758 | 44 |
| (3) | Dispense Lysis buffer | 756a | 34a |
| (4) | Open Binding Buffer Lance Blister | 760e | 36b |

TABLE 1-continued

| Follower Element | Process Step | Compression Mechanism/Valve Actuator | Compressible Chamber/Active Valve |
|---|---|---|---|
| (5) | Dispense Binding Buffer | 756e | 36a |
| (6) | Open Oil Lance Blister | 760b | 38b |
| (7) | Dispense Oil | 756b | 38a |
| (8) | Open Elution/Reconstitution Lance Blister | 760c | 40b |
| (9) | Dispense Elution/Reconstitution Buffer | 756c | 40a |
| (10) | Close sample Valve assembly | 762b | 204 |
| (11) | Open Wash Buffer Lance Blister | 760d | 42b |
| (12) | Dispense 50% wash buffer | 756d | 42a |
| (13) | Close waste valve assembly | 762a | 219 |
| (14) | Dispense 100% wash buffer | 756d | 42a |

*step (2) is optional and may be omitted if magnetic beads are provided directly, e.g., by a lyophilized pellet, in the mixing well 90.

Sample Reaction Process

The sample material that is dispensed from the sample processing module 70 into the sample compartment 266 of the reaction module 268 is subjected to a reaction process with the reaction module 240. In one exemplary embodiment, that reaction process includes PCR amplification and analyte detection.

Figure 60:
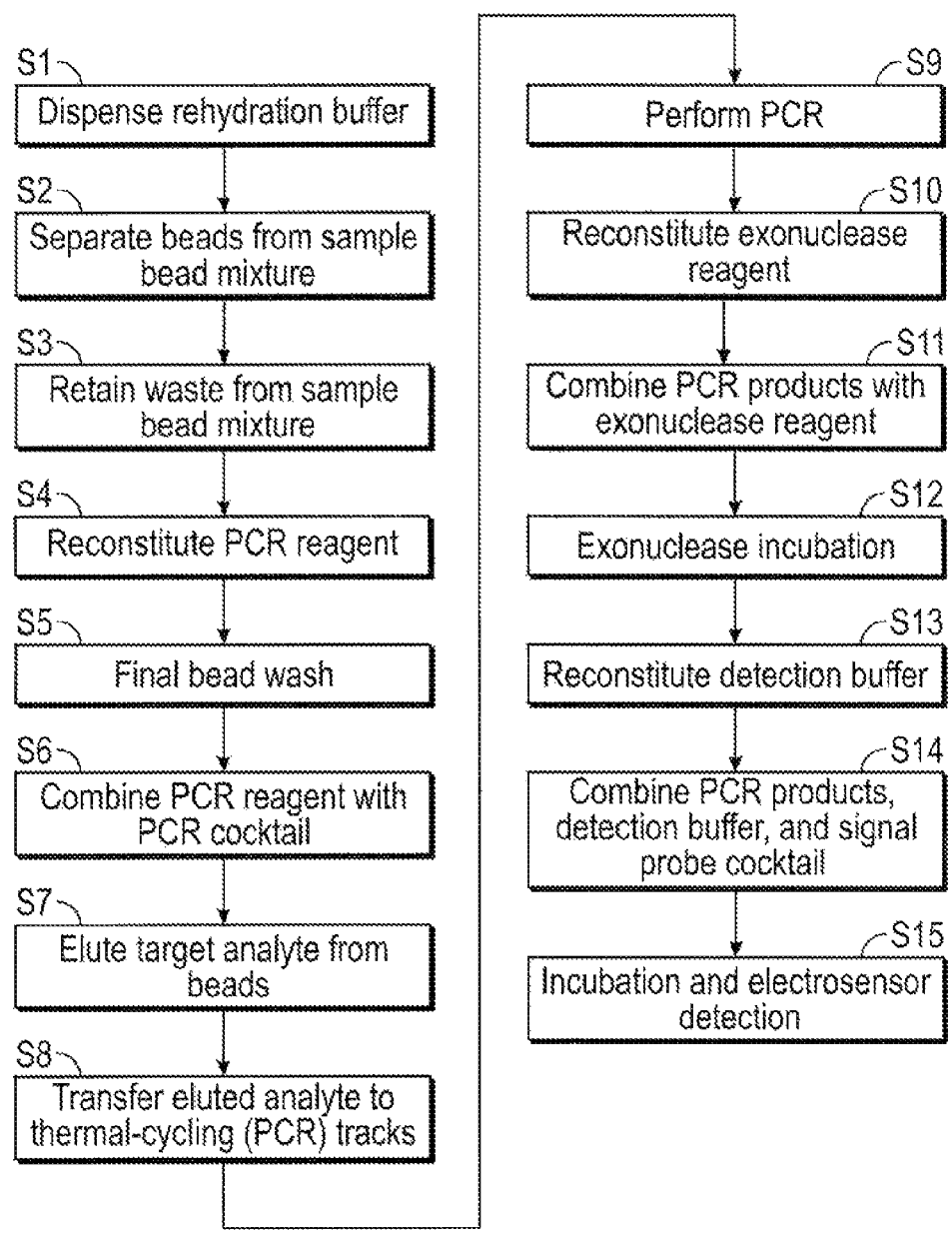
FIG. 60 is a flow chart illustrating an exemplary process that can be performed in the fluidic processing panel.

An exemplary process will be described with reference to flow chart 900 in FIG. 60. Although the various elements (steps) of flow chart 900 in FIG. 60 are shown as sequential steps having a prescribed order, it should be understood that the process 900 as illustrated is exemplary and not intended to be limiting. Persons of ordinary skill will recognize that many of the various elements (steps) of the process 900 can be performed in different orders than are shown and described herein, can be performed simultaneously or substantially simultaneously with other elements (steps), or can be omitted altogether. Thus, the order of the elements (steps) as shown in FIG. 60 should not be viewed as limiting unless a specific order for two or more elements (steps) is specifically prescribed or otherwise suggested by the context of the description (e.g., a mixture must first be formed before that mixture can be incubated or otherwise manipulated).

In step S1, an aliquot of the elution/reconstitution buffer (e.g., 15 μl) is dispensed by electrowetting droplet manipulation from the rehydration buffer zone 372 (FIG. 59) (and rehydration buffer compartment 376 of top plate 241 (FIGS. 26, 27)) to an electrowetting pathway defining the exonuclease zone 384 (FIG. 59).

As noted above, in an embodiment of the invention, the region of the reaction module 240 between the top plate 241 and the fluidic processing panel 354 may be filled with a process fluid, such as an immiscible fluid such as oil, and the droplets are manipulated through the oil.

In step S2, an aliquot of the sample mixture (comprising magnetic beads with DNA material bound thereto and wash solution from the sample preparation module 70) is retained by electrowetting manipulation within the sample bead zone 368 (FIG. 59) (and the sample compartment 266 of the top plate 241 (FIGS. 26, 27)), while the magnetic beads are pulled out of the aqueous solution held within the sample bead zone 368 by a magnet that is focused on position 369 (referred to as the bead collection area). The bead collection area 369 corresponds to the position of the focusing magnet 558 of the cartridge magnet assembly 552 (See FIG. 49B) adjacent to the fluid processing panel 554 of the multiplex cartridge 10 when the cartridge magnet assembly 552 is in the deployed position. During the process of collecting the magnetic beads at the bead collection area 369, the aqueous solution may be moved throughout the sample bead zone 368 by selective activation of different electrowetting pads to move the aqueous droplets containing the magnet beads to positions in closer proximity to the magnetic force at the bead collection area 369.

In Step S3, sample waste (i.e., wash buffer and other materials from which the magnetic beads have been removed in Step S2), is retained by electrowetting droplet manipulation within the sample bead zone 368 (and the sample compartment 266), thereby separating the magnet beads, and the target analyte material bound thereto, from the other constituent substances of the sample bead mixture that was delivered from the sample preparation module 70 to the sample bead zone 368.

In Step S4, an amount of the reconstitution buffer that was dispensed from the rehydration buffer zone 372 in Step S1 may be moved by electrowetting droplet manipulation to the PCR reagent zone 376 (FIG. 59) (and the buffer compartment 296 of the top plate 241 (FIGS. 26, 27)). Resuspension of the dried PCR reagent contained within the PCR reagent zone 376 occurs by oscillating movements of the droplets between the electrowetting pads within the PCR reagent zone 376.

In Step S5, an amount of the reconstitution buffer that was dispensed from the rehydration buffer zone 372 and which was not transported to the PCR reagent zone 376 is transported by electrowetting droplet manipulation over the magnetic beads held by the magnetic force at the bead collection area 369 for a final bead wash. After the final bead wash, the reconstitution buffer is then moved by electrowetting droplet manipulation to an end of the center pathway corresponding to the exonuclease zone 384 where it is held by electrowetting droplet manipulation apart from the magnetic beads held at the bead collection area 369.

In the Step S6, the reconstituted PCR buffer within the PCR reagent zone 376 is distributed by electrowetting droplet manipulation to the primer cocktail positions of each of the thermal cycling tracks 364a, 364b, 364c, and 364d. One primer cocktail position 366a at a proximal end of the thermal cycling track 364d is labeled in FIG. 59. Each of the other thermal cycling tracks 364a, 364b, and 364c has a similar primer cocktail location. The combination of reconstituted PCR reagent with the dried primer cocktail at the primer cocktail position (e.g., position 366) reconstitutes the primer cocktail at that position. In this configuration, the reaction module 240 is configured to perform one PCR reaction in each of the thermal cycling tracks 364a, 364b, 364c, and 364d.

In an alternate embodiment, a primer cocktail may also be provided at the distal end of each thermal cycling track 364a, 364b, 364c, and 364d. One primer cocktail position 366b at a distal end of thermal cycling track 364d is labeled in FIG. 59. Each of the other thermal cycling tracks 364a, 364b, and 364c may have a similar primer cocktail location. In such a configuration, the reaction module 240 is configured to perform two PCR reactions in each of the thermal cycling tracks 364a, 364b, 364c, and 364d.

In Step S7, the magnetic force is removed from the bead collection area 369 (e.g., by moving the cartridge magnet assembly 552 to its retracted position). Reconstitution/elution buffer is moved by electrowetting droplet manipulation from the central pathway 384 to the bead collection area 369, and a mixture of the magnetic beads and reconstitution/elution buffer from the rehydration buffer zone 372 is shuttled back and forth along the path 384 by electrowetting droplet manipulation to elute the DNA material (or other target analyte) from the magnetic beads.

After a sufficient elution period, in Step S8, the cartridge magnet assembly 552 is again deployed to apply a magnetic force (via the focusing magnet 558) to the bead collection area 369 to attract and retain (immobilize) the magnetic beads from which the DNA material has been eluted, and the eluted DNA material is transferred by electrowetting droplet manipulation to a PCR staging area at a proximal end of each of the thermal cycling tracks 364a, 364b, 364c, and 364d. In the embodiment and orientation shown in FIG. 59, the PCR staging area is at the left end of thermal cycling tracks 364a, 364b, 364c, and 364d.

In Step S9, PCR droplets—comprising the eluted DNA material, the reconstituted PCR reagent, and the reconstituted PCR primer—are formed by electrowetting droplet manipulation at the PCR staging area of each of the thermal cycling tracks 364a, 364b, 364c, and 364d. Each PCR droplet is moved into a corresponding one of the thermal cycling tracks 364a, 364b, 364c, and 364d, and a PCR process is performed by shuttling the droplets between two of the PCR (thermal cycling) regions 382a (at about, e.g., 60° C. for annealing and extension) and 382b (at about, e.g., 95° C. for denaturation) or 382c (at about 60° C. for annealing and extension) and 382b (at about, e.g., 95° C. for denaturation). In another embodiment, two PCR droplets are transported into each thermal cycling track 364a, 364b, 364c, and 364d, and one droplet is shuttled between heater areas 382c and 382b, whereas the other droplet is shuttled between heater areas 382a and 382b. The PCR process may last for about 40 minutes or less.

In Step S10, an amount of elution/reconstitution buffer is dispensed by electrowetting droplet manipulation from the rehydration buffer zone 372 and is transported by electrowetting droplet manipulation to the exonuclease reagent zone 374 (FIG. 59) (and the second buffer compartment 300 of the top plate 241 (FIG. 26, 27)) for resuspension of the dried exonuclease reagent. Resuspension of the dried exonuclease reagent contained within the exonuclease reagent zone 374 occurs by oscillating movements of the droplets between the electrowetting pads within the exonuclease reagent zone 374. The reconstituted exonuclease reagent is then transported by electrowetting droplet manipulation from the exonuclease reagent zone 374 to PCR staging areas of the thermal cycling track 364a, 364b, 364c, and 364d.

In Step S11, following PCR (Step 9), each droplet that has gone through the PCR process is combined with an amount of the exonuclease agent resuspended in Step S10, transported by electrowetting droplet manipulation to the exonuclease zone 384, and held in a separate location within the exonuclease zone 384. In various embodiments, an amount of elution/reconstitution buffer from the buffer zone 372 is added to each PCR droplet by electrowetting droplet manipulation to bring the total volume of each droplet up to a preferred amount.

In Step S12, the droplet mixtures formed in Step S11, comprising the PCR products and the reconstituted exonuclease reagent, are then incubated within the exonuclease region 380 and the exonuclease zone 384 at a prescribed temperature and for a prescribed period of time.

In Step S13, detection reagent within the hybridization zone 370 (FIG. 59) (and the detection buffer compartment 280 of the top plate 241 (FIGS. 26, 27)) is reconstituted with an amount of rehydration buffer from the rehydration buffer zone 372. In one embodiment, an amount of rehydration buffer from the rehydration buffer zone 372 is moved via electrowetting droplet manipulation through the connecting passage 274 (FIGS. 26, 27) between the detection buffer compartment 280 and the rehydration buffer compartment 276.

In Step S14, an amount of the reconstituted detection reagent (e.g. 25 μl) from the hybridization zone 370 is combined by electrowetting droplet manipulation with each of the PCR droplets. Each PCR droplet is then combined with a signal probe cocktail stored at positions 362*a*, 362*b*, 362*c*, and 362*d* of the fluid processing panel 354. To effect mixing of the PCR droplet and the signal probe cocktail, and to resuspend the signal probe cocktail, each droplets may be transported by electrowetting droplet manipulation around or within one of the detection mixing zones 385*a*, 385*b*, 385*c*, and 385*d*.

In Step S15, the droplets are transported by electrowetting manipulation to the electrosensor arrays 363*a*, 363*b*, 363*c*, and 363*d*, where they are subjected to further incubation within the detection region 378 and various analytes of interest are detected by electrosensing techniques, such as described above and/or described in publications incorporated by reference above.

EXEMPLARY EMBODIMENTS

The following embodiments are encompassed by the foregoing disclosure.

Embodiment 1

A fluid sample processing cartridge comprising:
a substrate;
a sample well formed in the substrate and configured to receive a volume of fluid sample;
a closure configured to be selectively placed over the sample well;
a deformable fluid chamber supported on the substrate and configured to hold a fluid therein when in an undeformed state and to collapse upon application of an external compression force to expel at least a portion of the fluid from the fluid chamber, the deformable fluid chamber being in fluid communication with the sample well via a channel formed in the substrate;
a mixing well formed in the substrate, the mixing well being in fluid communication with the sample well via a channel formed in the substrate, the mixing well comprising a first peripheral wall and a first floor defining a well and a fluid inlet snorkel extending up a side of the first peripheral wall extending from the channel communicating the mixing well to the sample well and terminating below a top edge of the first peripheral wall; and
a driven mixing apparatus disposed within the mixing well and constructed and arranged to mix the contents of the mixing well.

Embodiment 2

The fluid sample processing cartridge of embodiment 1, wherein the fluid inlet snorkel extends up an outer surface of the first peripheral wall and terminates at an opening formed in the first peripheral wall.

Embodiment 3

The fluid sample processing cartridge of embodiment 1 or embodiment 2, wherein the sample well comprising a second peripheral wall and a second floor defining a well and a fluid inlet snorkel extending up a side of the second peripheral wall and terminating below a top edge of the second peripheral wall.

Embodiment 4

The fluid sample processing cartridge of any one of embodiments 1-3, wherein the mixing well further comprises an exit port comprising one or more openings formed in the second floor, wherein the floor tapers downwardly toward the exit port.

Embodiment 5

The fluid sample processing cartridge of any one of embodiments 1-4, wherein the driven mixing apparatus comprises a first impeller rotatably disposed within the mixing well and a gear configured to be drivingly engaged by a mating gear of an instrument into which the liquid sample processing cartridge is inserted and to rotate the first impeller when engaged by the mating gear.

Embodiment 6

The fluid sample processing cartridge of any one of embodiments 1-5, further comprising:
a lysis chamber containing a plurality of lysis beads, the lysis chamber being formed in the substrate and disposed along the channel connecting the mixing well and the sample well whereby fluid flowing from the sample well to the mixing well will flow through the lysis chamber; and
a bead mixer disposed at least partially within the lysis chamber and constructed and arranged to agitate the lysis beads and fluid flowing through the lysis chamber.

Embodiment 7

The fluid sample processing cartridge of embodiment 6, further comprising:
a first optical interface comprising an enlarged portion of the channel connecting the lysis chamber to the sample well; and
a second optical interface comprising an enlarged portion of the channel connecting the lysis chamber to the mixing well.

Embodiment 8

The fluid sample processing cartridge of embodiment 6 or 7, wherein the bead mixer comprises:
a motor mounted within the substrate; and
a second impeller disposed within the lysis chamber and mounted on an output shaft of the motor.

Embodiment 9

The fluid sample processing cartridge of any one of embodiments 6-8 wherein the lysis chamber includes a fluid inlet and a fluid outlet and further comprises a mesh filter disposed over each of the fluid inlet and the fluid outlet and configured to retain the lysis beads within the lysis chamber.

Embodiment 10

The fluid sample processing cartridge of any one of embodiments 1-9, further comprising:

a pressure port formed in the substrate and configured to couple the substrate to an external fluid pressure source; and a channel formed in the substrate connecting the pressure port to the sample well.

Embodiment 11

The fluid sample processing cartridge of embodiments 1-10, further comprising:
- a waste chamber formed in the substrate, the waste chamber being in fluid communication with the mixing well via a channel formed in the substrate;
- a fluid exit port formed in the substrate, the fluid exit port being in fluid communication with the mixing well via a channel formed in the substrate;
- a first externally actuatable control valve disposed within the substrate and constructed and arranged to selectively permit or prevent fluid flow from the mixing well to the waste chamber; and
- a second externally actuatable control valve disposed within the substrate and constructed and arranged to selectively permit or prevent fluid flow from the mixing well to the fluid exit port.

Embodiment 12

The fluid sample processing cartridge of embodiment 11, further comprising a capture chamber disposed along a channel connecting the mixing well and the waste chamber Embodiment 13

The fluid sample processing cartridge of embodiments 1-12, further comprising:
- a passive valve assembly disposed within the substrate and constructed and arranged to be closed and prevent fluid flow from the mixing well when pressure within the mixing well is not higher than a threshold pressure and to open and permit fluid flow from the mixing well when pressure within the mixing well rises above the threshold pressure; and
- a pressure port formed in the substrate and in pressure communication with the passive valve assembly by a pressure conduit formed in the substrate, wherein when the pressure port is closed, pressure within the mixing well is allowed to reach the threshold pressure that will open the passive valve assembly and permit fluid flow from the mixing well, and when the pressure port is open pressure within the mixing cannot not reach the threshold pressure so the passive valve assembly is closed.

Embodiment 14

The fluid sample processing cartridge of any one of embodiments 1-13, further comprising a lance blister associated with the deformable fluid chamber; the lance blister being connected or connectable to the associated deformable fluid chamber and containing a bead retained within the lance blister by a breakable septum, wherein the lance blister is configured to collapse upon application of an external compression force to thereby push the bead through the breakable septum.

Embodiment 15

The fluid sample processing cartridge of any one of embodiments 1-14, further comprising an external shroud externally enclosing at least a portion of the cartridge.

Embodiment 16

The fluid sample processing cartridge of any one of embodiments 1-15, comprising a plurality of deformable fluid chambers, each of the fluid chambers containing one or more substances selected from the group consisting of a lysis buffer, a wash buffer, an oil, a rehydration buffer, target capture beads, and a binding buffer.

Embodiment 17

The fluid sample processing cartridge of any one of embodiments 1-10, further comprising:
- a first fluid exit port formed in the substrate, the first fluid exit port being in fluid communication with the mixing well via a channel formed in the substrate;
- a second fluid exit port formed in the substrate; and
- at least two deformable fluid chambers, one of the two deformable fluid chambers being in fluid communication with the mixing well via a channel formed in the substrate, and the other of the two deformable fluid chambers being in fluid communication with the second fluid exit port via a channel formed in the substrate that is different from the channel communicating the first fluid exit port with the mixing well.

Embodiment 18

The fluid sample processing cartridge of embodiment 17, wherein the deformable fluid chamber in fluid communication with the mixing well contains a lysis buffer, a wash buffer, target capture beads, or a binding buffer, and the deformable fluid chamber in fluid communication with the second fluid exit contains an oil or a rehydration buffer.

Embodiment 19

A fluid sample processing cartridge comprising:
a) a sample preparation module comprising:
 i) a substrate;
 ii) a sample well formed in the substrate and configured to receive a volume of fluid sample;
 iii) a closure configured to be selectively placed over the sample well;
 iv) a first deformable fluid chamber supported on the substrate and configured to hold a fluid therein when in an undeformed state and to collapse upon application of an external compression force to expel at least a portion of the fluid from the first fluid chamber, the first deformable fluid chamber being in fluid communication with the sample well via a channel formed in the substrate;
 v) a mixing well formed in the substrate, the mixing well being in fluid communication with the sample well via a channel formed in the substrate;
 vi) a driven mixing apparatus disposed within the mixing well and constructed and arranged to mix the contents of the mixing well; and
 vii) a first fluid exit port formed in the substrate, the first fluid exit port being in fluid communication with the mixing well via a channel formed in the substrate; and b) a reaction module attached to the sample preparation module and configured to receive a fluid from the sample preparation module via the fluid exit port formed in the sample preparation module, the reaction module comprising:
  i) a top plate comprising
   1) a top surface;
   2) a raised wall at least partially circumscribing the top surface and in fluid sealing contact with a surface of the sample preparation module to form an interstitial space between the top surface and the surface of the sample preparation module;
   3) a sample chamber fluidly coupled to the first fluid exit port of the sample preparation module;
   4) a reagent chamber; and
   5) a detection chamber; and
  ii) a fluidic processing panel coupled to a bottom surface of the top plate and defining a reaction and processing space between the fluidic processing panel and the top plate, wherein the reaction and processing space is open or openable to the sample chamber, the reaction chamber, and the detection chamber.

Embodiment 20

The fluid sample processing cartridge of embodiment 19, wherein the sample chamber of the reaction module includes an inlet port through which fluid sample enters the sample chamber and including a gap between the first fluid exit port of the sample preparation module and the inlet port of the sample chamber, the gap being open to the interstitial space.

Embodiment 21

The fluid sample processing cartridge of embodiment 19, wherein the first fluid exit port of the sample preparation module comprises an outlet channel formed through a frustoconical nipple.

Embodiment 22

The fluid sample processing cartridge of any one of embodiments 19-21, wherein the reaction module further comprises an electrosensor array disposed in each detection chamber.

Embodiment 23

The fluid sample processing cartridge of any one of embodiments 19-22, wherein the top plate of the reaction module further comprises one or more bubble traps, each bubble trap comprising a bubble capture hood open to the reaction and processing space and a vent opening open to the interstitial space.

Embodiment 24

The fluid sample processing cartridge of any one of embodiments 19-23, wherein the sample preparation module further comprises:
 a second deformable fluid chamber supported on the substrate and configured to hold a fluid therein when in an undeformed state and to collapse upon application of an external compression force to expel at least a portion the fluid from the fluid chamber; and
 a second fluid exit port formed in the substrate, wherein the second fluid exit port is in fluid communication with the second deformable fluid chamber via a channel formed in the substrate, and
 wherein the reaction and processing space is fluidly coupled to the second fluid exit port of the sample preparation module.

Embodiment 25

The fluid sample processing cartridge of any one of embodiments 19-24, wherein the mixing well comprises:
 a peripheral wall and a floor defining a well; and
 a fluid inlet snorkel extending up a side of the peripheral wall extending from the channel communicating the mixing well to the sample well and terminating below a top edge of the peripheral wall.

Embodiment 26

The fluid sample processing cartridge of embodiment 25, wherein the fluid inlet snorkel extends up an outer surface of the peripheral wall and terminates at an opening formed in the peripheral wall.

Embodiment 27

The fluid sample processing cartridge of embodiment 25 or 26, wherein the mixing well further comprises an exit port comprising one or more openings formed in the floor of the mixing well, wherein the floor tapers downwardly toward the exit port.

Embodiment 28

The fluid sample processing cartridge of any one of embodiments 19-25, wherein the driven mixing apparatus comprises a first impeller rotatably disposed within the mixing well and a gear configured to be drivingly engaged by a mating gear of an instrument into which the liquid sample processing cartridge is inserted and to rotate the first impeller when engaged by the mating gear.

Embodiment 29

The fluid sample processing cartridge of any one of embodiments 19-28, wherein the sample preparation module further comprises:
 a lysis chamber comprising a plurality of lysis beads, the lysis chamber being formed in the substrate and disposed along the channel connecting the mixing well and the sample well whereby fluid flowing from the sample well to the mixing well will flow through the lysis chamber; and
 a bead mixer disposed at least partially within the lysis chamber and constructed and arranged to agitate the lysis beads and fluid flowing through the lysis chamber.

Embodiment 30

The fluid sample processing cartridge of embodiment 29, further comprising:
 a first optical interface comprising an enlarged portion of the channel connecting the lysis chamber to the sample well; and a second optical interface comprising an enlarged portion of the channel connecting the lysis chamber to the mixing well.

Embodiment 31

The fluid sample processing cartridge of embodiment 29 or 30, wherein the bead mixer comprises:
a motor mounted within the substrate; and
a second impeller disposed within the lysis chamber and mounted on an output shaft of the motor.

Embodiment 32

The fluid sample processing cartridge of any one of embodiments 29-31 wherein the lysis chamber includes a fluid inlet and a fluid outlet and further comprises a mesh filter disposed over each of the fluid inlet and the fluid outlet and configured to retain the lysis beads within the lysis chamber.

Embodiment 33

The fluid sample processing cartridge of any one of embodiments 19-32, wherein the sample preparation module further comprises:
a pressure port formed in the substrate and configured to couple the substrate to an external fluid pressure source; and
a channel formed in the substrate connecting the pressure port to the sample well.

Embodiment 34

The fluid sample processing cartridge of embodiments 19-33, wherein the sample preparation module further comprises:
a waste chamber formed in the substrate, the waste chamber being in fluid communication with the mixing well via a channel formed in the substrate;
a first externally actuatable control valve disposed within the substrate and constructed and arranged to selectively permit or prevent fluid flow from the mixing well to the waste chamber; and
a second externally actuatable control valve disposed within the substrate and constructed and arranged to selectively permit or prevent fluid flow from the mixing well to the exit port.

Embodiment 35

The fluid sample processing cartridge of embodiment 34, wherein the sample preparation module further comprises a capture chamber disposed along a channel connecting the mixing well and the waste chamber.

Embodiment 36

The fluid sample processing cartridge of embodiments 19-35, wherein the sample preparation module further comprises:
a passive valve assembly disposed within the substrate and constructed and arranged to be closed and prevent fluid flow from the mixing well when pressure within the mixing well is not higher than a threshold pressure and to open and permit fluid flow from the mixing well when pressure within the mixing well rises above the threshold pressure; and
a pressure port formed in the substrate and in pressure communication with the passive valve assembly by a pressure conduit formed in the substrate, wherein when the pressure port is closed, pressure within the mixing well is allowed to reach the threshold pressure that will open the passive valve assembly and permit fluid flow from the mixing well, and when the pressure port is open pressure within the mixing well cannot reach the threshold pressure so the passive valve assembly is closed.

Embodiment 37

The fluid sample processing cartridge of any one of embodiments 19-36, wherein the sample preparation module further comprises a lance blister associated with the deformable fluid chamber; the lance blister being connected or connectable to the associated deformable fluid chamber and containing a bead retained within the lance blister by a breakable septum, wherein the lance blister is configured to collapse upon application of an external compression force to thereby push the bead through the breakable septum.

Embodiment 38

The fluid sample processing cartridge of any one of embodiments 19-37, further comprising an external shroud externally enclosing at least a portion of the cartridge.

Embodiment 39

The fluid sample processing cartridge of any one of embodiments 19-38, wherein the sample preparation module further comprises a plurality of deformable fluid chambers, each of the fluid chambers containing a substance selected from the group consisting of a lysis buffer, a wash buffer, an oil, a rehydration buffer, target capture beads, and a binding buffer.

Embodiment 40

An instrument configured to process a fluid sample processing cartridge including a deformable fluid chamber supported on a planar substrate and configured to hold a fluid therein when in an undeformed state and to collapse upon application of an external compression force to expel at least a portion of the fluid from the fluid chamber, the instrument comprising:
a cartridge carriage assembly configured to receive and hold a fluid sample processing cartridge inserted into the instrument;
a heating and control assembly adjacent the cartridge carriage assembly and configured for movement with respect to the cartridge carriage assembly between a first position not in operative contact with the cartridge carried within the cartridge carriage assembly and a second position in operative contact with the cartridge carried within the cartridge carriage assembly;
one or more movable magnet assemblies, each mounted for movement with respect to the cartridge independently of the heating and control assembly between a first position applying substantially no magnetic force to the cartridge and a second position applying magnetic force to corresponding discrete portions of the cartridge;
a cam block assembly configured for powered movement and operatively coupled to the heating and control assembly for converting powered movement of the cam block assembly into movement of the heating and control assembly with respect to the cartridge carriage assembly between the first position of the heating and control assembly and the second position of the heating and control assembly and operatively coupled to the one or more moveable magnet assemblies for converting powered movement of the cam block assembly into movement of each magnet assembly with respect to cartridge carriage assembly between the first position of the magnet assembly and the second position of the magnet assembly and;

e) a deformable chamber compression assembly configured to selectively apply an external compression force to the deformable fluid chamber to collapse the deformable chamber and expel at least a portion of the fluid from the fluid chamber.

Embodiment 41

The instrument of embodiment 40, wherein the heating and control assembly comprises:
one or more heater assemblies configured to apply a thermal gradient to corresponding discrete portions of the cartridge when the heating and control assembly is in the second position; and
a connector board including one or more electrical connector elements configured to effect an electrical connection between the instrument and the cartridge when the heating and control assembly is in the second position.

Embodiment 42

The instrument of embodiment 40 or 41, wherein the deformable chamber compression assembly comprises:
a cam follower plate configured for powered movement in a first direction that is generally parallel to the plane of the substrate; and
a compression mechanism associated with the deformable chamber of the cartridge and configured to apply a force compressing the chamber against the substrate by movement in a second direction having a component that is generally normal to the plane of the substrate,
wherein the cam follower plate is operatively coupled to the compression mechanism to convert movement of the cam follower plate in the first direction into movement of the compression mechanism in the second direction to thereby apply an external compression force to the chamber.

Embodiment 43

The instrument of any one of embodiments 40-42, further comprising a pneumatic pump and a pneumatic port connected to the pneumatic pump, wherein the pneumatic port is configured to couple the pneumatic pump to a pressure port of the fluid sample processing cartridge when the cartridge is inserted into the instrument.

Embodiment 44

The instrument of any one of embodiments 40-43, further comprising an optical detector configured to detect fluid flow through a part of the fluid sample processing cartridge.

Embodiment 45

The instrument of any one of embodiments 40-42 wherein the fluid sample processing cartridge includes a driven mixing apparatus including a drive gear, and wherein the instrument further comprises a mixing motor assembly including a powered driving gear and moveable between a first position in which the driving gear is not engaged with the drive gear of the driven mixing apparatus and a second position in which the driving gear is operatively engaged with the drive gear to actuate the driven mixing apparatus, and wherein the cam block assembly is operatively coupled to the mixing motor assembly for converting powered movement of the cam block assembly into movement of the mixing motor assembly between the first position of the mixing motor assembly and the second position of the mixing motor assembly.

Embodiment 46

The instrument of any one of embodiments 41-45, further comprising a heater cooling assembly comprising:
a fan; and
a cooling duct configured to direct air flow from the fan to a portion of one of the heater assemblies.

Embodiment 47

The instrument of any one of embodiments 40-46, wherein the cartridge carriage assembly comprises:
a cartridge holder configured to hold a cartridge inserted therein;
a cartridge latch biased into a cartridge-latching position and configured to latch onto a cartridge inserted into the cartridge holder to retain the cartridge within the cartridge holder; and
a cartridge eject mechanism configured to automatically push a cartridge at least partially out of the cartridge holder when the cartridge latch is released from a cartridge-latching position.

Embodiment 48

The instrument of any one of embodiments 41-47, wherein the heating and control assembly comprises a support plate on which the one or more heater assemblies and the connector board are supported, the support plate being mounted in a constrain configuration preventing horizontal movement of the support plate but permitting vertical movement of the support plate to enable movement of the heating and control assembly between its first and second positions.

Embodiment 49

The instrument of any one of embodiments 41-48, wherein one of the heater assemblies of the heating and control assembly comprises a resistive heating element attached to the connector board and a heat spreader comprising a thermally-conductive material thermally coupled to the resistive heating element.

Embodiment 50

The instrument of any one of embodiments 41-49, wherein one of the heater assemblies of the heating and control assembly comprises:
a thermoelectric element;
a heat spreader comprising a thermally-conductive material thermally coupled to the thermoelectric element; and a heat sink including a panel that is in thermal contact with the thermoelectric element and a plurality of heat-dissipating rods.

Embodiment 51

The instrument of any one of embodiments 41-50, wherein the electrical connector elements of the connector board of the heating and control assembly comprise a plurality of connector pin arrays, each connector pin array comprising a plurality of pogo pins.

Embodiment 52

The instrument of any one of embodiments 40-51, wherein one of the movable magnet assemblies comprises:
a magnet holder mounted on a spindle so as to be rotatable about the spindle between the first position and the second position of the magnet assembly;
a magnet supported on the magnet holder;
an actuator bracket extending from the magnet holder; and
a torsion spring configured to bias the magnet holder to a rotational position corresponding to the first position of the magnet assembly.

Embodiment 53

The instrument of any one of embodiments 40-52, wherein one of the movable magnet assemblies comprises:
a magnet holder frame mounted on a spindle so as to be rotatable about the spindle between the first position and the second position of the magnet assembly;
a magnet array disposed within the magnet holder frame;
a focusing magnet disposed within an opening formed in the magnet holder frame and configured to focus magnetic forces of the magnet array;
an actuator bracket extending from the magnet holder frame; and
a torsion spring configured to bias the magnet holder frame to a rotational position corresponding to the first position of the magnet assembly.

Embodiment 54

The instrument of embodiment 52 or 53, wherein the cam block assembly is operatively coupled to each movable magnet assembly by a magnet actuator coupled at one portion thereof to the cam block assembly so as to be moveable by powered movement of the cam block assembly and including a tab configured to be engageable with the actuator bracket of each magnet assembly as the magnet actuator is moved with the cam block assembly to cause corresponding rotation of the magnet assembly from the first position to the second position.

Embodiment 55

The instrument of any one of embodiments 40-54, wherein the cam block assembly comprises:
a cam frame;
a cam block motor coupled to the cam frame and configured to effect powered movement of the cam frame; and
first and second cam rails attached to the cam frame, each of the cam rails having two cam slots, wherein the cam block assembly is operatively coupled to the heating and control assembly by cam followers extending from the heating and control assembly into the cam slots such that movement of the cam frame and the cam rails with respect to the heating and control assembly causes corresponding relative movement between the cam followers and the cam slots to move the cam followers between respective first segments of the cam slots corresponding to the first position of the heating and control assembly and respective second segments of the cam slots corresponding to the second position of the heating and control assembly.

Embodiment 56

The instrument of embodiment 55, wherein the cam frame comprises:
a first longitudinal spar extending along one side of the heating and control assembly;
a second longitudinal spar extending along an opposite side of the heating and control assembly; and
a cross spar extending between the first and second longitudinal spars, and wherein each cam rail is attached to one of the first and second longitudinal spars.

Embodiment 57

The instrument of any one of embodiments 42-56, wherein the compression mechanism of the deformable chamber compression assembly comprises:
a cam arm having a cam surface and mounted so as to be pivotable about one end of the cam arm; and
a compression pad disposed at an opposite end of the cam arm, wherein the cam arm is pivotable between a first position in which the compression pad does not contact the associated deformable chamber and a second position in which the compression pad applies a compressive force to the associated deformable chamber to at least partially collapse the chamber.

Embodiment 58

The instrument of embodiment 57, wherein the deformable chamber compression assembly further comprises a cam arm plate, and the cam arm of the compression mechanism is pivotably mounted within a slot formed in the cam arm plate for pivotable movement of the cam arm with respect to the cam arm plate, and wherein the cam surface of the cam arm projects out of the slot above a surface of the cam arm plate, and wherein the cam follower plate is operatively coupled to the compression mechanism by a cam follower element of the cam follower plate that is engaged with the cam surface of the compression mechanism during movement of the cam follower plate with respect to the cam arm plate to cause the cam arm to pivot from its first position to its second position.

Embodiment 59

The instrument of embodiment 58, wherein the cam follower plate comprises a cam groove that receives the cam surface of the cam arm projecting above the surface of the cam arm plate, and the cam follower element comprises a follower ridge disposed within the cam groove that contacts the cam surface as the cam follower plate moves with respect to the cam arm plate to cause the cam arm to pivot from its first position to its second position.

Embodiment 60

The instrument of embodiments 59, comprising a plurality of compression mechanisms each comprising a cam arm pivotably mounted within a slot formed in the cam arm plate and a cam arm surface, and the cam follower plate comprises a plurality of cam grooves, each cam groove being associated with at least one of the compression mechanisms and wherein each cam groove includes a follower ridge disposed within the cam groove that contacts the cam surface of the associated compression mechanism as the cam follower plate moves with respect to the cam arm plate to cause the cam arm of the associated compression mechanism to pivot from its first position to its second position.

Embodiment 61

The instrument of any one of embodiments 42-60, wherein the sample processing cartridge includes a plurality of deformable fluid chambers and wherein the deformable chamber compression assembly comprises a plurality of compression mechanisms, each compression mechanism being associated with one of the deformable fluid chambers, and wherein the cam follower plate is operatively coupled to the compression mechanisms to convert movement of the cam follower plate in the first direction into movement of each of the compression mechanisms in the second direction to thereby apply an external compression force to each of the associated chambers in a specified sequence Embodiment 62

The instrument of any one of embodiments 40-61, wherein the fluid sample processing cartridge includes an externally-actuatable control valve configured to selectively control fluid flow by permitting fluid flow through the valve when not externally actuated and preventing fluid flow through the valve when externally actuated, and wherein the instrument further comprises a valve actuator compression mechanism associated with the externally-actuatable control valve of the sample processing cartridge and configured to actuate the associated externally-actuatable control valve by movement in a second direction having a component that is generally normal to the plane of the substrate, and wherein the cam follower plate is operatively coupled to the valve actuator compression mechanism to convert movement of the cam follower plate in the first direction into movement of the valve actuator compression mechanism in the second direction to thereby actuate the associated externally-actuatable control valve.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present invention. Moreover, the descriptions of such embodiments, combinations, and sub-combinations is not intended to convey that the inventions requires features or combinations of features other than those expressly recited in the claims. Accordingly, the scope of this disclosure is intended to include all modifications and variations encompassed within the spirit and scope of the following appended claims.

The invention claimed is:
1. An instrument configured to process a fluid sample processing cartridge including a deformable fluid chamber supported on a planar substrate and configured to hold a fluid therein when in an undeformed state and to collapse upon application of an external compression force to expel at least a portion of the fluid from the fluid chamber, said instrument comprising:
 a cartridge carriage assembly configured to receive and hold a fluid sample processing cartridge inserted into the instrument;
 a heating and control assembly adjacent the cartridge carriage assembly and configured for movement with respect to the cartridge carriage assembly between a first position not in operative contact with the cartridge carried within the cartridge carriage assembly and a second position in operative contact with the cartridge carried within the cartridge carriage assembly;
 one or more movable magnet assemblies, each mounted for movement with respect to the cartridge carriage assembly independently of the heating and control assembly between a first position applying substantially no magnetic force to the cartridge and a second position applying magnetic force to corresponding discrete portions of the cartridge;
 a cam block assembly configured for powered movement and operatively coupled to the heating and control assembly for converting powered movement of the cam block assembly into movement of the heating and control assembly with respect to the cartridge carriage assembly between the first position of the heating and control assembly and the second position of the heating and control assembly and operatively coupled to the one or more moveable magnet assemblies for converting powered movement of the cam block assembly into movement of each magnet assembly with respect to cartridge carriage assembly between the first position of the magnet assembly and the second position of the magnet assembly; and
 a deformable chamber compression assembly configured to selectively apply an external compression force to the deformable fluid chamber to collapse the deformable chamber and expel at least a portion of the fluid from the fluid chamber.

2. The instrument of claim 1, wherein said heating and control assembly comprises:
 one or more heater assemblies configured to apply a thermal gradient to corresponding discrete portions of the cartridge when the heating and control assembly is in the second position; and
 a connector board including one or more electrical connector elements configured to effect an electrical connection between the instrument and the cartridge when the heating and control assembly is in the second position.

3. The instrument of claim 1, wherein said deformable chamber compression assembly comprises:
 a cam follower plate configured for powered movement in a first direction that is generally parallel to the plane of the substrate; and
 a compression mechanism associated with the deformable chamber of the cartridge and configured to apply a force compressing the chamber against the substrate by movement in a second direction having a component that is generally normal to the plane of the substrate, wherein the cam follower plate is operatively coupled to the compression mechanism to convert movement of the cam follower plate in the first direction into movement of the compression mechanism in the second direction to thereby apply an external compression force to the chamber.

4. The instrument of claim 1, further comprising a pneumatic pump and a pneumatic port connected to the pneumatic pump, wherein the pneumatic port is configured to couple the pneumatic pump to a pressure port of the fluid sample processing cartridge when the cartridge is inserted into the instrument.

5. The instrument of claim 1, further comprising an optical detector configured to detect fluid flow through a part of the fluid sample processing cartridge.

6. The instrument of claim 1, wherein the fluid sample processing cartridge includes a driven mixing apparatus including a drive gear, and wherein the instrument further comprises a mixing motor assembly including a powered driving gear and moveable between a first position in which the driving gear is not engaged with the drive gear of the driven mixing apparatus and a second position in which the driving gear is operatively engaged with the drive gear to actuate the driven mixing apparatus, and wherein the cam block assembly is operatively coupled to the mixing motor assembly for converting powered movement of the cam block assembly into movement of the mixing motor assembly between the first position of the mixing motor assembly and the second position of the mixing motor assembly.

7. The instrument of claim 2, further comprising a heater cooling assembly comprising:
  a fan; and
  a cooling duct configured to direct air flow from the fan to a portion of one of said heater assemblies.

8. The instrument of claim 1, wherein said cartridge carriage assembly comprises:
  a cartridge holder configured to hold a cartridge inserted therein;
  a cartridge latch biased into a cartridge-latching position and configured to latch onto a cartridge inserted into the cartridge holder to retain the cartridge within the cartridge holder; and
  a cartridge eject mechanism configured to automatically push a cartridge at least partially out of the cartridge holder when the cartridge latch is released from a cartridge-latching position.

9. The instrument of claim 2, wherein said heating and control assembly comprises a support plate on which said one or more heater assemblies and said connector board are supported, said support plate being mounted in a constrained configuration preventing horizontal movement of the support plate but permitting vertical movement of the support plate to enable movement of the heating and control assembly between its first and second positions.

10. The instrument of claim 2, wherein one of said heater assemblies of the heating and control assembly comprises a resistive heating element attached to the connector board and a heat spreader comprising a thermally-conductive material thermally coupled to the resistive heating element.

11. The instrument of claim 2, wherein one of said heater assemblies of the heating and control assembly comprises:
  a thermoelectric element;
  a heat spreader comprising a thermally-conductive material thermally coupled to the thermoelectric element; and
  a heat sink including a panel that is in thermal contact with the thermoelectric element and a plurality of heat-dissipating rods.

12. The instrument of claim 2, wherein the electrical connector elements of the connector board of the heating and control assembly comprise a plurality of connector pin arrays, each connector pin array comprising a plurality of pogo pins.

13. The instrument of claim 1, wherein one of the movable magnet assemblies comprises:
  a magnet holder mounted on a spindle so as to be rotatable about the spindle between the first position and the second position of the magnet assembly;
  a magnet supported on the magnet holder;
  an actuator bracket extending from the magnet holder; and
  a torsion spring configured to bias the magnet holder to a rotational position corresponding to the first position of the magnet assembly.

14. The instrument of claim 1, wherein one of the movable magnet assemblies comprises:
  a magnet holder frame mounted on a spindle so as to be rotatable about the spindle between the first position and the second position of the magnet assembly;
  a magnet array disposed within the magnet holder frame;
  a focusing magnet disposed within an opening formed in the magnet holder frame and configured to focus magnetic forces of the magnet array;
  an actuator bracket extending from the magnet holder frame; and
  a torsion spring configured to bias the magnet holder frame to a rotational position corresponding to the first position of the magnet assembly.

15. The instrument of claim 13, wherein the cam block assembly is operatively coupled to each movable magnet assembly by a magnet actuator coupled at one portion thereof to the cam block assembly so as to be moveable by powered movement of the cam block assembly and including a tab configured to be engageable with the actuator bracket of each magnet assembly as the magnet actuator is moved with the cam block assembly to cause corresponding rotation of the magnet assembly from the first position to the second position.

16. The instrument of claim 1, wherein the cam block assembly comprises:
  a cam frame;
  a cam block motor coupled to the cam frame and configured to effect powered movement of the cam frame; and
  first and second cam rails attached to the cam frame, each of the cam rails having two cam slots, wherein the cam block assembly is operatively coupled to the heating and control assembly by cam followers extending from the heating and control assembly into the cam slots such that movement of the cam frame and the cam rails with respect to the heating and control assembly causes corresponding relative movement between the cam followers and the cam slots to move the cam followers between respective first segments of the cam slots corresponding to the first position of the heating and control assembly and respective second segments of the cam slots corresponding to the second position of the heating and control assembly.

17. The instrument of claim 16, wherein the cam frame comprises:
  a first longitudinal spar extending along one side of the heating and control assembly;
  a second longitudinal spar extending along an opposite side of the heating and control assembly; and
  a cross spar extending between the first and second longitudinal spars, and wherein each cam rail is attached to one of the first and second longitudinal spars.

18. The instrument of claim 3, wherein the compression mechanism of the deformable chamber compression assembly comprises:

a cam arm having a cam surface and mounted so as to be pivotable about one end of the cam arm; and a compression pad disposed at an opposite end of the cam arm, wherein the cam arm is pivotable between a first position in which the compression pad does not contact the associated deformable chamber and a second position in which the compression pad applies a compressive force to the associated deformable chamber to at least partially collapse the chamber.

19. The instrument of claim 18, wherein the deformable chamber compression assembly further comprises a cam arm plate, and the cam arm of the compression mechanism is pivotably mounted within a slot formed in the cam arm plate for pivotable movement of the cam arm with respect to the cam arm plate, and wherein the cam surface of the cam arm projects out of the slot above a surface of the cam arm plate, and wherein the cam follower plate is operatively coupled to the compression mechanism by a cam follower element of the cam follower plate that is engaged with the cam surface of the compression mechanism during movement of the cam follower plate with respect to the cam arm plate to cause the cam arm to pivot from its first position to its second position.

20. The instrument of claim 19, wherein the cam follower plate comprises a cam groove that receives the cam surface of the cam arm projecting above the surface of the cam arm plate, and the cam follower element comprises a follower ridge disposed within the cam groove that contacts the cam surface as the cam follower plate moves with respect to the cam arm plate to cause the cam arm to pivot from its first position to its second position.

21. The instrument of claim 20, comprising a plurality of compression mechanisms each comprising a cam arm pivotably mounted within a slot formed in the cam arm plate and a cam arm surface, and the cam follower plate comprises a plurality of cam grooves, each cam groove being associated with at least one of the compression mechanisms and wherein each cam groove includes a follower ridge disposed within the cam groove that contacts the cam surface of the associated compression mechanism as the cam follower plate moves with respect to the cam arm plate to cause the cam arm of the associated compression mechanism to pivot from its first position to its second position.

22. The instrument of claim 3, wherein the sample processing cartridge includes a plurality of deformable fluid chambers and wherein the deformable chamber compression assembly comprises a plurality of compression mechanisms, each compression mechanism being associated with one of the deformable fluid chambers, and wherein the cam follower plate is operatively coupled to the compression mechanisms to convert movement of the cam follower plate in the first direction into movement of each of the compression mechanisms in the second direction to thereby apply an external compression force to each of the associated chambers in a specified sequence.

23. The instrument of claim 3, wherein the fluid sample processing cartridge includes an externally-actuatable control valve configured to selectively control fluid flow by permitting fluid flow through the valve when not externally actuated and preventing fluid flow through the valve when externally actuated, and wherein the instrument further comprises a valve actuator compression mechanism associated with the externally-actuatable control valve of the sample processing cartridge and configured to actuate the associated externally-actuatable control valve by movement in a second direction having a component that is generally normal to the plane of the substrate, and wherein the cam follower plate is operatively coupled to the valve actuator compression mechanism to convert movement of the cam follower plate in the first direction into movement of the valve actuator compression mechanism in the second direction to thereby actuate the associated externally-actuatable control valve.

* * * * *